(12) United States Patent
Mitsuya et al.

(10) Patent No.: US 7,629,362 B2
(45) Date of Patent: Dec. 8, 2009

(54) 2-PYRIDINE CARBOXAMIDE DERIVATIVES

(75) Inventors: Morihiro Mitsuya, Tsukuba (JP); Makoto Bamba, Tsukuba (JP); Fumiko Sakai, Sapporo (JP); Hitomi Watanabe, Tsukuba (JP); Yasuhiro Sasaki, Tsukuba (JP); Teruyuki Nishimura, Ushiku (JP); Jun-ichi Eiki, Tsutiura (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 586 days.

(21) Appl. No.: 10/545,424

(22) PCT Filed: Feb. 13, 2004

(86) PCT No.: PCT/JP2004/001568

§ 371 (c)(1),
(2), (4) Date: Apr. 24, 2006

(87) PCT Pub. No.: WO2004/081001

PCT Pub. Date: Sep. 23, 2004

(65) Prior Publication Data

US 2006/0258701 A1 Nov. 16, 2006

(30) Foreign Application Priority Data

Feb. 13, 2003 (JP) ............................. 2003-034987
Oct. 1, 2003 (JP) ............................. 2003-342860
Jan. 22, 2004 (JP) ............................. 2004-014799

(51) Int. Cl.
*A61K 31/4436* (2006.01)
*C07D 417/14* (2006.01)
*C07D 401/14* (2006.01)

(52) U.S. Cl. .................................. 514/342; 546/268.7

(58) Field of Classification Search ............. 546/268.7; 514/342
See application file for complete search history.

(56) References Cited

U.S. PATENT DOCUMENTS

| | | | |
|---|---|---|---|
| 4,404,214 A | 9/1983 | Takeda et al. | |
| 7,390,908 B2 | 6/2008 | Boyd et al. | |
| 7,432,287 B2 | 10/2008 | Iino et al. | |
| 7,524,957 B2 | 4/2009 | Boyd et al. | |
| 2005/0080106 A1 | 4/2005 | Boyd et al. | |
| 2006/0258701 A1 | 11/2006 | Mitsuya et al. | |
| 2008/0207636 A1 | 8/2008 | Boyd et al. | |

FOREIGN PATENT DOCUMENTS

| | | |
|---|---|---|
| GB | 2 277 930 | 11/1994 |
| JP | 57-95984 | 6/1982 |
| JP | 58-121215 A | 7/1983 |
| JP | 2002-47278 | 2/2002 |
| WO | WO 03/015774 | 2/2003 |
| WO | WO 2004/076420 | 9/2004 |
| WO | WO 2004/081001 | 9/2004 |

OTHER PUBLICATIONS

Vippagunta et al., "Crystalline Solid", Advanced Drug Delivery Reviews 48 (2001) 3-26.*
Guillory (in Brittain ed.), "Polymorphism, etc.," NY: Marcel Dekker, Inc., 1999, 1-2, 183-226.*
D. Garfinkel et al., "Computer modeling identifies glucokinase as glucose sensor of pancreatic beta-cells", American Journal Physiology, vol. 247, pp. 527-536 (1984).
A. Grupe et al., "Transgenic Knockouts Reveal a Critical Requirement for Pancreatic beta Cell Glucokinase in Maintaining Glucose Homeostasis", Cell, vol. 83, pp. 69-78 (1995).

(Continued)

*Primary Examiner*—Patricia L Morris
(74) *Attorney, Agent, or Firm*—Richard C. Billups; Catherine D. Fitch

(57) ABSTRACT

The present invention relates to a compound which has a glucokinase-activating effect and is useful as a therapeutic agent for diabetes mellitus, being represented by a formula (I):

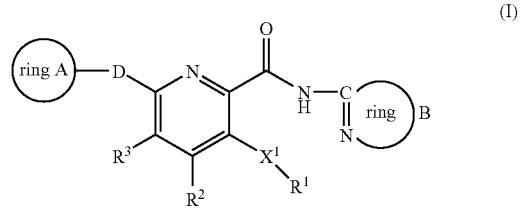

[wherein $X^1$ represents a nitrogen atom, sulfur atom, oxygen atom or the like; $R^1$ represents a 6- to 10-membered aryl group, 5- to 7-membered heteroaryl group or the like; D represents an oxygen atom or sulfur atom; $R^2$ and $R^3$ are the same or different, each representing a hydrogen atom, lower alkyl group or the like; a formula (II)

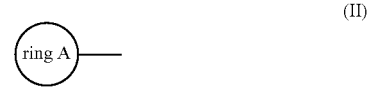

represents an optionally substituted 5- to 7-membered heteroaryl group or the like; a formula (III)

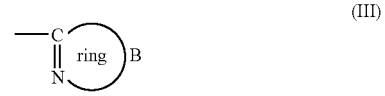

represents a monocyclic or bicyclic heteroaryl group] or a pharmaceutically acceptable salt thereof.

14 Claims, No Drawings

OTHER PUBLICATIONS

T. Ferre et al.m "Correction of diabetic alterations by glocokinase", Proceedings of the National Academy of Sciences of the USA, vol. 93, pp. 7225-7230 (1996).

N. Vionnet et al., "Nonsense mutation in the glucokinase gene causes early-onset non-insulin-dependent diabetes mellitus", Nature, vol. 356, pp. 721-722 (1992).

B. Glaser et al., "Familial Hyperinsulinism Caused by an Activating Glucokinase Mutation", New England Journal of Medicine, vol. 338, pp. 226-230 (1998).

S. W. Kaldor et al., "Viracept (Nelfmavir Mesylate, AG1343): A Potent, Orally Bioavailable Inhibitor of HIV-1 Protease", J. Med. Chem., vol. 40, pp. 3979-3985 (1997).

N. Zheng et al., "Palladium-Catalyzed Synthesis of Aryl Sulfides from Aryl Triflates", J. Org. Chem., vol. 63, pp. 9606-9607 (1998).

G. Y. Li et al., "Highly Active, Air-Stable Versatile Palladium Catalysts for the C-C, C-N, and C-S Bond Formations via Cross-Coupling Reactions of Aryl Chlorides", J. Org. Chem., vol. 66, pp. 8677-8681 (2001).

U. Schopfer et al., "A general palladium-catalysed synthesis of aromatic and heteroaromatic thioethers", Tetrahedron, vol. 57, pp. 3069-3073 (2001).

T. Migita et al., "The Palladium Catalyzed Nucleophilic Substitution of Aryl Halides by Thiolate Anions", Bull. Chem. Soc. Japan, vol. 53, pp. 1385-1389 (1980).

F. Y. Kwong et al., "A General, Efficient, and Inexpensive Catalyst System for the Coupling of Aryl Iodides adn Thiols", Organic Letters, vol. 4, No. 20, pp. 3517-3520 (2002).

S. Rajagopalan et al., "Synthesis of N-t-BOC-4-S-t-Butyl-L-Thiophenylalanine Via Pallidium Catalyzed Cross-Coupling Reaction of N-t-BOC-4-IODO-L-Phenylalanine with t-Butylthiol or Sodium t-Butylthiolate", Synthetic Communications, vol. 26, No. 7, pp. 1431-1440 (1996).

J. E. T. Corrie et al., "Synthesis of a Cephalosporin Analogue", Journal of Chemical Society, Perkin Transaction, Chapter I, p. 1421-1425 (1977).

S. Sakakibara et al., "Use of Anhydrous Hydrogen Fluoride in Peptide Synthesis. I. Behavior of Various Protective Groups in Anhydrous Hydrogen Fluoride", Bulletin of the Chemical Society of Japan, vol. 40, pp. 2164-2167 (1967).

D. A. J. Ives, "Electrolysis in liquid ammonia solution in peptide chemistry", Canadian Journal of Chemistry, vol. 47, pp. 3697-3699 (1969).

A. Ogawa et al., "Highly Regio- and Stereocontrolled Synthesis of Vinyl Sulfides via Transition-Metal-Catalyzed Hydrothiolation of Alkynes with Thiols", J. Am. Chem. Soc., vol. 121, pp. 5108-5114 (1999).

* cited by examiner

2-PYRIDINE CARBOXAMIDE DERIVATIVES

CROSS-REFERENCE TO RELATED APPLICATIONS

This application is a U.S. National Phase application under 35 U.S.C. §371 of PCT Application No. PCT/JP2004/001568, filed Feb. 13, 2004, which claims priority from Japanese patent application Nos. JP2003-34987, filed Feb. 13, 2003, JP2003-342860 filed Oct. 1, 2003, and JP2004-14799, filed Jan. 22, 2004, priority of which is claimed hereunder.

TECHNICAL FIELD

The present invention relates to a glucokinase activating agent containing a pyridine-2-carboxamide derivative as an effective component. Moreover, it relates to novel 2-pyridine carboxamide derivatives and salts thereof.

BACKGROUND ART

Glucokinase (GK) (ATP: D-hexose 6-phosphotransferase, EC 2.7.1.1) is one of 4 types of hexokinase (hexokinase IV) in mammals. Hexonase is an enzyme acting in the first stage of a glycolytic pathway which catalyzes the reaction from glucose to glucose 6-phosphate. Occurrence of glucokinase is localized mainly in liver and the beta cells of pancreas, in which glucokinase controls the rate-determining step of glucose metabolism, whereby it plays an important role in the generalized saccharometabolism. Glucokinase in liver and that in the beta cells of pancreas are the same in their enzymatic properties, though the sequences of the N-terminal 15 amino acids are different from each other due to the difference of splicing. In 3 types of hexokinase (I, II, and III) other than glucokinase, the enzyme activities are saturated at a 1 mM or lower concentration of glucose, whereas the Km of glucokinase for glucose is 8 mM, which value is proximate to the physiological blood sugar level. Therefore, the intracellular glucose metabolism is accelerated through glucokinase in response to the change of blood sugar level from normal (5 mM) to postprandial elevation (10-15 mM).

About 10 years ago, a hypothesis has been proposed that glucokinase works as a glucose sensor in the beta cells of pancreas or liver (Garfinkel D, et al., "Computer modeling identifies glucokinase as glucose sensor of pancreatic beta-cells", American Journal Physiology, 247, 3Pt2. 1984, P. 527-536). From the recent results in mice in which glucokinase has been genetically engineered, it has been found that glucokinase in fact has an important role in the generalized homeostasis of glucose. Though mice of which the glucokinase gene has been destroyed result in death shortly after birth (Grupe A, et al., "Transgenic knockouts reveal a critical requirement for pancreatic beta cell glucokinase in maintaining glucose homeostasis", Cell, 83, 1995, P. 69-78, the blood sugar level is decreased in normal and diabetic mice in which glucokinase has been generated in excess (Ferre T, et al., "Correction of diabetic alterations by glucokinase", Proceedings of the National Academy of Sciences of the U.S.A., 93, 1996, P. 7225-7230). With increase of the glucose concentration, the reactions of the pancreatic beta cells and hepatocytes move toward decreasing the blood sugar level though the degree is different respectively. The pancreatic beta cells work to secrete much more insulin, and on the other hand the liver uptakes sugar and store it as glycogen, resulting in decrease of sugar release.

Thus, the change of the enzymatic activity of glucokinase plays an important role in mammalian glucose homeostasis through liver and the beta cells of pancreas. In a case of causing juvenile diabetes which is called MODY2 (maturity-onset diabetes of the young), it has been found that a mutation occurs in the glucokinase gene and decrease of the glucokinase activity increases the blood sugar level (Vionnet N, et al., "Nonsense mutation in the glucokinase gene causes early-onset non-insulin-dependent diabetes mellitus", Nature Genetics, 356, 1992, P. 721-722). It has also been found that there is a kindred which has a mutation increasing the glucokinase activity and shows hypoglycemia (Glaser B, et al., "Familial hyperinsulinism caused by an activating glucokinase mutation", New England Journal Medicine, 338, 1998, P. 226-230).

This means that glucokinase works as a glucose sensor in human and plays an important role in glucose homeostasis. On the other hand, it is considered that in a large number of the II-type diabetic patients it will be possible to regulate the blood sugar level utilizing a system of glucokinase sensor. The glucokinase-activating substances are expected to have an effect of accelerating the insulin secretion in the pancreatic beta cells and an effect of accelerating the sugar uptake and inhibiting the sugar release in liver, and they are considered useful as therapeutic agents in the II-type diabetic patients.

In recent years, it has been elucidated that the occurrence of glucokinase of the pancreatic beta cell type is localized in the brain of rats, particularly in the feeding center (ventromedial hypothalamus; VMH). It has long been considered that about 20% of the neurocytes in VMH, called the glucose responsive neuron, have an important role in control of body weight. Feeding of rats is decreased when glucose is administered into the brain, while inhibition of the glucose metabolism by intracerebral administration of a glucose analog, glucosamine, causes hyperphagia. From electrophysiological experiments, it has been recognized that the glucose responsive neuron is activated in response to the physiological change of glucose concentration (5-20 mM), but its activity is inhibited by inhibiting the glucose metabolism with glucosamine. The same mechanism through glucokinase has been assumed in the sensor system for the glucose concentration in VHM as in the insulin secretion in the pancreatic beta cells. Therefore, in addition to the action in the liver and pancreatic beta cells, a glucokinase-activating substance in VMH is expected to improve not only the blood sugar lever but also obesity which is a problem in a large number of II-type diabetic patients.

As seen from the above description, glucokinase-activating compounds are useful as therapeutic agents and/or preventive agents for diabetes mellitus or for chronic diabetic complications such as retinopathy, nephropathy, neurosis, ischemic heart disease or arteriosclerosis, as well as for obesity.

As for a compound having a pyridine skeleton and an amide linkage attached to the pyridine skeleton which are contained in the compounds (I) of the invention, the following compound represented by the structural formula (IV) has been described (see, for example, Japanese Laid-Open Patent Application No. 5-213382).

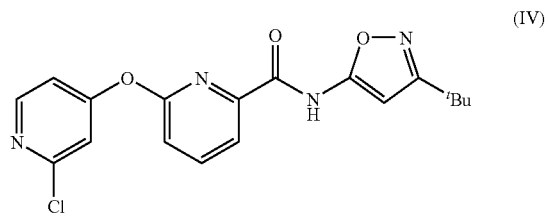

(IV)

In the compound (IV) described in Japanese Laid-Open Patent Application No. 5-213382, however, the location of the C═N and the amide linkage in the isoxazole group is different from that of the compounds of the invention. In addition, it is also different in that while the utility of the compounds of the invention includes diabetes mellitus, the utility described in Japanese Laid-Open Patent Application No. 5-213382 relates to herbicide.

As for the structurally analogous compounds having the utility for diabetes mellitus, the following compounds represented by the formulae (V):

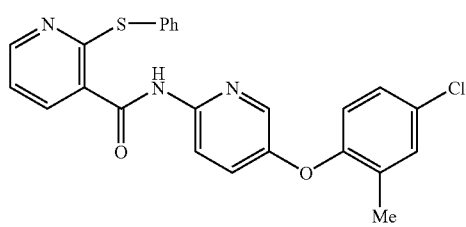

(V)

and (VI):

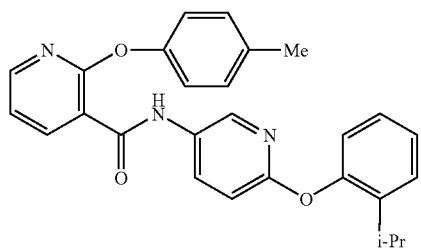

(VI)

have been described (see, for example, Published Japanese Translation of PCT International Publication No. 2001-522834).

One of the utility of the compounds described in the Published Japanese Translation of PCT International Publication No. 2001-522834 is for diabetes mellitus, the same as that of the compounds (I) of the present invention.

The compound (V) or (VI) described in the Published Japanese Translation of PCT International Publication No. 2001-522834 and the compounds (I) of the present invention have a pyridine skeleton in common as the fundamental skeleton and an amide linkage on the pyridine ring.

It is different, however, in that the compounds (I) of the present invention have a substituent at the 6 position of the pyridine ring, while the compound (V) or (VI) has no substituent at the 6 position of the pyridine ring.

In addition, it is also different that the compounds (I) of the invention have an amide linkage adjacent to the nitrogen atom constituting the pyridine ring, while the compound (VI) described in Published Japanese Translation of PCT International Publication No. 2001-522834 has an amide linkage at the position separated by one carbon from the nitrogen atom constituting the pyridine ring. Moreover, the location of the amide linkage relative to the C═N moiety of the pyridine ring corresponding to the ring B in the compounds (I) of the present invention is different from that of the compound (VI) of the Published Japanese Translation of PCT International Publication No. 2001-522834.

As for a compound having the same pyridine-2-carboxamide skeleton as the compounds (I) of the present invention, the compound of the formula (VII):

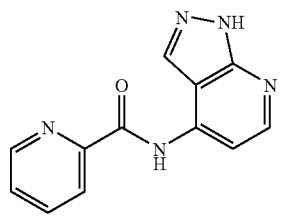

(VII)

has been described (see, for example, WO01/81345). However, the location of the amide linkage relative to the nitrogen atom of 1H-pyrazolo[3,4-b]pyridine-4-yl which is attached to the nitrogen atom of the amide linkage in the compound (VII) is different from the location of the amide linkage relative to the C═N in the ring B of the compounds (I) of the present invention. In addition, it is different that, while the 3 and 6 positions of the pyridine skeleton in the formula (VII) are occupied by hydrogen atoms, those of the compounds (I) are occupied by other groups than hydrogen atoms. Thus, the compound of the formula (VII) is different from the compounds (I) of the present invention in the entire structure.

Therefore, the compounds (I) of the present invention are different from the compound described in WO01/81345 in the aspect of the substituent attached to the pyridine skeleton, though both compounds have the pyridine-2-carboxamide as fundamental skeleton. Thus, the compounds (I) are different from the compound (VII) in total.

The purpose of the invention is to provide a therapeutic agent and/or preventive agent for diabetes mellitus which can bind to glucokinase to increase the glucokinase activity, as well as an anti-obesity agent which activates glucokinase to stimulate the satiety center.

As mentioned above, it is advantageous that the compounds of the invention have a better drug effect than the existing diabetic agents and provide a possibility of resulting in development of new drug effects which have not been possessed by the existing diabetic agents.

The present inventors, accordingly, worked assiduously to develop a new diabetic agent which has a better new drug effect than the existing diabetic agents based on a mechanism of action that is different from that of the existing drugs. As a result, they have found that the compounds represented by the formula (I) have a glucokinase-activating effect. Thus, the invention has been completed.

DISCLOSURE OF THE INVENTION

That is, the invention provides the following:
(1) A compound of the formula (I):

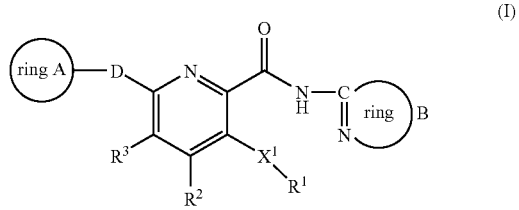

(I)

[wherein $X^1$ represents N, S or O, or a divalent saturated hydrocarbon group of 1 to 6 carbon atoms (when the carbon number of the divalent saturated hydrocarbon group is 2 or more, one of the carbon atoms therein may be replaced by a nitrogen atom, oxygen atom or sulfur atom); $R^1$ represents a 6- to 10-membered aryl group, 5- to 10-membered heteroaryl group, cycloalkyl group of 3 to 7 carbon atoms, or lower alkyl group (wherein $R^1$ may be substituted on $R^1$ by 1 or 2 groups selected from the group consisting of amino, lower alkyl group (the hydrogen atom of the lower alkyl group may be substituted by a group comprised of hydroxyl group, lower alkoxy group, halogen atom, carbamoyl group, mono- or di-lower alkyl carbamoyl group, carboxyl group alkoxy carboyl group, alkanoyl group, amino group, mono- or di-alkylamino group), lower alkoxy group (the hydrogen atom of the methylene or methyl group constituting the lower alkoxy group may be substituted by hydroxyl group, halogen atom, carbamoyl group, mono- or di-loweralkyl carbamoyl group, carboxyl group, alkoxy carbonyl group, alkanoyl group, amino group, mono- or di-lower alkylamino group), carbamoyl group, lower alkylcarbamoyl group, di-lower alkylcarbamoyl group, carbamoylamino group, carbamoyloxy group, carboxyl group, cyano group, sulfamoyl group, trifluoromethyl group, halogen atom, hydroxyl group, formyl group, C2-C6 alkanoyl group, N—C2-C6 alkanoylamino group, C1-C6 alkylthio group, N—C1-C6 alkylsulfamoyl group, N,N-di-C1-C6 alkylsulfamoyl group, C1-C6 alkylsulfinyl group, C1-C6 alkylsulfonyl group, N—C1-C6 alkylsulfonylamino group, C1-C6 alkoxycarbonyl group, N—C1-C6 alkylamino group, N,N-di-C1-C6 alkylamino group, 6- to 1-membered aryl group and 5- to 10-membered heteroaryl group); D represents O or S; $R^2$ and $R^3$ are the same or different, each representing a hydrogen atom, lower alkyl group, lower alkoxy group or halogen atom; the formula (II):

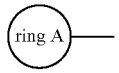

(II)

represents a 5- to 7-membered heteroaryl group or 6- to 10-membered aryl group which may have on the ring 1 or 2 groups selected from the group consisting of lower alkyl group, lower alkoxy group, hydroxyl group, hydroxyalkyl group (the hydrogen atom of the hydroxy group of the hydroxyalkyl group may further be substituted by a lower alkyl group) and halogen atom; the formula (III):

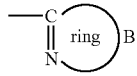

(III)

represents a monocyclic or bicyclic heteroaryl group in which the carbon atom attached to the amide nitrogen atom contained in the formula (I) forms C═N together with the nitrogen atom in the ring (wherein the heteroaryl group may have in the ring B 1 or 2 substituents selected from the group consisting of lower alkyl group, lower alkoxy group, halogen atom, trifluoromethyl group, hydroxyalkyl group (the hydrogen atom of the hydroxy group in the hydroxyalkyl group may further be substituted by a lower alkyl group), aminoalkyl group (the amino group in the group may be substituted by a lower alkyl group), alkanoyl group, carboxyl group, alkoxycarbonyl group and cyano group)]

or a pharmaceutically acceptable salt thereof.

(2) The compound according to (1), wherein D is S.

(3) The compound according to (1) or (2), wherein both of $R^2$ and $R^3$ are hydrogen atoms.

(4) The compound according to any one of (1) to (3), wherein the ring A is phenyl group, isothiazolyl group, imidazolyl group, oxazolyl group, thiadiazolyl group, thienyl group, triazolyl group, tetrazolyl group, pyridyl group, pyrimidinyl group, furyl group, thiazolyl group, isoxazolyl group or pyrazolyl group, which may contain on the ring 1 or 2, groups selected from the group consisting of lower alkyl group, lower alkoxy group, hydroxy group, hydroxyalkyl group (the hydrogen atom of the hydroxy group in the hydroxyalkyl group may further be substituted by a lower alkyl group) and halogen atom.

(5) The compound according to any one of the above items (1) to (4), wherein $X^1$ is a group selected from the group consisting of nitrogen atom, sulfur atom, oxygen atom, —CH$_2$—, —N—CH$_2$—, —S—CH$_2$—, —O—CH$_2$—, —CH$_2$—N—, —CH$_2$—O— and —CH$_2$—S—.

(6) The compound according to any one of (1) to (5), wherein the ring B is a 5- or 6-membered heteroaryl group which contains at least one nitrogen atom of C═N constituting the ring as a heteroatom, or a 9- or 10-membered heteroaryl group which is formed by condensation of the former heteroaryl group with phenyl group or pyridyl group.

(7) The compound according to any one of (1) to (6), wherein $R^1$ is a 6- to 10-membered aryl group, 5- to 10-membered heteroaryl group, or cycloalkyl group of 3 to 7 carbons.

(8) The compound according to any one of (1) to (6), wherein $R^1$ is a 6- to 10-membered aryl group or 5- to 10-membered heteroaryl group.

(9) The compound according to any one of (1) to (6), wherein $R^1$ is a 6- to 10-membered aryl group.

(10) The compound according to any one of (1) to (6), wherein $R^1$ is a 5- to 10-membered heteroaryl group.

(11) The compound according to (9) or (10), wherein the substituent of the ring A is a hydrogen atom, lower alkyl group, lower alkoxy group, hydroxyl group, or hydroxy lower alkyl group (the hydrogen atom of the hydroxy group of the hydroxy lower alkyl group may further be substituted by a lower alkyl group).

(12) The compound according to any one of (9) to (11), wherein the ring B is a thiazolyl group, imidazolyl group, isothiazolyl group, thiadiazolyl group, triazolyl group, oxazolyl group, isoxazolyl group, pyrazinyl group, pyridyl group, pyridazinyl group, pyrazolyl group, pyrimidinyl group, pyridothiazolyl group, or benzothiazolyl group.

(13) The compound according to any one of (1) to (10), wherein the substituent of the ring B is a hydrogen atom, lower alkyl group, halogen atom, hydroxyalkyl group, aminoalkyl group, or alkanoyl group.

(14) The compound according to any one of (9) to (12), wherein the substituent in $R^1$ is hydrogen atom, hydroxyalkyl group, lower alkyl group, lower alkoxy group, carbamoyl group, alkylcarbamoyl group, dialkylcarbamoyl group, cyano group, trifluoromethyl group, halogen atom, C2-C6 alkanoyl group, N—C2-C6 alkanoylamino group, C1-C6 alkylsulfonyl group, C1-C6 alkylamino group, or aminoalkyl group.

(15) The compound according to any one of (1) to (14), wherein the compound represented by the formula (I):

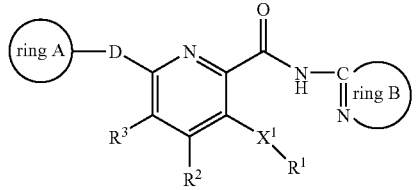

(I)

(wherein the respective symbols have the same meanings as defined above)

is: 3-(4-methoxy-phenylsulfanyl)-6-(4H-[1,2,4]triazole-3-yl)-N-(thiazole-2-yl)-2-pyridine carboxamide, 3-(4-fluoro-phenylsulfanyl)-6-(4-methyl-4H-[1,2,4]triazole-3-yl-sulfanyl-N-(4-methyl-thiazole-2-yl)-2-pyridine carboxamide, 3-(4-fluoro-phenylsulfanyl)-6-(4H-[1,2,4]triazole-3-yl-sulfanyl)-N-(4-methyl-thiazole-2-yl)-2-pyridine carboxamide, 3-(4-fluoro-phenylsulfanyl)-6-(1-methyl-imidazole-2-yl-sulfanyl)-N-(4-methyl-thiazole-2-yl)-2-pyridine carboxamide, 3-(4-fluoro-phenylsulfanyl)-6-(1-methyl-1H-tetrazole-5-yl-sulfanyl)-N-(4-methyl-thiazole-2-yl)-2-pyridine carboxamide, 3-(cyclohexylsulfanyl)-6-(4H-[1,2,4]triazole-3-yl-sulfanyl)-N-(4-methyl-thiazole-2-yl)-2-pyridine carboxamide, 3-(4-fluoro-phenylsulfanyl)-6-(4H-[1,2,4]triazole-3-yl-sulfanyl)-N-(thiazole-2-yl)-2-pyridine carboxamide, 3-(thiazole-2-yl-sulfanyl)-6-(4H-[1,2,4]triazole-3-yl)-N-(4-methyl-thiazole-2-yl)-2-pyridine carboxamide, 3-(2-fluoro-phenylsulfanyl)-6-(4H-[1,2,4]triazole-3-yl-sulfanyl)-N-thiazole-2-yl-pyridine carboxamide, 3-phenylsulfanyl-6-(4H-[1,2,4]triazole-3-yl-sulfanyl)-N-(thiazole-2-yl)-2-pyridine carboxamide, 3-(4-fluoro-phenyloxy)-6-(4H-[1,2,4]triazole-3-yl-sulfanyl)-N-(thiazole-2-yl)-2-pyridine carboxamide, 3-(4-methoxy-phenylmethylsulfanyl)-6-(4-methyl-4H-[1,2,4]triazole-3-yl-sulfanyl)-N-(thiazole-2-yl)-2-pyridine carboxamide, 3-(3-fluoro-phenylsulfanyl)-6-(4H-[1,2,4]triazole-3-yl-sulfanyl)-N-(thiazole-2-yl)-2-pyridine carboxamide, 3-(2,4-difluoro-phenyl-sulfanyl)-6-(4H-[1,2,4]-triazole-3-yl-sulfanyl)-N-(thiazole-2-yl)-2-pyridine carboxamide, 3-(4-fluoro-phenylsulfanyl)-6-(5-methyl-4H-[1,2,4]triazole-3-yl-sulfanyl)-N-(thiazole-2-pyridine carboxamide, 3-(4-cyanophenylsulfanyl)-6-(4H-[1,2,4]triazole-3-yl-sulfanyl)-N-(thiazole-2-yl)-2-pyridine carboxamide, 3-(pyridine-4-yl-sulfanyl)-6-(4H-[1,2,4]triazole-3-yl-sulfanyl)-N-(thiazole-2-yl)-2-pyridine carboxamide, 3-(4-fluoro-phenylsulfanyl)-6-(4H-[1,2,4]triazole-3-yl-sulfanyl)-N-(4-thiazoleo[5,4-b]pyridine-2-yl)-2-pyridine carboxamide, 3-(4-methoxy-phenylsulfanyl)-6-(4H-[1,2,4]triazole-3-yl-sulfanyl)-N-(4-methoxymethyl-thiazole-2-yl)-2-pyridine carboxamide, 3-(4-acetyl-phenylsulfanyl)-6-(4H-[1,2,4]triazole-3-yl-sulfanyl)-N-(thiazole-2-yl)-2-pyridine carboxamide, 3-(thiophene-2-yl-sulfanyl)-6-(4H[1,2,4]triazole-3-yl-sulfanyl)-N-(thiazole-2-yl)-2-pyridine carboxamide, 3-(4-methoxymethyl-phenylsulfanyl)-6-(4H-[1,2,4]triazole-3-yl-sulfanyl)-N-(thiazole-2-yl)-2-pyridine carboxamide, 3-(4-fluoro-phenylsulfanyl)-6-(5-methyl-4H-[1,2,4]triazole-3-yl-sulfanyl)-N-(thiazoleo[5,4-b]pyridine-2-yl)-2-pyridine carboxamide, 3-(4-methyl-phenylsulfanyl)-6-(4H-[1,2,4]triazole-3-yl-sulfanyl)-N-(4-methoxymethyl-thiazole-2-yl)-2-pyridine carboxamide, 3-(4-chloro-phenylsulfanyl)-6-(4H-[1,2,4]triazole-3-yl-sulfanyl)-N-(4-methoxymethyl-thiazole-2-yl)-2-pyridine carboxamide, 3-(4-fluoro-phenylsulfanyl)-6-(3H-[1,2,3]triazole-4-yl-sulfanyl)-N-(thiazole-2-yl)-2-pyridine carboxamide, 3-(4-methylsulfonyl-phenylsulfanyl)-6-(4H-[1,2,4]triazole-3-yl-sulfanyl)-N-(thiazole-2-yl)-2-pyridine carboxamide, 3-(4-methoxy-phenylsulfanyl)-6-(4H-[1,2,4]triazole-3-yl-sulfanyl)-N-(5-hydroxymethyl-thiazole-2-yl)-2-pyridine carboxamide, 3-(4-fluoro-phenylsulfanyl)-6-(5-methoxymethyl-4H-[1,2,4]triazole-3-yl-sulfanyl)-N-(thiazole-2-yl)-2-pyridine carboxamide, 3-(6-methyl-pyridine-3-yl-sulfanyl)-6-(4H-[1,2,4]triazole-3-yl-sulfanyl)-N-(thiazole-2-yl)-2-pyridine carboxamide, 3-(4-dimethylcarbamoyl-phenylsulfanyl)-6-(4H-[1,2,4]triazole-3-yl-sulfanyl)-N-(thiazole-2-yl)-2-pyridine carboxamide, 3-(4-trifluoromethyl-phenylsulfanyl)-6-(4H-[1,2,4]triazole-3-yl-sulfanyl)-N-(thiazole-2-yl)-2-pyridine carboxamide, 3-(4-methylcarbamoyl-phenylsulfanyl)-6-(4H-[1,2,4]triazole-3-yl-sulfanyl)-N-(thiazole-2-yl)-2-pyridine carboxamide, 3-(hydroxyethyloxy-phenylsulfanyl)-6-(4H-[1,2,4]triazole-3-yl-sulfanyl)-N-(thiazole-2-yl)-2-pyridine carboxamide, 3-(4-methoxy-phenylsulfanyl)-6-(4H-[1,2,4]triazole-3-yl-sulfanyl)-N-(5-dimethylaminomethyl-thiazole-2-yl)-2-pyridine carboxamide, 3-(4-dimethylaminoethyloxy-phenylsulfanyl)-6-(4H-[1,2,4]triazole-3-yl-sulfanyl)-N-(thiazole-2-yl)-2-pyridine carboxamide, 3-(4-hydroxyethyl-phenylsulfanyl)-6-(4H-[1,2,4]triazole-3-yl-sulfanyl)-N-(thiazole-2-yl)2-pyridine carboxamide, 3-(4-methylsulfamoyl-phenylsulfanyl)-6-(4H-[1,2,4]triazole-3-yl-sulfanyl)-N-(thiazole-2-yl)-2-pyridine carboxamide, 3-(4-dimethylcarbamoyl-phenylsulfanyl)-6-(4H-[1,2,4]-triazole-3-yl-sulfanyl)-N-(isoxazol-3-yl)-2-pyridine carboxamide, 3-(4-hydroxy-cyclohexylsulfanyl)-6-(4H-[1,2,4]triazole-3-yl-sulfanyl)-N-(thiazole-2-yl)-2-pyridine carboxamide, 3-(4-fluoro-phenylsulfanyl)-6-(4H-[1,2,4]-triazole-3-yl-sulfanyl)-N-pyridazine-3-yl)-2-pyridine carboxamide, 3-(pyrazine-2-yl-sulfanyl)-6-(4H-[1,2,4]triazole-3-yl-sulfanyl)-N-(thiazole-2-yl)-2-pyridine carboxamide, 3-(6-methyl-pyridine-3-yl-sulfanyl)-6-(4H-[1,2,4]triazole-3-yl-sulfanyl)-N-(pyrazine-2-pyridine carboxamide, 3-(6-methyl-pyridine-3-yl-sulfanyl)-6-(4H-[1,2,4]triazole-3-yl-sulfanyl)-N-(4-methyl-thiazole-2-yl)-2-pyridine carboxamide, 3-[4-(1-hydroxyethyl-phenylsulfanyl)-6-(4H-[1,2,4]triazole-3-yl-sulfanyl)-N-(thiazole-2-yl)-2-pyridine carboxamide, 3-(6-methyl-pyridine-3-yl-sulfanyl)-6-(4H-[1,2,4]triazole-3-yl-sulfanyl)-N-(2-methyl-thiazole-4-yl)-2-pyridine carboxamide, 3-(4-dimethylcarbamoyl-phenylsulfanyl)-6-(4H-[1,2,4]triazole-3-yl-sulfanyl)-N-(2-methyl-thiazole-4-yl)-2-pyridine carboxamide, 3-(6-methyl-pyridine-3-yl-sulfanyl)-6-(4H-[1,2,4]triazole-3-yl-sulfanyl)-N-(4-methoxymethyl-thiazole-2-yl)-2-pyridine carboxamide, 3-(1-methyl-1H-tetrazole-5-yl-sulfanyl)-6-(4H-[1,2,4]triazole-3-yl-sulfanyl)-N-(thiazole-2-yl)-2-pyridine carboxamide, 3-(4-hydroxyethyloxy-phenylsulfanyl)-6-(4H-[1,2,4]triazole-3-yl-sulfanyl)-N-(isoxazol-3-yl)-2-pyridine carboxamide, 3-(4-dimethylaminoethyloxy-phenylsulfanyl)-6-(4H-[1,2,4]triazole-3-yl-sulfanyl)-N-(isoxazol-3-yl)-2-pyridine carboxamide, 3-(4-fluoro-phenylsulfanyl)-6-phenoxy-N-(4-methyl-thiazole-2-yl)-2-pyridine carboxamide, 3-(2-chloro-phenylmethyl-amino)-6-(4-methyl-4H-[1,2,4]triazole-3-yl-sulfanyl)-N-(4-methyl-thiazole-2-yl)-2-pyridine carboxamide, 3,6-bis-(pyridine-2-yl-sulfanyl)-N-(4-methyl-thiazole-2-yl)-2-pyridine carboxamide, 3,6-bis-(4-fluoro-phenylsulfanyl)-N-(4-methyl-thiazole-2-yl)-2-pyridine carboxamide, 3,6-bis-(thiazole-2-yl-sulfanyl)-N-(thiazole-2-yl)-2-pyridine carboxamide, 3,6-bis-(5-methyl-[1,3,4]thiadiazol-2-yl-sulfanyl)-N-(thiazole-2-yl)-2-pyridine carboxamide, 3-(4-methoxy-phenylsulfanyl)-6-(4H-[1,2,4]triazole-3-yl-sulfanyl)-N-(5-methyl-thiazole-2-yl)-2-pyridine carboxamide, 3-(4-methoxy-phenylsulfanyl)-6-(4H-[1,2,4]triazole-3-yl-sulfanyl)-N-(isoxazol-3-yl)-2-pyridine carboxamide, 3-(4-methoxy-phenylsulfanyl)-6-(4H-[1,2,4]triazole-3-yl-sulfanyl)-N-([1,3,4]thiadiazol-2-yl)-2-pyridine carboxamide, 3-(4-methoxy-phenylsulfanyl)-6-(4H-[1,2,4]triazole-3-yl-sulfanyl)-N-([1,2,4]thiadiazol-5-yl)-2-pyridine carboxamide, 3-(4-methoxy-phenylsulfanyl)-6-(4H-[1,2,4]triazole-3-yl-sulfanyl)-N-(4-methylcarbonyl-thiazole-2-yl)-2-pyridine carboxamide, 3-(4-methoxy-phenylsulfanyl)-6-(4H-[1,2,4]triazole-3-yl-sulfanyl)-N-(pyrimidine-4-yl)-2-pyridine carboxamide, 3-(4-methoxy-phenylsulfanyl)-6-(4H-[1,2,4]triazole-3-yl-sulfanyl)-N-(pyridine-2-yl)-2-pyridine carboxamide, 3-(4-methoxy-phenylsulfanyl)-6-(4H-[1,2,4]triazole-3-yl-sulfanyl)-N-(5-ethoxylcarbonyl-thiazole-2-yl)-2-pyridine carboxamide, 3-(pyridine-3-yl-sulfanyl)-6-(4H-[1,2,4]triazole-3-yl-sulfanyl)-N-(thiazole-2-yl)-2-pyridine carboxamide, 3-(6-methoxy-pyridine-3-yl-sulfanyl)-6-(4H-[1,2,4]triazole-3-yl-sulfanyl)-N-(thiazole-2-yl)-2-pyridine carboxamide, 3-(pyridine-3-yl-sulfanyl)-6-(4H-[1,2,4]triazole-3-yl-sulfanyl)-N-(4-methoxymethyl-thiazole-2-yl)-2-pyridine carboxamide, 3-phenyloxymethyl-6-(4-methyl-4H-[1,2,4]triazole-3-yl-sulfanyl)-N-(thiazole-2yl)-2-pyridine carboxamide, 3-phenylsulfanylmethyl-6-(4-methyl-4H-[1,2,4]triazole-3-yl-sulfanyl)-N-(thiazole-2-yl)-2-pyridine carboxamide, 3-phenylmethyl-6-(4H-[1,2,4]triazole-3-yl-sulfanyl)-N-(thiazole-2-yl)-2-pyridine carboxamide, 3-(4-fluoro-phenylmethyl)-6-(4H-[1,2,4]triazole-3-yl-sulfanyl)-N-(thiazole-2-yl)-2-pyridine carboxamide, 3-(4-dimethylaminoethyl-phenylsulfanyl)-6-(4H-[1,2,4]triazole-3-yl-sulfanyl)-N-(thiazole-2-pyridine carboxamide, 3-(4-dimethylaminomethyl-phenylsulfanyl)-6-(4H-[1,2,4]triazole-3-yl-sulfanyl)-N-(thiazole-2-yl)-2-pyridine carboxamide, 3-(4-methoxy-phenylsulfanyl)-6-(4H-[1,2,4]triazole-3-yl-sulfanyl)-N-(thiazole-4-yl)-2-pyridine carboxamide, 3-(4-dimethylcarbamoylmethyloxy-phenylsulfanyl)-6-(4H-[1,2,4]triazole-3-ylsulfanyl)-N-(thiazole-2-yl)-2-pyridine carboxamide, 3-(4-methoxy-phenylsulfanyl)-6-(4H-[1,2,4]triazole-3-ylsulfanyl)-N-(4-hydroxyethyl-thiazole-2-yl)-2-pyridine carboxamide, 3-(6-methyl-pyridine-3-ylsulfanyl)-6-(5-hydroxy-4H-[1,2,4]triazole-3-ylsulfanyl)-N-(thiazole-2-yl)-2-pyridine carboxamide, 3-(6-methoxycarbonyl-pyridine-3-ylsulfanyl)-6-(4H-[1,2,4]triazole-3-yl-sulfanyl)-N-(thiazole-2-yl)-2-pyridine carboxamide, 3-(4-dimethylaminoethyloxy-phenylsulfanyl)-6-(4H-[1,2,4]triazole-3-yl-sulfanyl)-N-([1,2,4]triadiazol-5-yl)-2-pyridine carboxamide, 3-(pyrimidine-5-ylsulfanyl)-6-(4H-[1,2,4]triazole-3-ysulfanyl)-N-(thiazole-2-yl)-2-pyridine carboxamide, 3-(6-hydroxymethyl-pyridine-3-ylsulfanyl)-6-(4H-[1,2,4]triazole-3-ylsulfanyl)-N-(thiazole-2-yl)-2-pyridine carboxamide, 3-[4-(1-methylpyrrolidine-3-yloxy)-phenylsulfanyl]-6-(4H-[1,2,4]triazole-3-yl-sulfanyl)-N-thiazole-2-yl)-2-pyridine carboxamide, 3-(6-methyl-pyridine-3-ylsulfanyl)-6-(4H-[1,2,4]triazole-3-ylsulfanyl)-N-([1,2,4]thiadiazol-5-yl)-2-pyridine carboxamide, 3-(4-dimethylaminoethyloxy-phenylsulfanyl)-6-(5-methyl-4H-[1,2,4]triazole-3-yl-sulfanyl)-N-([1,2,4]thiadiazol-5-yl)-2-pyridine carboxamide, 3-(1-oxy-6-methyl-pyridine-3-ylsulfanyl)-6-(4H-[1,2,4]triazole-3-ylsulfanyl)-N-(thiazole-2-yl)-2-pyridine carboxamide, 3-(4-diethylaminoethyloxy-phenylsulfanyl)-6-(4H-[1,2,4]triazole-3-ylsulfanyl)-N-(thiazole-2-yl)-2-pyridine carboxamide, 3-(4-pyrrolidinoethyloxy-phenylsulfanyl)-6-(4H-[1,2,4]triazole-3-ylsulfanyl)-N-(thiazole-2-yl)-2-pyridine carboxamide, 3-(6-dimethylaminoethyloxy-pyridine-3-yl-sulfanyl)-6-(4H-[1,2,4]triazole-3-ylsulfanyl)-N-(thiazole-2-yl)-2-pyridine carboxamide, 3-(pyrazol-4-ylsulfanyl)-6-(4H-[1,2,4]triazole-3-yl-sulfanyl)-N-(thiazole-2-yl)-2-pyridine carboxamide, 3-(4-dimethylaminoethyloxy-phenylsulfanyl)-6-(4H-[1,2,4]triazole-3-ylsulfanyl)-N-(3-methyl-[1,2,4]thiadiazol-5-yl)-2-pyridine carboxamide, 3-(4-carbamoylmethyloxy-phenylsulfanyl)-6-(4H-[1,2,4]triazole-3-ylsulfanyl)-N-(thiazole-2-yl)-2-pyridine carboxamide, 3-(5-bromo-6-methyl-pyridine-3-ylsulfanyl)-6-(4H-[1,2,4]triazole-3-ylsulfanyl)-N-(thiazole-2-yl)-2-pyridine carboxamide, 3-[4-(2-hydroxyethyl-phenylsulfanyl)-6-(4H-[1,2,4]-triazole-3-ylsulfanyl)-N-(3-methyl-[1,2,4]thiadiazol-5-yl)-2-pyridine carboxamide, 3-[4-(2-hydroxyethyl-phenylsulfanyl)-6-(5-methyl-4H-[1,2,4]-triazole-3-ylsulfanyl)-N-(3-methyl-[1,2, 4]thiadiazol-5-yl)-2-pyridine carboxamide, 3-(pyridine-3-ylsulfanyl)-6-(4H-[1,2,4]triazole-3-ylsulfanyl)-N-(3-methyl-[1,2,4]thiazole-5-yl)-2-pyridine carboxamide, 3-(6-methyl-pyridine-3-y-sulfanyl)-6-(4H-[1,2,4]triazole-3-ylsulfanyl)-N-(3-methyl-[1,2,4]thiadiazol-5-yl)-2-pyridine carboxamide, 3-(4-dimethylaminoethyloxy-phenylsulfanyl)-6-(4H-[1,2,4]triazole-3-ylsulfanyl)-N-(thiazoleo[5,4-b]pyridine-2-yl)-2-pyridine carboxamide, 3-(6-methyl-pyridine-3-ylsulfanyl)-6-(5-methyl-4H-[1,2,4]triazole-3-ylsulfanyl)-N-(3-methyl-[1,2,4]thiadiazol-5-yl)-2-pyridine carboxamide, 3-(6-methyl-pyridine-3-ylsulfanyl)-6-(4H-[1,2,4]triazole-3-ylsulfanyl)-N-([1,2,5]thiadiazol-3-yl)-2-pyridine carboxamide, 3-(2,3-dihydrobenzofuran-5-ylsulfanyl)-6-(4H-[1,2,4]triazole-3-ylsulfanyl)-N-(thiazole-2-yl)-2-pyridine carboxamide, 3-(6-methyl-pyridine-3-ylsulfanyl)-6-(4H-[1,2,4]triazole-3-ylsulfanyl)-N-(3-methoxy-[1,2,4]thiadiazol-5-yl)-2-pyridine carboxamide, 3-(6-methyl-pyridine-3-yl-sulfanyl)-6-(4H-[1,2,4]triazole-3-ylsulfanyl)-N-(3-cyclopropyl-[1,2,4]thiadiazol-5-yl)-2-pyridine carboxamide, 3-(4-dimethylaminoethyloxy-phenylsulfanyl)-6-(5-methyl-4H-[1,2,4]triazole-3-ylsulfanyl)-N-(3-methyl-[1,2,4]thiadiazol-5-yl)-2-pyridine carboxamide, 3-(2-fluoro-pyridine-4-ylsulfanyol)-6-(4H-[1,2,4]triazole-3-ylsulfanyl)-N-(thiazole-2-pyridine carboxamide, 3-(2-methoxy-pyrimidine-5-ylsulfanyl)-6-(2H-[1,2,4]triazole-3-ylsulfanyl)-N-(thiazole-2-pyridine carboxamide, 3-(6-methyl-pyridine-3-ylsulfanyl)-6-(5-methyl-4H-[1,2,4]triazole-3-ylsulfanyl)-N-([1,2,4]thiadiazol-5-yl)-2-pyridine carboxamide, 3-(4-hydroxyethyloxy-phenylsulfanyl)-6-(4H-[1,2,4]triazole-3-ylsulfanyl)-N-(3-methyl-[1,2,4]thiadiazol-5-yl)-2-pyridine carboxamide, 3-(4-diethylcarbamoylmethyloxy-phenylsulfanyl)-6-(4H-[1,2,4]triazole-3-ylsulfanyl)-N-(thiazole-2-yl)-2-pyridine carboxamide, 3-(6-cyclopropyl-pyridine-3-ylsulfanyl)-6-(4H-[1,2,4]triazole-3-ylsulfanyl)-N-(thiazole-2-yl)-2-pyridine carboxamide, 3-(6-methyl-pyridine-3-ylsulfanyl)-6-(5-methyl-4H-[1,2,4]triazole-3-ylsulfanyl)-N-(thiazole-2-yl)-2-pyridine carboxamide, 3-(6-methyl-pyridine-3-ylsulfanyl)-6-(pyrazol-4-ylsulfanyl)-N-(thiazole-2-yl)-2-pyridine carboxamide, 3-(6-ethoxy-pyridine-3-ylsulfanyl)-6-(4H-[1,2,4]-triazole-3-ylsulfanyl)-N-(3-methyl-[1,2,4]thiadiazol-5-yl)-2-pyridine carboxamide, 3-(4-dimethylaminosulfonyl-phenylsulfanyl)-6-(4H-[1,2,4]-triazole-3-ylsulfanyl)-N-(thiazole-2-yl)-2-pyridine carboxamide, 3-(5-fluoro-pyridine-3-ylsulfanyl)-6-(4H-[1,2,4]-triazole-3-ylsulfanyl)-N-(3-methyl-[1,2,4]-thiadiazol-5-yl)-2-pyridine carboxamide, 3-(2,3-dihydrobenzofuran-5-ylsulfanyl)-6-(4H-[1,2,4]-triazole-3-ylsulfanyl)-N-(3-methyl-[1,2,4]thiadiazol-5-yl)-2-pyridine carboxamide, 3-(4-methoxy-phenylsulfanyl)-6-(4H-[1,2,4]-triazole-3-ylsulfanyl)-N-([1,2,4]triazine-3-yl)-2-pyridine carboxamide, 3-(4-carboxy-phenylsulfanyl)-6-(5-methyl-[1,2,4]-triazole-3-ylsulfanyl)-N-(3-methyl-[1,2,4]thiadiazol-5-yl)-2-pyridine carboxamide, 3-(6-ethoxy-pyridine-3-ylsulfanyl)-6-(4H-[1,2,4]triazole-3-ylsulfanyl)-N-(pyrazine-2-yl)-2-pyridine carboxamide, 3-(imidazo-[1,2-a]pyridine-6-ylsulfanyl)-6-(4H-[1,2,4]-triazole-3-ylsulfanyl)-N-(3-methyl-[1,2,4]thiadiazol-5-yl)-2-pyridine carboxamide, 3-(2-methyl-pyridine-3-ylsulfanyl)-6-(4H-[1,2,4]-triazole-3-ylsulfanyl)-N-(3-methyl-[1,2,4]-thiadiazol-5-yl)-2-pyridine carboxamide, 3-(4-methoxy-phenylsulfanyl)-6-(4H-[1,2,4]triazole-3-ylsulfanyl)-N-(thiazoleo[4,5-b]pyridine-2-yl)-2-pyridine carboxamide, 3-(5-methyl-pyridine-3-ylsulfanyl)-6-(4H-[1,2,4]-triazole-3-ylsulfanyl)-N-(3-methyl-[1,2,4]-thiadiazol-5-yl)-2-pyridine carboxamide, 3-(4,4-difluoromethyloxy-phenylsulfanyl)-6-(4H-[1,2,4]-triazole-3-ylsulfanyl)-N-(pyradine-2-yl)-2-pyridine carboxamide, 3-(6-methyl-pyridine-3-ylphenylsulfanyl)-6-(4H-[1,2,4]triazole-3-ylsulfanyl)-N-(1-methyl-1H-[1,2]pyrazol-3-yl)-2-pyridine carboxamide, 3-(6-hydroxyethyl-pyridine-3-ylsulfanyl)-6-(4H-[1,2,4]triazole- 3-ylsulfanyl)-N-(3-methyl-[1,2,4]thiadiazol-5-yl)-2-pyridine carboxamide, 3-(4-fluoro-phenylsulfanyl)-6-(4H-[1,2,4]triazole-3-ylsulfanyl)-N-(1-methyl-1H-[1,2]pyrazol-3-yl)-2-pyridine carboxamide, 3-(2-methyl-imidazo-[1,2-a]pyridine-6-ylsulfanyl)-6-(4H-[1,2,4]triazole-3-ylsulfanyl)-N-(3-methyl-[1,2,4]-thiadiazol-5-yl)-2-pyridine carboxamide, 3-(6-methyl-pyridine-3-ylsulfanyl)-6-(4H-[1,2,4]triazole-3-ylsulfanyl)-N-(3-hydroxymethyl-[1,2,4]-thiadiazol-5-yl)-2-pyridine carboxamide, 3-[4-(2-hydroxyethyl-phenylsulfanyl)-6-(4-methyl-4H-[1,2,4]triazole-3-ylsulfanyl)-N-(3-methyl-[1,2,4]thiadiazol-5-yl)-2-pyridine carboxamide, 3-(6-methyl-pyridine-3-ylsulfanyl)-6-(5-hydroxy-4H-[1,2,4]triazole-3-ylsulfanyl)-N-(3-methyl-[1,2,4]thiadiazol-5-yl)-2-pyridine carboxamide, 3-(1-methyl-1H-indazol-5-ylsulfanyl)-6-(4H-[1,2,4]triazole-3-ylsulfanyl)-N-(3-methyl-[1,2,4]thiadiazol-5-yl)-2-pyridine carboxamide, 3-(3-methyl-[1,2,4]-triazoleo-[4,3-a]pyridine-7-ylsulfanyl)-6-(4H-[1,2,4]triazole-3-ylsulfanyl)-N-(3-methyl-[1,2,4]thiadiazol-5-yl)-2-pyridine carboxamide, 3-(1-oxy-6-methyl-pyridine-3-ylsulfanyl)-6-(4H-[1,2,4]triazole-3-ylsulfanyl)-N-(3-methyl-[1,2,4]thiadiazol-5-yl)-2-pyridine carboxamide, 3-(6-hydroxymethyl-pyridine-3-ylsulfanyl)-6-(4H-[1,2,4]triazole-3-ylsulfanyl)-N-(3-methyl-[1,2,4]thiadiazol-5-yl)-2-pyridine carboxamide, 3-(4-methoxy-phenylsulfanyl)-6-(4H-[1,2,4]triazole-3-ylsulfanyl)-N-(1-methyl-1H-[1,2]pyrazol-3-yl)-2-pyridine carboxamide, 3-(4-fluoro-phenylsulfanyl)-6-(4H-[1,2,4]triazole-3-ylsulfanyl)-N-(1H-[1,2]-pyridine carboxamide, 3-(6-methoxy-pyridine-3-ylsulfanyl)-6-(4H-[1,2,4]triazole-3-ylsulfanyl)-N-(3-methyl-[1,2,4]thiadiazol-5-yl)-2-pyridine carboxamide, 3-[4-(1H-imidazol-1-yl)-phenylsulfanyl]-6-(4H-[1,2,4]triazole-3-ylsulfanyl)-N-(3-methyl-[1,2,4]thiadiazol-5-yl)-2-pyridine carboxamide, 3-(4-methoxy-phenylsulfanyl)-6-(4H-[1,2,4]triazole-3-ylsulfanyl)-N-(1H-[1,2]-pyrazol-3-yl)-2-pyridine carboxamide, 3-(6-methoxy-pyridine-3-ylsulfanyl)-6-(4H-[1,2,4]triazole-3-ylsulfanyl)-N-(1-methyl-1H-pyrazol-3-yl)-2-pyridine carboxamide, 3-(6-ethoxy-pyridine-3-ylsulfanyl)-6-(4H-[1,2,4]triazole-3-yl-sulfanyl)-N-(1-methyl-1H-pyrazol-3-yl)-2-pyridine carboxamide, 3-(4-methoxymethyl-phenylsulfanyl)-6-(4H-[1,2,4]triazole-3-ylsulfanyl)-N-(1-methyl-1H-pyrazol-3-yl)-2-pyridine carboxamide, 3-(4-methoxy-phenylsulfanyl)-6-(4H-[1,2,4]triazole-3-ylsulfanyl)-N-(4,5-dimethyl-thiazole-2-yl)-2-pyridine carboxamide, 3-(4-fluoro-phenylsulfanyl)-6-(4,5-dimethyl-4H-[1,2,4]triazole-3-yl-sulfanyl)-N-(4-methoxymethyl-thiazole-2-yl)-2-pyridine carboxamide, 3-[4-(1-methoxyethyl)-phenylsulfanyl]-6-(4H-[1,2,4]triazole-3-yl-sulfanyl)-N-(thiazole-2-yl)-2-pyridine carboxamide, 3-(4-fluoro-phenylsulfanyl)-6-(4H-[1,2,4]triazole-3-ysulfanyl)-N-(4-hydroxymethyl-thiazole-2-yl)-2-pyridine carboxamide, 3-(4-methoxy-phenylsulfanyl)-6-(4H-[1,2,4]triazole-3-yl-sulfanyl)-N-(5-trifluoromethylthiazole-2-yl)-2-pyridine carboxamide, 3-(4-methoxy-phenylsulfanyl)-6-(4H-[1,2,4]triazole-3-yl-sulfanyl)-N-(4-trifluoromethylthiazole-2-yl)-2-pyridine carboxamide, 3-(3-fluoro-4-methoxy-phenylsulfanyl)-6-(4H-[1,2,4]triazole-3-yl-sulfanyl)-N-(thiazole-2-yl)-2-pyridine carboxamide, 3-[4-(1,1-dimethyl-1-hydroxymethyl)-phenylsulfanyl]-6-(4H-[1,2,4]triazole-3-ylsulfanyl)-N-thiazole-2-yl)-2-pyridine carboxamide, 3-(3,4-difluoro-phenylsulfanyl)-6-(4H-[1,2,4]triazole-3-ylsulfanyl)-N-(1-methyl-1H-[1,2]-pyrazol-3-yl)-2-pyridine carboxamide, 3-(3,5-difluoro-phenylsulfanyl)-6-(4H-[1,2,4]triazole-3-ylsulfanyl)-N-(1-methyl-1H-[1,2]pyrazol-3-yl)-2-pyridine carboxamide, 3-(1-methyl-2-oxo-2,3-dihydro-1H-indole-5-ylsulfanyl)-6-(4H-[1,2,4]triazole-3-ylsulfanyl)-N-(1-methyl-1H-[1,2]pyrazol-3-yl)-2-pyridine carboxamide, 3-(6-methyl-pyridine-3-sulfanyl)-6-(4H-[1,2,4]triazole-3-ylsulfanyl)-N-([1,2,4]triazoleopyridine-2-yl)-2-pyridine carboxamide, 3-(4-ethoxymethyl-phenylsulfanyl)-6-(4H-[1,2,4]triazole-3-ylsulfanyl)-N-(1-methyl-1H-[1,2]pyrazol-3-yl)-2-pyridine carboxamide, 3-(6-oxo-1,6-dihydro-pyridine-3-ylsulfanyl)-6-(4H-[1,2,4]triazole-3-ylsulfanyl)-N-(1-methyl-1H-[1,2]pyrazol-3-yl)-2-pyridine carboxamide, 3-(6-methoxy-pyridine-3-ylsulfanyl)-6-(4H-[1,2,4]triazole-3-ylsulfanyl)-N-(1H-[1,2]pyrazol-3-yl)-2-pyridine carboxamide, 3-(4-hydroxyethyloxy-phenylsulfanyl)-6-(4-methyl-4H-[1,2,4]triazole-3-ylsulfanyl)-N-(1-methyl-1H-[1,2]-pyrazol-3-yl)-2-pyridine carboxamide.

(17) A compound which is 3-(4-fluoro-phenylsulfanyl)-6-(4H-[1,2,4]triazole-3-yl-sulfanyl)-N-(thiazole-2-yl)-2-pyridine carboxamide or a pharmaceutically acceptable salt thereof.

(18) A compound which is 3-(4-methoxy-phenylsulfanyl)-6-(4H-[1,2,4]triazole-3-yl-sulfanyl)-N-(4-methoxymethyl-thiazole-2-yl)-2-pyridine carboxamide or a pharmaceutically acceptable salt thereof.

(19) A compound which is 3-(4-methoxymethyl-phenylsulfanyl)-6-(4H-[1,2,4]triazole-3-yl-sulfanyl)-(thiazole-2-yl)-2-pyridine carboxamide or a pharmaceutically acceptable salt thereof.

(20) A compound which is 3-(6-methyl-pyridine-3-yl-sulfanyl)-6-(4H-[1,2,4]triazole-3-yl-sulfanyl)-N-(thiazole-2-yl)-2-pyridine carboxamide or a pharmaceutically acceptable salt thereof.

(21) A compound which is 3-(hydroxyethyloxy-phenylsulfanyl)-6-(4H-[1,2,4]triazole-3-yl-sulfanyl)-N-(thiazole-2-yl)-2-pyridine carboxamide or a pharmaceutically acceptable salt thereof.

(22) A compound which is 3-(4-dimethylaminoethyloxy-phenylsulfanyl)-6-(4H-[1,2,4]triazole-3-yl-sulfanyl)-N-(thiazole-2-yl)-2-pyridine carboxamide or a pharmaceutically acceptable salt thereof.

(23) A compound which is 3-(4-hydroxyethyl-phenylsulfanyl)-6-(4H-[1,2,4]triazole-3-yl-sulfanyl)-N-(thiazole-2-yl)-2-pyridine carboxamide or a pharmaceutically acceptable salt thereof.

(24) A compound which is 3-(6-methyl-pyridine-3-yl-sulfanyl)-6-(4H-[1,2,4]triazole-3-yl-sulfanyl)-N-(4-methyl-thiazole-2-yl)-2-pyridine carboxamide or a pharmaceutically acceptable salt thereof.

(25) A compound which is 3-(4-dimethylaminoethyloxy-phenylsulfanyl)-6-(4H-[1,2,4]triazole-3-ylsulfanyl)-N-([1,2,4]thiadiazol-5-yl)-2-pyridine carboxamide or a pharmaceutically acceptable salt thereof.

(26) A compound which is 3-(6-methyl-pyridine-3-ylsulfanyl)-6-(4H-[1,2,4]triazole-3-ylsulfanyl)-N-([1,2,4]thiadiazol-5-yl)-2-pyridine carboxamide or a pharmaceutically acceptable salt thereof.

(27) A compound which is 3-(4-dimethylaminoethyloxy-phenylsulfanyl)-6-(5-methyl-4H-[1,2,4]triazole-3-ylsulfanyl)-N-([1,2,4]thiadiazol-5-yl)-2-pyridine carboxamide or a pharmaceutically acceptable salt thereof.

(28) A compound which is 3-(4-dimethylaminoethyloxy-phenylsulfanyl)-6-(4H-[1,2,4]-triazole-3-ylsulfanyl)-N-(3-methyl-[1,2,4]thiadiazol-2-yl)-2-pyridine carboxamide or a pharmaceutically acceptable salt thereof.

(29) A compound which is 3-[4-(2-hydroxyethyl-phenylsulfanyl)]-6-(5-methyl-4H-[1,2,4]triazole-3-ylsulfanyl)-N-(3-methyl-[1,2,4]thiadiazol-5-yl)-2-pyridine carboxamide or a pharmaceutically acceptable salt thereof.

(30) A compound which is 3-(6-methyl-pyridine-3-ylsulfanyl)-6-(4H-[1,2,4]triazole-3-ylsulfanyl)-N-(3-methyl-[1,2,4]-thiadiazol-5-yl)-2-pyridine carboxamide or a pharmaceutically acceptable salt thereof.

(31) A compound which is 3-(6-ethoxy-pyridine-3-ylsulfanyl)-6-(4H-[1,2,4]triazole-3-ylsulfanyl)-N-(3-methyl-[1,2,4]-thiadiazol-5-yl)-2-pyridine carboxamide or a pharmaceutically acceptable salt thereof.

(32) A compound which is 3-(6-ethoxy-pyridine-3-ylsulfanyl)-6-(4H-[1,2,4]triazole-3-ylsulfanyl)-N-(pyrazin-2-yl)-2-pyridine carboxamide or a pharmaceutically acceptable salt thereof.

(33) A compound which is 3-(6-methoxy-pyridine-3-ylsulfanyl)-6-(4H-[1,2,4]triazole-3-ylsulfanyl)-N-(1-methyl-1H-pyrazol-3-yl)-2-pyridine carboxamide or a pharmaceutically acceptable salt thereof.

(34) A compound which is 3-(4-methoxymethyl-phenylsulfanyl)-6-(4H-[1,2,4]triazole-3-ylsulfanyl)-N-(1-methyl-1H-pyrazol-3-yl)-2-pyridine carboxamide or a pharmaceutically acceptable salt thereof.

(35) A pharmaceutical composition comprising the following (1) to (3) used for treatment, prevention and/or retardation of onset of type II diabetes mellitus.
   (1) a compound represented by (D);
   (2) one or more compound(s) selected from the group consisting of the following (a) to (g):
      (a) other glucokinase activator,
      (b) bis-guanide,
      (c) a PPAR agonist,
      (d) insulin,
      (e) somatostatin,
      (f) an α-glucosidase inhibitor and
      (g) insulin secretarorues; and
   (3) a pharmaceutically acceptable carrier.

(36) A glucokinase activating agent which comprises as an effective component the compound according to any one (1) to (34).

(37) A therapeutic agent and/or preventive agent for diabetes mellitus which comprises as an effective component the compound according to any one of (1) to (34).

(38) A therapeutic agent and/or preventive agent for obesity which comprises as an effective component the compound according to any one of (1) to (34).

BEST MODE OF CARRYING OUT THE INVENTION

The followings will illustrate the meanings of the terms used in the present specification to explain the compounds of the invention in more details.

The "aryl group" includes aryl groups of cyclic hydrocarbons of 6 to 14 carbons, for example, phenyl group, naphthyl group, biphenyl group, anthryl group, and the like.

The "lower alkyl group" means preferably a straight or branched chain alkyl group of 1 to 6 carbons, including, for example, methyl group, ethyl group, propyl group, isopropyl group, butyl group, isobutyl group, sec-butyl group, tert-butyl group, pentyl group, isoamyl group, neopentyl group, isopentyl group, 1,1-dimethylpropyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,2,2-trimethylpropyl group, 1-ethyl-2-methylpropyl group, and the like.

The "cycloalkyl group" means a monocyclic saturated hydrocarbon group of 3 to 7 carbons, including, for example, cyclopropyl group, cyclobutyl group, cyclopentyl group, cyclohexyl group, cycloheptyl group, and the like.

The "lower alkoxy group" means a group wherein the hydrogen atom of the hydroxy group is substituted by the above-mentioned lower alkyl group, including, for example, methoxy group, ethoxy group, propoxy group, isopropoxy group, butoxy group, sec-butoxy group, tert-butoxy group, pentyloxy group, isopentyloxy group, hexyloxy group, isohexyloxy group, and the like.

The "alkylsulfamoyl group" means a group wherein the hydrogen atom of the sulfamoyl group is mono-substituted by the above-mentioned alkyl group, including preferably, for example, methylsulfamoyl group, ethylsulfamoyl group, isopropylsulfamoyl group, and the like.

The "dialkylsulfamoyl group" means a group wherein the hydrogen atoms of $NH_2$ of the alkylsulfamoyl group are di-substituted by the same or different above-mentioned alkyl group, including, for example, dimethylsulfamoyl group, diethylsulfamoyl group, methylethylsulfamoyl group, and the like.

The "heteroaryl group" means a 4- to 7-membered monocyclic heteroaryl group which has 1 to 3 hetero-atoms selected from the group consisting of oxygen atom, sulfur atom and nitrogen atom in the heteroaryl group, or alternatively bicyclic heteroaryl groups which are formed by condensation of the monocyclic heteroaryl group with a benzene ring or pyridine ring, including, for example, furyl group, thienyl group, pyrrolyl group, imidazolyl group, pyrazolyl group, thizaolyl group, thiadiazolyl group, isothiazolyl group, oxazolyl group, isoxazolyl group, pyridyl group, pyrimidinyl group, pyridazinyl group, pyrazolyl group, pyradinyl group, quinolyl group, isoquinolyl group, quinazolinyl group, quinolizinyl group, quinoxalinyl group, cinnolinyl group, benzimidazolyl group, imidazopyridyl group, benzofuranyl group, naphthylidinyl group, 1,2-benzisoxazolyl group, benzoxazolyl group, benzothiazolyl group, oxazolopyridyl group, pyridothiazolyl group, isothizaolopyridyl group, benzothienyl group, and the like.

The "halogen atom" includes, for example, fluorine atom, chlorine atom, bromine atom and iodine atom.

The "lower alkylcarbamoyl group" means the carbamoyl group mono-substituted by the above-mentioned lower alkyl group, including, for example, methylcarbamoyl group, ethylcarbamoyl group, propylcarbamoyl group, isopropylcarbamoyl group, butylcarbamoyl group, sec-butylcarbamoyl group, tert-butylcarbamoyl group, and the like.

The "di-lower alkylcarbamoyl group" means the carbamoyl group di-substituted by the same or different above-mentioned lower alkyl group, including, for example, dimethylcarbamoyl group, diethylcarbamoyl group, ethylmethylcarbamoyl group, dipropylcarbamoyl group, methylpropylcarbamoyl group, diisopropylcarbamoyl group, and the like.

The "lower alkylamino group" means the amino group mono-substituted by the above-mentioned lower alkyl group, including, for example, methylamino group, ethylamino group, propylamino group, isopropylamino group, butylamino group, sec-butylamino group, or tert-butylamino.

The "di-lower alkylamino group" means the amino group di-substituted by the same or different above-mentioned lower alkyl group, including, for example, dimethylamino group, diethylamino group, dipropylamino group, methylpropylamino group, or diisopropylamino group.

The "alkanoyl group" means the carbonyl group to which the above-mentioned lower alkyl group is attached, including, for example, methylcarbonyl group, ethylcarbonyl group, propylcarbonyl group, isopropylcarbonyl group; and the like.

The "alkanoylamino group" means a group wherein the above-mentioned alkanoyl group is attached an amino group, including, for example, methylcarbonylamino group, ethylcarbonylamino group, isopropylcarbonylamino group, and the like.

The "alkylthio group" means a group wherein the above-mentioned lower alkyl group is attached to a sulfur atom, including, for example, methylthio group, ethylthio group, propylthio group, isopropylthio group, and the like.

The "alkylsulfinyl group" means a group wherein the above-mentioned lower alkyl group is attached to a sulfinyl group, including, for example, methylsulfinyl group, ethylsulfinyl group, isopropylsulfinyl group, and the like.

The "alkylsulfonyl group" means a group wherein the above-mentioned alkyl group is attached to a sulfonyl group, including, for example, methylsulfonyl group, ethylsulfonyl group, propylsulfonyl group, isopropylsulfonyl group, and the like.

The "alkylsulfonylamino group" means a group wherein hydrogen atom of the amino group is mono-substituted by the above-mentioned alkylsulfonyl group, including, for example, methylsulfonylamino group, ethylsulfonylamino group, propylsulfonylamino group, or isopropylsulfonylamino group.

The "alkoxycarbonyl group" means a group wherein the hydrogen atom of the carboxyl group is substituted by the above-mentioned alkyl group, including, for example, methoxycarbonyl group, ethoxycarbonyl group, propyloxycarbonyl group, isopropyloxycarbony group, and the like.

The "divalent saturated hydrocarbon group of 1 to 6 carbons" means a straight or branched chain divalent saturated hydrocarbon group of 1 to 6 carbons, specifically including, for example, methylene group, ethylene group, propylene group, isopropylene group, butylene group, and the like.

In order to further show specific examples of the compounds of the formula (I) of the present invention, the respective symbols used in the formula (I) will be explained by the following examples.

The ring A represented by the formula (II):

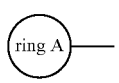

(II)

[wherein the respective symbols have the same meanings as defined above]

represents a 5- to 7-membered heteroaryl group or 6- to 10-membered aryl group which may have on the ring A, 1 or 2 groups selected from the group consisting of lower alkyl group, lower alkoxy group, hydroxyl group, hydroxyalkyl group (the hydrogen atom of the hydroxy group of the hydroxyalkyl group may further be substituted by a lower alkyl group) and halogen atom.

The "5- to 7-membered heteroaryl group or 6- to 10-membered aryl group" represented by the ring A is preferably a 5- to 6-membered heteroaryl group containing at least one nitrogen atom in the ring.

The ring A specifically includes, for example, phenyl group, isothiazolyl group, imidazolyl group, oxazolyl group, thiadiazolyl group, thienyl group, triazolyl group, tetrazolyl group, pyridyl group, pyrimidinyl group, furyl group, thiazolyl group, isoxazolyl group or pyrazolyl group, with triazolyl group, imidazolyl group, thiazolyl group and pyridyl group being preferred, and triazolyl group being more preferred.

The followings will explain the substituent attached to the ring A.

The ring A in the formula (I) may have a substituent or substituents on the ring.

The substituent on the ring A includes lower alkyl, alkoxy, halogen atom, hydroxy, and hydroxyalkyl group (the hydrogen atom of the hydroxy group may further be substituted by an alkyl group). Among these substitutents, lower alkyl group, lower alkoxy group, hydroxy group and hydroxyalkyl group are preferred, and the lower alkyl group is more preferred.

The substituent on the ring A, more specifically, includes, for example, methyl group, ethyl group, isopropyl group, methoxy group, ethoxy group, hydroxy group, hydroxymethyl group, hydroxyethyl group, methoxymethyl group, fluorine atom, and chlorine atom, with methyl group and ethyl group being preferred and methyl group being more preferred.

Accordingly, as the preferred ring A in total, the groups represented by the following formula (VIII):

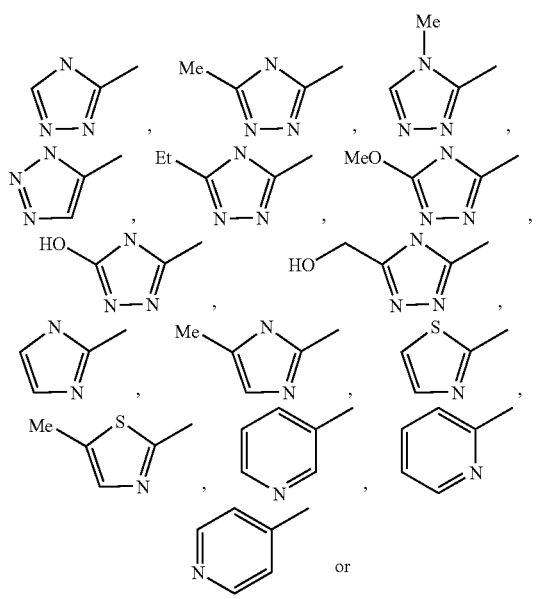

are preferable. The groups represented by the formula (IX):

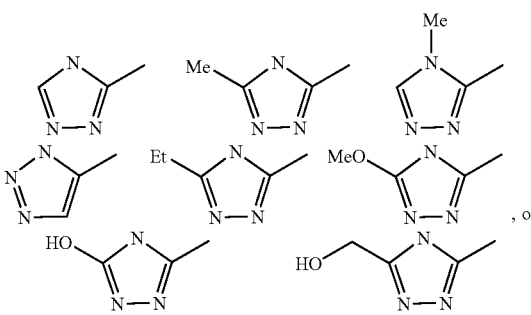

are more preferred.

D represents an oxygen atom or sulfur atom, with sulfur atom being preferred.

The ring B will be explained by the followings.

The ring B represented by the formula (III):

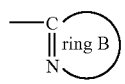

(III)

means a monocyclic or bicyclic heteroaryl group having such a relative location as shown in the following formula (X):

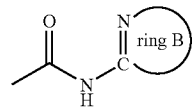

(X)

in which the C=N in the ring is bound to the nitrogen atom of the amide group in the above formula (I).

The "monocyclic or bicyclic heteroaryl group" represented by the ring B has the same meanings as the above-defined "heteroaryl group".

The ring B includes, for example, thiazolyl group, imidazolyl group, isothiazolyl group, thiadiazolyl group, triazolyl group, oxazolyl group, isoxazolyl group, pyrazinyl group, pyridyl group, pyridazinyl group, pyrazolyl group, pyrimidinyl group, pyridothiazolyl group and benzothiazolyl group. Among these groups, thiazolyl group, thiadiazolyl group, isoxazolyl group, pyrazinyl group, pyridothiazolyl group and pyridyl group are preferred, and thiazolyl group, pyridothiazolyl group and isoxazolyl group are more preferred.

The ring B may have in the ring 1 or 2 substituents, preferably 1 substituent, selected from the group consisting of lower alkyl group, lower alkoxy group, halogen atom, trifluoromethyl group, hydroxy group, hydroxyalkyl group (the hydrogen atom of the hydroxy group of the hydroxyalkyl group may be substituted by a lower alkyl group), aminoalkyl group, alkanoyl group, carboxyl group, alkoxycarbonyl group and cyano group.

Among them, as the substituent on the ring B, lower alkyl group, lower alkoxy group, halogen atom, hydroxyalkyl group (the hydrogen atom of the hydroxyl group of the hydroxyalkyl group, may be substituted by a lower alkyl group), aminoalkyl group and alkanoyl group are preferred; and lower alkyl group, hydroxyalkyl group (the hydrogen atom of the hydroxy of the hydroxyalkyl group may be substituted by a lower alkyl group) and alkanoyl group are more preferred.

The substituent on the ring B specifically includes, for example, methyl group, ethyl group, propyl group, isopropyl group, butyl group, methoxy group, ethoxy group, propoxy group, isopropoxy group, butoxy group, chlorine atom, fluorine atom, bromine atom, hydroxymethyl group, hydroxyethyl group, methoxymethyl group, ethoxyethyl group, methoxyethyl group, methoxycarbonyl group, ethoxycarbonyl group, propoxycarbonyl group, aminomethyl group, aminoethyl group, aminopropyl group, methylcarbonyl group, ethylcarbonyl group, propylcarbonyl group, and the like. Among them, methyl group, ethyl group, chlorine atom, fluorine atom, hydroxymethyl group, hydroxyethyl group, methoxymethyl group, methoxyethyl group, methoxycarbonyl group, ethoxycarbonyl group, aminomethyl group, aminoethyl group, methylcarbonyl group, and ethylcarbonyl group are preferred; and methyl group, hydroxymethyl group, methoxymethyl group, and methylcarbonyl group are more preferred.

Therefore, as the ring B in total, for example, thiazol-2-yl group, 4-methyl-thiazol-2-yl group, 4-hydroxymethyl-thiazol-2-yl group, 4-methoxycarbonyl-thiazol-2-yl group, 4-methoxymethyl-thiazol-2-yl group, 4-aminomethyl-thiazol-2-yl group, 4-cyano-thiazol-2-yl group, 4-cyano-thiazol-2-yl group, 4-fluoro-thiazol-2-yl group, imidazol-2-yl group, 4-methyl-imidazol-2-yl group, 4-methoxycarbonyl-imidazol-2-yl group, isothiazole-3-yl group, 4-hydroxymethyl-isothiazole-3-yl group, [1,3,4]thiadiazol-2-yl group, 5-methylcarbonyl[1,3,4]thiadiazol-2-yl group, [1,2,4]thiadiazol-5-yl group, 3-methyl-[1,2,4]thiadiazol-5-yl group, [1,2,4]triazole-2-yl group, 5-hydroxymethyl[1,2,4]triazol-3-yl group, pyrazin-2-yl group, pyridin-2-yl group, 4-methyl-pyridin-2-yl group, 4-methoxymethyl-imidazol-2-yl group, 4-methylcarbonyl-imidazol-2-yl group, 5-hydroxymethyl-imidazol-2-yl group, 5-methyl-[1,3,4]thiadiazol-2-yl group, 5-fluoro-[1,3,4]thiadiazol-2-yl group, 5-methyl[1,2,4]triazole-2-yl group, 5-methylcarbonyl-[1,2,4]triazole-3-yl, isoxazol-3-yl group, 4-methoxymethyl-isoxazol-2-yl group, 5-methyl-isoxazol-3-yl group, 5-hydroxymethyl-isoxazol-3-yl group, 5-methoxymethyl-isoxazol-3-yl group, 5-methylcarbonyl-isoxazol-3-yl group, 5-chloroisoxazol-3-yl group, 5-aminomethyl-isoxazol-3-yl group, 4-methyl-1H-pyrazol-3-yl group, 1-methyl-pyrazol-3-yl group, 6-methyl-pyridazin-3-yl group, thiazol-4-yl group, 2-methyl-thiazol-4-yl group, isoxazol-3-yl group, pyridothiazole group, and the like are preferred.

$X^1$ represents a nitrogen atom, sulfur atom or oxygen atom, or a divalent saturated hydrocarbon group of 1 to 6 carbons.

The "divalent saturated hydrocarbon group of 1 to 6 carbons" means an alkylene group of 1 to 6 carbons as defined above, including, for example, methylene group, propylene group, isopropylene group, butylene group, and the like. When the carbon number of the divalent saturated hydrocarbon group is 2 to 6, an optional carbon atom in the divalent saturated hydrocarbon group may be replaced by a nitrogen atom, sulfur atom or oxygen atom.

$X^1$ includes more specifically, for example, nitrogen atom, oxygen atom, sulfur atom $CH_2-$, $-N-CH_2-$, $-S-CH_2-$ $-O-CH_2-$, $-CH_2-N-$, $-CH_2-S-$ and $-CH_2-O-$ and the like. Among them, nitrogen atom, sulfur atom, oxygen atom, $-N-CH_2-$, and $-CH_2-$ are preferred, with sulfur atom being more preferred.

$R^2$ and $R^3$ are the same or different, each representing a hydrogen atom, lower alkyl group, alkoxy group or halogen atom.

The "lower alkyl groups" represented by $R^2$ and $R^3$ are the same or different, each being preferably methyl group or ethyl group; more preferably, both of $R^2$ and $R^3$ are methyl group.

The "lower alkoxy groups" represented by $R^2$ and $R^3$ are the same or different, each representing preferably methoxy group or ethoxy group more preferably, both of $R^2$ and $R^3$ are methoxy group.

The "halogen atom" represented by $R^2$ and $R^3$ is preferably fluorine atom, chlorine atom or bromine atom, with fluorine atom or chlorine atom being more preferred.

As for $R^2$ and $R^3$, both of $R^2$ and $R^3$ are preferably hydrogen atoms.

$R^1$ represents a 6- to 10-membered aryl group, 5- to 10-membered heteroaryl group, cycloalkyl group of 3 to 7 carbon atoms, or lower alkyl group.

The "6- to 10-membered aryl group" represented by $R^1$ indicates an aryl group of hydrocarbon ring of 6 to 10 carbon atoms, or 9- or 10-membered bicyclic aryl group which is formed by condensation of a benzene ring with a 5- or 6-membered aliphatic heterocycle (the aliphatic heterocycle ring may be substituted by an oxy group) having therein 1 or 2 heteroatoms selected from the group consisting of nitrogen atom, sulfur atom and oxygen atom.

The 6- to 10-membered aryl group of hydrocarbon ring more specifically includes, for example, phenyl group, naphthyl group, biphenyl group, and the like, with phenyl group being preferred.

The 9- or 10-membered bicyclic aryl group more specifically includes, for example, ethylenedioxyphenyl group, methylenedioxyphenyl group, tetrahydroquinolinyl group, tetrahydroisoquinolinyl group, dihydroindolyl group, 2,3-dihydrobenzofuranyl group, 1,3-dihydroisobenzofuranyl group, oxyindolyl group or isoindoyl group, and the like, with ethylenedioxyphenyl group or tetrahydroisoquinolinyl group being preferred.

The "5- to 10-membered heteroaryl group" represented by $R^1$ means a 5- to 7-membered monocyclic heteroaryl group or 9- or 10-membered bicyclic heteroaryl group which contains therein 1 to 3 heteroatoms selected from the group consisting of oxygen atom, nitrogen atom and sulfur atom.

The 5- to 7-membered monocyclic heteroaryl group more specifically includes, for example, isoxazolyl group, isothiazolyl group, imidazolyl group, oxazolyl group, thiazolyl group, thiadiazolyl group, thienyl group, triazolyl group, tetrazolyl group, pyridyl group, pyrazinyl group, pyrimidinyl group, pyridazinyl group, pyrazolyl group, pyrrolyl group, pyranyl group, furyl group, furazanyl group, imidazolidinyl group, and the like.

The 9- or 10-membered bicyclic heteroaryl group more specifically includes, for example, isoquinolyl group, isoindolyl group, indolyl group, quinolyl group, pyridothiazolyl group, benzoimidazolyl group, benzoxazolyl group, benzothiazolyl group, benzotriazolyl group, benzofuranyl group, imidazo-pyridinyl group, triazopyridinyl group and the like.

As for the 5- to 10-membered heteroaryl group, a 5- to 7-membered monocyclic heteroaryl group is preferred, more specifically, pyridyl group, imidazolyl group, thiazolyl group, or thienyl group is preferred.

The "cycloalkyl group of 3 to 7 carbons" represented by $R^1$ includes the same groups as defined above, and particularly cyclopentyl group or cyclohexyl group is preferred.

The "lower alkyl group" represented by $R^1$ includes the same groups as defined above, particularly propyl group and butyl group are preferred.

As for $R_1$, 6- to 10-membered aryl group, 5- to 10-membered heteroaryl group, 3- to 7-membered cycloalkyl group are preferred, and 6- to 10-membered aryl group, 5- to 10-membered heteroaryl group are more preferred.

Specific examples include phenyl group, naphthyl group, biphenyl group, isoxazolyl group, isothiazolyl group, imidazolyl group, oxazolyl group, thiazolyl group, thiadiazolyl group, thienyl group, triazolyl group, tetrazolyl group, pyridyl group, pyrazinyl group, pyrimidinyl group, pyridazinyl group, pyrazolyl group, pyrrolyl group, pyranyl group, furyl group, furazanyl group, imidazolidinyl group, isoquinolyl group, isoindolyl group, indolyl group, ethylenedioxyphenyl group, methylenedioxyphenyl group, quinolyl group, pyridothiazolyl group, dihydroindolyl group, tetrahydroquinolinyl group, tetrahydroisoquinolinyl group, benzoimidazolyl group, benzoxazolyl group, benzothiazolyl group, benzotriazolyl group, benzofuranyl group, cyclopropyl group, cyclobutyl group, cyclopenyl group, cyclohexyl group, cycloheptyl group, methyl group, ethyl group, propyl group, isopropyl group, butyl group, pentyl group, and the like. Among them, phenyl group, naphthyl group, pyridyl group, imidazolyl group, thiazolyl group, thienyl group, cyclopentyl group, and cyclohexyl group are preferred; and phenyl group, pyridyl group, imidazolyl group, thiazolyl group, and thienyl group are more preferred, with phenyl group or pyridyl group being particularly preferred.

The followings will illustrate the substituent contained in $R^1$.

The substituent contained in $R^1$ includes hydrogen atom, amino group, hydroxyl group, hydroxyalkyl group (the hydrogen atom of the hydroxyl group may be substituted by lower alkyl group), lower alkyl group (the hydrogen atom of the lower alkyl group may be substituted by hydroxyl group, alkoxy group, amino group, alkylamino group, dialkylamino group, halogen atom, carbamoyl group, mono- or di-alkyl carbamoyl group, carboxyl group, alkoxy carbonyl group, or alkanoyl group, lower alkoxy group (the hydrogen atom of the methylene group or methyl group constituting the lower alkoxy group may be substituted by hydroxyl group, halogen atom, carbamoyl group, mono- or di-lower alkyl carbamoyl group, carboxyl group, alkoxy carbonyl group, or alkanoyl group, carbamoyl group, alkylcarbamoyl group, di-alkylcarbamoyl group, carbamoyloxy group, carbamoylamino group, cyano group, sulfamoyl group, trifluoromethyl group, halogen atom, formyl, C2-C6 alkanoyl group, N—C2-C6 alkanoylamino group, C1-C6 alkylthio group, N—C1-C6 alkylsulfamoyl group, N,N-di-C1-C6 alkylsulfamoyl group, C1-C6 alkylsulfinyl group, C1-C6 alkylsulfonyl group, N—C1-C6 alkylsulfonylamino group, C1-C6 alkoxycarbonyl group, C1-C6 alkylamino group and N,N—C1-C6 di-alkylamino group.

$R^1$ may have a hydroxyalkyl group as a substituent. The preferred hydroxyalkyl group includes, for example, hydroxymethyl group, hydroxyethyl group, hydroxypropyl group, hydroxyisopropyl group, hydroxybutyl group, hydroxypentyl group, and the like, with hydroxymethyl group, hydroxyethyl group, hydroxypropyl group, or hydroxyisopropyl group being more preferred.

The hydrogen atom of the hydroxy group may be substituted by a lower alkyl group of 1 to 6 carbons. The substituted hydroxy alkyl group includes, for example, methoxymethyl group, 1-methoxyethyl group, ethoxymethyl group, methoxyethyl group, propyloxymethyl group, and the like. Among them, methoxymethyl group or methoxyethyl group is preferred, with methoxymethyl group being more preferred.

$R^1$ may have a lower alkyl group as a substituent. The lower alkyl group represented includes the same groups as defined above; among them, methyl group, ethyl group, propyl group, butyl group, isopropyl group, and the like are preferred, with methyl group or ethyl group being more preferred.

When $R^1$ has a lower alkyl group as a substituent, the hydrogen atom of the lower alkyl group may be substituted by hydroxyl group, lower alkoxy group, amino group, monoalkylamino group or dialkylamino group. The lower alkyl group includes, for example, hydroxymethyl group, hydroxyethyl group, methoxymethyl group, ethoxymethyl group, methoxyethyl group, aminomethyl group, aminoethyl group, aminopropyl group, methylaminomethyl group, ethylaminomethyl group, dimethylaminomethyl group, ethylmethylaminomethyl group, aminomethyl group, 2-aminoethyl group, 1-amino-ethyl group, 3-amino-propyl group, 2-amino-1-methyl-ethyl group, 2-amino-propyl group, 4-amino-butyl group, 2-amino-1-methyl-propyl group, 2-amino-butyl group, 5-amino-pentyl group, 3-amino-1,2-dimethyl-propyl group, 6-amino-hexyl group, and the like.

Among them, aminomethyl group, 2-amino-ethyl group, 1-amino-ethyl group, 3-amino-propyl group, 3-amino-1-methyl-ethyl group, and 2-amino-propyl group are preferred, with 2-amino-ethyl group or 3-aminopropyl group being more preferred.

$R^1$ may have a lower alkoxy group (wherein one of the hydrogen atoms of the lower alkoxy group may be substituted by hydroxy group or amino group) as a substituent.

The alkoxy group includes the same groups as defined above; among them, methoxy group, ethoxy group, propoxy group, isopropoxy group, and the like are preferred, with methoxy group or ethoxy group being more preferred.

When the hydrogen atom of the alkoxy group is substituted by hydroxyl group, for example, 2-hydroxy-ethoxy group, 3-hydroxy-propoxy group, 4-hydroxy-butoxy group, 2-hydroxy-1-methyl-ethoxy group, 2-hydroxy-propoxy group, 3-hydroxy-2-methyl-propoxy group, 3-hydroxy-butoxy group, and the like; among them, 2-hydroxy-ethoxy group, 3-hydroxy-propoxy group, and 2-hydroxy-1-methyl-ethoxy group are preferred, with 2-hydroxy-ethoxy group being preferred.

When the hydrogen atom of the alkoxy group is substituted by amino group, the amino group may further be substituted by 1 or 2 lower alkyl groups. When the amino group is substituted by 2 lower alkyl groups, the alkyl groups may be the same or different, preferably including alkylaminoalkoxy group or dialkylaminoalkoxy group, and more preferably dialkylaminoethoxy group.

More specifically, for example, aminoethoxy group, methylaminoethoxy group, dimethylaminoethoxy group, dimethylaminopropoxy group, and the like. Among them, methylaminoethoxy group or dimethylaminoethoxy group is preferred, with dimethylaminoethoxy group being more preferred.

$R^1$ may have a lower alkylcarbamoyl group as a substituent. The lower alkylcarbamoyl group includes the same groups as defined above, preferably lower alkylcarbamoyl groups of 1 to 5 carbons, more preferably lower alkylcarbamoyl groups of 1 to 3 carbons. The preferred lower alkylcarbamoyl group specifically includes methylcarbamoyl group, ethylcarbamoyl group, propylcarbamoyl group and the like, with methylcarbamoyl group being more preferred.

$R^1$ may have a di-lower alkylcarbamoyl group as a substituent. The lower alkylcarbamoyl group includes the same groups as defined above, and for example, dimethylcarbamoyl group, diethylcarbamoyl group, ethylmethylcarbamoyl group, and the like are preferred, with dimethylcarbamoyl group being more preferred.

$R^1$ may have a halogen atom as a substituent. The halogen atom includes the same ones as defined above, for example, fluorine atom, chlorine atom, bromine atom, and the like, with fluorine atom or chlorine atom being preferred.

$R^1$ may have a C2-C6 alkanoyl group as a substituent. The C2-C6 alkanoyl group includes the same groups as defined above, more specifically, for example, methylcarbonyl group, ethylcarbonyl group, propylcarbonyl group or isopropylcarbonyl group, with methylcarbonyl group or ethylcarbonyl group being more preferred.

$R^1$ may have an N—C2-C6 alkanoylamino group as a substituent. The preferred N—C2-C6 alkanoyl group specifically includes preferably, for example, ethylcarbonylamino group, propylcarbonylamino group, isopropylcarbonylamino group, and the like, with methylcarbonylamino group or ethylcarbonylamino group being more preferred.

$R^1$ may have a C1-C6 alkylthio group as a substituent. The alkylthio group includes the same groups as defined above. The preferred alkylthio group specifically includes preferably, for example, methylthio group, ethylthio group, propylthio group, isopropylthio group, and the like, with methylthio group or ethylthio group being more preferred.

$R^1$ may have an alkylsulfamoyl group as a substituent. The alkylsulfamoyl group includes the same groups as defined above. The preferred alkylsulfamoyl group includes preferably, for example, methylsulfamoyl group, ethylsulfamoyl group, propylsulfamoyl group, and the like, with methylsulfamoyl group or ethylsulfamoyl group being more preferred.

$R^1$ may have a dialkylsulfamoyl group as a substituent. The dialkylsulfamoyl group includes the same groups as defined above. The preferred dialkylsulfamoyl group specifically includes, for example, dimethylsulfamoyl group, diethylsulfamoyl group, and the like, with dimethylsulfamoyl group being more preferred.

$R^1$ may have an alkylsulfinyl group as a substituent. The alkylsulfinyl group includes the same groups as defined above. The preferred alkylsulfinyl group specifically includes, for example, methylsulfinyl group, ethylsulfinyl group, propylsulfinyl group, isopropylsulfinyl group, and the like, with methylsulfinyl group or ethylsulfinyl group being more preferred.

$R^1$ may have an alkylsulfonyl group as a substituent. The alkylsulfonyl group includes the same groups as defined above. The preferred alkylsulfonyl group specifically includes, for example, methylsulfonyl group, ethylsulfonyl group, propylsulfonyl group, isopropylsulfonyl group, and the like, with methylsulfonyl group or ethylsulfonyl group being more preferred.

$R^1$ may have an alkylsulfonylamino group as a substituent. The alkylsulfonylamino group includes the same groups as defined above. The preferred alkylsulfonylamino group specifically includes, for example, methylsulfonylamino group, ethylsulfonylamino group, propylsulfonylamino group, isopropylsulfonylamino group, and the like, with methylsulfonylamino group or ethylsulfonylamino group being more preferred.

$R^1$ may have an alkoxycarbonyl group as a substituent. The alkoxycarbonyl group includes the same groups as defined above. The preferred alkoxycarbonyl group specifically includes, for example, methoxycarbonyl group, ethoxycarbonyl group, isopropoxycarbonyl group, propoxycarbonyl group, and the like, with methoxycarbonyl group or ethoxycarbonyl group being more preferred.

$R^1$ may have an alkylamino group as a substituent. The alkylamino group includes the same groups as defined above. The preferred alkylamino group specifically includes, for example, methylamino group, ethylamino group, and the like, with methylamino group being more preferred.

$R^1$ may have an N,N-di-C1-C6 alkylamino group as a substituent. The preferred N,N-di-C1-C6 alkylamino group includes, for example, dimethylamino group, diethylamino group, ethyl-methyl-amino group, and the like, with dimethylamino group being more preferred.

$R^1$ may have a 5- or 6-membered cyclic amino group as a substituent. The 5- or 6-membered cyclic amino group includes the same groups as "cyclic amino group" as defined above. The preferred "substituent contained in $R^1$", includes, for example, pyrrolidinyl group, piperazinyl group, morpholinyl group, and the like, with piperidinyl group or morpholinyl group being more preferred.

With regard to the substituents in $R^1$, hydrogen atom, lower alkyl group, lower alkoxy group, carbamoyl group, alkylcarbamoyl group, cyano group, trifluoromethyl group, halogen atom, $C_2$-$C_6$ alkanoyl group, N—$C_2$-$C_6$ alkanoylamino group, $C_1$-$C_6$-alkylsulfonyl group, $C_1$-$C_6$ alkyl amino group or aminoalkyl group is preferred and among them lower alkyl group, lower alkoxy group, alkylcarbamoyl group, halogen atom, $C_1$-$C_6$ alkylsulfonyl group or aminoalkyl group is more preferred.

Therefore, with regard to —$X^1$—$R^1$, to be more specific, preferred ones are phenylsulfanyl group, 4-hydroxyethyl-phenylsulfanyl group, 3-hydroxymethyl-phenylsulfanyl group, 2-hydroxymethyl-phenylsulfanyl group, 4-methyl-phenylsulfanyl group, 3-methyl-phenylsulfanyl group, 2-methyl-phenylsulfanyl group, 4-isopropyl-phenylsulfanyl group, 4-methoxy-phenylsulfanyl group, 4-methoxymethyl-phenylsulfanyl group, 3-methoxy-phenylsulfanyl group, 2-ethoxy-phenylsulfanyl group, 4-ethoxy-phenylsulfanyl group, 4-hydroxymethyl-phenylsulfanyl group, 4-hydroxyethyloxy-phenylsulfanyl group, 4-carbamoyl-phenylsulfanyl group, 4-methylcarbamoyl-phenylsulfanyl group, 4-dimethylcarbamoyl-phenylsulfanyl group, 4-isopropylcarbamoyl-phenylsulfanyl group, 4-cyano-phenylsulfanyl group, 4-trifluoromethyl-phenylsulfanyl group, 4-fluoro-phenylsulfanyl group, 3-chloro-phenylsulfanyl group, 2-fluoro-phenylsulfanyl group, 4-methylcarbamoyl-phenylsulfanyl group, 4-ethylcarbamoyl-phenylsulfanyl group, 3-methylcarbonyl-phenylsulfanyl group, 3-ethylcarbonyl-phenylsulfanyl group, 4-methylcarbonylamino-phenylsulfanyl group, 4-ethylcarbonyl-phenylsulfanyl group, 4-isopropylcarbonyl-phenylsulfanyl group, 4-methylsulfonyl-phenylsulfanyl group, 3-ethylsulfonyl-phenylsulfanyl group, 4-methylsulfonyl-phenylsulfanyl group, 4-isopropylsulfonyl-phenylsulfanyl group, 4-methylamino-phenylsulfanyl group, 3-ethylamino-phenylsulfanyl group, 2-methylamino-phenylsulfanyl group, 4-aminomethyl-phenylsulfanyl group, 3-aminomethyl-phenylsulfanyl group, 4-aminoethyl-phenylsulfanyl group, 4-dimethylaminoethyloxy-phenylsulfanyl group, thiazol-2-yl-sulfanyl group, 4-hydroxymethyl-thiazol-2-yl group, 5-hydroxymethyl-thiazol-2-yl-sulfanyl group, 4-hydroxyethyl-thiazol-2-yl-sulfanyl group, 4-methyl-thiazol-2-yl-sulfanyl group, 5-methyl-thiazol-2-yl-sulfanyl group, 4-ethyl-thiazol-2-yl-sulfanyl group, 4-methoxy-thiazol-2-yl-sulfanyl group, 4-ethoxy-thiazol-2-yl-sulfanyl group, 4-carbamoyl-thiazol-2-yl-sulfanyl group, 5-carbamoyl-thiazol-2-yl-sulfanyl group, 4-methylcarbamoyl-thiazol-2-yl-sulfanyl group, 4-ethylcarbamoyl-thiazol-2-yl-sulfanyl group, 4-isopropyl-thiazol-2-yl-sulfanyl group, 4-cyano-thiazol-2-yl-sulfanyl group, 4-chloro-thiazol-2-yl-sulfanyl group, 4-fluoro-thiazol-2-yl-sulfanyl group, 4-methylcarbonyl-thiazol-2-yl-sulfanyl group, 4-ethylcarbonyl-thiazol-2-yl-sulfanyl group, 4-ethylcarbonylamino-thiazol-2-yl-sulfanyl group, 4-methylcarbonylamino-thiazol-2-yl-sulfanyl group, 4-methylsulfonyl-thiazol-2-yl-sulfanyl group, 4-ethylsulfonyl-thiazol-2-yl-sulfanyl group, 3-methylsulfonyl-thiazol-2-yl-sulfanyl group, 4-isopropylsulfonyl-thiazol-2-yl-sulfanyl group, 4-methylamino-thiazol-2-yl-sulfanyl group, 3-methylamino-thiazol-2-yl-sulfanyl group, 4-ethylamino-thiazol-2-yl-sulfanyl group, 4-aminomethyl-thiazol-2-yl-sulfanyl group, 4-aminoethyl-thiazol-2-yl-sulfanyl group, pyridine-2-yl-sulfanyl group, pyridin-3-yl-sulfanyl group, pyridin-4-yl-sulfanyl group, 6-hydroxymethyl-pyridin-3-yl-sulfanyl group, 4-hydroxymethyl-pyridine-5-yl-sulfanyl group, 4-hydroxymethyl-pyridine-6-yl-sulfanyl group, 3-hydroxyethyl-pyridin-6-yl-sulfanyl group, 4-methyl-pyridin-5-yl-sulfanyl group, 4-methyl-pyridin-6-yl-sulfanyl group, 6-methyl-pyridin-3-yl-sulfanyl group, 6-methoxy-pyridin-3-yl-sulfanyl group, 6-ethoxy-pyridin-3-ylsulfanyl group, 6-methyl-pyridin-3-yl-sulfanyl group, 2-carbamoyl-pyridin-4-yl-sulfanyl group, 6-carbamoyl-pyridin-3-yl-sulfanyl group, 6-methylcarbamoyl-pyridin-3-yl-sulfanyl group, 2-methylcarbamoyl-pyridin-4-yl-sulfanyl group, 2-cyano-pyridin-4-yl-sulfanyl group, 6-cyano-pyridin-3-yl-sulfanyl group, 2-trifluoromethyl-pyridin-4-yl-sulfanyl group, 6-trifluoromethyl-pyridin-3-yl-sulfanyl group, 2-chloro-pyridin-4-yl-sulfanyl group, 6-chloro-pyridin-3-yl-sulfanyl group, 2-fluoro-pyridin-4-yl-sulfanyl group, 6-fluoro-pyridin-3-yl-sulfanyl group, 2-methylcarbonyl-pyridin-4-yl-sulfanyl group, 6-methylcarbonyl-pyridin-3-yl-sulfanyl group, 2-ethylcarbonyl-pyridin-4-yl-sulfanyl group, 6-ethylcarbonyl-pyridin-3-yl-sulfanyl group, 2-methylsulfonyl-pyridin-4-yl-sulfanyl group, 6-methylsulfonyl-pyridin-3-yl-sulfanyl group, 2-ethylsulfonyl-pyridin-4-yl-sulfanyl group, 6-isopropylsulfonyl-pyridin-3-yl-sulfanyl group, 2-methylcarbonylamino-pyridin-4-ylsulfanyl group, 6-methylcarbonylamino-pyridin-3-yl-sulfanyl group, 2-methylamino-pyridin-4-yl-sulfanyl group, 6-methylamino-pyridin-3-yl-sulfanyl group, 2-ethylamino-pyridin-4-yl-sulfanyl group, 6-ethylamino-pyridin-3-yl-sulfanyl group, 2-aminomethyl-pyridin-4-yl-sulfanyl group, 6-aminomethyl-pyridin-3-yl-sulfanyl group, 4-hydroxyethyl-phenylamino group, 3-hydroxymethyl-phenylamino group, 2-hydroxymethyl-phenylamino group, 4-methyl-phenylamino group, 3-methyl-phenylamino group, 2-methyl-phenylamino group, 4-ethyl-phenylamino group, 4-isopropyl-phenylamino group, 4-methoxy-phenylamino group, 3-methoxy-phenylamino group, 2-ethoxy-phenylamino group, 4-ethoxy-phenylamino group, 4-hydroxymethyl-phenylamino group, 4-carbamoyl-phenylamino group, 4-methylcarbamoyl-phenylamino group, 4-isopropylcarbamoyl-phenylamino group, 4-cyano-phenylamino group, 4-trifluoromethyl-phenylamino group, 4-fluoro-phenylamino group, 3-chloro-phenylamino group, 2-fluoro-phenylamino group, 4-methylcarbonyl-phenylamino group, 4-ethylcarbonyl-phenylamino group, 3-methylcarbonyl-phenylamino group, 3-ethylcarbonyl-phenylamino group, 4-methylcarbonylamino-phenylamino group, 4-ethylcarbonylamino-phenylamino group, 4-isopropylcarbonylamino-phenylamino group, 4-methylsulfonyl-phenylamino group, 3-ethylsulfonyl-phenylamino group, 4-isopropylsulfonyl-phenylamino group, 4-methylamino-phenylamino group, 3-ethylamino-phenylamino group, 4-aminomethyl-phenylamino group, 3-aminomethyl-phenylamino group, 4-aminoethyl-phenylamino group, 3-aminoethyl-phenylamino group, 4-methyl-thiazol-2-ylamino group, 5-methyl-thiazol-2-ylamino group, 4-ethyl-thiazole-2-ylamino group, 5-ethyl-thiazol-2-ylamino group, 4-ethoxythiazol-2-ylamino group, 5-methoxy-thiazol-2-ylamino group, 4-carbamoyl-thiazol-2-ylamino group, 5-carbamoyl-thiazol-2-ylamino group, 4-methylcarbamoyl-thiazol-2-ylamino group, 4-ethylcarbamoyl-thiazol-2-ylamino group, 4-methyl-thiazol-2-ylamino group, 4-ethyl-thiazol-2-ylamino group, 4-cyano-thiazol-2-ylamino group, 4-chloro-thiazol-2-ylamino group, 4-fluoro-thiazol-2-ylamino group, 4-methylcarbamoyl-thiazol-2-ylamino group, 4-ethylcarbamoyl-thiazole-2-ylamino group, 4-isopropyl-thiazol-2-ylamino group, 4-cyano-thiazol-2-ylamino group, 4-chloro-thiazol-2-ylamino group, 4-fluoro-thiazol-2-ylamino group, 4-methylcarbonyl-thiazol-2-ylamino group, 4-ethylcarbonyl-thiazol-2-ylamino group, 4-ethylcarbonylamino-thiazol-2-ylamino group, 4-methylcarbonylamino-thiazol-2-ylamino group, 4-methylsulfonyl-thiazol-2-ylamino group, 4-ethylsulfonyl-thiazol-2-ylamino group, 3-methylsulfonyl-thiazol-2-ylamino group, 4-isopropyl-sulfonyl-thiazol-2-ylamino group, 4-methylamino-thiazol-2-ylamino group, 3-methylamino-thiazol-2-ylamino group, 4-ethylamino-thiazol-2-ylamino group, 4-aminomethyl-thiazol-2-ylamino group, 4-aminoethyl-thiazol-2-ylamino group, 3-aminomethyl-thiazol-2-ylamino group, pyridin-4-ylamino group, 6-hydroxymethyl-pyridin-3-ylamino group, 3-hydroxyethyl-pyridin-4-ylamino group, 4-hydroxymethyl-pyridin-2- ylamino group, 5-hydroxymethyl-pyridin-2-ylamino group, 3-methyl-pyridin-4-yl-sulfanyl group, 4-methyl-pyridin-2-ylamino group, 6-methyl-pyridin-3-ylamino group, 6-methoxy-pyridin-3-ylamino group, 6-methyl-pyridin-3-ylamino group, 2-carbamoyl-pyridin-4-ylamino group, 6-carbamoyl-pyridin-3-ylamino group, 6-methylcarbamoyl-pyridin-3-ylamino group, 2-methylcarbamoyl-pyridin-4-ylamino group, 2-cyano-pyridin-4-ylamino group, 6-cyano-pyridin-3-ylamino group, 2-trifluoromethyl-4-ylamino group, 6-trifluoromethyl-pyridin-3-ylamino group, 2-chloro-pyridin-4-ylamino group, 6-chloro-pyridin-3-ylamino group, 2-fluoro-pyridin-4-ylamino group, 6-fluoro-pyridin-3-ylamino group, 2-methylcarbonyl-pyridin-4-ylamino group, 6-methylcarbonyl-pyridin-3-ylamino group, 2-ethylcarbonyl-pyridin-4-ylamino group, 6-ethylcarbonyl-pyridin-3-ylamino group, 2-methylsulfonyl-pyridin-4-ylamino group, 6-methylsulfonyl-pyridin-3-ylamino group, 2-ethylsulfonyl-pyridin-4-ylamino group, 6-isopropylsulfonyl-pyridin-3-ylamino group, 2-methylcarbonyl-amino-pyridin-4-ylamino group, 6-methylcarbonylamino-pyridin-3-ylamino group, 2-methylamino-pyridin-4-ylamino group, 6-methylamino-pyridin-3-ylamino group, 2-ethylamino-pyridin-4-ylamino group, 6-ethylamino-pyridin-3-ylamino group, 2-aminomethyl-pyridin-4-ylamino group, 6-aminomethyl-pyridin-3-ylamino group, 4-hydroxymethyl-phenoxy group, 4-hydroxyethyl-phenoxy group, 3-hydroxymethyl-phenoxy group, 3-hydroxyethyl-phenoxy group, 4-methyl-phenoxy group, 3-ethyl-phenoxy group, 4-methoxy-phenoxy group, 3-methoxy-phenoxy group, 4-ethoxy-phenoxy group, 4-carbamoyl-phenoxy group, 3-carbamoyl-phenoxy group, 4-methylcarbamoyl-phenoxy group, 3-isopropylcarbamoyl-phenoxy group, 4-cyano-phenoxy group, 3-cyano-phenoxy group, 4-trifluoromethyl-phenoxy group, 3-trifluoromethyl-phenoxy group, 4-chloro-phenoxy group, 3-chloro-phenoxy group, 4-fluoro-phenoxy group, 3-fluoro-phenoxy group, 4-methylcarbonyl-phenoxy group, 3-methylcarbonyl-phenoxy group, 4-ethylcarbonyl-phenoxy group, 4-methylcarbonylamino-phenoxy group, 3-methylcarbonylamino-phenoxy group, 4-methylsulfonyl-phenoxy group, 3-methylsulfonyl-phenoxy group, 4-ethylsulfonyl-phenoxy group, 3-ethylsulfonyl-phenoxy group, 4-methylamino-phenoxy group, 3-methylamino-phenoxy group, 4-ethylamino-phenoxy group, 3-ethylamino-phenoxy group, 4-aminomethyl-phenoxy group, 3-aminomethyl-phenoxy group, 4-aminoethyl-phenoxy group, 3-aminoethyl-phenoxy group, 4-hydroxyethyl-phenylmethylamino group, 3-hydroxyethyl-phenylmethylamino group, 2-hydroxymethyl-phenylmethylamino group, 4-methyl-phenylmethylamino group, 3-methyl-phenylmethylamino group, 2-methyl-phenylmethylamino group, 4-ethyl-phenylmethylamino group, 4-isopropyl-phenylmethylamino group, 4-methoxy-phenylmethylamino group, 3-methoxy-phenylmethylamino group, 2-ethoxy-phenylmethylamino group, 4-ethoxy-phenylmethylamino group, 4-hydroxymethyl-phenylmethylamino group, 4-carbamoyl-phenylmethylamino group, 4-methylcarbamoyl-phenylmethylamino group, 4-isopropylcarbamoyl-phenylmethylamino group, 4-cyano-phenylmethylamino group, 4-trifluoromethyl-phenylmethylamino group, 4-fluoro-phenylmethylamino group, 3-chloro-phenylmethylamino group, 2-chloro-phenylmethylamino group, 2-fluoro-phenylmethylamino group, 4-methylcarbonyl-phenylmethylamino group, 4-ethylcarbonyl-phenylmethylamino group, 3-methylcarbonyl-phenylmethylamino group, 3-ethylcarbonyl-phenylmethylamino group, 4-methylcarbonylamino-phenylmethylamino group, 4-ethylcarbonylamino-phenylmethylamino group, 4-isopropylcarbonylamino-phenylmethylamino group, 4-methylsulfonyl-phenylmethylamino group, 3-ethylsulfonyl-phenylmethylamino group, 4-isopropylsulfonyl-phenylmethylamino group, 4-methylamino-phenylmethylamino group, 3-ethylamino-phenylmethylamino group, 4-aminomethyl-phenylmethylamino group, 3-aminomethyl-phenylmethylamino group, 4-aminoethyl-phenylmethylamino group, 3-aminoethyl-phenylmethylamino group, 4-methyl-thiazol-ylmethylamino group, 5-methyl-thiazol-2-ylmethylamino group, 4-ethyl-thiazol-2-ylmethylamino group, 5-ethyl-thiazol-2-ylmethylamino group, 4-ethoxy-thiazol-2-ylmethylamino group, 5-methoxy-thiazol-2-ylmethylamino group, 4-carbamoyl-thiazol-2-ylmethylamino group, 5-carbamoyl-thiazol-2-ylmethylamino group, 4-methylcarbamoyl-thiazol-2-ylmethylamino group, 4-ethylcarbamoyl-thiazol-2-ylmethylamino group, 4-methyl-thiazol-2-ylmethylamino group, 4-ethyl-thiazol-2-ylmethylamino group, 4-cyano-thiazol-2-ylmethylamino group, 4-chloro-thiazol-2-ylmethylamino group, 4-fluoro-thiazol-2-ylmethylamino group, 4-methylcarbamoyl-thiazol-2-ylmethylamino group, 4-ethylcarbamoyl-thiazole-2-ylmethylamino group, 4-isopropyl-thiazole-2-ylmethylamino group, 4-cyano-thiazole-2-ylmethylamino group, 4-chloro-thiazol-2-ylmethylamino group, 4-fluoro-thiazol-2-ylmethylamino group, 4-methylcarbonyl thiazol-2-ylmethylamino group, 4-ethylcarbonyl-thiazol-2-ylmethylamino group, 4-ethylcarbonylamino-thiazol-2-ylmethylamino group, 4-methylcarbonylamino-thiazol-2-ylmethylamino group, 4-methylsulfonyl thiazol-2-ylmethylamino group, 4-ethylsulfonyl-thiazol-2-ylmethylamino group, 3-methylsulfonyl-thiazol-2-ylmethylamino group, 4-isopropyl-sulfonyl-thiazol-2-ylmethylamino group, 4-methylamino-thiazol-2-ylmethylamino group, 3-methylamino-thiazol-2-ylmethylamino group, 4-ethylamino-thiazol-2-ylmethylamino group, 4-aminomethyl-thiazol-2-ylmethylamino group, 4-aminoethyl-thiazol-2-ylmethylamino group, 3-aminomethyl-thiazol-2-ylmethylamino group, pyridin-4-ylmethylamino group, 6-hydroxymethyl-pyridin-3-ylmethylamino group, 3-hydroxymethyl-pyridin-4-ylmethylamino group, 4-hydroxymethyl-pyridin-2-ylmethylamino group, 5-hydroxymethyl-pyridin-2-ylmethylamino group, 3-methyl-pyridin-4-yl-sulfanyl group, 4-methyl-pyridin-2-ylmethylamino group, 6-methyl-pyridin-3-ylmethylamino group, 6-methoxy-pyridin-3-ylmethylamino group, 6-methyl-pyridin-3-ylmethylamino group, 2-carbamoyl-pyridin-4-ylmethylamino group, 6-carbamoyl-pyridin-3-ylmethylamino group, 6-methylcarbamoyl-pyridin-3-ylmethylamino group, 2-methylcarbamoyl-pyridin-4-ylmethylamino group, 2-cyano-pyridin-4-ylmethylamino group, 6-cyano-pyridin-3-ylmethylamino group, 2-trifluoromethyl-4-ylmethylamino group, 6-trifluoromethyl-pyridin-3-ylmethylamino group, 2-chloro-pyridin-4-ylmethylamino group, 6-chloro-pyridin-3-ylmethylamino group, 2-fluoro-pyridin-4-ylmethylamino group, 6-fluoro-pyridin-3-ylmethylamino group, 2-methylcarbonyl-pyridin-4-ylmethylamino group, 6-methylcarbonyl-pyridin-3-ylmethylamino group, 2-ethylcarbonyl-pyridin-4-ylmethylamino group, 6-ethylcarbonyl-4-pyridin-3-ylmethylamino group, 2-methylsulfonyl-pyridin-4-ylmethylamino group, 6-methylsulfonyl-pyridin-3-ylmethylamino group, 2-ethylsulfonyl-pyridin-4-ylmethylamino group, 6-isopropylsulfonyl-pyridin-3-ylmethylamino group, 2-methylcarbonylamino-pyridin-4-ylmethylamino group, 6-methylcarbonylamino-pyridin-3-ylmethylamino group, 2-methylamino-pyridin-4-ylmethylamino group, 6-methylamino-pyridin-3-ylamino group, 2-ethylamino-pyridin-4-ylamino group, 6-ethylamino-pyridin-3-ylamino group, 2-aminomethyl-pyridin-4-ylamino group, 6-aminomethyl-pyridin-3-ylmethylamino group, 3-hydroxymethyl-phenylmethyl group, 2-hydroxyethyl-phenylmethyl group, 4-methyl-phenylmethyl group, 3-methyl-phenylmethyl group, 2-methyl-phenylmethyl group, 4-methyl-phenylmethyl group, 4-isopropyl-phenylmethyl group, 4-methoxy-phenylmethyl group, 3-methoxy-phenylmethyl group, 2-ethoxy-phenylmethyl group, 4-ethoxy-phenylmethyl group, 4-hydroxymethyl-phenylmethyl group, 4-carbamoyl-phenylmethyl group, 4-methylcarbamoyl-phenylmethyl group, 4-isopropylcarbamoyl-phenylmethyl group, 4-cyano-phenylmethyl group, 4-triflouoromethyl-phenylmethyl group, 4-fluoro-phenylmethyl group, 3-chloro-phenylmethyl group, 2-fluoro-phenylmethyl group, 4-methylcarbonyl-phenylmethyl group, 4-ethylcarbonyl-phenylmethyl group, 3-methylcarbonyl-phenylmethyl group, 3-ethylcarbonyl-phenylmethyl group, 4-methylcarbonylamino-phenylmethyl group, 4-ethylcarbonyl-phenylmethyl group, 4-isopropylcarbonyl-phenylmethyl group, 4-methylsulfonyl-phenylmethyl group, 3-ethylsulfonyl-phenylmethyl group, 4-methylsulfonyl-phenylmethyl group, 4-isopropylsulfonyl-phenylmethyl group, 4-methylamino-phenylmethyl group, 3-ethylamino-phenylmethyl group, 2-methylamino-phenylmethyl group, 4-aminomethyl-phenylmethyl group, 3-aminomethyl-phenylmethyl group, 4-aminoethyl-phenylmethyl group, thiazol-2-ylmethyl group, 4-hydroxymethyl-thiazol-2-yl group, 5-hydroxymethyl-thiazol-2-ylmethyl group, 4-hydroxyethyl-thiazol-2-ylmethyl group, 4-methyl-thiazol-2-ylmethyl group, 5-methyl-thiazol-2-ylmethyl group, 4-ethyl-thiazol-2-ylmethyl group, 4-methoxy-thiazol-2-ylmethyl group, 4-ethoxy-thiazol-2-ylmethyl group, 4-carbamoyl-thiazol-2-ylmethyl group, 5-carbamoyl-thiazol-2-ylmethyl group, 4-methylcarbamoyl-thiazol-2-ylmethyl group, 4-ethylcarbamoyl-thiazol-2-ylmethyl group, 4-isopropyl-thiazol-2-ylmethyl group, 4-cyano-thiazol-2-ylmethyl group, 4-chloro-thiazol-2-ylmethyl group, 4-fluoro-thiazol-2-ylmethyl group, 4-methylcarbonyl-thiazol-2-ylmethyl group, 4-ethylcarbonyl-thiazol-2-ylmethyl group, 4-ethylcarbonylamino-thiazol-2-ylmethyl group, 4-methylcarbonylamino-thiazol-2-ylmethyl group, 4-methylsulfonyl-thiazol-2-ylmethyl group, 4-ethylsulfonyl-thiazol-2-ylmethyl group, 3-methylsulfonyl-thiazol-2-ylmethyl group, 4-isopropyl-sulfonyl-thiazol-2-ylmethyl group, 4-methylamino-thiazol-2-ylmethyl group, 3-methylamino-thiazol-2-ylmethyl group, 4-ethylamino-thiazol-2-ylmethyl group, 4-aminomethyl-thiazol-2-ylmethyl group, 4-aminoethyl-thiazol-2-ylmethyl group, pyridin-4-ylmethyl group, 6-hydroxymethyl-pyridin-3-ylmethyl group, 3-hydroxymethyl-pyridin-4-ylmethyl group, 4-hydroxymethyl-pyridin-2-ylmethyl group, 6-hydroxymethyl-pyridin-3-ylmethyl group, 3-methyl-pyridin-4-ylsulfanyl group, 4-methyl-pyridin-2-ylmethyl group, 6-methyl-pyridin-3-ylmethyl group, 6-methoxy-pyridin-3-ylmethyl group, 6-methyl-pyridin-3-ylmethyl group, 2-carbamoyl-pyridin-4-ylmethyl group, 6-carbamoyl-pyridin-3-ylmethyl group, 6-methylcarbamoyl-pyridin-3-ylmethyl group, 2-methylcarbamoyl-pyridin-4-ylmethyl group, 2-cyano-pyridin-4-ylmethyl group, 6-cyano-pyridin-3-ylmethyl group, 2-trifluoromethyl-4-ylmethyl group, 6-trifluoromethyl-pyridin-3-ylmethyl group, 2-chloro-pyridin-4-ylmethyl group, 6-chloro-pyridin-3-ylmethyl group, 2-fluoro-pyridin-4-ylmethyl group, 6-fluoro-pyridin-3-ylmethyl group, 2-methylcarbonyl-pyridin-4-ylmethyl group, 6-methylcarbonyl-pyridin-3-ylmethyl group, 2-ethylcarbonyl-pyridin-4-ylmethyl group, 6-ethylcarbonyl-pyridin-3-ylmethyl group, 2-methylsulfonyl-pyridin-4-ylmethyl group, 6-methylsulfonyl-pyridin-3-ylmethyl group, 2-ethylsulfonyl-pyridin-4-ylmethyl group, 6-isopropylsulfonyl-pyridin-3-ylmethyl group, 2-methylcarbonylamino-pyridin-4-ylmethyl group, 6-methylcarbonylamino-pyridin-3-ylmethyl group, 2-methylamino-pyridin-4-ylmethyl group, 6-methylamino-pyridin-3-ylamino group, 2-ethylamino-pyridin-4-ylamino group, 2-ethylamino-pyridin-5-ylamino group, 2-aminomethyl-pyridin-4-ylamino group, 6-aminomethyl-pyridin-3-ylmethyl group, etc. Among them, preferred ones are phenylsulfanyl group, 4-hydroxyethyl-phenylsulfanyl group, 4-methyl-phenylsulfanyl group, 3-methyl-phenylsulfanyl group, 4-methoxy-phenylsulfanyl group, 3-methoxy-phenylsulfanyl group, 4-ethoxy-phenylsulfanyl group, 4-hydroxymethyl-phenylsulfanyl group, hydroxyethyloxy-phenylsulfanyl group, 4-carbamoyl-phenylsulfanyl group, 4-methylcarbamoyl-phenylsulfanyl group, 4-dimethylcarbamoyl-phenylsulfanyl group, 4-cyano-phenylsulfanyl group, 4-trifluoromethyl-phenylsulfanyl group, 4-fluoro-phenylsulfanyl group, 3-chloro-phenylsulfanyl group, 2-fluoro-phenylsulfanyl group, 4-methylcarbonyl-phenylsulfanyl group, 4-ethylcarbonyl-phenylsulfanyl group, 4-methylcarbonylamino-phenylsulfanyl group, 4-methylsulfonyl-phenylsulfanyl group, 4-methylamino-phenylsulfanyl group, 4-aminomethyl-phenylsulfanyl group, 4-aminoethyl-phenylsulfanyl group, 4-dimethylaminoethyloxy-phenylsulfanyl group, thiazol-2-yl-sulfanyl group, 4-methyl-thiazol-2-yl-sulfanyl group, 5-methyl-thiazol-2-yl-sulfanyl group, pyridin-4-yl-sulfanyl group, pyridin-3-yl-sulfanyl group, pyridin-2-yl-sulfanyl group, 6-hydroxymethyl-pyridin-3-yl-sulfanyl group, 6-methyl-pyridin-3-yl-sulfanyl group, 6-methoxy-pyridin-3-yl-sulfanyl group, 6-methyl-pyridin-3-yl-sulfanyl group, 6-carbamoyl-pyridin-3-yl-sulfanyl group, 6-methylcarbamoyl-pyridin-3-yl-sulfanyl group, 2-cyano-pyridin-4-yl-sulfanyl group, 6-cyano-pyridin-3-yl-sulfanyl group, 6-trifluoromethyl-pyridin-3-yl-sulfanyl group, 2-chloro-pyridin-4-yl-sulfanyl group, 6-chloro-pyridin-3-yl-sulfanyl group, 2-fluoro-pyridin-4-yl-sulfanyl group, 6-fluoro-pyridin-3-yl-sulfanyl group, 6-methylcarbonyl-pyridin-3-yl-sulfanyl group, 6-ethylcarbonyl-pyridin-3-yl-sulfanyl group, 6-methylsulfonyl-pyridin-3-yl-sulfanyl group, 6-methylcarbonylamino-pyridin-3-yl-sulfanyl group, 6-methylamino-pyridin-3-yl-sulfanyl group, 6-ethylamino-pyridin-3-yl-sulfanyl group, 6-aminomethyl-pyridin-3-yl-sulfanyl group, 4-methyl-phenylamino group, 4-methoxy-phenylamino group, 4-fluoro-phenylamino group, 4-methyl-thiazol-2-ylamino group, 5-methyl-thiazol-2-ylamino group, pyridin-4-ylamino group, 2-methyl-pyridin-5-ylamino group, 4-methyl-phenoxy group, 4-methoxy-phenoxy group, 4-fluoro-phenoxy group, 4-methyl-phenylaminomethyl group, 3-methyl-phenylaminomethyl group, 2-methyl-phenylaminomethyl group, 4-fluoro-phenylaminomethyl group, 2-chloro-phenylmethylamino group, 2-fluoro-phenylaminomethyl group, 4-methyl-thiazol-2-ylaminomethyl group, 5-methyl-thiazol-2-ylaminomethyl group, pyridin-4-ylaminomethyl group, 6-methyl-pyridin-3-ylaminomethyl group, 2-methyl-pyridin-5-ylaminomethyl group, 4-methyl-phenylmethyl group, 4-methoxy-phenylmethyl group and 4-fluoro-phenylmethyl group; more preferred ones are phenylsulfanyl group, 4-hydroxyethyl-phenylsulfanyl group, 4-methyl-phenylsulfanyl group, 3-methyl-phenylsulfanyl group, 4-methoxy-phenylsulfanyl group, 3-methoxy-phenylsulfanyl group, 4-ethoxy-phenylsulfanyl group, 4-hydroxymethyl-phenylsulfanyl group, hydroxyethyloxy-phenylsulfanyl group, 4-carbamoyl-phenylsulfanyl group, 4-methylcarbamoyl-phenylsulfanyl group, 4-dimethylcarbamoyl-phenylsulfanyl group, 4-cyano-phenylsulfanyl group, 4-trifluoromethyl-phenylsulfanyl group, 4-fluoro-phenylsulfanyl group, 3-chloro-phenylsulfanyl group, 2-fluoro-phenylsulfanyl group, 4-methylcarbonyl-phenylsulfanyl group, 4-methylsulfonyl-phenylsulfanyl group, 4-dimethylaminoethyloxyphenylsulfanyl group, pyridin-4-yl-sulfanyl group, pyridin-3-yl-sulfanyl group, 6-methoxy-pyridin-3-yl-sulfanyl group, 6-methyl-pyridin-3-yl-sulfanyl group and 6-trifluoromethyl-pyridin-3-yl-sulfanyl group; and still more preferred ones are phenylsulfanyl group, 4-hydroxyethyl-phenylsulfanyl group, 4-methyl-phenylsulfanyl group, 4-methoxy-phenylsulfanyl group, 4-ethoxy-phenylethylsulfanyl group, 4-methylcarbamoyl-phenylsulfanyl group, 4-dimethylcarbamoyl-phenylsulfanyl group, 4-cyano-phenylsulfanyl group, 4-trifluoromethyl-phenylsulfanyl group, 4-fluoro-phenylsulfanyl group, 2-fluoro-phenylsulfanyl group, 4-methylcarbonyl-phenylsulfanyl group, 4-methylsulfonyl-phenylsulfanyl group, 4-dimethylaminoethyloxy-phenylsulfanyl group, pyridin-4-yl-sulfanyl group, pyridin-3-yl-sulfanyl group, 6-methoxy-4-yl-sulfanyl group, 6-methoxy-pyridin-3-yl-sulfanyl group and 6-methyl-pyridin-3-yl-sulfanyl group.

As mentioned above, the compounds of the invention represented by the formula (I):

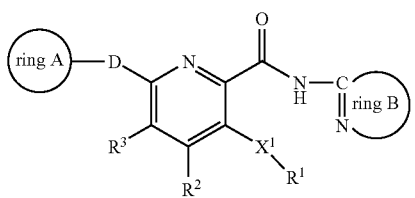

(I)

(wherein the respective symbols have the same meanings as defined above)

more specifically include, for example, 3-(4-methoxy-phenylsulfanyl)-6-(4H-[1,2,4]triazol-3-yl)-N-(thiazol-2-yl)-2-pyridine carboxamide, 3-(4-fluoro-phenylsulfanyl)-6-(4-methyl-4H-[1,2,4]triazol-3-yl-sulfanyl-N-(4-methyl-thiazol-2-yl)-2-pyridine carboxamide; 3-(4-fluoro-phenylsulfanyl)-6-(4H-[1,2,4]triazol-3-yl-sulfanyl)-N-(4-methyl-thiazol-2-yl)-2-pyridine carboxamide, 3-(4-fluoro-phenylsulfanyl)-6-(1-methyl-imidazol-2-yl-sulfanyl)-N-(4-methyl-thiazol-2-yl)-2-pyridine carboxamide; 3-(4-fluoro-phenylsulfanyl)-6-(1-methyl-1H-tetrazol-5-yl-sulfanyl)-N-(4-methyl-thiazol-2-yl)-2-pyridine carboxamide; 3-(cyclohexylsulfanyl)-6-(4H-[1,2,4]triazol-3-yl-sulfanyl)-N-(4-methyl-thiazol-2-yl)-2-pyridine carboxamide; 3-(4-fluoro-phenylsulfanyl)-6-(4H-[1,2,4]triazol-3-yl-sulfanyl)-N-(thiazol-2-yl)-2-pyridine carboxamide; 3-(thiazol-2-yl-sulfanyl)-6-(4H-[1,2,4]triazol-3-yl)-N-(4-methyl-thiazol-2-yl)-2-pyridine carboxamide; 3-(2-fluoro-phenylsulfanyl)-6-(4H-[1,2,4]triazol-3-yl-sulfanyl)-N-(thiazol-2-yl)-pyridine carboxamide; 3-phenylsulfanyl-6-(4H-[1,2,4]triazol-3-yl-sulfanyl)-N-(thiazol-2-yl)-2-pyridine carboxamide; 3-(4-fluoro-phenyloxy)-6-(4H-[1,2,4]triazol-3-yl-sulfanyl)-N-(thiazol-2-yl)-2-pyridine carboxamide; 3-(4-methoxy-phenylmethylsulfanyl)-6-(4-methyl-4H-[1,2,4]triazol-3-yl-sulfanyl)-N-(thiazol-2-yl)-2-pyridine carboxamide; 3-(3-fluoro-phenylsulfanyl)-6-(4H-[1,2,4]triazol-3-yl-sulfanyl)-N-(thiazol-2-yl)-2-pyridine carboxamide; 3-(2,4-difluoro-phenylsulfanyl)-6-(4H-[1,2,4]-triazol-3-yl-sulfanyl)-N-(thiazol-2-yl)-2-pyridine carboxamide; 3-(4-fluoro-phenylsulfanyl)-6-(5-methyl-4H-[1,2,4]triazol-3-yl-sulfanyl)-N-(thiazol-2-yl)-2-pyridine carboxamide; 3-(4-cyano-phenylsulfanyl)-6-(4H-[1,2,4]triazol-3-yl-sulfanyl)-N-(thiazol-2-yl)2-pyridine carboxamide; 3-(pyridine-4-yl-sulfanyl)-6-(4H-[1,2,4]triazol-3-yl-sulfanyl)-N-(thiazol-2-yl)-2-pyridine carboxamide; 3-(4-fluoro-phenylsulfanyl)-6-(4H-[1,2,4]triazol-3-yl-sulfanyl)-N-(4-thiazolo[5,4-b]pyridine-2-yl)-2-pyridine carboxamide; 3-(4-methoxy-phenylsulfanyl)-6-(4H-[1,2,4]triazol-3-yl-sulfanyl)-N-(4-methoxymethyl-thiazol-2-yl)-2-pyridine carboxamide; 3-(4-acetyl-phenylsulfanyl)-6-(4H-[1,2,4]triazol-3-yl-sulfanyl)-N-(thiazol-2-yl)-2-pyridine carboxamide; 3-(thiophene-2-yl-sulfanyl)-6-(4H[1,2,4]triazol-3-yl-sulfanyl)-N-(thiazol-2-yl)-2-pyridine carboxamide; 3-(4-methoxymethyl-phenylsulfanyl)-6-(4H-[1,2,4]triazol-3-yl-sulfanyl)-N-(thiazol-2-yl)-2-pyridine carboxamide; 3-(4-fluoro-phenylsulfanyl)-6-(5-methyl-4H-[1,2,4]triazol-3-yl-sulfanyl)-N-(thiazolo[5,4-b]pyridin-2-yl)-2-pyridine carboxamide; 3-(4-methyl-phenylsulfanyl)-6-(4H-[1,2,4]triazol-3-yl-sulfanyl)-N-(4-methoxymethyl-thiazol-2-yl)-2-pyridine carboxamide; 3-(4-chloro-phenylsulfanyl)-6-(4H-[1,2,4]triazol-3-yl-sulfanyl)-N-(4-methoxymethyl-thiazol-2-yl)-2-pyridine carboxamide; 3-(4-fluoro-phenylsulfanyl)-6-(3H-[1,2,3]triazol-4-yl-sulfanyl)-N-(thiazol-2-yl)-2-pyridine carboxamide; 3-(4-methylsulfonyl-phenylsulfanyl)-6-(4H-[1,2,4]triazol-3-yl-sulfanyl)-N-(thiazol-2-yl)-2-pyridine carboxamide; 3-(4-methoxy-phenylsulfanyl)-6-(4H-[1,2,4]triazol-3-yl-sulfanyl)-N-(5-hydroxymethyl-thiazol-2-yl)-2-pyridine carboxamide; 3-(4-fluoro-phenylsulfanyl)-6-(5-methoxymethyl-4H-[1,2,4]triazol-3-yl-sulfanyl)-N-(thiazol-2-yl)-2-pyridine carboxamide; 3-(6-methyl-pyridin-3-yl-sulfanyl)-6-(4H-[1,2,4]triazol-3-yl-sulfanyl)-N-(thiazol-2-yl)-2-pyridine carboxamide; 3-(4-dimethylcarbamoyl-phenylsulfanyl)-6-(4H-[1,2,4]triazol-3-yl-sulfanyl)-N-(thiazol-2-yl)-2-pyridine carboxamide; 3-(4-trifluoromethyl-phenylsulfanyl)-6-(4H-[1,2,4]triazol-3-yl-sulfanyl)-N-(thiazol-2-yl)-2-pyridine carboxamide; 3-(4-methylcarbamoyl-phenylsulfanyl)-6-(4H-[1,2,4]triazol-3-yl-sulfanyl)-N-(thiazol-2-yl)-2-pyridine carboxamide; 3-(hydroxyethyloxy-phenylsulfanyl)-6-(4H-[1,2,4]triazol-3-yl-sulfanyl)-N-(thiazol-2-yl)-2-pyridine carboxamide; 3-(4-methoxy-phenylsulfanyl)-6-(4H-[1,2,4]triazol-3-yl-sulfanyl)-N-(5-dimethylaminomethyl-thiazol-2-yl)-2-pyridine carboxamide; 3-(4-dimethylaminoethyloxy-phenylsulfanyl)-6-(4H-[1,2,4]triazol-3-yl-sulfanyl)-N-(thiazol-2-yl)-2-pyridine carboxamide; 3-(4-hydroxyethyl-phenylsulfanyl)-6-(4H-[1,2,4]triazol-3-yl-sulfanyl)-N-(thiazol-2-yl)-2-pyridine carboxamide; 3-(4-methylsulfamoyl-phenylsulfanyl)-6-(4H-[1,2,4]triazol-3-yl-sulfanyl)-N-(thiazol-2-yl)-2-pyridine carboxamide; 3-(4-dimethylcarbamoyl-phenylsulfanyl)-6-(4H-[1,2,4]-triazol-3-yl-sulfanyl)-N-(isoxazol-3-yl)-2-pyridine carboxamide; 3-(4-hydroxy-cyclohexylsulfanyl)-6-(4H-[1,2,4]triazol-3-yl-sulfanyl)-N-(thiazol-2-yl)-2-pyridine carboxamide; 3-(4-fluoro-phenylsulfanyl)-6-(4H-[1,2,4]-triazol-3-yl-sulfanyl)-N-pyridazin-3-yl)-2-pyridine carboxamide; 3-(pyrazine-2-yl-sulfanyl)-6-(4H-[1,2,4]triazol-3-yl-sulfanyl)-N-(thiazol-2-yl)-2-pyridine carboxamide; 3-(6-methyl-pyridin-3-yl-sulfanyl)-6-(4H-[1,2,4]triazol-3-yl-sulfanyl)-N-(pyrazin-2-yl)-2-pyridine carboxamide; 3-(6-methyl-pyridin-3-yl-sulfanyl)-6-(4H-[1,2,4]triazol-3-yl-sulfanyl)-N-(4-methyl-thiazol-2-yl)-2-pyridine carboxamide; 3-[4-(1-hydroxyethyl-phenylsulfanyl)-6-(4H-[1,2,4]triazol-3-yl-sulfanyl)-N-(thiazol-2-yl)-2-pyridine carboxamide; 3-(6-methyl-pyridin-3-yl-sulfanyl)-6-(4H-[1,2,4]triazol-3-yl-sulfanyl)-N-(2-methyl-thiazol-4-yl)-2-pyridine carboxamide; 3-(4-dimethylcarbamoyl-phenylsulfanyl)-6-(4H-[1,2,4]triazol-3-yl-sulfanyl)-N-(2-methyl-thiazol-4-yl)-2-pyridine carboxamide; 3-(6-methyl-pyridin-3-yl-sulfanyl)-6-(4H-[1,2,4]triazol-3-yl-sulfanyl)-N-(4-methoxymethyl-thiazol-2-yl)-2-pyridine carboxamide; 3-(1- methyl-1H-tetrazole-5-yl-sulfanyl)-6-(4H-[1,2,4]triazol-3-yl-sulfanyl)-N-(thiazol-2-yl)-2-pyridine carboxamide; 3-(4-hydroxyethyloxy-phenylsulfanyl)-6-(4H-[1,2,4]triazol-3-yl-sulfanyl)-N-(isoxazol-3-yl)-2-pyridine carboxamide; 3-(4-dimethylaminoethyloxy-phenylsulfanyl)-6-(4H-[1,2,4]triazol-3-yl-sulfanyl)-N-(isoxazol-3-yl)-2-pyridine carboxamide; 3-(4-fluoro-phenylsulfanyl)-6-phenoxy-N-(4-methyl-thiazol-2-yl)-2-pyridine carboxamide; 3-(2-chloro-phenylmethyl-amino)-6-(4-methyl-4H-[1,2,4]triazol-3-yl-sulfanyl)-N-(4-methyl-thiazol-2-yl)-2-pyridine carboxamide; 3,6-bis-(pyridin-2-yl-sulfanyl)-N-(4-methyl-thiazol-2-yl)-2-pyridine carboxamide; 3,6-bis-(4-fluoro-phenylsulfanyl)-N-(4-methyl-thiazol-2-yl)-2-pyridine carboxamide; 3,6-bis-(thiazol-2-yl-sulfanyl)-N-(thiazol-2-yl)-2-pyridine carboxamide; 3,6-bis-(5-methyl-[1,3,4]thiadiazol-2-yl-sulfanyl-sulfanyl)-N-(thiazol-2-yl)-2-pyridine carboxamide; 3-(4-methoxy-phenylsulfanyl)-6-(4H-[1,2,4]triazol-3-yl-sulfanyl)-N-(5-methyl-thiazol-2-yl)-2-pyridine carboxamide; 3-(4-methoxy-phenylsulfanyl)-6-(4H-[1,2,4]triazol-3-yl-sulfanyl)-N-(isoxazol-3-yl)-2-pyridine carboxamide; 3-(4-methoxy-phenylsulfanyl)-6-(4H-[1,2,4]triazol-3-yl-sulfanyl)-N-([1,3,4]thiadiazol-2-yl)-2-pyridine carboxamide; 3-(4-methoxy-phenylsulfanyl)-6-(4H-[1,2,4]triazol-3-yl-sulfanyl)-N-([1,2,4]thiadiazol-5-yl)-2-pyridine carboxamide; 3-(4-methoxy-phenylsulfanyl)-6-(4H-[1,2,4]triazol-3-yl-sulfanyl)-N-(4-methylcarbonyl-thiazol-2-yl)-2-pyridine carboxamide; 3-(4-methoxy-phenylsulfanyl)-6-(4H-[1,2,4]triazol-3-yl-sulfanyl)-N-(pyrimidin-4-yl)-2-pyridine carboxamide; 3-(4-methoxy-phenylsulfanyl)-6-(4H-[1,2,4]triazol-3-yl-sulfanyl)-N-(pyridin-2-yl)-2-pyridine carboxamide; 3-(4-methoxy-phenylsulfanyl)-6-(4H-[1,2,4]triazol-3-yl-sulfanyl)-N-(5-ethoxylcarbonyl-thiazol-2-yl)-2-pyridine carboxamide; 3-(pyridine-3-yl-sulfanyl)-6-(4H-[1,2,4]triazol-3-yl-sulfanyl)-N-(thiazol-2-yl)-2-pyridine carboxamide; 3-(6-methoxy-pyridin-3-yl-sulfanyl)-6-(4H-[1,2,4]triazol-3-yl-sulfanyl)-N-(thiazol-2-yl)-2-pyridine carboxamide; 3-(pyridin-3-yl-sulfanyl)-6-(4H-[1,2,4]triazol-3-yl-sulfanyl)-N-(4-methoxymethyl-thiazol-2-yl)-2-pyridine carboxamide; 3-phenyloxymethyl-6-(4-methyl-4H-[1,2,4]triazol-3-yl-sulfanyl)-N-(thiazol-2-yl)-2-pyridine carboxamide; 3-phenylsulfanylmethyl-6-(4-methyl-4H-[1,2,4]triazol-3-yl-sulfanyl)-N-(thiazol-2-yl)-2-pyridine carboxamide; 3-phenylmethyl-6-4H-[1,2,4]triazol-3-yl-sulfanyl)-N-(thiazol-2-yl)-2-pyridine carboxamide; 3-(4-fluoro-phenylmethyl)-6-(4H-[1,2,4]triazol-3-yl-sulfanyl)-N-(thiazol-2-yl)-2-pyridine carboxamide; 3-(4-dimethylaminoethyl-phenylsulfanyl)-6-(4H-[1,2,4]triazol-3-yl-sulfanyl)-N-(thiazol-2-yl)-2-pyridine carboxamide; 3-(4-dimethylaminomethyl-phenylsulfanyl)-6-(4H-[1,2,4]triazol-3-yl-sulfanyl)-N-(thiazol-2-yl)-2-pyridine carboxamide; 3-(4-methoxy-phenylsulfanyl)-6-(4H-[1,2,4]triazol-3-yl-sulfanyl)-N-(thiazol-4-yl)-2-pyridine carboxamide; 3-(4-dimethylcarbamoylmethyloxy-phenylsulfanyl)-6-(4H-[1,2,4]triazol-3-yl-sulfanyl)-N-(thiazol-2-yl)-2-pyridine carboxamide; 3-(4-methoxy-phenylsulfanyl)-6-(4H-[1,2,4]triazol-3-yl-sulfanyl)-N-(4-hydroxyethyl-thiazol-2-yl)-2-pyridine carboxamide; 3-(6-methyl-pyridin-3-yl-sulfanyl)-6-(5-hydroxy-4H-[1,2,4]triazol-3-ylsulfanyl)-N-(thiazol-2-yl)-2-pyridine carboxamide; 3-(6-methoxycarbonyl-pyridin-3-ylsulfanyl)-6-(4H-[1,2,4]triazol-3-ylsulfanyl)-N-(thiazol-2-yl)-2-pyridine carboxamide; 3-(4-dimethylaminoethyloxy-phenylsulfanyl)-6-(4H-[1,2,4]triazol-3-yl-sulfanyl)-N-([1,2,4]thiadiazol-5-yl)-2-pyridine carboxamide; 3-(pyrimidine-5-ylsulfanyl)-6-(4H-[1,2,4]triazol-3-yl-sulfanyl)-N-(thiazol-2-yl)-2-pyridine carboxamide; 3-(6-hydroxymethyl-pyridin-3-ylsulfanyl)-6-(4H-[1,2,4]triazol-3-yl-sulfanyl)-N-(thiazol-2-yl)-2-pyridine carboxamide; 3-[4-(1-methylpyrrolidine-3-yloxy)-phenylsulfanyl]-6-(4H-[1,2,4]triazol-3-ylsulfanyl)-N-(thiazol-2-yl)-2-pyridine carboxamide; 3-(6-methyl-pyridin-3-ylsulfanyl)-6-(4H-[1,2,4]triazol-3-ylsulfanyl)-N-([1,2,4]thiadiazol-5-yl)-2-pyridine carboxamide; 3-(4-dimethylaminoethyloxy-phenylsulfanyl)-6-(5-methyl-4H-[1,2,4]triazol-3-ylsulfanyl)-N-([1,2,4]thiadiazol-5-yl)-2-pyridine carboxamide; 3-(1-oxy-6-methyl-pyridin-3-yl-sulfanyl)-6-(4H-[1,2,4]triazol-3-ylsulfanyl)-N-(thiazol-2-yl)-2-pyridine carboxamide; 3-(4-diethylaminoethyloxy-phenylsulfanyl)-6-(4H-[1,2,4]triazol-3-yl-sulfanyl)-N-(thiazol-2-yl)-2-pyridine carboxamide; 3-(4-pyrrolidinoethyloxy-phenylsulfanyl)-6-(4H-[1,2,4]triazol-3-yl-sulfanyl)-N-(thiazol-2-yl)-2-pyridine carboxamide; 3-(6-dimethylaminoethyloxy-pyridin-3-ylsulfanyl)-6-(4H-[1,2,4]triazol-3-ylsulfanyl)-N-(thiazol-2-yl)-2-pyridine carboxamide; 3-(pyrazol-4-yl-sulfanyl)-6-(4H-[1,2,4]triazol-3-ysulfanyl)-N-(thiazol-2-yl)-2-pyridine carboxamide; 3-(4-dimethylaminoethyloxy-phenylsulfanyl)-6-(4H-[1,2,4]triazol-3-ylsulfanyl)-N-(3-methyl-[1,2,4]thiadiazol-5-yl)-2-pyridine carboxamide; 3-(4-carbamoylmethyloxy-phenylsulfanyl)-6-(4H-[1,2,4]triazol-3-yl-sulfanyl)-N-(thiazol-2-yl)-2-pyridine carboxamide; 3-(5-bromo-6-methyl-pyridin-3-ylsulfanyl)-6-(4H-[1,2,4]triazol-3-yl-sulfanyl)-N-(thiazol-2-yl)-2-pyridine carboxamide; 3-[4-(2-hydroxyethyl)-phenylsulfanyl]-6-(4H-[1,2,4]-triazol-3-ylsulfanyl)-N-(3-methyl-[1,2,4]thiadiazol-5-yl)-2-pyridine carboxamide; 3-[4-(2-hydroxyethyl-phenylsulfanyl)-6-(5-methyl-4H-[1,2,4]triazol-3-ylsulfanyl)-N-(3-methyl-[1,2,4]thiadiazol-5-yl)-2-pyridine carboxamide; 3-(pyridin-3-yl-sulfanyl)-6-(4H-[1,2,4]triazol-3-ylsulfanyl)-N-(3-methyl-[1,2,4]thiadiazol-5-yl)-2-pyridine carboxamide; 3-(6-methyl-pyridin-3-ylsulfanyl)-6-(4H-[1,2,4]triazol-3-ylsulfanyl)-N-(3-methyl-[1,2,4]thiadiazol-5-yl)-2-pyridine carboxamide; 3-(4-dimethylaminoethyloxy-phyenylsulfanyl)-6-(4H-[1,2,4]triazol-3-ylsulfanyl)-N-(thiazolo[5,4-b]pyridin-2-yl)-2-pyridine carboxamide; 3-(6-methyl-pyridin-3-ylsulfanyl)-6-(5-methyl-4H-[1,2,4]triazol-3-ylsulfanyl)-N-(3-methyl-[1,2,4]thiadiazol-5-yl)-2-pyridine carboxamide; 3-(6-methyl-pyridin-3-yl-sulfanyl)-6-(4H-[1,2,4]triazol-3-ylsulfanyl)-N-([1,2,5]thiadiazol-3-yl)-2-pyridine carboxamide; 3-(2,3-dihydrobenzofuran-5-ylsulfanyl)-6-(4H-[1,2,4]triazol-3-ylsulfanyl)-N-(thiazol-2-yl)-2-pyridine carboxamide; 3-(6-methyl-pyridin-3-yl-sulfanyl)-6-(4H-[1,2,4]triazol-3-ylsulfanyl)-N-(3-methoxy-[1,2,4]-thiadiazol-5-yl)-2-pyridine carboxamide; 3-(6-methyl-pyridin-3-yl-sulfanyl)-6-(4H-[1,2,4]triazol-3-ylsulfanyl)-N-(3-cyclopropyl-[1,2,4]thiadiazol-5-yl)-2-pyridine carboxamide; 3-(4-dimethylaminoethyloxy-phenylsulfanyl)-6-(5-methyl-4H-[1,2,4]triazol-3-ylsulfanyl)-N-(3-methyl-[1,2,4]thiadiazol-5-yl)-2-pyridine carboxamide; 3-(2-fluoro-pyridin-4-ylsulfanyol)-6-(4H-[1,2,4]triazol-3-yl-sulfanyl)-N-(thiazol-2-yl)-2-pyridine carboxamide; 3-(2-methoxy-pyrimidin-5-ylsulfanyl)-6-(2H-[1,2,4]triazol-3-ylsulfanyl)-N-(thiazol-2-yl)-2-pyridine carboxamide; 3-(6-methyl-pyridin-3-ylsulfanyl)-6-(5-methyl-4H-[1,2,4]triazol-3-ylsulfanyl)-N-([1,2,4]thiadiazol-5-yl)-2-pyridine carboxamide; 3-(4-hydroxyethyloxy-phenylsulfanyl)-6-(4H-[1,2,4]triazol-3-ylsulfanyl)-N-(3-methyl-[1,2,4]thiadiazol-5-yl)-2-pyridine carboxamide; 3-(4-diethylcarbamoylmethyloxy-phenylsulfanyl)-6-(4H-[1,2,4]triazol-3-ylsulfanyl)-N-(thiazol-2-yl)-2-pyridine carboxamide; 3-(6-cyclopropyl-pyridin-3-ylsulfanyl)-6-(4H-[1,2,4]triazol-3-ylsulfanyl)-N-(thiazol-2-yl)-2-pyridine carboxamide; 3-(6-methyl-pyridin-3-ylsulfanyl)-6-(5-methyl-4H-[1,2,4]triazol-3-ylsulfanyl)-N-(thiazol-2-yl)-2-pyridine carboxamide; 3-(6-methyl-pyridin-3-ylsulfanyl)-6-(pyrazol-4-ylsulfanyl)-

N-(thiazol-2-yl)-2-pyridine carboxamide; 3-(6-ethoxy-pyridin-3-ylsulfanyl)-6-(4H-[1,2,4]-triazol-3-ylsulfanyl)-N-(3-methyl-[1,2,4]thiadiazol-5-yl)-2-pyridine carboxamide; 3-(4-dimethylaminosulfonyl-phenylsulfanyl)-6-(4H-[1,2,4]-triazol-3-ylsulfanyl)-N-(thiazol-2-yl)-2-pyridine carboxamide; 3-(5-fluoro-pyridin-3-ylsulfanyl)-6-(4H-[1,2,4]-triazol-3-ylsulfanyl)-N-(3-methyl-[1,2,4]-thiadiazol-5-yl)-2-pyridine carboxamide; 3-(2,3-dihydrobenzofuran-5-ylsulfanyl)-6-(4H-[1,2,4]-triazol-3-ylsulfanyl)-N-(3-methyl-[1,2,4]thiadiazol-5-yl)-2-pyridine carboxamide; 3-(4-methoxy-phenylsulfanyl)-6-(4H-[1,2,4]-triazol-3-yl-sulfanyl)-N-([1,2,4]triazin-3-yl)-2-pyridine carboxamide; 3-(4-carboxy-phenylsulfanyl)-6-(5-methyl-[1,2,4]-triazol-3-ylsulfanyl)-N-(3-methyl-[1,2,4]thiadiazol-5-yl)-2-pyridine carboxamide; 3-(6-ethoxy-pyridin-3-ylsulfanyl)-6-(4H-[1,2,4]triazol-3-ylsulfanyl)-N-(pyrazin-2-yl)-2-pyridine carboxamide; 3-(imidazo-[1,2-a]pyridin-6-ylsulfanyl)-6-(4H-[1,2,4]-triazol-3-ylsulfanyl)-N-(3-methyl-[1,2,4]thiadiazol-5-yl)-2-pyridine carboxamide; 3-(2-methyl-pyridin-3-ylsulfanyl)-6-(4H-[1,2,4]-triazol-3-ylsulfanyl)-N-(3-methyl-[1,2,4]thiadiazol-5-yl)-2-pyridine carboxamide; 3-(4-methoxy-phenylsulfanyl)-6-(4H-[1,2,4]triazol-3-ylsulfanyl)-N-(thiazolo[4,5-b]pyridin-2-yl)-2-pyridine carboxamide; 3-(5-methyl-pyridin-3-ylsulfanyl)-6-(4H-[1,2,4]-triazol-3-ylsulfanyl)-N-(3-methyl-[1,2,4]thiadiazol-5-yl)-2-pyridine carboxamide; 3-(4,4-difluoromethyloxy-phenylsulfanyl)-6-(4H-[1,2,4]triazol-3-ylsulfanyl)-N-(pyridin-2-yl)-2-pyridine carboxamide; 3-(6-methyl-pyridin-3-ylphenylsulfanyl)-6-(4H-[1,2,4]triazol-3-ylsulfanyl)-N-(1-methyl-1H-[1,2]pyrazol-3-yl)-2-pyridine carboxamide; 3-(6-hydroxyethyl-pyridin-3-ylsulfanyl)-6-(4H-[1,2,4]triazol-3-ylsulfanyl)-N-(3-methyl-[1,2,4]thiadiazol-5-yl)-2-pyridine carboxamide; 3-(4-fluoro-phenylsulfanyl)-6-(4H-[1,2,4]triazol-3-ylsulfanyl)-N-(1-methyl-1H-[1,2]pyrazol-3-yl)-2-pyridine carboxamide; 3-(2-methyl-imidazo[1,2-a]pyridin-6-ylsulfanyl)-6-(4H-[1,2,4]triazol-3-ylsulfanyl)-N-(3-methyl-[1,2,4]thiadiazol-5-yl)-2-pyridine carboxamide; 3-(6-methyl-pyridin-3-ylsulfanyl)-6-(4H-[1,2,4]triazol-3-ylsulfanyl)-N-(3-hydroxymethyl-[1,2,4]thiadiazol-5-yl)-2-pyridine carboxamide; 3-[4-(2-hydroxyethyl-phenylsulfanyl)-6-(4-methyl-4H-[1,2,4]triazol-3-ylsulfanyl)-N-(3-methyl-[1,2,4]thiadiazol-5-yl)-2-pyridine carboxamide; 3-(6-methyl-pyridin-3-ylsulfanyl)-6-(5-hydroxy-4H-[1,2,4]triazol-3-ylsulfanyl)-N-(3-methyl-[1,2,4]thiadiazol-5-yl)-2-pyridine carboxamide; 3-(1-methyl-1H-indazol-5-ylsulfanyl)-6-(4H-[1,2,4]triazol-3-ylsulfanyl)-N-(3-methyl-[1,2,4]thiadiazol-5-yl)-2-pyridine carboxamide; 3-(3-methyl-[1,2,4]-triazolo-[4,3-a]pyridin-7-ylsulfanyl)-6-(4H-[1,2,4]triazol-3-ylsulfanyl)-N-(3-methyl-[1,2,4]thiadiazol-5-yl)-2-pyridine carboxamide; 3-(1-oxy-6-methyl-pyridin-3-ylsulfanyl)-6-(4H-[1,2,4]triazol-3-ylsulfanyl)-N-(3-methyl-[1,2,4]thiadiazol-5-yl)-2-pyridine carboxamide; 3-(6-hydroxymethyl-pyridin-3-ylsulfanyl)-6-(4H-[1,2,4]triazole-3-ylsulfanyl)-N-(3-methyl-[1,2,4]thiadiazol-5-yl)-2-pyridine carboxamide; 3-(4-methoxy-phenylsulfanyl)-6-(4H-[1,2,4]triazol-3-ylsulfanyl)-N-(1-methyl-1H-[1,2]pyrazol-3-yl)-2-pyridine carboxamide; 3-(4-fluoro-phenylsulfanyl)-6-(4H-[1,2,4]triazol-3-ylsulfanyl)-N-(1H-[1,2]pyrazol-3-yl)-2-pyridine carboxamide; 3-(6-methoxy-pyridin-3-ylsulfanyl)-6-(4H-[1,2,4]triazol-3-ylsulfanyl)-N-(3-methyl-[1,2,4]thiadiazol-5-yl)-2-pyridine carboxamide; 3-[4-(1H-imidazol-1-yl)-phenylsulfanyl]-6-(4H-[1,2,4]triazol-3-ylsulfanyl)-N-(3-methyl-[1,2,4]thiadiazol-5-yl)-2-pyridine carboxamide; 3-(4-methoxy-phenylsulfanyl)-6-(4H-[1,2,4]triazol-3-ylsulfanyl)-N-(1H-[1,2]pyrazol-3-yl)-2-pyridine carboxamide; 3-(6-methoxy-pyridin-3-ylsulfanyl)-6-(4H-[1,2,4]triazol-3-ylsulfanyl)-N-(1-methyl-1H-pyrazol-3-yl)-2-pyridine carboxamide; 3-(6-ethoxy-pyridin-3-ylsulfanyl)-6-(4H-[1,2,4]triazol-3-ylsulfanyl)-N-(1-methyl-1H-pyrazol-3-yl)-2-pyridine carboxamide; 3-(4-methoxymethyl-phenylsulfanyl)-6-(4H-[1,2,4]triazol-3-ylsulfanyl)-N-(1-methyl-1H-pyrazol-3-yl)-2-pyridine carboxamide; 3-(4-methoxy-phenylsulfanyl)-6-(4H-[1,2,4]triazol-3-ylsulfanyl)-N-(4,5-dimethyl-thiazol-2-yl)-2-pyridine carboxamide; 3-(4-fluoro-phenylsulfanyl)-6-(4,5-dimethyl-4H-[1,2,4]triazol-3-ylsulfanyl)-N-(4-methoxymethyl-thiazol-2-yl)-2-pyridine carboxamide; 3-[4-(1-methoxyethyl)-phenylsulfanyl]-6-(4H-[1,2,4]triazol-3-ylsulfanyl)-N-(thiazol-2-yl)-2-pyridine carboxamide; 3-(4-fluoro-phenylsulfanyl)-6-(4H-[1,2,4]triazol-3-ylsulfanyl)-N-(4-hydroxymethyl-thiazol-2-yl)-2-pyridine carboxamide; 3-(4-methoxy-phenylsulfanyl)-6-(4H-[1,2,4]triazol-3-ylsulfanyl)-N-(5-trifluoromethylthiazol-2-yl)-2-pyridine carboxamide; 3-(4-methoxy-phenylsulfanyl)-6-(4H-[1,2,4]triazol-3-ylsulfanyl)-N-(4-trifluoromethylthiazol-2-yl)-2-pyridine carboxamide; 3-(3-fluoro-4-methoxy-phenylsulfanyl)-6-(4H-[1,2,4]triazol-3-ylsulfanyl)-N-(thiazol-2-yl)-2-pyridine carboxamide; 3-[4-(1,1-dimethyl-1-hydroxymethyl)-phenylsulfanyl]-6-(4H-[1,2,4]triazol-3-ylsulfanyl)-N-(thiazol-2-yl)-2-pyridine carboxamide; 3-(3,4-difluoro-phenylsulfanyl)-6-(4H-[1,2,4]triazol-3-ylsulfanyl)-N-(1-methyl-1H-[1,2]pyrazol-3-yl)-2-pyridine carboxamide; 3-(3,5-difluoro-phenylsulfanyl)-6-(4H-[1,2,4]triazol-3-ylsulfanyl)-N-(1-methyl-1H-[1,2]pyrazol-3-yl)-2-pyridine carboxamide; 3-(1-methyl-2-oxo-2,3-dihydro-1H-indol-5-ylsulfanyl)-6-(4H-[1,2,4]triazol-3-ylsulfanyl)-N-(1-methyl-1H-[1,2]pyrazol-3-yl)-2-pyridine carboxamide; 3-(6-methyl-pyridin-3-ylsulfanyl)-6-(4H-[1,2,4]triazol-3-ylsulfanyl)-N-([1,2,4]triazolopyridin-2-yl)-2-pyridine carboxamide; 3-(4-ethoxymethyl-phenylsulfanyl)-6-(4H-[1,2,4]triazol-3-ylsulfanyl)-N-(1-methyl-1H-[1,2]pyrazol-3-yl)-2-pyridine carboxamide; 3-(6-oxo-1,6-dihydropyridin-3-ylsulfanyl)-6-(4H-[1,2,4]triazol-3-ylsulfanyl)-N-(1-methyl-1H-[1,2]pyrazol-3-yl)-2-pyridine carboxamide; 3-(6-methoxy-pyridin-3-ylsulfanyl)-6-(4H-[1,2,4]triazol-3-ylsulfanyl)-N-(1H-[1,2]pyrazol-3-yl)-2-pyridine carboxamide; 3-(4-hydroxyethyloxy-phenylsulfanyl)-6-(4-methyl-4H-[1,2,4]triazol-3-yl-sulfanyl)-N-(1-methyl-1H-[1,2]pyrazol-3-yl)-2-pyridine carboxamide.

Among them, the preferred compounds are 3-(4-fluoro-phenylsulfanyl)-6-(4-methyl-4H-[1,2,4]triazol-3-yl-sulfanyl)-N-(4-methyl-thiazol-2-yl)-2-pyridine carboxamide; 3-(4-fluoro-phenylsulfanyl)-6-(4H-[1,2,4]triazol-3-yl-sulfanyl)-N-(4-methyl-thiazol-2-yl)-2-pyridine carboxamide; 3-(4-fluoro-phenylsulfanyl)-6-(4H-[1,2,4]triazol-3-yl-sulfanyl)-N-(4-methoxymethyl-thiazol-2-yl)-2-pyridine carboxamide; 3-(4-methoxy-phenylsulfanyl)-6-(4H[1,2,4]triazol-3-yl-sulfanyl)-N-(thiazol-2-yl)2-pyridine carboxamide; 3-(4-fluoro-phenylsulfanyl)-6-(5-methyl-4H-[1,2,4]triazol-3-yl-sulfanyl)-N-(thiazol-2-yl)2-pyridine carboxamide; 3-(pyridin-4-yl-sulfanyl)-6-(4H-[1,2,4]triazol-3-yl-sulfanyl)-N-(thiazol-2-yl)2-pyridine carboxamide; 3-(4-methoxy-phenylsulfanyl)-6-(4H-[1,2,4]triazol-3-yl-sulfanyl)-N-(4-methoxymethyl-thiazol-2-yl)-2-pyridine carboxamide; 3-(4-methoxymethyl-phenylsulfanyl)-6-(4H-[1,2,4]triazol-3-yl-sulfanyl)-N-(thiazol-2-yl)-2-pyridine carboxamide; 3-(4-chloro-phenylsulfanyl)-6-(4H-[1,2,4]triazol-3-yl-sulfanyl)-N-(4-methoxymethyl-thiazol-2-yl)-2-pyridine carboxamide; 3-(4-fluoro-phenylsulfanyl)-6-(3H-[1,2,3]triazol-4-yl-sulfanyl)-N-(thiazol-2-yl)-2-pyridine carboxamide; 3-(4-methoxy-phenylsulfanyl)-6-(4H-[1,2,4]triazol-3-yl-sulfanyl)-N-(isoxazol-3-yl)-2-pyridine carboxamide; 3-(4-methoxy-phenylsulfanyl)-6-(4H-[1,2,4]triazol-3-yl-sulfanyl)-N-([1,3,4]thiadiazol-2-yl)-2-pyridine carboxamide; 3-(4-methylsulfonyl-phenylsulfanyl)-6-(4H-

[1,2,4]triazol-3-yl-sulfanyl)-N-(thiazol-2-yl)-2-pyridine carboxamide; 3-(4-methoxy-phenylsulfanyl)-6-(4H-[1,2,4]triazol-3-yl-sulfanyl)-N-(5-hydroxymethyl-thiazol-2-yl)-2-pyridine carboxamide; 3-(4-methyl-pyridin-3-yl-sulfanyl)-6-(4H-[1,2,4]triazol-3-yl-sulfanyl)-N-(thiazol-2-yl)-2-pyridine carboxamide; 3-(4-dimethylcarbamoyl-phenylsulfanyl)-6-(4H-[1,2,4]triazol-3-yl-sulfanyl)-N-(thiazol-2-yl)-2-pyridine carboxamide; 3-(4-methoxy-phenylsulfanyl)-6-(4H-[1,2,4]triazol-3-yl-sulfanyl)-N-([1,2,4]thiadiazol-5-yl)-2-pyridine carboxamide; 3-(4-hydroxyethyloxy-phenylsulfanyl)-6-(4H-[1,2,4]triazol-3yl-sulfanyl)-N-(thiazol-2-yl)-2-pyridine carboxamide; 3-(4-N,N-dimethylamino-ethyloxy-phenylsulfanyl)-6-(4H-[1,2,4]triazol-3-yl-sulfanyl)-N-(thiazol-2-yl)-2-pyridine carboxamide; 3-(4-methoxy-phenylsulfanyl)-6-(4H-[1,2,4]triazol-3-yl)-N-(thiazol-2-yl)-2-pyridine carboxamide; 3-(4-fluoro-phenylsulfanyl)-6-(4H-[1,2,4]triazol-3-yl-sulfanyl)-N-(thiazol-2-yl)-2-pyridine carboxamide; 3-(4-methoxy-phenylsulfanyl)-6-(4H-[1,2,4]triazol-3-yl-sulfanyl)-N-(4-methoxymethyl-thiazol-2-yl)-2-pyridine carboxamide; 3-(4-methoxymethyl-phenylsulfanyl)-6-(4H-[1,2,4]triazol-3-yl-sulfanyl)-thiazol-2-yl)-2-pyridine carboxamide; 3-(6-methyl-pyridin-3-yl-sulfanyl)-6-(4H-[1,2,4]triazol-3-yl-sulfanyl)-N-(thiazol-2-yl)-2-pyridine carboxamide; 3-(hydroxyethyloxy-phenylsulfanyl)-6-(4H-[1,2,4]triazol-3-yl-sulfanyl)-N-(thiazol-2-yl)-2-pyridine carboxamide; 3-(4-dimethylaminoethyloxy-phenylsulfanyl)-6-(4H-[1,2,4]triazol-3-yl-sulfanyl)-N-(thiazol-2-yl)-2-pyridine carboxamide; 3-(4-hydroxyethyl-phenylsulfanyl)-6-(4H-[1,2,4]triazol-3-yl-sulfanyl)-N-(thiazol-2-yl)-2-pyridine carboxamide; 3-(6-methyl-pyridin-3-yl-sulfanyl)-6-(4H-[1,2,4]triazol-3-yl-sulfanyl)-N-(4-methyl-thiazole-2-yl)-2-pyridine carboxamide, 3-(4-dimethylaminoethyloxy-phenylsulfanyl)-6-(4H-[1,2,4]triazol-3-ylsulfanyl)-N-([1,2,4]thiadiazol-5-yl)-2-pyridine carboxamide, 3-(6-methyl-pyridin-3-ylsulfanyl)-6-(4H-[1,2,4]triazol-3-ylsulfanyl)-N-([1,2,4]thiadiazol-5-yl)-2-pyridine carboxamide, 3-(4-dimethylaminoethyloxy-phenylsulfanyl)-6-(5-methyl-4H-[1,2,4]triazol-3-ylsulfanyl)-N-([1,2,4]thiadiazol-5-yl)-2-pyridine carboxamide, 3-(4-dimethylaminoethyloxy-phenylsulfanyl)-6-(4H-[1,2,4]triazol-3-ylsulfanyl)-N-(3-methyl-[1,2,4]thiadiazol-2-yl)-2-pyridine carboxamide, 3-[4-(2-hydroxyethyl-phenylsulfanyl)]-6-(5-methyl-4H-[1,2,4]triazol-3-ylsulfanyl)-N-(3-methyl-[1,2,4]-thiadiazol-5-yl)-2-pyridine carboxamide, 3-(6-methyl-pyridine-3-ylsulfanyl)-6-(4H-[1,2,4]triazol-3-ylsulfanyl)-N-(3-methyl-[1,2,4]-thiadiazol-5-yl)-2-pyridine carboxamide, 3-(6-ethoxy-pyridin-3-ylsulfanyl)-6-(4H-[1,2,4]triazol-3-yl-sulfanyl)-N-(3-methyl-[1,2,4]-thiadiazole-5-yl)-2-pyridine carboxamide, 3-(6-ethoxy-pyridin-3-ylsulfanyl)-6-(4H-[1,2,4]triazol-3-ylsulfanyl)-N-(pyridin-2-yl)-2-pyridine carboxamide, 3-(6-methoxy-pyridin-3-ylsulfanyl)-6-(4H-[1,2,4]triazol-3-ylsulfanyl)-N-(1-methyl-1H-pyrazol-3-yl)-2-pyridine carboxamide and 3-(4-methoxymethyl-phenylsulfanyl)-6-(4H-[1,2,4]triazole-3-ylsulfanyl)-N-(1-methyl-1H-pyrazole-3-yl)-2-pyridine carboxamide. More preferred examples include: 3-(4-fluoro-phenylsulfanyl)-6-(4H-[1,2,4]triazole-3-yl-sulfanyl)-N-(4-methoxymethyl-thiazole-2-yl)-2-pyridine carboxamide, 3-(4-methoxy-phenylsulfanyl)-6-(4H-[1,2,4]triazole-3-yl-sulfanyl)-N-(thiazole-2-yl)2-pyridine carboxamide, 3-(4-methoxy-phenylsulfanyl)-6-(4H-[1,2,4]triazole-3-yl-sulfanyl)-N-(4-methoxymethyl-thiazole-2-yl)-2-pyridine carboxamide, 3-(4-methyl-pyridine-3-yl-sulfanyl)-6-(4H-[1,2,4]triazole-3-yl-sulfanyl)-N-(thiazole-2-yl)-2-pyridine carboxamide, 3-(4-dimethylcarbomoyl-phenylsulfanyl)-6-(4H-[1,2,4]triazole-3-yl-sulfanyl)-N-(thiazole-2-yl)-2-pyridine carboxamide, 3-(4-hydroxyethyloxy-phenylsulfanyl)-6-(4H-[1,2,4]triazole-3-yl-sulfanyl)-N-(thiazole-2-yl)-2-pyridine carboxamide, 3-(4-N,N-dimethylamino-ethyloxy-phenylsulfanyl)-6-(4H-[1,2,4]triazole-3-yl-sulfanyl)-N-(thiazole-2-yl)-2-pyridine carboxamide, 3-(4-methoxy-phenylsulfanyl)-6-(4H-[1,2,4]triazole-3-yl)-N-(thiazole-2-yl)-2-pyridine carboxamide, 3-(4-fluoro-phenylsulfanyl)-6-(4H-[1,2,4]triazole-3-yl-sulfanyl)-N-(thiazole-2-yl)-2-pyridine carboxamide, 3-(4-methoxy-phenylsulfanyl)-6-(4H-[1,2,4]triazole-3-yl-sulfanyl)-N-(4-methoxymethyl-thiazole-2-yl)-2-pyridine carboxamide, 3-(4-methoxymethyl-phenylsulfanyl)-6-(4H-[1,2,4]triazole-3-yl-sulfanyl)-(thiazole-2-yl)-2-pyridine carboxamide, 3-(6-methyl-pyridine-3-yl-sulfanyl)-6-(4H-[1,2,4]triazole-3-yl-sulfanyl)-N-(thiazole-2-yl)-2-pyridine carboxamide, 3-(hydroxyethyloxy-phenylsulfanyl)-6-(4H-[1,2,4]triazole-3-yl-sulfanyl)-N-(thiazole-2-yl)-2-pyridine carboxamide, 3-(4-dimethylaminoethyloxy-phenylsulfanyl)-6-(4H-[1,2,4]triazole-3-yl-sulfanyl)-N-(thiazole-2-yl)-2-pyridine carboxamide, 3-(4-hydroxyethyl-phenylsulfanyl)-6-(4H-[1,2,4]triazole-3-yl-sulfanyl)-N-(thiazole-2-yl)-2-pyridine carboxamide, 3-(6-methyl-pyridine-3-yl-sulfanyl)-6-(4H-[1,2,4]triazole-3-yl-sulfanyl)-N-(4-methyl-thiazole-2-yl)-2-pyridine carboxamide, 3-(4-dimethylaminoethyloxy-phenylsulfanyl)-6-(4H-[1,2,4]triazole-3-ylsulfanyl)-N-([1,2,4]thiadiazole-5-yl)-2-pyridine carboxamide, 3-(6-methyl-pyridine-3-ylsulfanyl)-6-(4H-[1,2,4]triazole-3-ylsulfanyl)-N-([1,2,4]thiadiazole-5-yl)-2-pyridine carboxamide, 3-(4-dimethylaminoethyloxy-phenylsulfanyl)-6-(5-methyl-4H-[1,2,4]triazole-3-ylsulfanyl)-N-([1,2,4]thiadiazole-5-yl)-2-pyridine carboxamide, 3-(4-dimethylaminoethyloxy-phenylsulfanyl)-6-(4H-[1,2,4]triazole-3-ylsulfanyl)-N-(3-methyl-[1,2,4]thiadiazole-2-yl)-2-pyridine carboxamide, 3-[4-(2-hydroxyethyl-phenylsulfanyl)]-6-(5-methyl-4H-[1,2,4]triazole-3-ylsulfanyl)-N-(3-methyl-[1,2,4]-thiadiazole-5-yl)-2-pyridine carboxamide, 3-(6-methyl-pyridine-3-ylsulfanyl)-6-(4H-[1,2,4]triazole-3-ylsulfanyl)-N-(3-methyl-[1,2,4]-thiadiazole-5-yl)-2-pyridine carboxamide, 3-(6-ethoxy-pyridine-3-ylsulfanyl)-6-(4H-[1,2,4]triazole-3-ylsulfanyl)-N-(3-methyl-[1,2,4]-thiadiazole-5-yl)-2-pyridine carboxamide, 3-(6-ethoxy-pyridine-3-ylsulfanyl)-6-(4H-[1,2,4]triazole-3-ylsulfanyl)-N-(pyradine-2-yl)-2-pyridine carboxamide, 3-(6-methoxy-pyridine-3-ylsulfanyl)-6-(4H-[1,2,4]triazole-3-ylsulfanyl)-N-(1-methyl-1H-pyrazole-3-yl)-2-pyridine carboxamide and 3-(4-methoxymethyl-phenylsulfanyl)-6-(4H-[1,2,4]triazole-3-ylsulfanyl)-N-(1-methyl-1H-pyrazole-3-yl)-2-pyridine carboxamide.

The pyridine-2-carboxamide derivatives of the present invention can also exist as pharmaceutically acceptable salts, including the acid addition salts and base addition salts.

In some cases, the compounds of the present invention exist as stereoisomers or tautomers such as optical isomers, diastereomers, or geometrical isomers depending on the location of the substituents. Such isomers all are naturally included in the present invention. In addition, the mixtures of these isomers in the optional ratio are also included in the present invention.

The compounds of the present invention have a glucokinase activation activity, and therefore they are useful as therapeutic agents and/or preventive agents for diabetes mellitus as well as for diabetic complication.

The diabetic complication means diseases caused by development of diabetes mellitus and includes, for example, diabetic nephropathy, diabetic retinopathy, diabetic neurosis, diabetic arteriosclerosis, and so on.

The compounds of the present invention are applicable to both of insulin dependent diabetes mellitus (IDDM) and non-insulin dependent diabetes mellitus (NIDDM).

The insulin dependent diabetes mellitus (IDDM) is considered to be developed by increase of insulin resistance due to obesity in addition to a genetic predisposition of decrease of insulin secretion and insulin resistance in the skeletal muscle mainly in adults. The insulin dependent diabetes mellitus has been proposed to classify into type I and type II depending on the predisposition.

The compounds of the present invention are considered to be effective not only to type I insulin-dependent diabetes mellitus but also to type II diabetes for which the so far used diabetic drugs have not been able to decrease sufficiently the blood sugar level.

In the type II diabetes mellitus, the blood sugar after meals is markedly maintained at a high level for a long period of time in comparison with that of healthy persons. The compounds of the present invention are useful for such type II diabetes.

The followings will illustrate the process for producing the compounds of the present invention.

The compounds (I) of the present invention can be produced easily according to a well-known reaction method or a per se known method. The compounds (I) of the invention can be produced in a conventional method carried out in a liquid phase, or in a recently developed striking solid phase method, such as combinatorial synthetic method or parallel synthetic process. Preferably, they can be produced, for example, according to the following processes.

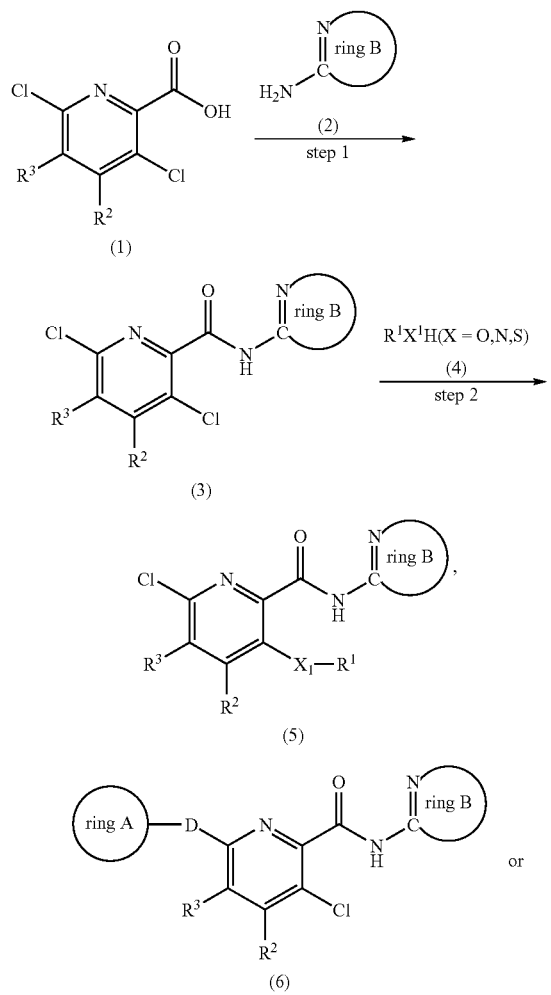

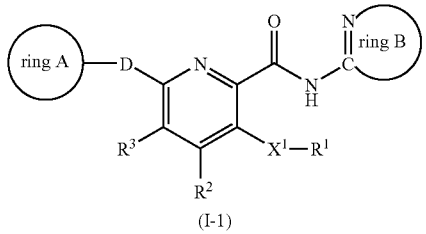

(wherein the respective symbols have the same meanings as defined above)

(Step 1)

In this step, the dichloropyridinecarboxylic acid derivative or its reactive derivative is allowed to react with the amino compound (2) to give the compound (3). The reaction may be carried by performing amide-forming reaction by a method as described previously (for example, Basic Principle and Experiments in Peptide Syntheses, Nobuo Izumiya et al., Maruzen Co., Ltd., 1983; Comprehensive Organic Synthesis, 6, Pergamon Press, 1991), by a method according thereto, or by a combination of these and ordinary methods. That is, the reaction is achieved in the presence of a condensing agent well-known to a person skilled in the art or in such a method as ester activation method, mixed acid anhydride method, acid chloride method, or carbodiimide method, which can be utilized by a person skilled in the art. Such an amide-forming agent includes, for example, thionyl chloride, oxalyl chloride, N,N-dicyclohexylcarbodiimide, 1-methyl-2-bromopyridineium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate or benzotriazo-1-yl-oxy-tris(dimethylamino)phosphonium hexafluorophospate. Among these agents, for example, thionyl chloride, 1-ethyl-3-(3-dimethylaminopropyl)carbodiimide hydrochloride, N,N-dicyclohexylcarbodiimide, or benzotriazo-1-yl-oxy-tris(dimethylamino)phosphonium hexafluorophospate are preferred. In the amide-forming reaction, a base and a condensation auxiliary agent may be used together with the amide-forming agent.

The base used includes, for example, tertiary aliphatic amines such as trimethylamine, tri-ethylamine, N,N-diisopropylethylamine, N-methylmorpholine, N-methylpyrrolidine, N-methylpiperidine, N,N-dimethyl-aniline, 1,8-diazabicyclo[5.4.0]undeca-7-ene (DBU), or 1,5-azobicyclo[4.3.0]nona-5-ene (DBN); and aromatic amines such as pyridine, 4-dimethylaminopyridine, picoline, lutidine, quinoline, or isoquinoline. Among them, tertiary aliphatic amines, particularly, triethylamine or N,N-diisopropylethylamine, are preferred.

The condensation auxiliary agent used includes, for example, N-hydroxybenzotriazole hydrate, N-hydroxysuccinimide, N-hydroxy-5-norbornene-2,3-dicarboximide, or 3-hydroxy-3,4-dihydro-4-oxo-1,2,3-benzotriazole. Among them, for example, N-hydroxybenzotriazole and the like are preferred.

The compound (2) may be used usually in an amount of 0.1 to 10 equivalent, preferably 0.5 to 3 equivalent for 1 equivalent of the carboxylic acid compound (1) or its reactive derivative, though it depends on the type of the compound and solvent and the other reaction conditions.

The amide-forming agent may be used in an amount of 1 to 10 equivalent, preferably 1 to 3 equivalent for 1 equivalent of the carboxylic acid compound (1) or its reactive derivative, though it depends on the type of the compound and solvent and the other reaction conditions.

The condensation auxiliary agent may be used in an amount of 1 to 10 equivalent, preferably 1 to 3 equivalent for 1 equivalent of the carboxylic acid compound (1) or its reactive derivative, though it depends on the type of the compound and solvent and the other reaction conditions.

The base may be usually used in an amount of 1 to 10 equivalent, preferably 1 to 5 equivalent, though it depends on the type of the compound and solvent and the other reaction conditions.

There is no particular limitation in the reaction solvent used in this step as far as it gives no adverse effect on the reaction; such a solvent includes, for example, inert solvents, specifically, methylene chloride, chloroform, 1,2-dichloroethane, N,N-dimethylformamide, ethyl acetate, methyl acetate, acetonitrile, benzene, xylene, toluene, 1,4-dioxane, tetrahydrofuran, dimethoxyethane, or a mixture of them. In view of the maintenance of a suitable temperature of the reaction, methylene chloride, chloroform, 1,2-dichloroethane, acetonitrile or N,N-dimethylformamide is preferred.

The reaction temperature of this step may usually be a temperature of −78° C. to the reflux temperature of the solvent, preferably 0 to 30° C.

The reaction time of this step may usually a period of 0.5 to 96 hours, preferably 3 to 24 hours.

The base, amide-forming agent, and condensation auxiliary agent used in this step may be used alone or in a combination of 2 or more species.

When the compound (3) produced in this step has a protecting group on the substituent of the ring B, the protecting group may be removed if necessary. Removal of the protecting group may be achieved according to a method as described previously (Protective Groups in Organic Synthesis, T. W. Green, 2nd edition, John Wiley & Sons, 1991), by a method according thereto or by a combination of these and ordinary methods.

Thus resulting compound (3) may be isolated and purified by means of a conventional way, for example, concentration, vacuum condensation, crystallization, extract with solvents, reprecipitation, chromatography, and so on. Alternatively, the compound (3) may be used in the subsequent step without purification.

(Step 2)

In this step, the compound (3) produced in the Step 1 is allowed to react with a compound (4) represented by $R^1X^1H$ ($X^1$ represents an oxygen atom, nitrogen atom or sulfur atom; $R^1$ has the same meanings as defined above) or a compound of the formula (II):

(II)

to give the compound (5), (6) or (I-1).

The compound (4) used in this reaction is a phenol derivative, thiol derivative or amine derivative. The phenol derivative includes those in which a hydroxyl group is attached to an aryl group as well as those in which a hydroxyl group is attached to a 5- to 7-membered heteroaryl group.

In this step, when the compound (4) is used, the compound (5) can be produced.

By reacting with the compound represented by (wherein the respective symbols have the same meanings as defined above) (5), the compound of the formula (II-1) is a phenol derivative or thiol derivative in which —DH (wherein D is an oxygen atom or sulfur atom) is attached to the ring A of the compound (II) (wherein the phenol derivative has the same meanings as defined above).

In this step, when the compound (II) is used, the compound (6) or (I-1) can be produced.

The compound (I-1) is included in the compounds (I) of the invention. In this step, the compound (4) or (II) may be used usually in an amount of 0.2 to 10 equivalent, preferably 1 to 3 equivalent, for 1 equivalent of the compound (3).

The compound (I-1) is included in the compounds (I) of the invention.

The base used in this step includes, for example, tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undeca-7-ene (DBU), or 1,5-azobicyclo[4.3.0]nona-5-ene (DBN); aromatic amines such as pyridine, 4-dimethylaminopyridine, picoline, lutidine, quinoline, or isoquinoline; alkali metals such as metal potassium, metal sodium, or metal lithium; alkali metal hydrides such as sodium hydride or potassium hydride; alkyl metal compounds such as butyllithium; alkali metal alkoxides such as potassium tert-butylate, sodium ethylate, or sodium methylate; alkali metal hydroxides such as potassium hydroxide or sodium hydroxide; and alkali metal carbonates such as potassium carbonate, sodium carbonate, or cesium carbonate. Among them, particularly preferred are tertiary aliphatic amines, alkali metal hydrides, alkali metal carbonates or alkali metal alkoxides, and specifically triethylamine, N,N-diisopropylethylamine, sodium hydride or potassium carbonate, or alkali metal alkoxides such as potassium tert-butylate, sodium ethylate, or sodium methylate.

The base used in this step may be used usually in an amount of 0.2 to 10 equivalent, preferably 1 to 5 equivalent, for 1 equivalent of the compound (3), though it depends on the type of the compound and solvent used.

There is no particular limitation in the reaction solvent used as far as it gives no adverse effect on the reaction; such a solvent includes, for example, inert organic solvents. Specifically, it includes, for example, methylene chloride, chloroform, 1,2-dichloroethane, trichloroethane, N,N-dimethylformamide, N,N-dimethylacetamide, N-methylpyrrolidone, acetone, ethanol, isopropanol, tert-butanol, tert-amyl alcohol, ethyl acetate, methyl acetate, acetonitrile, benzene, xylene, toluene, 1,4-dioxane, tetrahydrofuran, dimethoxyethane, or a mixture of them. Among them, N,N-dimethylformamide, N,N-dimethylacetamide, N-methylpyrrolidone, acetonitrile, isopropanol, and tert-amyl alcohol, are preferred, and N,N-dimethylformamide, acetonitrile and isopropanol are more preferred.

The reaction time is usually 0.2 to 100 hours, preferably 1 to 40 hours.

The reaction temperature is usually from −20° C. to the boiling temperature of the solvent used, preferably from 0° C. to the boiling temperature of the solvent.

In this step, the reaction may be carried out according to the method as described previously (Organic Letters, 2002, vol. 4, no. 20, pp. 3517-3520), by a method according thereto or by a combination of these and ordinary methods. If required, it is possible to add a catalyst and an additive to the reaction medium.

As for the catalyst used in this step, any type of catalyst accelerating the reaction may be used, including, for example, copper chloride, copper bromide, copper iodide, copper oxide, copper acetate, and the like, with copper iodide being more preferred.

As for the additive used in this step, any type of additive accelerating the reaction may be used, including, for example, ethylene glycol, dimethoxyethane, and the like, with ethylene glycol being more preferred.

Thus resulting compound (5) or (6) may be isolated and purified by means of a conventional way, for example, concentration, vacuum condensation, reprecipitation, extract with solvents, crystallization, chromatography, and so on. Alternatively, the compound (5) or (6) may be used in the subsequent step without purification.

The compounds (I-1) of the present invention may be isolated and purified by means of a conventional way, for example, concentration, vacuum condensation, reprecipitation, extract with solvents, crystallization, chromatography, and so on.

Alternatively, the compound (I-1) may be used in the subsequent step without purification.

(Step 3-2)

In this step, the compound (6) produced in Step 2 is allowed to react with a compound (4) represented by $R^1X^1H$ (wherein the respective symbols have the same meanings as defined above) to give the compound (I-3).

In this step, the reaction may be carried out in the same way as in Step 2, in the condition using the same reaction solvent, reaction time and reaction temperature and the same equivalent of the starting compounds and base.

Thus resulting compound (I-3) may be isolated and purified by means of a conventional way, for example, concentration, vacuum condensation, crystallization, extract with solvents, reprecipitation, chromatography, and so on. Alternatively, the compound (I-3) may be used in the subsequent step without purification.

The compounds (I-4) of the invention may also be produced according to the following process.

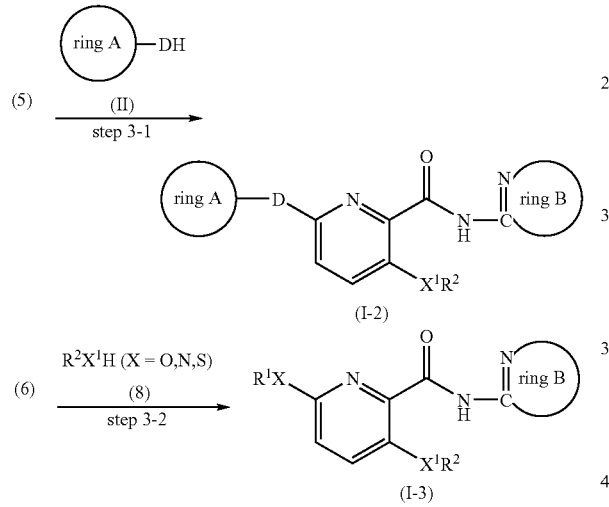

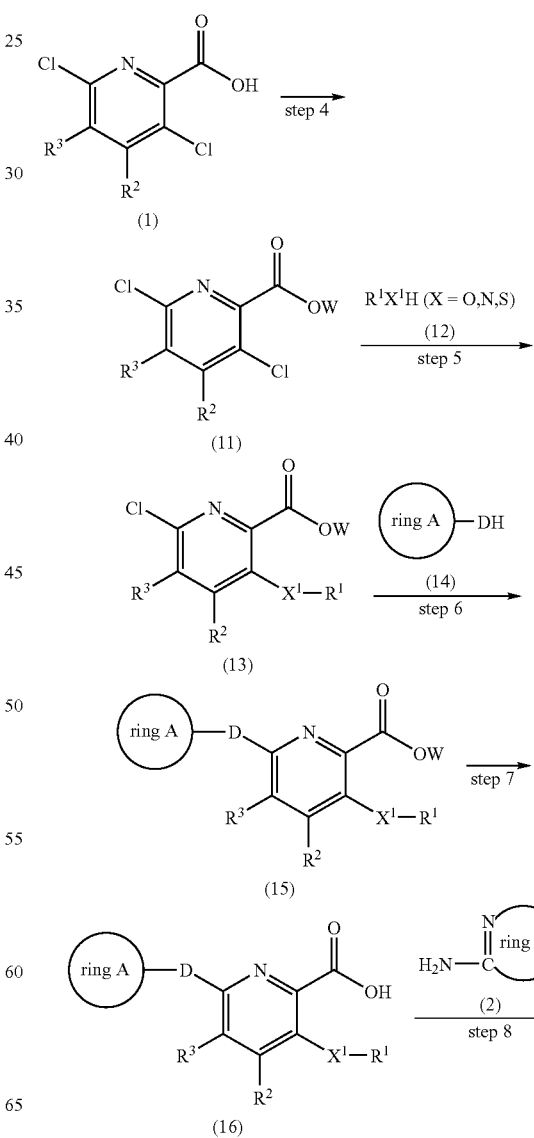

(wherein the respective symbols have the same meanings as defined above)

(Step 3-1)

In this step, the compound (5) produced in Step 2 is allowed to react with a phenol or thiol derivative having the ring A of the formula (II):

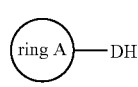

(II)

(wherein the respective symbols have the same meanings as defined above)

in the presence of a base to give the compounds (1-2) of the invention.

In this step, the reaction may be carried out in the same way as in Step 2, in the condition using the same reaction solvent, reaction time and reaction temperature and the same equivalent of the starting compounds.

Thus resulting compound (I-1) may be isolated and purified by means of a conventional way, for example, concentration, vacuum condensation, extract with solvents, crystallization, reprecipitation, chromatography, and so on.

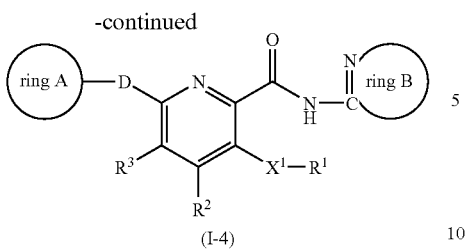

(I-4)

(wherein W represents a carboxyl-protecting group; and the other symbols have the same meanings as defined above)

(Step 4)

In this step, a protecting group is introduced into the carboxyl group of the dichloropyridine-2-carboxylic acid derivative (1) to give the compound (11). The compound (11) may be produced in a publicly known method or a method according thereto. There is no particular limitation in the protecting group W of the carboxyl group in the compound (11) as far as it works as a protective group for the carboxyl in the steps 5 and 6 and can readily be removed in Step 7. Such a protecting group includes, for example, straight or branched chain lower alkyl groups such as methyl group, ethyl group and tert-butyl group; halogenated lower alkyl groups such as 2-iodoethyl and 2,2,2-trichloroethyl; lower alkenyl groups such as allyl group, 2-propenyl group and 2-methyl-2-propenyl group; and aralkyl groups such as benzyl group and PMB group.

Introduction and removal of the protecting group W in the carboxyl group may be achieved according to the method as described previously (Protective Groups in Organic Synthesis, T. W. Green, 2nd edition, John Wiley & Sons, 1991), by a method according thereto or by a combination of these and ordinary methods.

Thus resulting compound (11) may be isolated and purified by means of a conventional way, for example, concentration, vacuum condensation, extract with solvents, reprecipitation, crystallization, chromatography, and so on. Alternatively, the compound (11) may be used in the subsequent step without purification.

(Step 5)

In this step, the compound (11) produced in the Step 4 is allowed to react with a compound (12) represented by $R^1X^1H$ (wherein the respective symbols have the same meanings as defined above) to give the compound (13).

In this step, the reaction may be carried out in the same way as in Step 2, in the condition using the same reaction temperature, reaction time and reaction solvent and the same equivalent of the starting compounds and base.

Thus resulting compound (13) may be isolated and purified by means of a conventional way, for example, concentration, vacuum condensation, extract with solvents, crystallization, reprecipitation, chromatography, and so on. Alternatively, the compound (13) may be used in the subsequent step without purification.

(Step 6)

In this step, the compound (13) produced in Step 5 is allowed to react with a phenol or thiol derivative represented by the formula (II):

(II)

(wherein the respective symbols have the same meanings as defined above) to give the compound (15).

The compounds (15) are prepared by reacting a phenol derivative or a thiol derivative. In this reaction, the phenol derivative has the same meanings as defined above.

In this step, the reaction may be carried out in the same way as in Step 2, in the condition using the same reaction time, reaction temperature and reaction solvent and the same equivalent of the starting compounds and the same amount of the base.

Thus resulting compound (15) may be isolated and purified by means of a conventional way, for example, concentration, vacuum condensation, reprecipitation, extract with solvents, crystallization, chromatography, and so on. Alternatively, the compound (15) may be used in the subsequent step without purification.

(Step 7)

In this step, the carboxyl-protecting group W of the compound (15) produced in Step 6 is removed to give the compound (16).

Removal of the protecting group W in the carboxyl group in this step may be achieved according to the method as described previously (Protective Groups in Organic Synthesis, T. W. Green, 2nd edition, John Wiley & Sons, 1991), by a method according thereto or by a combination of these and ordinary methods.

Thus resulting compound (16) may be isolated and purified by means of a conventional way, for example, concentration, vacuum condensation, extract with solvents, crystallization, reprecipitation, chromatography, and so on. Alternatively, the compound (16) may be used in the subsequent step without purification.

(Step 8)

In this step, the carboxylic acid derivative (16) produced in the step 7 is allowed to react with the compound (2) to give the compound (I-4) of the invention.

The reaction employed in this step is the so-called amide-forming reaction, which may be carried out in the same way as in Step 1, in the condition using the same reaction temperature and reaction time and the same equivalent of the starting compounds and the same amount of the condensing agent and auxiliary agent.

Thus resulting compound (I-4) may be isolated and purified by means of a conventional way, for example, concentration, vacuum condensation, extract with solvents, crystallization, reprecipitation, chromatography, and so on. Alternatively, the compound (I-4) may be used in the subsequent step without purification.

The compounds (I-5) of the present invention may also be produced according to the following process.

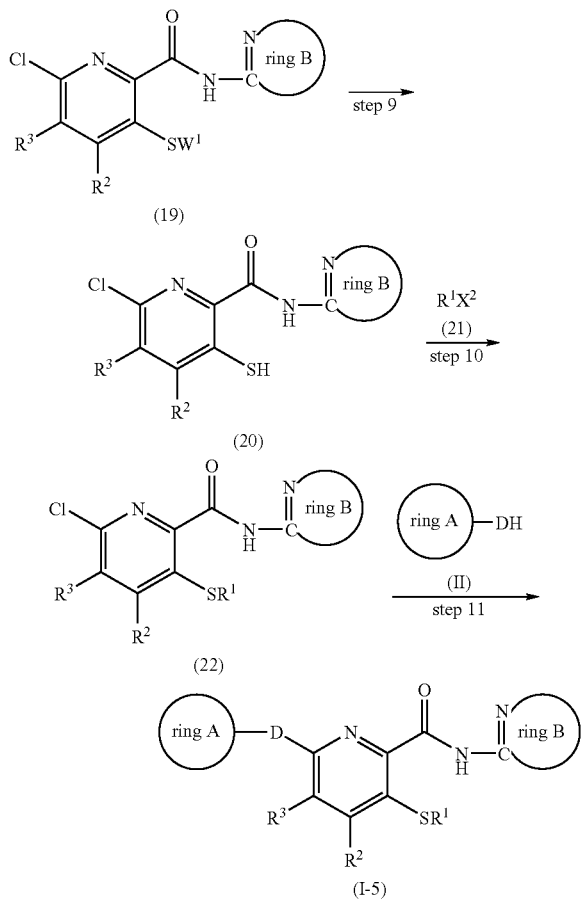

(wherein W1 represents a thiol-protecting group; $X^2$ represents a leaving group; and the other symbols have the same meanings as defined above)

(Step 9)

In this step, the thiol-protective group of the compound (19) is removed to give the compound (20).

Removal of the protecting group in the thiol group in this step may be achieved according to the method as described previously (Protective Groups in Organic Synthesis, T. W. Green, 2nd edition, John Wiley & Sons, 1991), by a method according thereto or by a combination of these and ordinary methods.

As for the thiol-protective group W1, any type of groups may be employed as far as it can readily be removed in this step to give the SH group. Such a thiol-protective group W1 includes, for example, acyl groups such as acetyl group or benzoyl group, or substituted aralkyl groups such as trityl group or 4-methoxybenzyl group.

Thus resulting compound (20) may be isolated and purified by means of a conventional way, for example, concentration, vacuum condensation, extract with solvents, crystallization, reprecipitation, chromatography, and so on. Alternatively, the compound (20) may be used in the subsequent step without purification.

(Step 10)

In this step, the compound (20) produced in Step 9 is allowed to react with the compound (21) in the presence of a base to give the compound (22).

As for the compound (21) used in this step, any type of compounds may be employed as far as $X^2$ acts as a leaving group in Step 21 to give the compound (22). As $X^2$, for example, a halogen atom such as fluorine atom, chlorine atom, bromine atom, or iodine atom, or sulfonate or phosphonate is included, with fluorine atom, chlorine atom, iodine atom, or trifluoromethanesulfonate being preferred, and fluorine atom, chlorine atom, or iodine atom being more preferred.

In this step, the reaction may be carried out in the same way as in Step 2, in the condition using the same reaction time; amount of the starting compounds and the base.

Thus resulting compound (22) may be isolated and purified by means of a conventional way, for example, concentration, vacuum condensation, crystallization, extract with solvents, reprecipitation, chromatography, and so on. Alternatively, the compound (22) may be used in the subsequent step without purification.

(Step 11)

In this step, the compound (22) produced in Step 10 is allowed to react with the compound (8) in the presence of a base to give the compound (I-5).

In this step, the reaction may be carried out in the same way as in Step 2, in the condition using the same reaction time, reaction temperature and reaction solvent and the same amount of the starting compounds and base.

Thus resulting compound (I-5) may be isolated and purified by means of a conventional way, for example, concentration, vacuum condensation, crystallization, extract with solvents, reprecipitation, chromatography, and so on.

Among the compounds of the invention, when $-X^1-R^1$ in the formula (I) is $-CH_2-O-R^1$ or $-CH_2-S-R^1$, the compounds (I-6) of the present invention may be produced according to the following process.

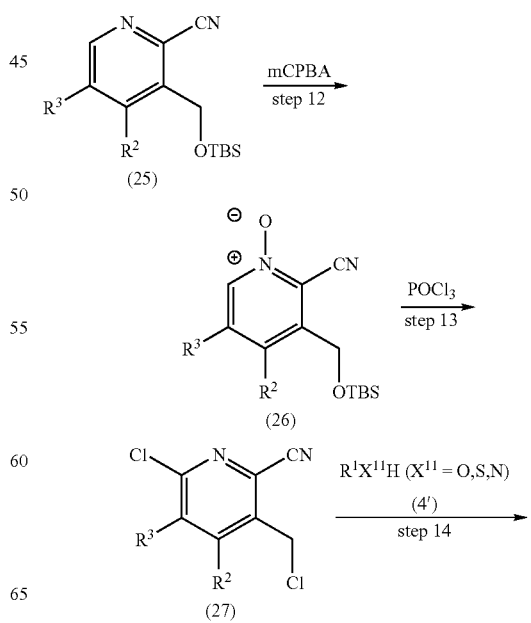

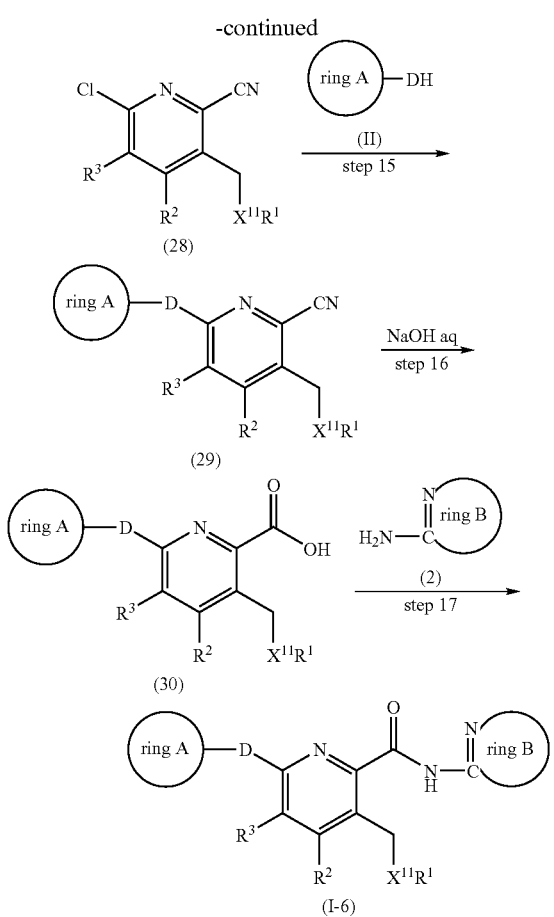

(wherein the respective symbols have the same meanings as defined above)

(Step 12)

In this step, the cyanopyridine derivative (25) is allowed to react with mCPBA to give the compound (26). The oxidation reaction of this step may be achieved according to the method as described previously (Tetrahedron, vol. 42, no. 5, pp. 1475-1485), by a method according thereto or by a combination of these and ordinary methods. mCPBA may be used usually in 0.5 to 1 equivalent, preferably 1 to 3 equivalent for 1 equivalent of the compound (25).

The reaction may be conducted usually for a period of 10 minutes to 24 hours, preferably 30 minutes to 12 hours, at a temperature of −20° C. to the boiling temperature of the solvent, preferably 0° C. to the boiling temperature of the solvent.

As for the reaction solvent, any type of solvents may be used as far as no adverse effect is given to the reaction, including, for example, chloroform, methylene chloride, 1,2-dichloroethane, and the like.

Thus resulting compound (26) may be isolated and purified by means of a conventional way, for example, concentration, vacuum condensation, extract with solvents, crystallization, reprecipitation, chromatography, and so on. Alternatively, the compound (26) may be used in the subsequent step without purification.

(Step 13)

In this step, the compound (26) produced in Step (12) is allowed to react with POCl₃ to give the compound (27).

POCl₃ used in this reaction may be used usually in an amount of 0.5 to 100 equivalent, preferably 1 to 20 equivalent for 1 equivalent of the compound (26).

The reaction may be conducted usually at a temperature of −20° C. to the boiling temperature of the solvent, preferably 20° C. to the boiling temperature of the solvent. The reaction time is usually a period of 0.5 to 50 hours, preferably 1 to 24 hours.

As for the reaction solvent, any type of solvents may be used as far as no adverse effect is given to the reaction, including preferably for example, methylene chloride, chloroform, dichloroethane, acetonitrile, N,N-dimethylformamide, and the like. Thus resulting compound (27) may be isolated and purified by means of a conventional way, for example, concentration, vacuum condensation, extract with solvents, reprecipitation, crystallization, chromatography, and so on. Alternatively, the compound (27) may be used in the subsequent step without purification.

(Step 14)

In this step, the compound (27) produced in Step 13 is allowed to react with the compound (12) produced in Step 5 in the presence of a base to give the compound (28). In this step, the reaction may be carried out in the same way as in Step 5, in the condition using the same reaction temperature, reaction time, and reaction temperature and the same amount of the starting compound (12) and the base.

Thus resulting compound (28) may be isolated and purified by means of a conventional way, for example, concentration, vacuum condensation, extract with solvents, crystallization, reprecipitation, chromatography, and so on. Alternatively, the compound (28) may be used in the subsequent step without purification.

(Step 15)

In this step, the compound (28) produced in Step 14 is allowed to react with the compound (14) to give the compound (29).

The reaction of this step may be carried out in the same way as in Step 2, in the condition using the same reaction temperature, reaction time, and reaction solvent and the same amount of the starting compound and base.

Thus resulting compound (29) may be isolated and purified by means of a conventional way, for example, concentration, vacuum condensation, extract with solvents, crystallization, reprecipitation, chromatography, and so on. Alternatively, the compound (29) may be used in the subsequent step without purification.

(Step 16)

In this step, the compound (29) produced in Step 15 is hydrolyzed to give the carboxylic acid compound (30). In this step, the hydrolysis is achieved with an alkali. As for an alkali, any type of alkalis may be used as far as the cyano of the compound (29) is converted into a carboxyl group; such an alkali includes preferably an aqueous solution of sodium hydroxide, potassium hydroxide, barium hydroxide, lithium hydroxide, and the like, with an aqueous solution of sodium hydroxide or potassium hydroxide being more preferred.

The alkali may be used usually in an amount of 1 to 100 equivalent, preferably 1 to 30 equivalent for 1 equivalent of the compound (29), though it depends on the type of the compounds and solvent used and other reaction conditions.

The reaction may be conducted usually at temperature of 0° C. to the boiling temperature of the solvent, preferably 50° C. to 100° C.

The reaction time is a period of 0.5 to 50 hours, preferably 1 to 24 hours.

The solvent used in this step includes, preferably, methanol, ethanol, isopropanol, dioxane, dimethoxyethane, ethylene glycol, and the like, with ethanol, isopropanol or dioxane being more preferred.

Thus resulting compound (30) may be isolated and purified by means of a conventional way, for example, concentration, vacuum condensation, extract with solvents, crystallization, reprecipitation, chromatography, and so on. Alternatively, the compound (30) may be used in the subsequent step without purification.

(Step 17)

In this step, the carboxylic acid compound (30) produced in Step 16 is allowed to react with the compound (2) to give the compound (31). The reaction of this step may be carried out in the same way as in Step 1, 8 or the like, using the amide linkage-forming reaction according to the method described previously (Basic Principle and Experiments in Peptide Syntheses, Nobuo Izumiya et al., Maruzen Co., Ltd., 1983; Comprehensive Organic Synthesis, 6, Pergamon Press, 1991), by a method according thereto or by a combination of these and ordinary methods.

The amount of the compound (2) to be used and the condition such as the reaction solvent and reaction temperature may be the same as in the amide linkage-forming reaction in Step 1, 8 or the like. Thus resulting compound (31) may be isolated and purified by means of a conventional way, for example, concentration, vacuum condensation, extract with solvents, crystallization, reprecipitation, chromatography, and so on.

The compound (1-7), that is, the compounds (I) of the present invention in which —$X^1$—$R^1$ is —$CH_2$—Cm—$R^1$, may be produced according to the following process (here, Cm is a divalent saturated hydrocarbon group of 2 to 5 carbons, wherein one of the carbon atoms may be substituted by a nitrogen atom, oxygen atom or sulfur atom; $R^1$ has the same meanings as defined above).

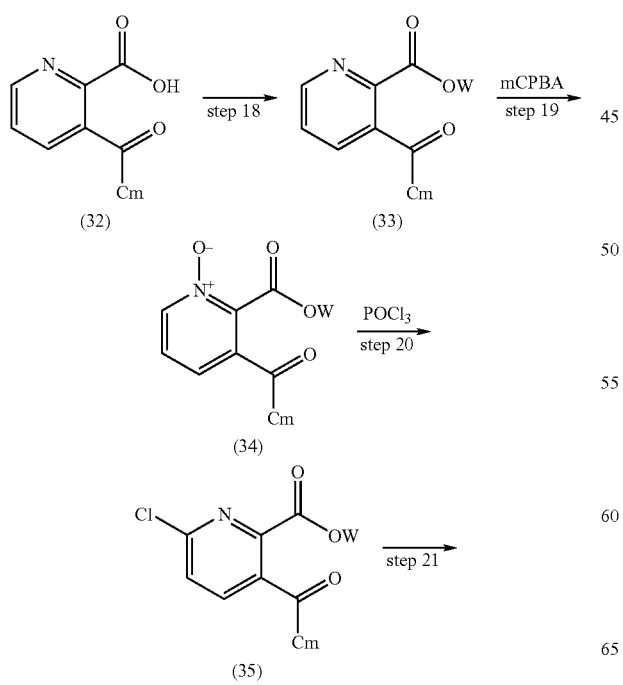

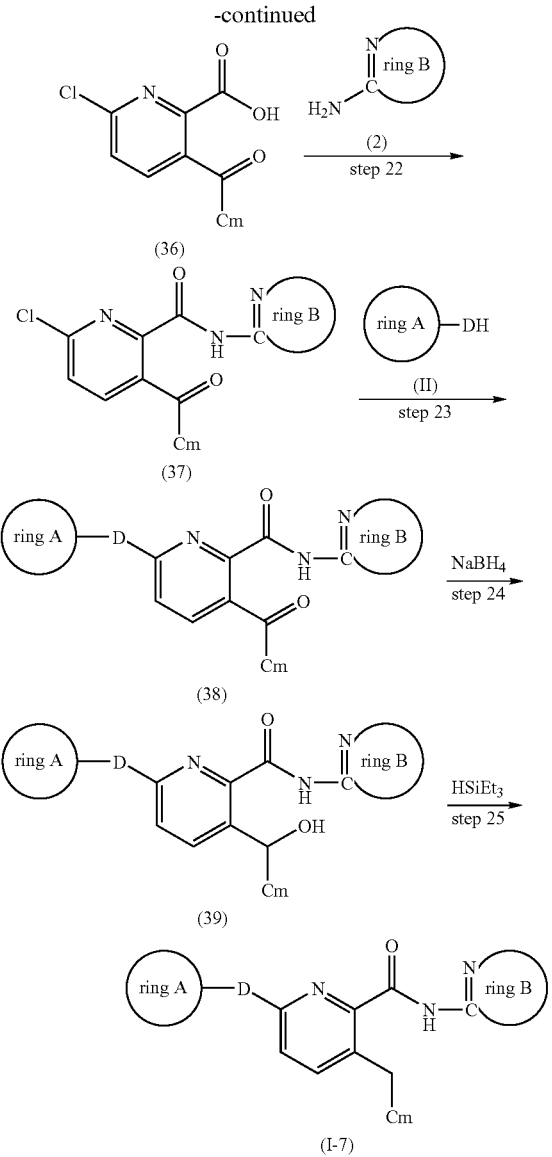

(wherein the respective symbols have the same meanings as defined above)

(Step 18)

In this step, a protecting group is introduced to the carboxyl group of the compound (32) to give the compound (33). Introduction of the carboxyl-protecting group may be achieved, for example, in the same way as in Step 4, as described previously (Protective Groups in Organic Synthesis, T. W. Green, 2nd edition, John Wiley & Sons, 1991), by a method according thereto or by a combination of these and ordinary methods.

Thus resulting compound (33) may be isolated and purified by means of a conventional way, for example, concentration, vacuum condensation, extract with solvents, crystallization, reprecipitation, chromatography, and so on. Alternatively, the compound (33) may be used in the subsequent step without purification.

(Step 19)

In this step, the compound (33) produced in Step 1 is allowed to react with mCPBA to give the compound (34). The amount of mCPBA to be used in this step and the condition such as the reaction temperature and reaction solvent may be the same as in Step 12. Thus resulting compound (34) may be isolated and purified by means of a conventional way, for example, concentration, vacuum condensation, extract with solvents, reprecipitation, crystallization, chromatography, and so on. Alternatively, the compound (34) may be used in the subsequent step without purification.

(Step 20)

In this step, the compound (34) produced in Step 19 is allowed to react with $POCl_3$ to give the compound (35).

The amount of $POCl_3$ to be used for 1 equivalent of the compound (34) in this step and the condition such as the reaction temperature and reaction time may be the same as in Step 13. Thus resulting compound (35) may be isolated and purified by means of a conventional way, for example, concentration, vacuum condensation, extract with solvents, reprecipitation, crystallization, chromatography, and so on. Alternatively, the compound (35) may be used in the subsequent step without purification.

(Step 21)

In this step, the carboxyl-protective group of the compound (35) produced in Step 20 is removed to give the compound (36).

Removal of the protecting group W in the carboxyl group used in this step may be achieved in the same way as in Step 7 according to the method as described previously (Protective Groups in Organic Synthesis, T. W. Green, 2nd edition, John Wiley & Sons, 1991), by a method according thereto or by a combination of these and ordinary methods. Thus resulting compound (36) may be isolated and purified by means of a conventional way, for example, concentration, vacuum condensation, extract with solvents, crystallization, reprecipitation, chromatography, and so on. Alternatively, the compound (36) may be used in the subsequent step without purification.

(Step 22)

In this step, the compound (36) produced in Step 21 is allowed to react with the compound (2) to give the compound (37). The reaction in this step may be carried out in the same way as in the amide linkage-forming reaction in Step 1, 8 or the like. Thus resulting compound (37) may be isolated and purified by means of a conventional way, for example, concentration, vacuum condensation, extract with solvents, crystallization, reprecipitation, chromatography, and so on. Alternatively, the compound (37) may be used in the subsequent step without purification.

(Step 23)

In this step, the compound (37) produced in Step 22 is allowed to react with the compound (14) in the presence of a base to give the compound (38). The reaction in this step may be carried out in the same way as in Step 2. Thus resulting compound (38) may be isolated and purified by means of a conventional way, for example, concentration, vacuum condensation, extract with solvents, reprecipitation, crystallization, chromatography, and so on. Alternatively, the compound (38) may be used in the subsequent step without purification.

(Step 24)

In this step, the compound (38) produced in Step 23 is allowed to react with $NaBH_4$ to give the compound (39). The reaction in this stage may be carried out according to the method as described previously (Comprehensive Organic Synthesis), by a method according thereto or by a combination of these and ordinary methods. The amount of $NaBH_4$ to be used is usually 0.2 to 30 equivalent, preferably 1 to 10 equivalent, for 1 equivalent of the compound (38), though it depends on the type of the compound (38) and the solvent used and other reaction condition.

The reaction may be conducted usually at temperature of −78° C. to the boiling temperature of the solvent, preferably −10° C. to 40° C.

The reaction time is usually a period of 0.1 to 24 hours, preferably 0.2 to 5 hours.

As for the solvent used in this step, any type of solvents may be used as far as no adverse effect is given to the reaction, for example, preferably including methanol, ethanol, isopropanol, tetrahydrofuran, and the like, with methanol or ethanol being more preferred. Thus resulting compound (39) may be isolated and purified by means of a conventional way, for example, concentration, vacuum condensation, extract with solvents, reprecipitation, crystallization, chromatography, and so on. Alternatively, the compound (39) may be used in the subsequent step without purification.

(Step 25)

In this step, the compound (39) produced in Step 24 is allowed to react with $HSiEt_3$ to give the compound (I-7). The reduction used in this step may be carried out according to the method as described previously (J.O.C., vol. 53, no. 22, pp. 5301-5304, 1988), by a method according thereto or by a combination of these and ordinary methods.

The amount of $HSiEt_3$ to be used is usually 0.5 to 100 equivalent, preferably 1 to 10 equivalent, for 1 equivalent of the compound (39), though it depends on the type of the compound (39) and the solvent used and other reaction condition.

The reaction may be conducted usually for a period of 0.2 to 30 hours, preferably 0.5 to 10 hours.

The reaction temperature is −10° C. to the boiling temperature of the solvent, preferably 0° C. to the boiling temperature of the solvent.

As for the solvent used in this step, any type of solvents may be used as far as no adverse effect is given to the reaction, for example, preferably including trifluoroacetic acid. Thus resulting compound (I-7) may be isolated and purified by means of a conventional way, for example, concentration, vacuum condensation, extract with solvents, crystallization, reprecipitation, chromatography, and so on.

In this step, when $R^2$ or $R^3$ is a lower alkoxy group, the hydrogen atom of the alkyl group in the alkoxy group may be substituted by a hydroxy group or amino group, and in such a case if required, introduction or removal of a protecting group for the hydroxy group or amino group may be conducted at any one of Steps 1 to 25.

The introduction or removal of the protecting group may be conducted according to the method as described previously (Protective Groups in Organic Synthesis), by a method according thereto or by a combination of these and ordinary methods.

In addition, when the ring A, $R^1$ or the ring B has one or more substituent(s), it would be possible to carry out the reaction in each step by introducing or removing a protecting group or groups according to need, to each substituent.

The reaction for introduction or removal of the protecting group may be conducted according to the method as described previously (Protective Groups in Organic Synthesis, T. W. Green, 2nd edition, John Wiley & Sons, 1991), by a method according thereto or by a combination of these and ordinary methods.

The pyridine-2-carboxamide derivatives provided by the invention sometimes exist in forms of pharmaceutically acceptable salts, which may be produced by an ordinary method with the use of the compounds of the formulae (I-1), (I-2), (I-3), (I-4), (I-5), (I-6) and (I-7) involved in the compounds (I) of the present invention.

Particularly, when the compounds of the formulae (I-1), (I-2), (I-3), (I-4), (I-5), (I-6) and (I-7) have a basic group or groups originated in an amino or pyridyl group within the molecule, they may be converted on treatment with an acid into the corresponding pharmaceutically acceptable salts.

The acid addition salts include, for example, hydrohalic acid salts such as hydrochloride, hydrofluoride, hydrobromide and hydroiodide; inorganic acid salts such as nitrate, perchlorate, sulfate, phosphate and carbonate; lower alkylsulfonates such as methanesulfonate, trifluoromethanesulfonate and ethanesulfonate; arylsulfonates such as benzenesulfonate and p-toluenesulfonate; organic acid salts such as fumarate, succinate, citrate, tartrate, oxalate and maleate; and amino acid addition salts such as glutamate and aspartate. When the compounds of the present invention have an acid group or groups in their substituents, for example, carboxyl group, they may be converted on treatment with a base into the corresponding pharmaceutically acceptable salts. The base addition salts include, for example, alkali metal salts such as sodium salt and potassium salt; alkaline earth metal salts such as calcium salts or magnesium salts; and organic base salts such as ammonium salt, guanidine, triethylamine and dicyclohexylamine. In addition, the compounds of the present invention may exist in optional forms of the hydrates or solvates of the free compounds or salts.

The compounds of formula (I) can be used in the manufacture of a medicament for the prevention of, or prophylactic or therapeutic treatment of type 2 diabetes mellitus or a disease or condition associated therewith, by combining the compound of formula (I) with the carrier materials.

The prophylactic or therapeutic dose of a compound of formula (I) will, of course, vary with the nature of the condition to be treated, the particular compound selected and its route of administration.

It will also vary according to the age, weight and response of the individual patient. In general, the daily dosage ranges from about 0.001 mg to about 100 mg per kg body weight, preferably about 0.01 mg to about 50 mg per kg, and more preferably about 0.1 to 10 mg per kg, in single or divided doses. It may be necessary to use dosages outside of these limits in some cases.

An example of a suitable oral dosage is from as low as about 0.01 mg. to as high as about 2.0 g, given orally in single or divided dosages, twice to four times daily. Preferably the dosage ranges from about 1.0 to about 200 mg per day given once or twice daily. More preferably the dosage is about 10-100 mg given once daily.

When intravenous or oral administration is employed, a representative dosage range is from about 0.001 mg to about 100 mg (preferably from 0.01 mg to about 10 mg) of a compound of formula (I) per kg of body weight per day, and more preferably, about 0.1 mg to about 10 mg of a compound of Formula I per kg of body weight per day.

As mentioned above, the pharmaceutical composition comprises a compound of formula (I) and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients.

Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, intravenous, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like in the case of oral liquids, e.g., suspensions, elixirs and solutions can be exemplified; or carriers may include starches, sugars, microcrystalline cellulose, diluents, granulating agents, lubricants, binders, disintegrating agents and the like; oral solids may include powders, capsules and tablets, with the solid oral preparations being preferred.

Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be exemplified by capsules, cachets or tablets each containing a predetermined amount of the active ingredient, as a powder or granules or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier comprising one or more necessary ingredients.

In general, the compositions are prepared by uniformly and intimately admixing the active ingredient with liquid carriers or finely divided solid carriers or both, and then, if necessary, shaping the product appropriately. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent.

Molded tablets may be made by molding in a suitable machine, a mixture of the powdered compound moistened with an inert liquid diluent. Desirably, each tablet contains from about 1 mg to about 1 g of the active ingredient and each cachet or capsule contains from about 1 to about 500 mg of the active ingredient.

The following are examples of pharmaceutical dosage forms for the compounds of formula (I):

TABLE 1

Injectable Suspension (I.M.)

| | mg/mL |
|---|---|
| Compound of Formula I | 10 |
| Methylcellulose | 5.0 |
| Tween 80 | 0.5 |

TABLE 1-continued

Injectable Suspension (I.M.)

| | mg/mL |
|---|---|
| Benzyl alcohol | 9.0 |
| Benzalkonium chloride | 1.0 |

Water for injection is added to make 1.0 mL

TABLE 2

Tablet

| | mg/tablet |
|---|---|
| Compound of Formula I | 25 |
| Methylcellulose | 415 |
| Tween 80 | 14.0 |
| Benzyl alcohol | 43.5 |
| Magnesium Sterate | 2.5 |
| Total | 500 mg |

TABLE 3

Capsule

| | mg/capsule |
|---|---|
| Compound of Formula I | 25 |
| Lactose Powder | 573.5 |
| Magnesium Stearate | 1.5 |
| Total | 600 mg |

TABLE 4

Aerosol

| | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of formula (I) may be used in combination with other drugs that are used in the treatment/prevention/delaying the onset of type 2 diabetes mellitus, as well as the diseases and conditions associated with type 2 diabetes mellitus. Other drugs may be administered, by a route and in an amount commonly used therefor, contemporaneously or sequentially with a compound of Formula (I).

When a compound of formula (I) is used contemporaneously with one or more other drugs, a pharmaceutical composition containing such other drugs in addition to the compound of formula (I) is preferred. Accordingly, the pharmaceutical compositions of the present invention include those that also contain one or more other active ingredients, in addition to a compound of formula (I). Examples of other active ingredients that may be combined with a compound of formula (I), either administered separately or in the same pharmaceutical compositions, include, but are not limited to:
(a) bis-guanides (e.g., buformin, metformin, phenformin),
(b) PPAR agonists (e.g., troglitazone, pioglitazone, rosiglitazone),
(c) insulin,
(d) somatostatin,
(e) α-glucosidase inhibitors (e.g., voglibose, miglitol, acarbose), and
(f) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide, repaglinide).

The weight ratio of the compound of the formula (I) to the second active ingredient may be varied within wide limits and depends upon the effective dose of each ingredient. Thus, for example, when a compound of the formula (I) is combined with a PPAR agonist the weight ratio of the compound of the Formula (I) to the PPAR agonist will generally range from about 1000:1 to about 1:1000, preferably about 200:1 to about 1:200. Combinations of a compound of the formula (I) and other active ingredients will generally also be within the aforementioned range, but in each case, an effective dose of each active ingredient should be used.

The followings show the glucokinase-activating capability of the compounds (I) of the present invention and a test method therefor.

The excellent glucokinase-activating capability of the compounds (I) may be determined according to the method as described previously (Diabetes, 45, 1671-1677, 1996), or by a method according thereto.

The glucokinase activity can be determined without directly measuring glucose-6-phosphate by measuring the amount of Thio-NADH generated during the production of phosphogluconolactone from glucose-6-phosphate by a reporter enzyme glucose-6-phosphate dehydrogenase. Thus, the degree of the glucokinase activity can be determined.

The recombinant human liver GK used in this assay expressed as a FLAG fusion protein in *E. coli*, was purified on ANTIFLAG M2 AFFINITY GEL (Sigma).

Assay was carried out at 30° C. in a 96-well plate. In the plate was distributed 69 µl each of assay buffer (25 mM Hepes Buffer: pH=7.2, 2 mM $MgCl_2$, 1 mM ATP, 0.5 mM TNAD, 1 mM dithiothreitol), to which was added 1 µl of a DMSO solution of the compound or DMSO as control. Then, 20 µl of pre-ice-cooled enzyme mixture (FLAG-GK, 20 U/ml G6PDH) was distributed thereto, to which was added 10 µl of 25 mM glucose as substrate to initiate the reaction (final glucose concentration=2.5 mM).

After starting the reaction, the absorbance at 405 nm was measured every 30 seconds for 10 minutes to evaluate the compound based on the initial increase for 5 minutes. FLAG-GK was added so that the increase of absorbance after 5 minutes fell between 0.05 to 0.1 in the presence of 1% DMSO.

The OD values of the respective compounds to be evaluated were measured in the respective concentrations, wherein the OD value of DMSO as control was regarded as 100%. From the OD values at the respective concentrations, Emax (%) and EC50 (µM) were calculated and used as indicators of the GK activation capability of the compounds. According to the above assay, the GK activation capability of the compounds in the present invention was determined. Table 5 shows the results.

TABLE 5

| Compound No. | Emax (%) | EC50 (µM) |
|---|---|---|
| Production Example 1 | 997 | 0.05 |
| Production Example 7 | 1067 | 0.06 |
| Production Example 30 | 818 | 0.12 |

As shown in Table 1, the compounds of the present invention have a sufficient GK activation capability when Emax and EC50 are employed as indicators.

Hereunder, the present invention will be illustrated in more specific by way of Preparation Examples and Production Examples although the present invention is not limited thereby at all.

PREPARATION EXAMPLE 1

The compound of Production Example 1 (10 parts), 15 parts of heavy magnesium oxide and 75 parts of lactose were homogeneously mixed to prepare a diluted powdery preparation in powder or fine powder of not larger than 350 μm. The diluted powdery preparation was placed in capsule containers to prepare capsule preparations.

PREPARATION EXAMPLE 2

The compound of Production Example 1 (45 parts), 15 parts of starch, 16 parts of lactose, 21 parts of crystalline cellulose, 3 parts of polyvinyl alcohol and 30 parts of distilled water were homogeneously mixed, disintegrated, granulated, dried and sieved to give a granular preparation having a size of 1410 to 177 μm diameter.

PREPARATION EXAMPLE 3

After a granular preparation was manufactured by the same method as in Production Example 2, 3 parts of calcium stearate were added to 96 parts of the granular preparation followed by subjecting to a compression molding to prepare tablets having 10 mm diameter.

PREPARATION EXAMPLE 4

To 90 parts of the granular preparation manufactured by the method of Production Example 2 were added 10 parts of crystalline cellulose and 3 parts of calcium stearate followed by subjecting to a compression molding to give tablets of 8 mm diameter. A mixed suspension of syrup gelatin and precipitated calcium carbonate was added thereto to prepare sugar-coated tablets.

In a thin-layer chromatography of Examples, Silicagel 60F$_{245}$ (Merck) was used as a plate and a UV detector was used in a detection method. As silica gel for a column, Wakogel™ C-300 (Wako Pure Chemical) was used while, as silica gel for a reversed-phase column, LC-Sorb™ SP-B-ODS (Chemco) or YMC-Gel™ ODS-AQ 120-S50 (Yamamura Kagaku Kenkyusho) was used.

Meanings of the abbreviations in the following Examples are as shown below.
i-Bu: isobutyl group
n-Bu: n-butyl group
t-Bu: t-butyl group
Me: methyl group
Et: ethyl group
Ph: phenyl group
i-Pr: isopropyl group
n-Pr: n-propyl group
CDCl$_3$: heavy chloroform
CD$_3$OD: heavy methanol
DMSO-d$_6$: heavy dimethyl sulfoxide Meanings of abbreviations in nuclear magnetic resonance spectrum are as shown below.
s: singlet
d: doublet
dd: double doublets
t: triplet
m: multiplet
br: broad
q: quartet
J: coupling constant
Hz: Herz

PRODUCTION EXAMPLE 1

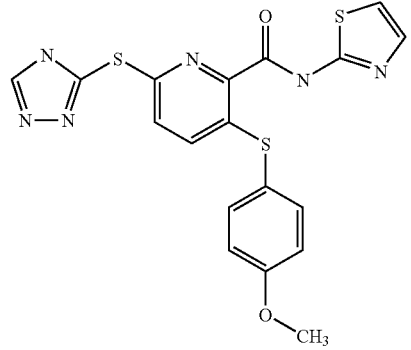

Manufacture of 3-(4-methoxy-phenylsulfanyl)-6-(4H-[1,2,4]triazole-3-yl)-N-(thiazole-2-yl)-2-pyridine carboxamide To a solution (400 ml) of 14.1 g (73.0 mmol) of 3,6-dichloro-2-pyridinecarboxylic acid in chloroform were successively added 9.00 g (89.9 mmol) of aminothiazole, 12.1 g (89.7 mmol) of N-hydroxybenzotriazole hydrate and 19.0 g (99.2 mmol) of 1-(3-dimethylaminopropyl)-3-ethylcarbodiimide hydrochloride followed by stirring at room temperature for 24 hours. After the reaction solution was concentrated, ethyl acetate was added to the residue followed by washing with 0.2N aqueous solution of hydrochloric acid, water and saturated aqueous solution of sodium hydrogen carbonate. After drying and concentrating, the resulting residue was crystallized from a mixed solvent of hexane and ethyl acetate (5:1) to give 12.8 g (yield: 64%) of 3,6-dichloro-N-(thiazole-2-yl)-2-pyridine carboxamide as a white solid.

To a solution (10 ml) of 1.27 g (4.64 mmol) of the resulting dichloro compound in N,N-dimethylformamide were added 1.25 g (9.04 mmol) of potassium carbonate and 605 μl (4.87 mmol) of 4-methoxythiophenol followed by stirring at room temperature for 24 hours. Water was added to the reaction solution followed by extracting with ethyl acetate and washing with a saturated aqueous saline solution. After drying and concentrating, the resulting residue was purified by a silica gel column chromatography (hexane:ethyl acetate=4:1 to 1:1) to give 1.70 g (yield: 97%) of 6-chloro-3-(4-methoxy-phenylsulfanyl)-N-(thiazole-2-yl)-2-pyridine carboxamide as a white solid.

To a solution (10 ml) of 705 mg (1.87 mmol) of the resulting 6-chloro derivative in N,N-dimethylformamide were added 350 mg (2.53 mmol) of potassium carbonate and 285 mg (2.82 mmol) of 3-mercapto-1,2,4-triazole followed by heating to reflux for 35 hours. Water was added to the reaction solution and, after extracting with chloroform for three times, the organic layer was dried and concentrated in vacuo. The resulting residue was purified by a silica gel column chromatography (chloroform:methanol=100:1) and by crystallization from a mixed solvent of hexane and ethyl acetate (1:1) to give 410 mg (yield: 50%) of the title compound as a white solid.

$^1$H-NMR (CDCl$_3$) δ: 3.87 (3H, s), 6.07-7.07 (4H, m), 7.22 (1H, d, J=8.7 Hz), 7.45 (1H, d, J=3.6 Hz), 7.49 (2H, d, J=9.0 Hz), 8.35 (1H, s).

ESI-MS (m/e): 443 [M+H]$^+$

Compounds of Production Examples 2 to 51 were produced by the same method as in the above Production Example 1. Analytical data of those compounds are shown hereunder.

PRODUCTION EXAMPLE 2

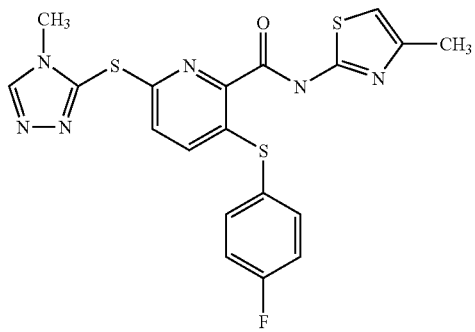

Manufacture of 3-(4-fluoro-phenylsulfanyl)-6-(4-methyl-4H-[1,2,4]triazole-3-yl-sulfanyl)-N-(4-thiazole-2-yl)-2-pyridine carboxamide The compound of Production Example 2 can be produced by the same method as Production Example 1, by a method according thereto or by a combination of these and ordinary methods, with a common method using 3,6-dichloro-2-pyridinecarboxylic acid, 2-amino-4-methylthiazole, 4-fluorothiophenol and 3-mercapto-4-methyl-1,2,4-triazole.

$^1$H-NMR (CDCl$_3$) δ: 2.42 (3H, s), 3.74 (3H, s), 6.62 (1H, s), 7.00 (1H, d, J=9.0 Hz), 7.10 (1H, d, J=9.0 Hz), 7.17 (2H, m), 7.53 (2H, m), 8.40 (1H, s)

ESI-MS (m/e): 459 [M+H]$^+$

PRODUCTION EXAMPLE 3

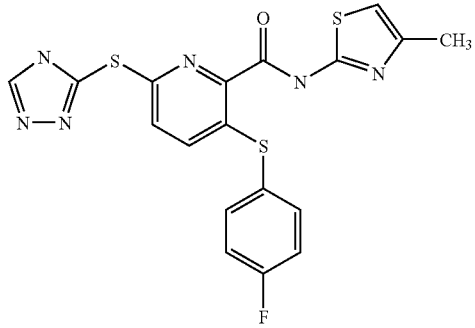

Manufacture of 3-(4-fluoro-phenylsulfanyl)-6-(4H-[1,2,4]triazole-3-yl-sulfanyl)-N-(4-methyl-thiazole-2-yl)-2-pyridine carboxamide Compound of Production Example 3 can be produced by the same method as Production Example 1, by a method according thereto, or by a combination of these and ordinary methods with the use of 3,6-dichloro-2-pyridinecarboxylic acid, 2-amino-4-methylthiazole, 4-fluoro-thiophenol and 3-mercapto-1,2,4-triazole.

$^1$HNMR (CDCl$_3$) δ: 2.40 (3H, s), 6.61 (1H, s), 7.01 (1H, d, J=9.3 Hz), 7.17-7.25 (3H, m), 7.58 (2H, m), 8.35 (1H, s)

ESI-MS (m/e): 445 [M+H]$^+$

PRODUCTION EXAMPLE 4

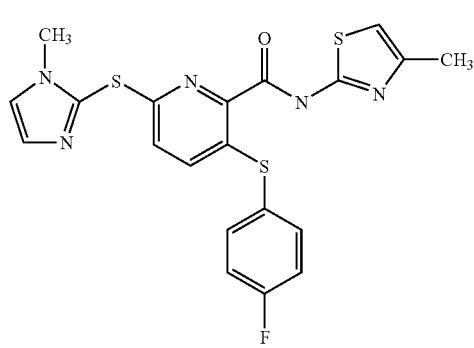

Manufacture of 3-(4-fluoro-phenylsulfanyl)-6-(1-methyl-imidazole-2-yl-sulfanyl)-N-(4-methyl-thiazole-2-yl)-2-pyridine carboxamide Compound of Production Example 4 can be produced by the same method as Production Example 1, by a method according thereof, or by a combination of these and ordinary methods, with the use of 3,6-dichloro-2-pyridinecarboxylic acid, 2-amino-4-methylthiazole, 4-fluorothiophenol and 3-mercapto-4-methyl-1,2,4-triazole.

$^1$HNMR (CDCl$_3$) δ: 2.41 (3H, s), 3.73 (3H, s), 6.60 (1H, s), 6.77 (1H, d, J=8.7 Hz), 6.92 (1H, d, J=8.7 Hz), 7.10-7.22 (4H, m), 7.52 (2H, m)

ESI-MS (m/e): 458[M+H]$^+$

PRODUCTION EXAMPLE 5

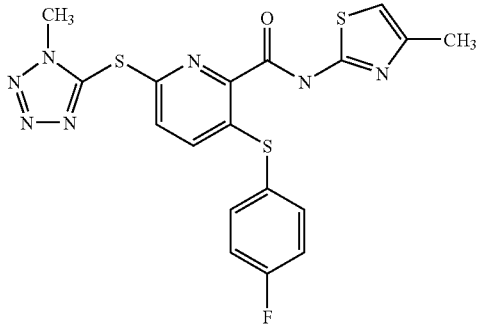

Manufacture of 3-(4-fluoro-phenylsulfanyl)-6-(1-methyl-1H-tetrazole-5-yl-sulfanyl)-N-(4-methyl-thiazole-2-yl)-2-pyridine carboxamide Compound of Production Example 5 can be produced by the same method as Production Example 1, by a method according thereto, or by a combination of these and ordinary methods, with the use of 3,6-dichloro-2-pyridinecarboxylic acid, 2-amino-4-methylthiazole, 4-fluorothiophenol and 5-mercapto-1-methyltriazole.

$^1$HNMR (CDCl$_3$)

δ: 2.43 (3H, s), 4.12 (3H, s), 6.65 (1H, s), 7.12 (1H, d, J=9.0 Hz), 7.21 (2H, m), 7.45 (1H, d, J=9.0 Hz), 7.58 (2H, m)

ESI-MS (m/e): 460[M+H]$^+$

PRODUCTION EXAMPLE 6

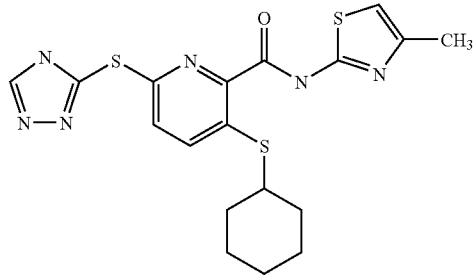

Manufacture of 3-(cyclohexylsulfanyl)-6-(4H-[1,2,4]triazole-3-yl-sulfanyl)-N-(4-methyl-thiazole-2-yl)-2-pyridine carboxamide Compound of Production Example 6 can be produced by the same method as Production Example 1, by a method according thereto, or by a combination of these and ordinary methods, with the use of 3,6-dichloro-2-pyridinecarboxylic acid, 2-amino-4-methylthiazole, cyclohexanthiol and 3-mercapto-1,2,4-triazole.

$^1$HNMR (CDCl$_3$) δ: 1.20-1.75 (6H, m), 1.84 (2H, m), 2.06 (2H, m), 2.36 (3H, s), 3.25 (1H, m), 6.56 (1H, s), 7.43 (1H, d, J=8.7 Hz), 7.64 (1H, d, J=8.7 Hz), 8.33 (1H, s)

ESI-MS (m/e): 433[M+H]$^+$

PRODUCTION EXAMPLE 7

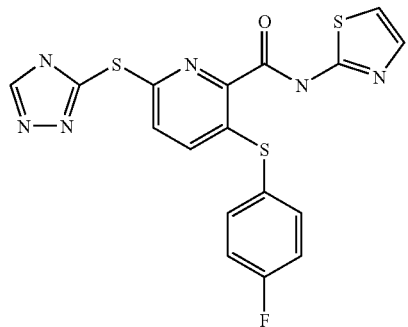

Manufacture of 3-(4-fluoro-phenylsulfanyl)-6-(4H-[1,2,4]triazole-3-yl-sulfanyl)-N-(thiazole-2-pyridine carboxamide Compound of Production Example 7 can be produced by the same method as Production Example 1, by a method according thereto, or by a combination of these and ordinary methods, with the use of 3,6-dichloro-2-pyridinecarboxylic acid, 2-aminothiazole, 4-fluorothiophenol and 3-mercapto-1,2,4-triazole.

$^1$HNMR (CDCl$_3$)

δ: 7.01 (1H, d, J=8.7 Hz), 7.09 (1H, d, J=3.6 Hz), 7.19 (2H, m), 7.25 (1H, d, J=8.7 Hz), 7.50 (1H, d, J=3.6 Hz), 7.50 (2H, m), 8.35 (1H, s)

ESI-MS (m/e): 431[M+H]$^+$

PRODUCTION EXAMPLE 8

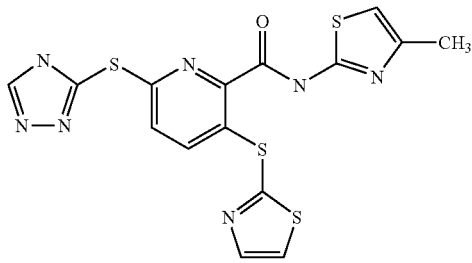

Manufacture of 3-(thiazole-2-yl-sulfanyl)-6-(4H-[1,2,4]-triazole-3-yl)-N-(4-methyl-thiazole-2-yl)-2-pyridine carboxamide Compound of Production Example 8 can be produced by the same method as Production Example 1, by a method according thereto, or by a combination of these and ordinary methods, with the use of 3,6-dichloro-2-pyridinecarboxylic acid, 2-amino-4-methylthiazole, 2-mercapto-thiazole and 3-mercapto-1,2,4-triazole.

$^1$HNMR (CDCl$_3$) δ: 2.40 (3H, s), 6.60 (1H, m), 7.30-7.36 (2H, m), 7.59 (1H, d, J=3.6 Hz), 8.02 (1H, d, J=3.6 Hz), 8.34 (1H, s)

ESI-MS (m/e): 434[M+H]$^+$

PRODUCTION EXAMPLE 9

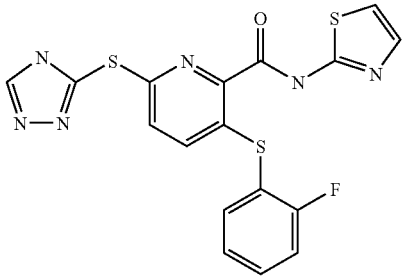

Manufacture of 3-(2-fluoro-phenylsulfanyl)-6-(4H-[1,2,4]-triazole-3-yl-sulfanyl)-N-(thiazole-2-yl)-2-pyridine carboxamide Compound of Production Example 9 can be produced by the same method as Production Example 1, by a method according thereto, or by a combination of these and ordinary methods, with the use of 3,6-dichloro-2-pyridinecarboxylic acid, 2-aminothiazole, 2-fluorothiophenol and 3-mercapto-1,2,4-triazole.

$^1$HNMR (CDCl$_3$) δ: 7.01-7.04 (2H, m), 7.20-7.28 (3H, m), 7.46 (1H, d, J=3.6 Hz), 7.51-7.64 (2H, m), 8.36 (1H, s)

ESI-MS (m/e): 431 [M+H]$^+$

PRODUCTION EXAMPLE 10

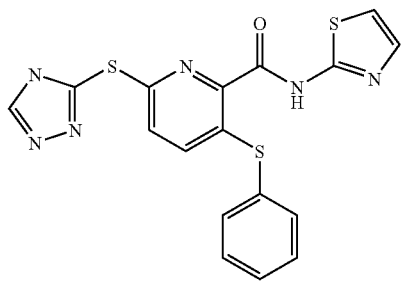

Manufacture of 3-phenylsulfanyl-6-(4H-[1,2,4]-triazole-3-yl-sulfanyl)-N-(thiazole-2-yl)-2-pyridine carboxamide Compound of Production Example 10 can be produced by the same method as Production Example 1, by a method according thereto, or by a combination of these and ordinary methods, with the use of 3,6-dichloro-2-pyridinecarboxylic acid, 2-aminothiazole, thiophenol and 3-mercapto-1,2,4-triazole.

$^1$HNMR (CDCl$_3$) δ: 7.02-7.09 (2H, m), 7.24 (1H, d, J=8.7 Hz), 7.47-7.53 (4H, m), 7.57-7.63 (2H, m), 8.38 (1H, s)

ESI-MS (m/e): 413[M+H]$^+$

PRODUCTION EXAMPLE 11

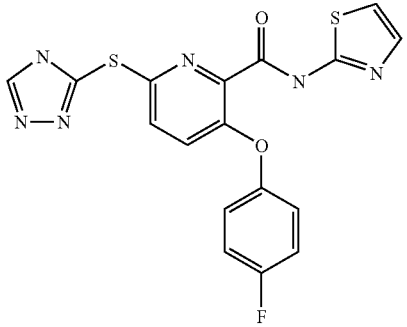

Manufacture of 3-(4-fluoro-phenyloxy)-6-(4H-[1,2,4]-triazole-3-yl-sulfanyl)-N-(thiazole-2-yl)-2-pyridine carboxamide Compound of Production Example 11 can be produced by the same method as Production Example 1, by a method according thereto, or by a combination of these and ordinary methods, with the use of 3,6-dichloro-2-pyridinecarboxylic acid, 2-aminothiazole, 4-fluorophenol and 3-mercapto-1,2,4-triazole.

$^1$HNMR (CDCl$_3$) δ: 7.04 (1H, d, J=3.6 Hz), 7.05-7.13 (4H, m), 7.24 (1H, d, J=8.7 Hz), 7.46-7.51 (2H, m), 8.32 (1H, s)

ESI-MS (m/e): 415[M+H]$^+$

PRODUCTION EXAMPLE 12

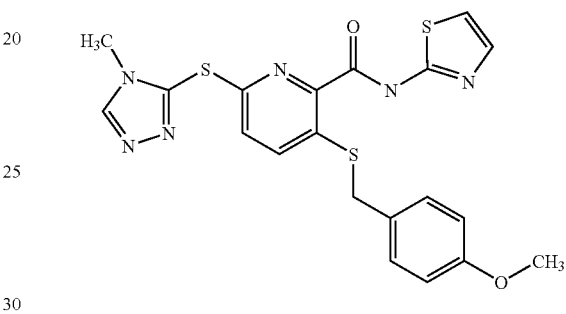

Manufacture of 3-(4-methoxy-phenylmethylsulfanyl)-6-(4-methyl-4H-[1,2,4]triazole-3-yl-sulfanyl)-N-(thiazole-2-yl)-2-pyridine carboxamide Compound of Production Example 12 can be produced by the same method as Production Example 1, by a method according thereto, or by a combination of these and ordinary methods, with the use of 3,6-dichloro-2-pyridinecarboxylic acid, 2-aminothiazole, 4-methoxybenzylmercaptan and 3-mercapto-4-methyl-1,2,4-triazole.

$^1$HNMR (CDCl$_3$)

δ: 3.76 (3H, s), 3.79 (3H, s), 4.11 (2H, s), 6.84 (2H, d, J=8.8 Hz), 7.01 (H, d, J=3.2 Hz), 7.30 (1H, d, J=8.8 Hz), 7.32 (2 H, d, J=8.8 Hz), 7.51 (1H, d, J=3.2 Hz), 7.65 (1H, d, J=8.8 Hz), 8.44 (1H, s)

ESI-MS (m/e): 471[M+H]$^+$

PRODUCTION EXAMPLE 13

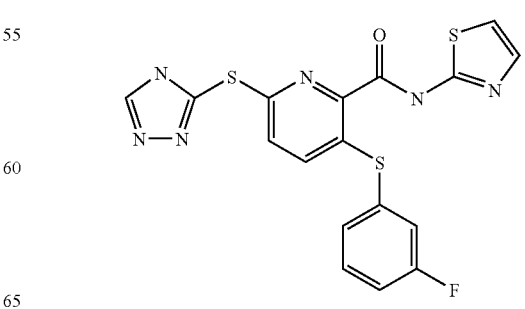

Manufacture of 3-(3-fluoro-phenylsulfanyl)-6-(4H-[1,2,4]triazole-3-yl-sulfanyl)-N-(thiazole-2-yl)-2-pyridine carboxamide Compound of Production Example 13 can be produced by the same method as Production Example 1, by a method according thereto, or by a combination of these and ordinary methods, with the use of 3,6-dichloro-2-pyridinecarboxylic acid, 2-aminothiazole, 3-fluorothiophenol and 3-mercapto-1,2,4-triazole.

¹HNMR (CDCl₃)

δ: 7.02 (1H, d, J=3.6 Hz), 7.05 (1H, d, J=8.4 Hz), 7.18 (1H, td, J=8.4 Hz, 3.2 Hz), 7.24 (1H, d, J=8.4 Hz), 7.29 (1H, ddd, J=8.4 Hz, 2.8 Hz, 2.8 Hz), 7.36 (1H, d, J=7.6 Hz), 7.42-7.48 (2H, m), 8.35 (1H, s)

ESI-MS (m/e): 431 [M+H]⁺

PRODUCTION EXAMPLE 14

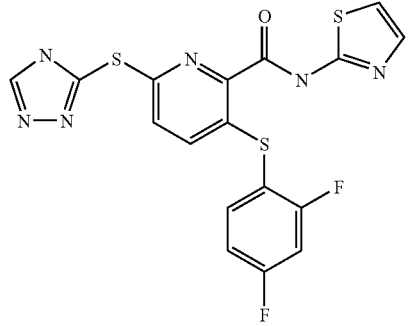

Manufacture of 3-(2,4-difluoro-phenylsulfanyl)-6-(4H-[1,2,4]-triazole-3-yl-sulfanyl)-N-(thiazole-2-yl)-2-pyridine carboxamide Compound of Production Example 14 can be produced by the same method as Production Example 1, by a method according thereto, or by a combination of these and ordinary methods, with the use of 3,6-dichloro-2-pyridinecarboxylic acid, 2-aminothiazole, 2,4-difluorothiophenol and 3-mercapto-1,2,4-triazole.

¹HNMR (CDCl₃) δ: 6.98-7.05 (4H, m), 7.28 (1H, d, J=8.8 Hz), 7.46 (1H, d, J=3.6 Hz), 7.58-7.64 (1H, m), 8.36 (1H, s)

ESI-MS (m/e): 449[M+H]⁺

PRODUCTION EXAMPLE 15

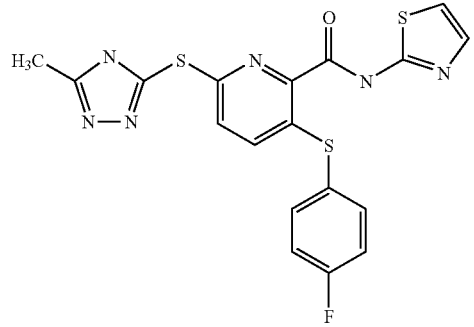

Manufacture of 3-(4-fluoro-phenylsulfanyl)-6-(5-methyl-4H-[1,2,4]-triazole-3-yl-sulfanyl)-N-(thiazole-2-yl)-2-pyridine carboxamide Compound of Production Example 15 can be produced by the same method as Production Example 1, by a method according thereto, or by a combination of these and ordinary methods, with the use of 3,6-dichloro-2-pyridinecarboxylic acid, 2-aminothiazole, 4-fluorothiophenol and 3-mercapto-5-methyl-1,2,4-triazole.

¹HNMR (CDCl₃) δ: 2.58 (3H, s), 6.97 (1H, d, J=8.4 Hz), 7.04 (1H, d, J=3.6 Hz), 7.15-7.23 (3H, m), 7.48 (1H, d, J=3.6 Hz), 7.54-7.58 (2H, m)

ESI-MS (m/e): 445 [M+H]⁺

PRODUCTION EXAMPLE 16

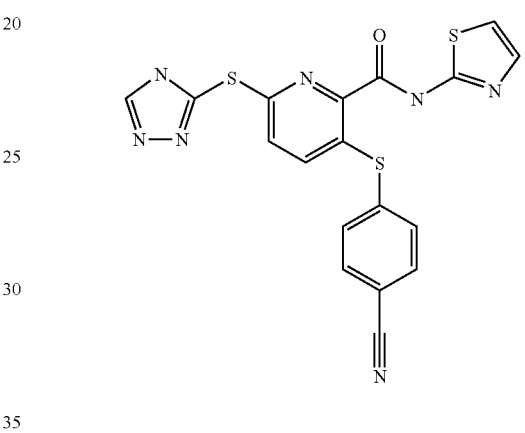

Manufacture of 3-(4-cyano-phenylsulfanyl)-6-(4H-[1,2,4]-triazole-3-yl-sulfanyl)-N-(thiazole-2-yl)-2-pyridine carboxamide Compound of Production Example 16 can be produced by the same method as Production Example 1, by a method according thereto, or by a combination of these and ordinary methods, with the use of 3,6-dichloro-2-pyridinecarboxylic acid, 2-aminothiazole, 4-cyanothiophenol and 3-mercapto-1,2,4-triazole.

¹HNMR (CDCl₃)

δ: 7.06 (1H, d, J=3.6 Hz), 7.11 (1H, d, J=8.8 Hz), 7.30 (1H, d, J=8.8 Hz), 7.49 (1H, d, J=3.6 Hz), 7.65 (2H, d, J=8.8 Hz), 7.73 (2H, d, J=8.8 Hz), 8.40 (1H, s)

ESI-MS (m/e): 438[M+H]⁺

PRODUCTION EXAMPLE 17

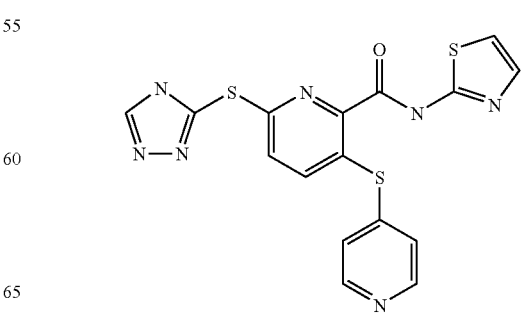

Manufacture of 3-(pyridine-4-yl-sulfanyl)-6-(4H-[1,2,4]triazole-3-yl-sulfanyl)-N-(thiazole-2-yl)-2-pyridine carboxamide Compound of Production Example 17 can be produced by the same method as Production Example 1, by a method according thereto, or by a combination of these and ordinary methods, with the use of 3,6-dichloro-2-pyridinecarboxylic acid, 2-aminothiazole, 4-mercapto-pyridine and 3-mercapto-1,2,4-triazole.

$^1$HNMR (CDCl$_3$) δ: 7.09 (1H, d, J=3.6 Hz), 7.28-7.35 (2H, m), 7.43 (2H, d, J=6.0 Hz), 7.51 (1H, d, J=3.6 Hz), 8.39 (1H, s), 8.62 (2H, d, J=6.0 Hz)

ESI-MS (m/e): 414[M+H]$^+$

PRODUCTION EXAMPLE 18

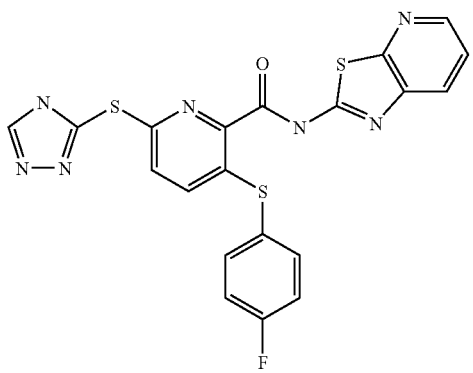

Manufacture of 3-(4-fluoro-phenylsulfanyl)-6-(4H-[1,2,4]triazole-3-yl-sulfanyl)-N-(thiazoleo[5,4-b]pyridine-2-yl)-2-pyridine carboxamide Compound of Production Example 18 can be produced by the same method as Production Example 1, by a method according thereto, or by a combination of these and ordinary methods, with the use of 3,6-dichloro-2-pyridinecarboxylic acid, 2-amino-thiazoleo[5,4-b]pyridine, 4-fluorothiophenol and 3-mercapto-1,2,4-triazole.

$^1$HNMR (CDCl$_3$) δ: 7.00 (1H, d, J=8.8 Hz), 7.16-7.20 (2H, m), 7.25 (1H, d, J=8.8 Hz), 7.37-7.41 (1H, m), 7.55-7.58 (2H, m), 8.02 (1H, d, J=8.4 Hz), 8.42 (1H, s), 8.51 (1H, d, J=4.4 Hz)

ESI-MS (m/e): 482[M+H]$^+$

PRODUCTION EXAMPLE 19

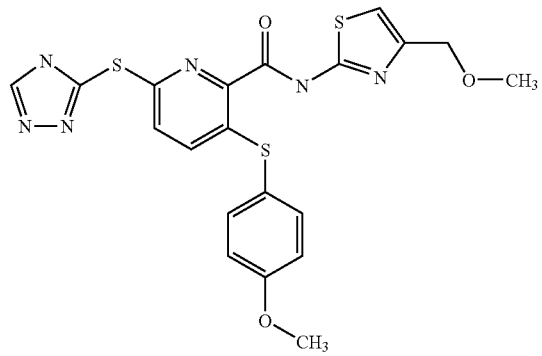

Manufacture of 3-(4-methoxy-phenylsulfanyl)-6-(4H-[1,2,4]triazole-3-yl-sulfanyl)-N-(4-methoxymethyl-thiazole-2-yl)-2-pyridine carboxamide Compound of Production Example 19 can be produced by the same method as Production Example 1, by a method according thereto, or by a combination of these and ordinary methods, with the use of 3,6-dichloro-2-pyridinecarboxylic acid, 2-amino-4-methoxymethyl-thiazole, 4-methoxy-thiophenol and 3-mercapto-1,2,4-triazole.

$^1$HNMR (CDCl$_3$) δ: 3.43 (3H, s), 3.86 (3H, s), 4.51 (2H, s), 6.92 (1H, s), 6.96-7.02 (3H, m), 7.22 (1H, d, J=8.7 Hz), 7.49 (2H, d, J=8.7 Hz), 8.35 (1H, s)

ESI-MS (m/e): 487[M+H]$^+$

PRODUCTION EXAMPLE 20

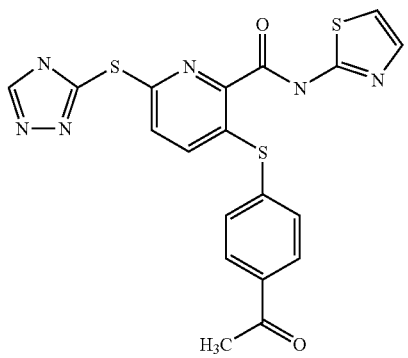

Manufacture of 3-(4-acetyl-phenylsulfanyl)-6-(4H-[1,2,4]triazole-3-yl-sulfanyl)-N-(thiazole-2-yl)-2-pyridine carboxamide Compound of Production Example 20 can be produced by the same method as Production Example 1, by a method according thereto, or by a combination of these and ordinary methods, with the use of 3,6-dichloro-2-pyridinecarboxylic acid, 2-amino-thiazole, 4-acetylthiophenol and 3-mercapto-1,2,4-triazole.

$^1$HNMR (CDCl$_3$)

δ: 2.65 (3H, s), 7.05 (1H, d, J=3.6 Hz), 7.10 (1H, d, J=8.4 Hz), 7.25 (1H, d, J=8.4 Hz), 7.47 (1H, d, J=3.6 Hz), 7.65 (2H, d, J=8.6 Hz), 8.01 (2H, d, J=8.6 Hz), 8.36 (1H, s)

ESI-MS (m/e): 455 [M+H]$^+$

PRODUCTION EXAMPLE 21

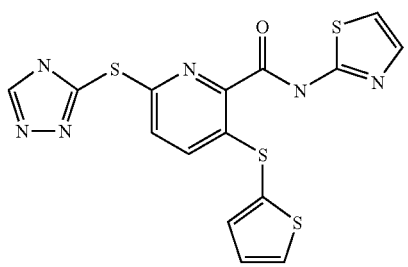

Manufacture of 3-(thiophene-2-yl-sulfanyl)-6-(4H-[1,2,4]triazole-3-yl-sulfanyl)-N-(thiazole-2-yl)-2-pyridine carboxamide Compound of Production Example 21 can be produced by the same method as Production Example 1, by a method according thereto, or by a combination of these and ordinary methods, with the use of 3,6-dichloro-2-pyridinecarboxylic acid, 2-amino-thiazole, 2-mercapto-thiophene and 3-mercapto-1,2,4-triazole.

$^1$HNMR (CDCl$_3$)

δ: 7.01 (1H, d, J=3.2 Hz), 7.06 (1H, d, J=8.8 Hz), 7.16 (1H, dd, J=3.6, 5.2 Hz), 7.26 (1H, d, J=8.8 Hz), 7.35 (1H, dd, J=1.2, 3.6 Hz), 7.43 (1H, d, J=3.2 Hz), 7.60 (1H, dd, J=1.2, 5.2 Hz), 8.35 (1H, s)

ESI-MS (m/e): 419[M+H]$^+$

PRODUCTION EXAMPLE 22

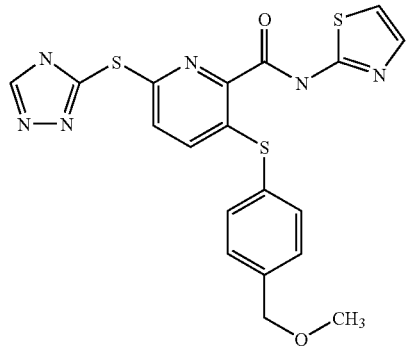

Manufacture of 3-(4-methoxymethyl-phenylsulfanyl)-6-(4H-[1,2,4]triazole-3-yl-sulfanyl)-(thiazole-2-yl)-2-pyridine carboxamide Compound of Production Example 22 can be produced by the same method as Production Example 1, by a method according thereto, or by a combination of these and ordinary methods, with the use of 3,6-dichloro-2-pyridinecarboxylic acid, 2-amino-thiazole, 4-methoxymethyl-thiophenol and 3-mercapto-1,2,4-triazole.

$^1$HNMR (CDCl$_3$)

δ: 3.46 (3H, s), 4.50 (2H, s), 7.00 (1H, d, J=3.2 Hz), 7.02 (1H, d, J=8.8 Hz), 7.17 (1H, d, J=8.8 Hz), 7.42 (1H, d, J=3.2 Hz), 7.43 (2H, d, J=8.0 Hz), 7.54 (2H, d, J=8.0 Hz), 8.33 (1H, s)

ESI-MS (m/e): 457[M+H]$^+$

PRODUCTION EXAMPLE 23

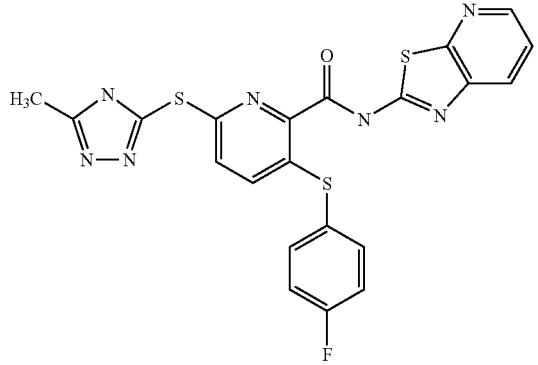

Manufacture of 3-(4-fluoro-phenylsulfanyl)-6-(5-methyl-4H-[1,2,4]triazole-3-yl-sulfanyl)-N-(thiazolo[5,4-b]pyridine-2-yl)-2-pyridine carboxamide Compound of Production Example 23 can be produced by the same method as Production Example 1, by a method according thereto, or by a combination of these and ordinary methods, with the use of 3,6-dichloro-2-pyridinecarboxylic acid, 2-amino-thiazolo[5,4-b]pyridine, 4-fluorothiophenol and 3-mercapto-5-methyl-1,2,4-triazole.

$^1$HNMR (CDCl$_3$) δ: 2.54 (3H, s), 6.96 (1H, d, J=8.8 Hz), 7.11-7.16 (2H, m), 7.17 (1H, d, J=8.8 Hz), 7.37 (1H, dd, J=4.8, 8.0 Hz), 7.50-7.54 (2H, m), 8.00 (1H, d, J=8.0 Hz), 8.45 (1H, d, J=4.8 Hz)

ESI-MS (m/e): 496[M+H]$^+$

PRODUCTION EXAMPLE 24

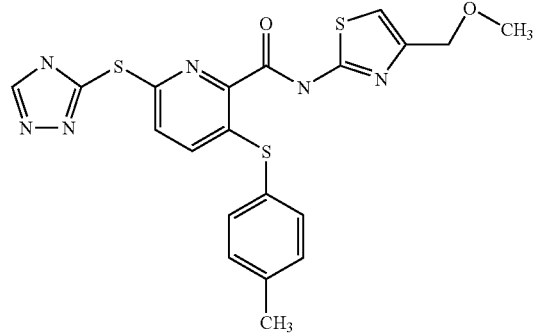

Manufacture of 3-(4-methyl-phenylsulfanyl)-6-(4H-[1,2,4]triazole-3-yl-sulfanyl)-N-(4-methoxymethyl-thiazole-2-yl)-2-pyridine carboxamide Compound of Production Example 24 can be produced by the same method as Production Example 1, by a method according thereto, or by a combination of these and ordinary methods, with the use of 3,6-dichloro-2-pyridinecarboxylic acid, 2-amino-4-methoxymethyl-thiazole, 4-methylthiophenol and 3-mercapto-1,2,4-triazole.

$^1$HNMR (CDCl$_3$)

δ: 2.42 (3H, s), 3.43 (3H, s), 4.51 (2H, s), 6.91 (1H, s), 7.00 (1H, d, J=8.8 Hz), 7.19 (1H, d, J=8.8 Hz), 7.26 (2H, d, J=8.4 Hz), 7.44 (2H, d, J=8.4 Hz), 8.34 (1H, s)

ESI-MS (m/e): 471[M+H]$^+$

PRODUCTION EXAMPLE 25

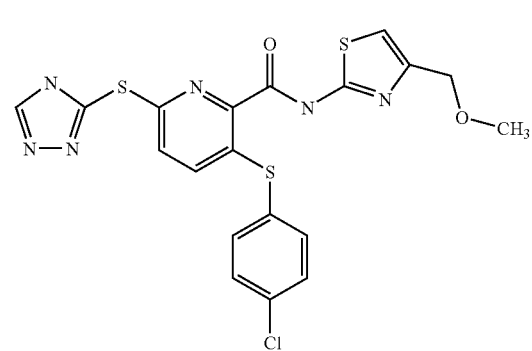

Manufacture of 3-(4-chloro-phenylsulfanyl)-6-(4H-[1,2,4]-triazole-3-yl-sulfanyl)-N-(4-methoxymethyl-thiazole-2-yl)-2-pyridine carboxamide Compound of Production Example 25 can be produced by the same method as Production Example 1, by a method according thereto, or by a combination of these and ordinary methods, with the use of 3,6-dichloro-2-pyridinecarboxylic acid, 2-amino-4-methoxymethyl-thiazole, 4-chlorothiophenol and 3-mercapto-1,2,4-triazole.

$^1$HNMR (CDCl$_3$)

δ: 3.43 (3H, s), 4.50 (2H, s), 6.91 (1H, s), 6.97 (1H, d, J=8.8 Hz), 7.20 (1H, d, J=8.8 Hz), 7.42 (2H, d, J=8.4 Hz), 7.49 (2 H, d, J=8.4 Hz), 8.33 (1H, s)

ESI-MS (m/e): 491[M+H]$^+$

PRODUCTION EXAMPLE 26

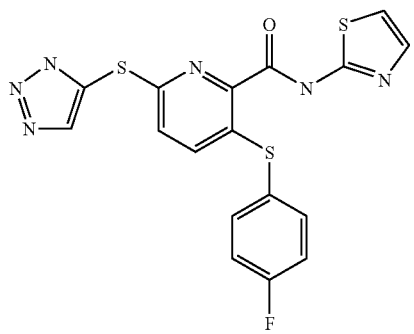

Manufacture of 3-(4-fluoro-phenylsulfanyl)-6-(3H-[1,2,4]triazole-4-yl-sulfanyl)-N-(thiazole-2-yl)-2-pyridine carboxamide Compound of Production Example 26 can be produced by the same method as Production Example 1, by a method according thereto, or by a combination of these and ordinary methods, with the use of 3,6-dichloro-2-pyridinecarboxylic acid, 2-amino-4-methoxymethyl-thiazole, 4-fluorothiophenol and 4-mercapto-1,2,4-triazole.

$^1$HNMR (CDCl$_3$) δ: 6.66 (1H, d, J=8.8 Hz), 6.72 (1H, d, J=8.8 Hz), 6.86 (1H, d, J=4.0 Hz), 6.89-6.94 (2H, m), 7.25 (1H, d, J=4.0 Hz), 7.27-7.30 (2H, m), 7.72 (1H, s),

ESI-MS (m/e): 431[M+H]$^+$

PRODUCTION EXAMPLE 27

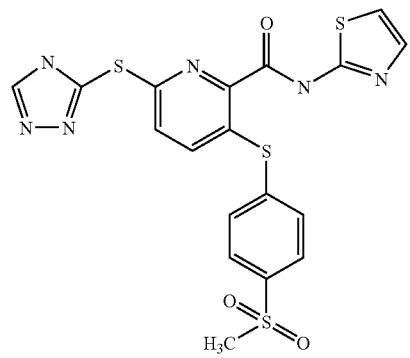

Manufacture of 3-(4-methylsulfonyl-phenylsulfanyl)-6-(4H-[1,2,4]triazole-3-yl-sulfanyl)-N-(thiazole-yl)-2-pyridine carboxamide Compound of Production Example 27 can be produced by the same method as Production Example 1, by a method according thereto, or by a combination of these and ordinary methods, with the use of 3,6-dichloro-2-pyridinecarboxylic acid, 2-amino-thiazole, 4-methylsulfonylthiophenol and 3-mercapto-1,2,4-triazole.

$^1$HNMR (CDCl$_3$)

δ: 3.12 (3H, s), 7.05 (1H, d, J=3.6 Hz), 7.11 (1H, d, J=8.8 Hz), 7.28 (1H, d, J=8.8 Hz), 7.48 (1H, d, J=3.6 Hz), 7.74 (2H, d, J=8.0 Hz), 8.00 (2H, d, J=8.0 Hz) 8.39 (1H, s)

ESI-MS (m/e): 491[M+H]$^+$

PRODUCTION EXAMPLE 28

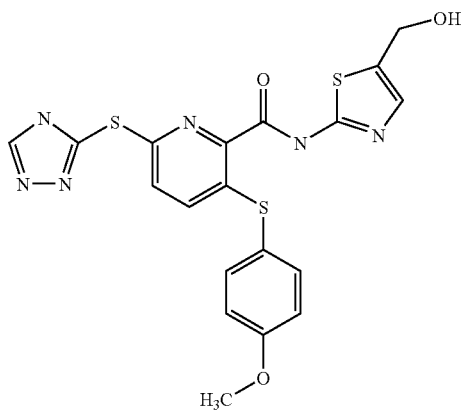

Manufacture of 3-(4-methoxy-phenylsulfanyl)-6-(4H-[1,2,4]triazole-3-yl-sulfanyl)-N-(5-hydroxymethyl-thiazole-2-yl)-2-pyridine carboxamide Compound of Production Example 28 can be produced by the same method as Production Example 1, by a method according thereto, or by a combination of these and ordinary methods, with the use of 3,6-dichloro-2-pyridinecarboxylic acid, 2-amino-4-hydroxymethyl-thiazole, 4-methoxythiophenol and 3-mercapto-1,2,4-triazole.

$^1$HNMR (CDCl$_3$)

δ: 3.86 (3H, s), 4.78 (2H, s), 6.99 (2H, d, J=8.8 Hz), 7.02 (1H, d, J=8.8 Hz), 7.18 (1H, d, J=8.8 Hz), 7.35 (1H, s), 7.46 (2 H, d, J=8.8 Hz), 8.39 (1H, s)

ESI-MS (m/e): 473[M+H]$^+$

PRODUCTION EXAMPLE 29

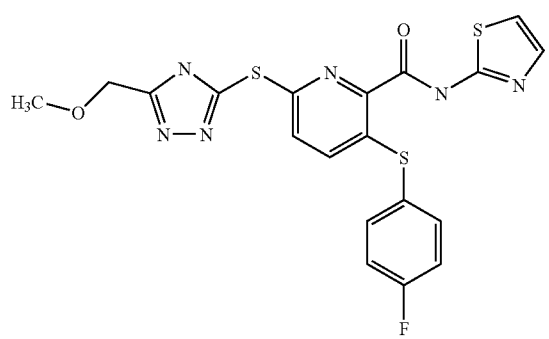

Manufacture of 3-(4-fluoro-phenylsulfanyl)-6-(5-methoxymethyl-4H-[1,2,4]triazole-3-yl-sulfanyl)-N-(thiazole-2-yl)-2-pyridine carboxamide Compound of Production Example 29 can be produced by the same method as Production Example 1, by a method according thereto, or by a combination of these and ordinary methods, with the use of 3,6-dichloro-2-pyridinecarboxylic acid, 2-amino-thiazole, 4-fluorothiophenol and 3-mercapto-5-methoxymethyl-1,2,4-triazole.

$^{1}$HNMR (CDCl$_3$) δ: 3.50 (3H, s), 4.76 (2H, s), 6.98 (1H, d, J=8.8 Hz), 7.03 (1H, d, J=3.2 Hz), 7.14-7.22 (3H, m), 7.48 (1H, d, J=3.2 Hz), 7.54-7.57 (2H, m)

ESI-MS (m/e): 475[M+H]$^+$

PRODUCTION EXAMPLE 30

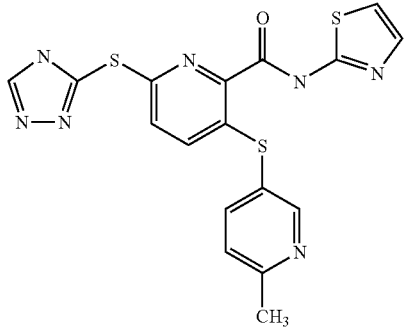

Manufacture of 3-(6-methyl-pyridine-3-yl-sulfanyl)-6-(4H-[1,2,4]triazole-3-yl-sulfanyl)-N-(thiazole-2-yl)-2-pyridine carboxamide Compound of Production Example 30 can be produced by the same method as Production Example 1, by a method according thereto or by a combination of these and ordinary methods, with the use of 3,6-dichloro-2-pyridinecarboxylic acid, 2-amino-thiazole, 3-mercapto-6-methyl-pyridine and 3-mercapto-1,2,4-triazole.

$^{1}$HNMR (DMSO-d$_6$)

δ: 2.51 (3H, s), 7.17 (1H, d, J=8.8 Hz), 7.21 (1H, d, J=8.8 Hz), 7.35 (1H, d, J=3.6 Hz), 7.36 (1H, d, J=8.8 Hz), 7.57 (1H, d, J=3.6 Hz), 7.83 (1H, dd, J=2.4, 8.8 Hz), 8.53 (1H, d, J=2.4 Hz), 8.72 (1H, s),

ESI-MS (m/e): 428[M+H]

PRODUCTION EXAMPLE 31

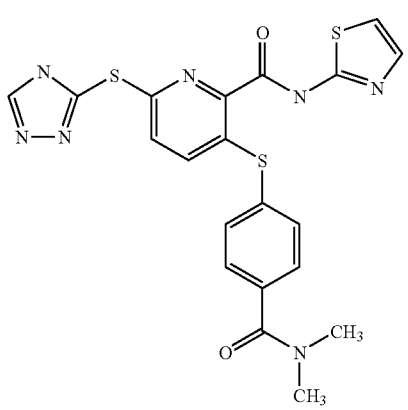

Manufacture of 3-(4-dimethylcarbamoyl-phenylsulfanyl)-6-(4H-[1,2,4]triazole-3-yl-sulfanyl)-N-(thiazole-2-yl)-2-pyridine carboxamide Compound of Production Example 31 can be produced by the same method as Production Example 1, by a method according thereto, or by a combination of these and ordinary methods, with the use of 3,6-dichloro-2-pyridinecarboxylic acid, 2-amino-thiazole, 4-dimethylcarbamoylthiophenol and 3-mercapto-1,2,4-triazole.

$^{1}$HNMR (CDCl$_3$)

δ: 3.02 (3H, s) 3.15 (3H, s), 7.04 (1H, d, J=3.6 Hz), 7.06 (1H, d, J=8.8 Hz), 7.23 (1H, d, J=8.8 Hz), 7.49 (1H, d, J=3.6 Hz), 7.50 (2H, d, J=8.4 Hz), 7.61 (2H, d, J=8.4 Hz), 8.39 (1H, s)

ESI-MS (m/e): 484[M+H]$^+$

PRODUCTION EXAMPLE 32

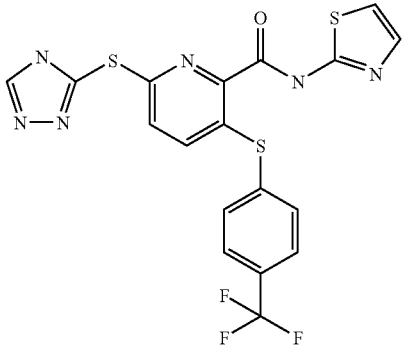

Manufacture of 3-(4-trifluoromethyl-phenylsulfanyl)-6-(4H-[1,2,4]triazole-3-yl-sulfanyl)-N-(thiazole-2-yl)-2-pyridine carboxamide Compound of Production Example 32 can be produced by the same method as Production Example 1, by a method according thereto, or by a combination of these and ordinary methods, with the use of 3,6-dichloro-2-pyridinecarboxylic acid, 2-amino-thiazole, 4-trifluoromethylthiophenol and 3-mercapto-1,2,4-triazole.

$^{1}$HNMR (CDCl$_3$)

δ: 7.04 (1H, d, J=3.6 Hz) 7.06 (1H, d, J=8.8 Hz), 7.26 (1H, d, J=8.8 Hz), 7.47 (1H, d, J=3.3.6 Hz), 7.66-7.74 (4H, m), 8.38 (1H, s),

ESI-MS (m/e): 481[M+H]$^+$

PRODUCTION EXAMPLE 33

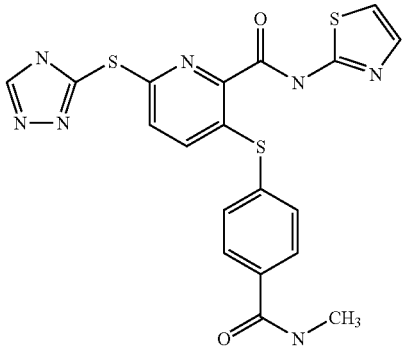

Manufacture of 3-(4-methylcarbamoyl-phenylsulfanyl)-6-(4H-[1,2,4]triazole-3-yl-sulfanyl)-N-(thiazole-2-yl)-2-pyridine carboxamide Compound of Production Example 33 can be produced by the same method as Production Example 1, by a method according thereto, or by a combination of these and ordinary methods, with the use of 3,6-dichloro-2-pyridinecarboxylic acid, 2-amino-thiazole, 4-methylcarbamoylthiophenol and 3-mercapto-1,2,4-triazole.

$^1$HNMR (CDCl$_3$)

δ: 3.00 (3H, d, J=4.8 Hz), 7.02 (1H, d, J=8.8 Hz), 7.05 (1H, d, J=3.6 Hz), 7.20 (1H, d, J=8.8 Hz), 7.47 (1H, d, J=3.6 Hz), 7.59 (2H, d, J=8.4 Hz), 7.81 (2H, d, J=8.4 Hz), 8.32 (1H, s), ESI-MS (m/e): 470[M+H]$^+$

PRODUCTION EXAMPLE 34

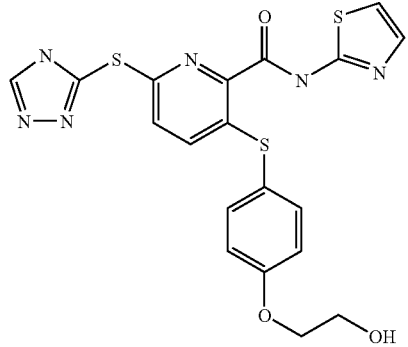

Manufacture of 3-(hydroxyethyloxy-phenylsulfanyl)-6-(4H-[1,2,4]triazole-3-yl-sulfanyl)-N-(thiazole-2-yl)-2-pyridine carboxamide Compound of Production Example 34 can be produced by the same method as Production Example 1, by a method according thereto, or by a combination of these and ordinary methods, with the use of 3,6-dichloro-2-pyridinecarboxylic acid, 2-amino-thiazole, 4-hydroxyethyloxy-thiophenol and 3-mercapto-1,2,4-triazole.

$^1$HNMR (CDCl$_3$) δ: 3.97 (2H, m), 4.13 (2H, m), 7.00-7.11 (4H, m), 7.23 (1H, d, J=9.0 Hz), 7.46-7.54 (3H, m), 8.36 (1H, s)

ESI-MS (m/e): 473[M+H]$^+$

PRODUCTION EXAMPLE 35

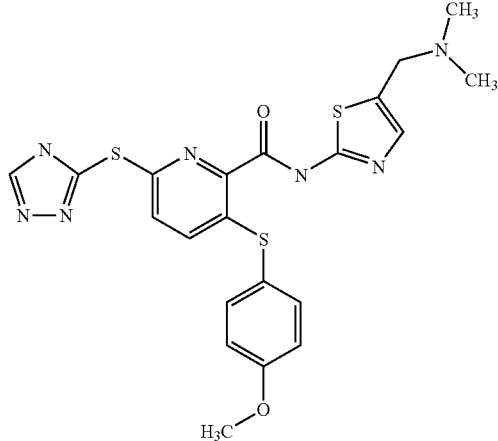

Manufacture of 3-(4-methoxy-phenylsulfanyl)-6-(4H-[1,2,4]triazole-3-yl-sulfanyl)-N-(5-dimethylaminomethyl-thiazole-2-yl)-2-pyridine carboxamide Compound of Production Example 35 can be produced by the same method as Production Example 1, by a method according thereto, or by a combination of these and ordinary methods, with the use of 3,6-dichloro-2-pyridinecarboxylic acid, 2-amino-5-dimethylaminomethylthiazole, 4-methoxythiophenol and 3-mercapto-1,2,4-triazole.

$^1$HNMR (CDCl$_3$)

δ: 2.32 (6H, s), 3.70 (2H, s), 3.85 (3H, s), 6.97 (2H, d, J=8.8 Hz), 7.00 (1H, d, J=8.5 Hz), 7.19 (1H, d, J=8.5 Hz), 7.26 (1 H, s), 7.46 (2H, d, J=8.8 Hz), 8.31 (1H, s)

ESI-MS (m/e): 500[M+H]$^+$

PRODUCTION EXAMPLE 36

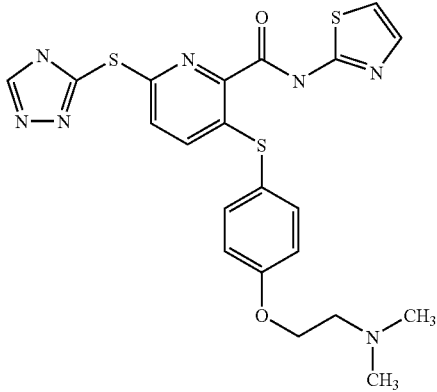

Manufacture of 3-(4-dimethylaminoethyloxy-phenylsulfanyl)-6-(4H-[1,2,4]triazole-3-yl-sulfanyl)-N-(thiazole-2-yl)-2-pyridine carboxamide Compound of Production Example 36 can be produced by the same method as Production Example 1, by a method according thereto, or by a combination of these and ordinary methods, with the use of 3,6-dichloro-2-pyridinecarboxylic acid, 2-amino-thiazole, 4-dimethylaminoethylthiophenol and 3-mercapto-1,2,4-triazole.

$^1$HNMR (CDCl$_3$) δ: 2.40 (6H, s), 2.82 (2H, t, J=5.6 Hz), 4.13 (2H, t, J=5.6 Hz), 6.95-7.05 (4H, m), 7.21 (1H, d, J=8.7 Hz), 7.42-7.50 (3H, m), 8.36 (1H, s)

ESI-MS (m/e): 500[M+H]$^+$

PRODUCTION EXAMPLE 37

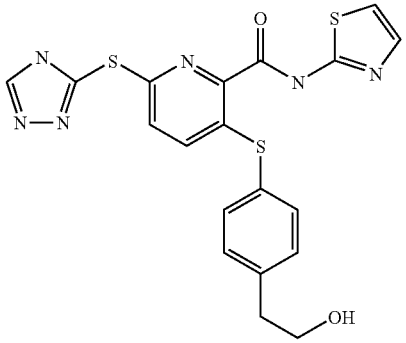

Manufacture of 3-(4-hydroxyethyl-phenylsulfanyl)-6-(4H-[1,2,4]triazole-3-yl-sulfanyl)-N-(thiazole-2-yl)-2-pyridine carboxamide Compound of Production Example 37 can be produced by the same method as Production Example 1, by a method according thereto, or by a combination of these and ordinary methods, with the use of 3,6-dichloro-2-pyridinecarboxylic acid, 2-amino-thiazole, 4-hydroxyethylthiophenol and 3-mercapto-1,2,4-triazole.

$^1$HNMR (CDCl$_3$) δ: 2.93 (2H, m), 3.90 (2H, m), 7.04-7.10 (2H, m), 7.23 (1H, d, J=9.0 Hz), 7.36 (2H, d, J=7.8 Hz), 7.48-7.56 (3H, m), 8.34 (1H, s)

ESI-MS (m/e): 457[M+H]$^+$

PRODUCTION EXAMPLE 38

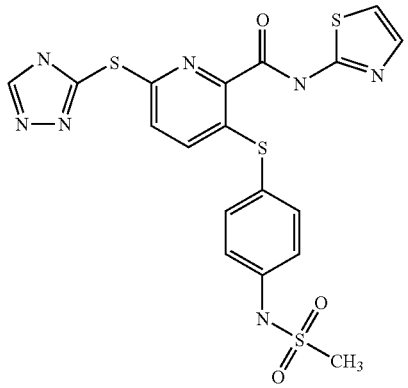

Manufacture of 3-(4-methylsulfamoyl-phenylsulfanyl)-6-(4H-[1,2,4]triazole-3-yl-sulfanyl)-N-(thiazole-2-yl)-2-pyridine carboxamide Compound of Production Example 38 can be produced by the same method as Production Example 1, by a method according thereto, or by a combination of these and ordinary methods, with the use of 3,6-dichloro-2-pyridinecarboxylic acid, 2-amino-thiazole, 4-methylsulfamoylthiophenol and 3-mercapto-1,2,4-triazole.

$^1$HNMR (CDCl$_3$) δ: 2.97 (3H, s), 6.98 (1H, d, J=3.6 Hz), 7.21-7.25 (3H, m), 7.30-7.50 (4H, m), 8.28 (1H, s)

ESI-MS (m/e): 505[M]$^+$

PRODUCTION EXAMPLE 39

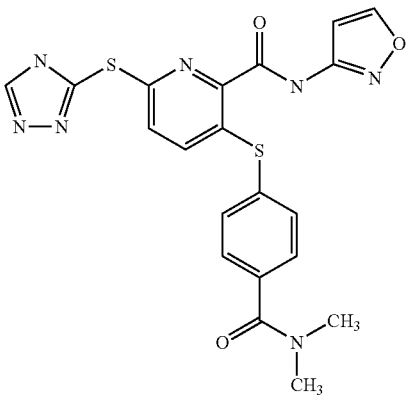

Manufacture of 3-(4-dimethylcarbamoyl-phenylsulfanyl)-6-(4H-[1,2,4]triazole-3-yl-sulfanyl)-N-(isoxazole-3-yl)-2-pyridine carboxamide Compound of Production Example 39 can be produced by the same method as Production Example 1, by a method according thereto, or by a combination of these and ordinary methods, with the use of 3,6-dichloro-2-pyridinecarboxylic acid, 3-amino-oxazole, 4-dimethylcarbamoylthiophenol and 3-mercapto-1,2,4-triazole.

$^1$HNMR (CDCl$_3$)

δ: 3.01 (3H, s), 3.15 (3H, s), 6.99 (1H, d, J=8.8 Hz), 7.19 (1H, d, J=8.8 Hz), 7.25 (1H, d, J=1.6 Hz), 7.48 (2H, d, J=8.1 Hz), 7.56 (2H, d, J=8.1 Hz), 8.31 (1H, d, J=1.6 Hz), 8.41 (1H, s)

ESI-MS (m/e): 468[M+H]$^+$

PRODUCTION EXAMPLE 40

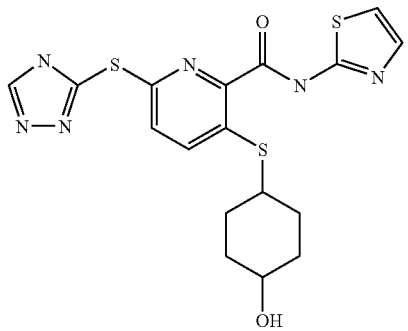

Manufacture of 3-(4-hydroxy-cyclohexylsulfanyl)-6-(4H-[1,2,4]triazole-3-yl-sulfanyl)-N-(thiazole-2-yl)-2-pyridine carboxamide Compound of Production Example 40 can be produced by the same method as Production Example 1, by a method according thereto, or by a combination of these and ordinary methods, with the use of 3,6-dichloro-2-pyridinecarboxylic acid, 2-amino-thiazole, 4-mercapto-cyclohexanol and 3-mercapto-1,2,4-triazole.

$^1$HNMR (CDCl$_3$) δ: 1.30-1.60 (4H, m), 1.90-2.15 (4H, m), 3.10-3.22 (1H, m), 3.60-3.70 (1H, m), 6.99 (1H, d, J=3.6 Hz), 7.40 (1H, d, J=8.8 Hz), 7.43 (1H, d, J=3.6 Hz), 7.61 (1H, d, J=8.8 Hz), 8.32 (1H, s)

ESI-MS (m/e): 435[M+H]$^+$

PRODUCTION EXAMPLE 41

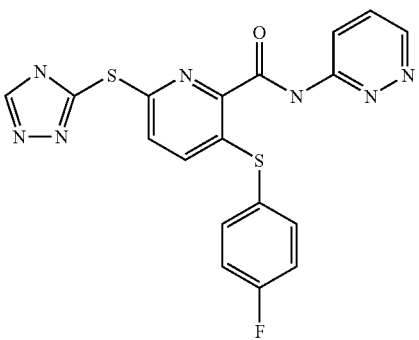

Manufacture of 3-(4-fluoro-phenylsulfanyl)-(4H-[1,2,4]triazole-3-yl-sulfanyl)-N-(pyridazine-3-yl)-2-pyridine carboxamide Compound of Production Example 41 can be produced by the same method as Production Example 1, by a method according thereto, or by a combination of these and ordinary methods, with the use of 3,6-dichloro-2-pyridinecarboxylic acid, 3-amino-pyridazine, 4-fluorothiophenol and 3-mercapto-1,2,4-triazole.

$^1$HNMR (CDCl$_3$) δ: 6.96 (1H, d, J=9.2 Hz), 7.12-7.16 (2H, m), 7.19 (1H, d, J=9.2 Hz), 7.50-7.55 (3H, m), 8.41 (1H, s), 8.65 (1H, d, J=9.2 Hz), 8.85 (1H, d, J=4.8 Hz)

ESI-MS (m/e): 426[M+H]$^+$

PRODUCTION EXAMPLE 42

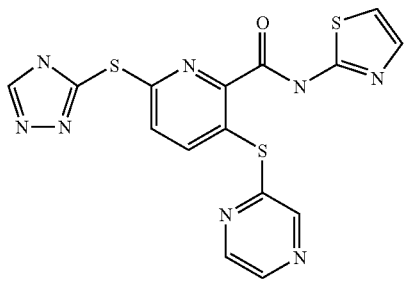

Manufacture of 3-(pyrazin-2-yl-sulfanyl)-6-(4H-[1,2,4]triazole-3-yl-sulfanyl)-N-(thiazole-2-yl)-2-pyridine carboxamide Compound of Production Example 42 can be produced by the same method as Production Example 1, by a method according thereto, or by a combination of these and ordinary methods, with the use of 3,6-dichloro-2-pyridinecarboxylic acid, 2-amino-thiazole, 2-mercapto-pyradine and 3-mercapto-1,2,4-triazole.

$^1$HNMR (CDCl$_3$)

δ: 7.02 (1H, d, J=3.6 Hz), 7.39 (1H, d, J=8.8 Hz), 7.45 (1H, d, J=3.6 Hz), 7.68 (1H, d, J=8.8 Hz), 8.38 (1H, s) 8.44-8.46 (2H, m), 8.70 (1H, d, J=1.6 Hz)

ESI-MS (m/e): 415[M+H]$^+$

PRODUCTION EXAMPLE 43

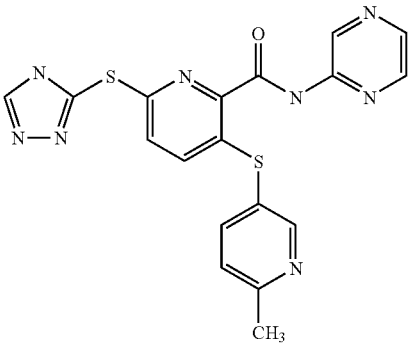

Manufacture of 3-(6-methyl-pyridine-3-yl-sulfanyl)-6-(4H-[1,2,4]triazole-3-yl-sulfanyl)-N-(pyridine-2-yl)-2-pyridine carboxamide Compound of Production Example 43 can be produced by the same method as Production Example 1, by a method according thereto, or by a combination of these and ordinary methods, with the use of 3,6-dichloro-2-pyridinecarboxylic acid, 2-amino-pyradine, 3-mercapto-6-methyl-pyridine and 3-mercapto-1,2,4-triazole.

$^1$HNMR (CDCl$_3$) δ: 2.64 (3H, s), 6.96 (1H, d, J=8.8 Hz), 7.17 (1H, d, J=8.8 Hz), 7.28 (1H, d, J=8.1 Hz), 7.77 (1H, dd, J=8.1, 2.2 Hz), 8.29 (1H, dd, J=2.6, 1.5 Hz), 8.35 (1H, d, J=2.6 Hz), 8.41 (1H, s), 8.61 (1H, d, J=2.2 Hz), 9.68 (1H, d, J=1.5 Hz)

ESI-MS (m/e): 423[M+H]$^+$

PRODUCTION EXAMPLE 44

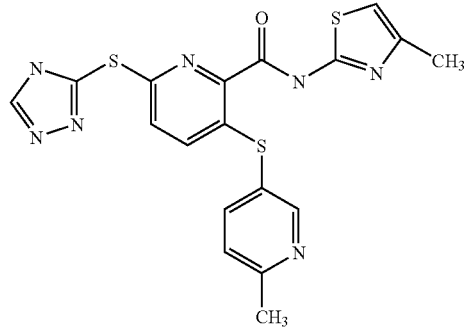

Manufacture of 3-(6-methyl-pyridine-3-yl-sulfanyl)-6-(4H-[1,2,4]triazole-3-yl-sulfanyl)-N-(4-methyl-thiazole-2-yl)-2-pyridine carboxamide Compound of Production Example 44 can be produced by the same method as Production Example 1, by a method according thereto, or by a combination of these and ordinary methods, with the use of 3,6-dichloro-2-pyridinecarboxylic acid, 2-amino-4-methyl-thiazole, 3-mercapto-6-methyl-pyridine and 3-mercapto-1,2,4-triazole.

$^1$HNMR (CDCl$_3$) δ: 2.39 (3H, s), 2.63 (3H, s), 6.58 (1H, s), 6.99 (1H, d, J=8.8 Hz), 7.20-7.30 (2H, m), 7.74 (1H, d, J=8.0 Hz), 8.32 (1H, s), 8.62 (1H, s)

ESI-MS (m/e): 442[M+H]$^+$

PRODUCTION EXAMPLE 45

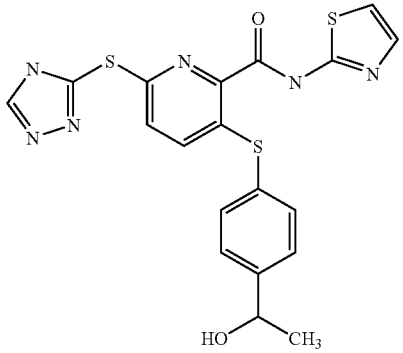

Manufacture of 3-[4-(1-hydroxyethyl-phenylsulfanyl)]-6-(4H-[1,2,4]-triazole-3-yl-sulfanyl)-N-(thiazole-2-yl)-2-pyridine carboxamide Compound of Production Example 45 can be produced by the same method as Production Example 1, by a method according thereto, or by a combination of these and ordinary methods, with the use of 3,6-dichloro-2-pyridinecarboxylic acid, 2-amino-thiazole, 4-(1-hydroxyethyl)thiophenol and 3-mercapto-1,2,4-triazole.

$^1$HNMR (CDCl$_3$)

δ: 1.52 (3H, d, J=6.4 Hz), 4.97 (1H, q, J=6.4 Hz), 7.03 (1H, d, J=8.4 Hz), 7.06 (1H, d, J=3.6 Hz), 7.18 (1H, d, J=8.4 Hz), 7.47 (2H, d, J=8.0 Hz), 7.48 (1H, d, J=3.6 Hz), 7.52 (2H, d, J=8.0 Hz), 8.34 (1H, s)

ESI-MS (m/e): 457[M+H]

PRODUCTION EXAMPLE 46

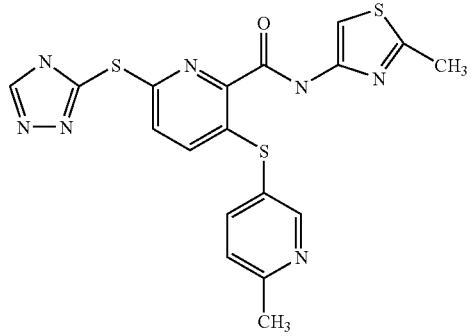

Manufacture of 3-(6-methyl-pyridine-3-yl-sulfanyl)-6-(4H-[1,2,4]triazole-3-yl-sulfanyl)-N-(2-methyl-thiazole-4-yl)-2-pyridine carboxamide Compound of Production Example 46 can be produced by the same method as Production Example 1, by a method according thereto, or by a combination of these and ordinary methods, with the use of 3,6-dichloro-2-pyridinecarboxylic acid, 2-amino-4-methylthiazole, 3-mercapto-6-methyl-pyridine and 3-mercapto-1,2,4-triazole.

$^1$HNMR (CDCl$_3$)

δ: 2.63 (3H, s), 2.72 (3H, s), 6.96 (1H, d, J=8.4 Hz), 7.19 (1H, d, J=8.1 Hz), 7.27 (1H, d, J=8.4 Hz), 7.68 (1H, s), 7.76 (1H, dd, J=8.4, 2.2 Hz), 8.26 (1H, s), 8.59 (1H, d, J=2.2 Hz)

ESI-MS (m/e): 442[M+H]$^+$

PRODUCTION EXAMPLE 47

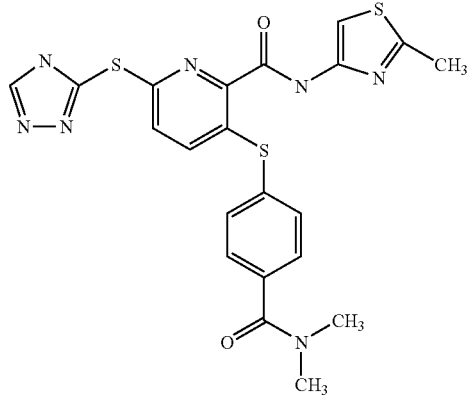

Manufacture of 3-(4-dimethylcarbamoyl-phenylsulfanyl)-6-(4H-[1,2,4]triazole-3-yl-sulfanyl)-N-(2-methyl-thiazole-4-yl)-2-pyridine carboxamide Compound of Production Example 47 can be produced by the same method as Production Example 1, by a method according thereto, or by a combination of these and ordinary methods, with the use of 3,6-dichloro-2-pyridinecarboxylic acid, 2-amino-4-methylthiazole, 4-dimethylcarbamoylthiophenol and 3-mercapto-1,2,4-triazole.

$^1$HNMR (CDCl$_3$)

δ: 2.69 (3H, s), 3.00 (3H, s), 3.14 (3H, s), 6.95 (1H, d, J=8.8 Hz), 7.11 (1H, d, J=8.8 Hz), 7.45 (2H, d, J=8.1 Hz), 7.56 (2H, d, J=8.1 Hz), 7.64 (1H, s), 8.29 (1H, s)

ESI-MS (m/e): 498[M+H]$^+$

PRODUCTION EXAMPLE 48

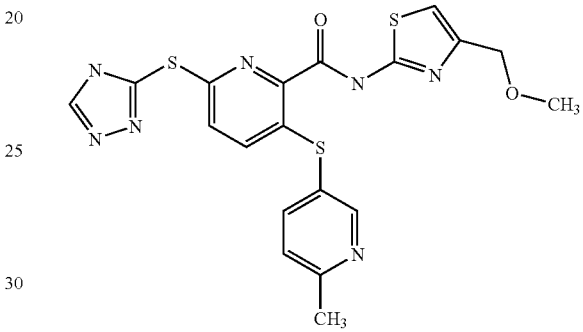

Manufacture of 3-(6-methyl-pyridine-3-yl-sulfanyl)-6-(4H-[1,2,4]triazole-3-yl-sulfanyl)-N-(4-methoxymethyl-thiazole-2-yl)-2-pyridine carboxamide Compound of Production Example 48 can be produced by the same method as Production Example 1, by a method according thereto, or by a combination of these and ordinary methods, with the use of 3,6-dichloro-2-pyridinecarboxylic acid, 2-amino-4-methoxymethyl-thiazole, 3-mercapto-6-methyl-pyridine and 3-mercapto-1,2,4-triazole.

$^1$HNMR (CDCl$_3$)

δ: 2.62 (3H, s), 3.44 (3H, s), 4.51 (2H, s), 6.91 (1H, s), 6.93 (1H, d, J=8.4 Hz), 7.19 (1H, d, J=8.4 Hz), 7.26 (1H, d, J=8.0 Hz), 7.77 (1H, dd, J=8.0 Hz, 2.4 Hz), 8.35 (1H, s), 8.61 (1H, d, J=2.4 Hz)

ESI-MS (m/e): 472[M+H]

PRODUCTION EXAMPLE 49

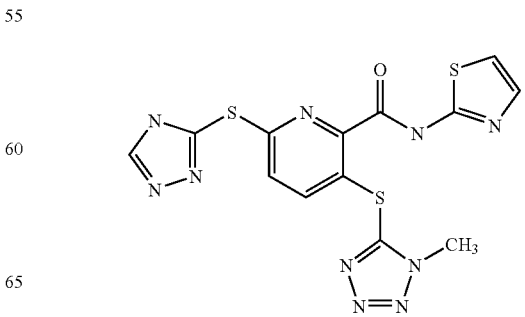

Manufacture of 3-(1-methyl-1H-tetrazole-5-yl-sulfanyl)-6-(4H-[1,2,4]triazole-3-yl-sulfanyl)-N-(thiazole-2-yl)-2-pyridine carboxamide Compound of Production Example 49 can be produced by the same method as Production Example 1, by a method according thereto, or by a combination of these and ordinary methods, with the use of 3,6-dichloro-2-pyridinecarboxylic acid, 2-amino-thiazole, 5-mercapto-1-methyl-1,2,4-triazole and 3-mercapto-1,2,4-triazole.

$^1$HNMR (CDCl$_3$) δ: 4.11 (3H, s), 7.11 (1H, d, J=3.2 Hz), 7.32 (1H, d, J=8.8 Hz), 7.36 (1H, d, J=8.8 Hz), 7.52 (1H, d, J=3.2 Hz), 8.42 (1H, s)

ESI-MS (m/e): 419[M+H]

PRODUCTION EXAMPLE 50

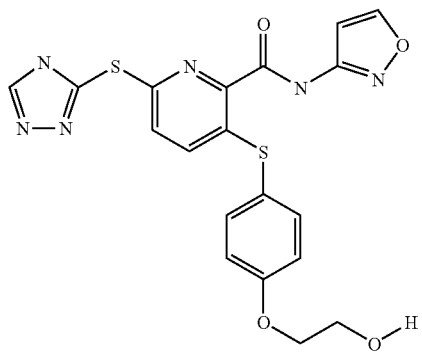

Manufacture of 3-(4-hydroxyethyloxy-phenylsulfanyl)-6-(4H-[1,2,4]triazole-3-yl-sulfanyl)-N-(isoxazole-3-yl)-2-pyridine carboxamide Compound of Production Example 50 can be produced by the same method as Production Example 1, by a method according thereto, or by a combination of these and ordinary methods, with the use of 3,6-dichloro-2-pyridinecarboxylic acid, 3-aminooxazole, 4-hydroxyethylthiophenol and 3-mercapto-1,2,4-triazole.

$^1$HNMR (CDCl$_3$)
δ: 3.91 (2H, t, J=4.6 Hz), 4.05 (2H, t, J=4.6 Hz), 6.91 (1H, d, J=8.8 Hz), 6.92 (2H, d, J=8.4 Hz), 7.11 (1H, d, J=8.8 Hz), 7.22 (1H, d, J=1.5 Hz), 7.39 (2H, d, J=8.4 Hz), 8.25 (1H, d, J=1.5 Hz), 8.29 (1H, s)

ESI-MS (m/e): 457[M+H]$^+$

PRODUCTION EXAMPLE 51

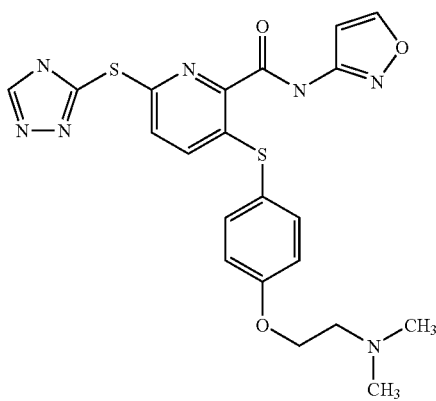

Manufacture of 3-(4-dimethylaminoethyloxy-phenylsulfanyl)-6-(4H-[1,2,4]triazole-3-yl-sulfanyl)-N-(isoxazole-3-yl)-2-pyridine carboxamide Compound of Production Example 51 can be produced by the same method as Production Example 1, by a method according thereto, or by a combination of these and ordinary methods, with the use of 3,6-dichloro-2-pyridinecarboxylic acid, 3-amino-oxazole, 4-dimethylaminoethyloxy-thiophenol and 3-mercapto-1,2,4-triazole.

$^1$HNMR (CDCl$_3$)

δ: 2.43 (6H, s), 2.85 (2H, t, J=5.5 Hz), 4.12 (2H, t, J=5.5 Hz), 6.90 (2H, d, J=8.8 Hz), 6.93 (1H, d, J=8.8 Hz), 7.15 (1H d, J=8.8 Hz), 7.24 (1H, s), 7.38 (2H, d, J=8.8 Hz), 8.30 (1H, s), 8.38 (1H, s)

ESI-MS (m/e): 484[M+H]$^+$

PRODUCTION EXAMPLE 52

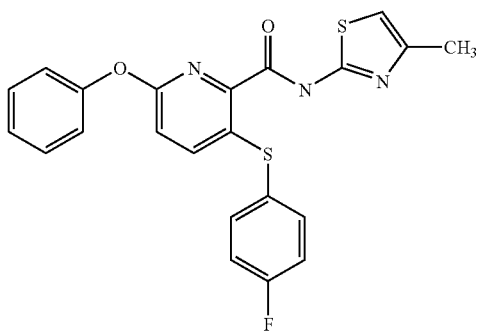

Manufacture of 3-(4-fluoro-phenylsulfanyl)-6-phenoxy-N-(4-methyl-thiazole-2-yl)-2-pyridine carboxamide Phenol (135 mg; 1.43 mmol) and 540 mg (1.66 mol) of cesium carbonate were added to a solution (3 ml) of 84 mg (0.292 mmol) of 3,6-dichloro-N-(4-methyl-thiazole-2-yl)-2-pyridine carboxamide in N,N-dimethylformamide followed by stirring at 120° C. for 24 hours. Aqueous solution (1N) of sodium hydroxide was added to the reaction solution followed by extracting with ethyl acetate. The organic layer was washed with water and a saturated aqueous saline solution, dried and concentrated in vacuo. The resulting residue was purified by a thin-layer silica gel chromatography (hexane:ethyl acetate=4:1) to give 61 mg (yield: 61%) of 3-chloro-6-phenoxy-N-(4-methyl-thiazole-2-yl)-2-pyridine carboxamide as a white solid.

Potassium carbonate (80 mg; 0.579 mmol) and 20 µl (0.188 mmol) of 4-fluorothiophenol were added to a solution (2 ml) of the resulting 3-chloro derivative in N,N-dimethylformamide followed by stirring at 100° C. for 16 hours. Water was added to the reaction solution followed by extracting with ethyl acetate and washing with a saturated aqueous saline solution. After drying and concentrating, the resulting residue was purified by a thin-layer silica gel chromatography (hexane:ethyl acetate=4:1) to give 11 mg (yield: 32%) of the title compound as a white solid.

¹H-NMR (CDCl₃) δ: 2.37 (3H, s), 6.58 (1H, s), 6.90 (1H, d, J=9.0 Hz), 7.10-7.23 (6H, m), 7.46 (1H, d, J=7.8, 7.8 Hz), 7.62 (2H, m)

ESI-MS (m/e): 438 [M+H]⁺

Compound of Production Example 53 was obtained by the same method as the above Production Example 52. Analytical data of those compounds are shown hereunder.

PRODUCTION EXAMPLE 53

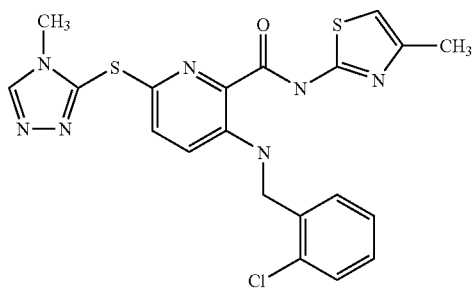

Manufacture of 3-(2-chloro-phenylmethyl-amino)-6-amino-(4-methyl-4H-[1,2,4]triazole-3-yl-sulfanyl)-N-(4-methyl-thiazole-2-yl)-2-pyridine carboxamide Compound of Production Example 53 can be produced by the same method as Production Example 1, by a method according thereto, or by a combination of these and ordinary methods, with the use of 3,6-dichloro-N-(4-methyl-thiazole-2-yl)-2-pyridine carboxamide, 2-chloro-benzylamine and 3-mercapto-4-methyl-1,2,4-triazole.

¹H-NMR(CDCl₃) δ: 2.41 (3H, s), 3.73 (3H, s), 4.55 (2H, d, J=6.0 Hz), 6.58 (1H, s), 6.92 (1H, d, J=9.3 Hz), 7.20-7.45 (5H, m), 8.32 (1H, s), 8.72 (1H, m)

ESI-MS (m/e): 472, 474[M+H]⁺

PRODUCTION EXAMPLE 54

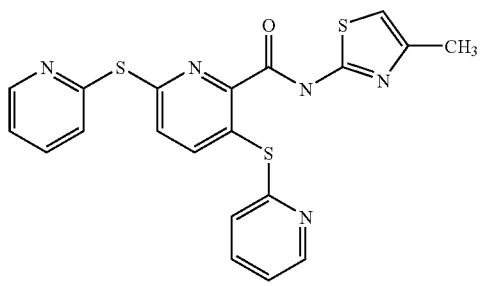

Manufacture of 3,6-bis-(pyridine-2-yl-sulfanyl)-N-(4-methyl-thiazole-2-yl)-2-pyridine carboxamide 2-Mercaptopyridine (24 mg; 0.205 mmol) and 68 g (0.492 mmol) of potassium carbonate were added to a solution (2 ml) of 3,6-dichloro-N-(4-methyl-thiazole-2-yl)-2-pyridine carboxamide produced by the same method as in Production Example 1 in N,N-dimethylformamide followed by stirring at 100° C. for 15 hours. Water was added to the reaction solution followed by extracting with ethyl acetate and washing with a saturated aqueous saline solution. After drying and concentrating, the resulting residue was purified by a thin-layer silica gel chromatography (chloroform:methanol=20:1) to give 15 mg (yield: 23%) of the title compound as a yellow solid.

¹H-NMR (CDCl₃) δ: 2.39 (3H, s), 6.58 (1H, s), 7.20-7.30 (2H, m), 7.40 (1H, d, J=8.6 Hz), 7.46 (1H, br, d, J=8.1 Hz), 7.52-7.75 (4H, m), 8.55-8.65 (2H, m)

ESI-MS (m/e): 438 [M+H]⁺

Compounds of Production Examples 55 to 57 were produced by the same method as in the above Production Example 54. Analytical data of those compounds are shown hereunder.

PRODUCTION EXAMPLE 55

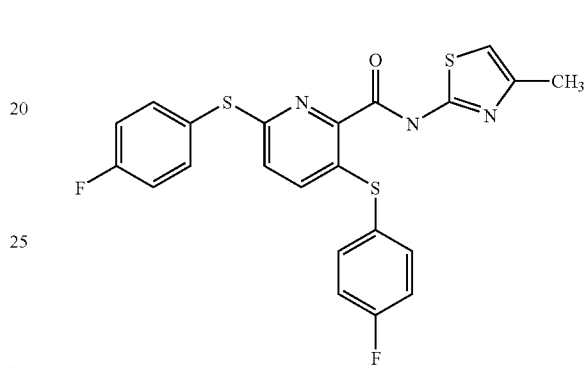

Manufacture of 3-6-bis-(4-fluoro-phenylsulfanyl)-N-(4-methyl-thiazole-2-yl)-2-pyridine carboxamide Compound of Production Example 55 can be produced by the same method as Production Example 1, by a method according thereto, or by a combination of these and ordinary methods, with the use of 3,6-dichloro-N-(4-methyl-thiazole-2-yl)-2-pyridine carboxamide, and 4-fluorothiophenol.

¹HNMR (CDCl₃) δ: 2.41 (3H, s), 6.59 (1H, s), 6.77 (1H, d, J=9.0 Hz), 6.88 (1H, d, J=9.0 Hz), 7.09-7.20 (4H, m), 7.49-7.60 (4H, m)

ESI-MS (m/e): 472[M+H]⁺

PRODUCTION EXAMPLE 56

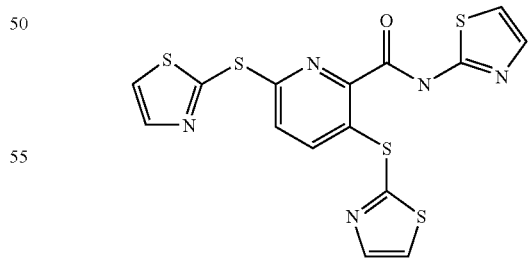

Manufacture of 3-6-bis-(thiazole-2-yl-sufanyl)-N-(thiazole-2-yl)-2-pyridine carboxamide Compound of Production Example 56 can be produced by the same method as Production Example 1, by a method according thereto, or by a combination of these and ordinary methods, with the use of 3,6-dichloro-N-(4-methyl-thiazole-2-yl)-2-pyridine carboxamide, and 2-mercapto-thiazole.

¹HNMR (CDCl₃)

δ: 7.06 (1H, d, J=3.6 Hz), 7.27 (1H, d, J=8.8 Hz), 7.37 (1H, d, J=8.8 Hz), 7.54 (1H, d, J=3.6 Hz), 7.59 (1H, d, J=3.6 Hz), 7.61 (1H, d, J=3.6 Hz), 7.98 (1H, d, J=3.6 Hz), 8.02 (1H, d, J=3.6 Hz)

ESI-MS (m/e): 436[M+H]⁺

PRODUCTION EXAMPLE 57

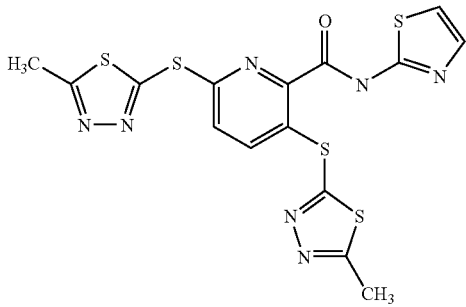

Manufacture of 3-6-bis-(5-methyl-[1,3,4]thiadiazole-2-yl-sufanyl)-N-(thiazole-2-yl)-2-pyridine carboxamide Compound of Production Example 57 can be produced by the same method as Production Example 1, by a method according thereto, or by a combination of these and ordinary methods, with the use of 3,6-dichloro-N-(4-methyl-thiazole-2-yl)-2-pyridine carboxamide, and 2-mercapto-5-methyl-1,3,4-thiazole.

¹HNMR (CDCl₃)

δ: 2.86 (3H, s), 2.91 (3H, s), 7.07 (1H, d, J=3.6 Hz), 7.44 (1H, d, J=8.8 Hz), 7.52 (1H, d, J=3.6 Hz), 7.64 (1H, d, J=8.8 Hz)

ESI-MS (m/e): 466[M+H]⁺

PRODUCTION EXAMPLE 58

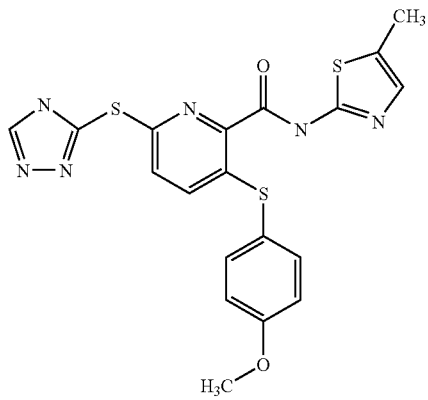

Manufacture of 3-(4-methoxy-phenylsulfanyl)-6-(4H-[1,2,4]triazole-3-yl-sulfanyl)-N-(5-methyl-thiazole-2-yl)-2-pyridine carboxamide Concentrated sulfuric acid (0.441 ml; 8.27 mmol) was dropped into a suspension (35 ml) of 3.86 g (32.2 mmol) of magnesium sulfate in dichloromethane and, after completion of the dropping, the mixture was stirred at room temperature for 20 minutes. After that, 750 mg (3.91 mmol) of 3,6-dichloro-2-pyridinecarboxylic acid and dichloromethane (10 ml) solution of 3.84 ml (40.2 mmol) of tert-butyl alcohol were added to the reaction solution at room temperature followed by stirring rapidly at room temperature for 15 hours. Under ice-cooling, an aqueous solution (40 ml) of 3.0 g of sodium carbonate was dropped thereinto followed by stirring until the reaction solution became a homogeneous solution. The reaction solution was extracted with chloroform and the organic layer was washed with a saturated aqueous saline solution, dried and concentrated in vacuo. The resulting residue was purified by a silica gel column chromatography (hexane:ethyl acetate=97:3) to give 644 mg (yield: 66%) of tert-butyl 3,6-dichloro-2-pyridinecarboxylate as a white solid.

4-Methoxythiophenol (0.927 ml; 7.55 mmol) and 1.14 g (8.26 mmol) of potassium carbonate were added, at room temperature, to a solution (70 ml) of 1.70 g (6.86 mmol) of the resulting ester compound in N,N-dimethylformamide followed by stirring for 1 hour. Chloroform was added to the reaction solution followed by washing with a saturated aqueous solution of sodium hydrogen carbonate and a saturated aqueous saline solution, drying and concentrating in vacuo. The resulting residue was purified by a silica gel column chromatography (hexane:ethyl acetate=9:1) to give 743 mg (yield: 31%) of tert-butyl 6-chloro-3-(4-methoxy-phenylsulfanyl)-2-pyridinecarboxylate as a colorless oily substance.

3-mercapto-1,2,4-triazole (258 mg; 2.55 mmol) and 353 mg (2.56 mmol) of potassium carbonate were added, at room temperature, to a solution (30 ml) of 451 mg (1.28 mmol) of the resulting chloro compound in N,N-dimethylformamide and the reaction solution was stirred at 130° C. for 10 hours. Chloroform was added to the reaction solution followed by washing with a saturated aqueous solution of sodium hydrogen carbonate and a saturated aqueous saline solution, drying and concentrating in vacuo. The resulting residue was purified by a silica gel column chromatography (hexane:ethyl acetate=2:1) to give 264 mg (yield: 49%) of tert-butyl 3-(4-methoxy-phenylsulfanyl)-6-(4H-[1,2,4]triazole-3-yl-sulfanyl)-2-pyridinecarboxylate as a colorless oily substance.

Trifluoroacetic acid (2.0 ml) was added, at room temperature, to a solution (5.0 ml) of 264 mg (0.633 mmol) of the resulting ester compound in dichloromethane and the reaction solution was stirred at room temperature for 1.5 hours. The reaction solution was concentrated in vacuo to give 228 mg of 3-(4-methoxy-phenylsulfanyl)-6-(4H-[1,2,4]triazole-3-yl-sulfanyl)-2-pyridinecarboxylic acid as a light yellow solid.

5-Methylaminothiazole (3.2 mg; 29 μmol), 3.8 mg (27 μmol) of N-hydroxybenzotriazole hydrate and 5.4 mg (28 μmol) of 1-(3-dimethylaminoproyl)-3-ethylcarbodiimide hydrochloride were successively added, at room temperature, to a solution (1.0 ml) of 5.9 mg (16 μmol) of the resulting carboxylic acid compound in dichloromethane and the reaction solution was stirred at room temperature for 3 hours. To the reaction solution was added a saturated aqueous solution of sodium hydrogen carbonate followed by extracting with chloroform. The organic layer was washed with a saturated aqueous saline solution, dried and concentrated in vacuo. The resulting residue was purified by a silica gel column chromatography (chloroform:methanol=95:5) to give 2.0 m g (yield: 15%) of the title compound as a light yellow solid.

¹HNMR (CDCl₃) δ: 2.43 (3H, s), 3.86 (3H, s), 6.98 (2H, d, J=8.4 Hz), 6.99 (1H, d, J=8.4 Hz), 7.09 (1H, s), 7.19 (1H, d, J=8.4 Hz), 7.47 (2 H, d, J=8.4 Hz), 8.32 (1H, s)

ESI-MS (m/e): 457[M+H]⁺

Compounds of Production Examples 59 to 65 were obtained by the same method as in the above Production Example 58. Analytical data of those compounds are shown hereunder.

PRODUCTION EXAMPLE 59

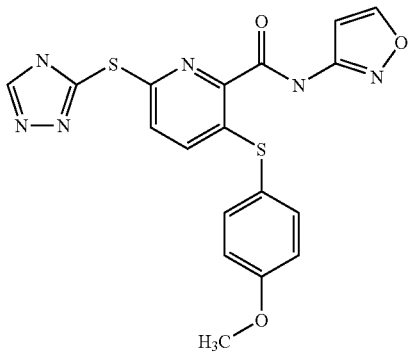

Manufacture of 3-(4-methoxy-phenylsulfanyl)-6-(4H-[1,2,4]triazole-3-yl-sulfanyl)-N-(isoxazole-3-yl)-2-pyridine carboxamide Compound of Production Example 59 can be produced by the same method as Production Example 58, by a method according thereto, or by a combination of these and ordinary methods, with the use of 3,6-dichloro-2-pyridine carboxamide, 4-methoxythiophenol, 3-mercapto-1,2,4-triazole and 3-amino-isoxazole.

$^1$HNMR (CDCl$_3$)

δ: 3.86 (3H, s), 6.98 (2H, d, J=8.4 Hz), 6.99 (1H, d, J=8.4 Hz), 7.19 (1H, d, J=8.4 Hz), 7.30 (1H, s), 7.47 (2H, d, J=8.4 Hz), 8.31 (1H, s), 8.41 (1H, s)

ESI-MS (m/e): 427[M+H]$^+$

PRODUCTION EXAMPLE 60

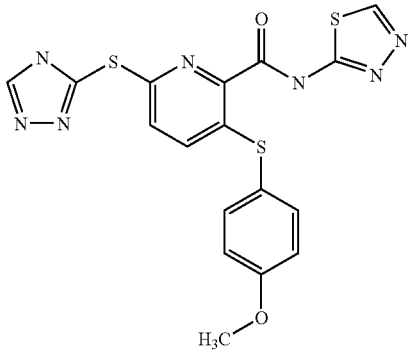

Manufacture of 3-(4-methoxy-phenylsulfanyl)-6-(4H-[1,2,4]triazole-3-yl-sulfanyl)-N-([1,3,4]thiadiazole-2-yl)-2-pyridine carboxamide Compound of Production Example 60 can be produced by the same method as Production Example 58, by a method according thereto, or by a combination of these and ordinary methods, with the use of 3,6-dichloro-2-pyridine carboxamide, 4-methoxythiophenol, 3-mercapto-1,2,4-triazole and 2-amino-1,3,4-thiadiazole.

$^1$HNMR (CDCl$_3$)

δ: 3.86 (3H, s), 6.99 (2H, d, J=8.5 Hz), 7.03 (1H, d, J=8.4 Hz), 7.23 (1H, d, J=8.4 Hz), 7.47 (2H, d, J=8.5 Hz), 8.45 (1H, s), 8.85 (1H, s)

ESI-MS (m/e): 444[M+H]$^+$

PRODUCTION EXAMPLE 61

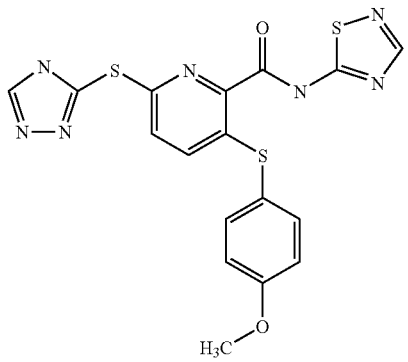

Manufacture of 3-(4-methoxy-phenylsulfanyl)-6-(4H-[1,2,4]triazole-3-yl-sulfanyl)-N-([1,2,4]-thiadiazole-5-yl)-2-pyridine carboxamide Compound of Production Example 61 can be produced by the same method as Production Example 58, by a method according thereto, or by a combination of these and ordinary methods, with the use of 3,6-dichloro-2-pyridine carboxamide, 4-methoxythiophenol, 3-mercapto-1,2,4-triazole and 5-amino-1,2,4-thiadiazole.

$^1$HNMR (CDCl$_3$)

δ: 3.87 (3H, s), 7.00 (2H, d, J=8.4 Hz), 7.01 (1H, d, J=8.4 Hz), 7.20 (1H, d, J=8.4 Hz), 7.48 (2H, d, J=8.5 Hz), 7.80 (1H, s), 8.36 (1H, s)

ESI-MS (m/e): 444[M+H]$^+$

PRODUCTION EXAMPLE 62

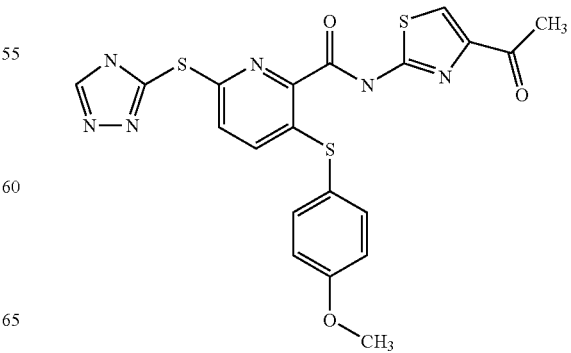

Manufacture of 3-(4-methoxy-phenylsulfanyl)-6-(4H-[1,2,4]triazole-3-yl-sulfanyl)-N-(4-methylcarbonyl-thiazole-2-yl)-2-pyridine carboxamide Compound of Production Example 62 can be produced by the same method as Production Example 58, by a method according thereto, or by a combination of these and ordinary methods, with the use of 3,6-dichloro-2-pyridine carboxamide, 4-methoxythiophenol, 3-mercapto-1,2,4-triazole and 4-acetyl-2-amino-thiazole.

$^1$HNMR (CDCl$_3$)

δ: 2.63 (3H, s), 3.86 (3H, s), 6.98 (1H, d, J=8.8 Hz), 7.01 (2H, d, J=8.8 Hz), 7.22 (1H, d, J=8.8 Hz), 7.46 (2H, d, J=8.8 Hz), 7.86 (1H, s), 8.33 (1H, s)

ESI-MS (m/e): 485[M+H]$^+$

PRODUCTION EXAMPLE 63

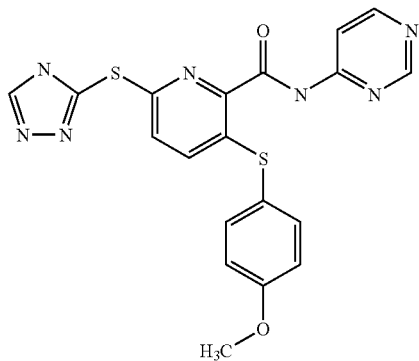

Manufacture of 3-(4-methoxy-phenylsulfanyl)-6-(4H-[1,2,4]triazole-3-yl-sulfanyl)-N-(pyrimidine-4-yl)-2-pyridine carboxamide Compound of Production Example 63 can be produced by the same method as Production Example 58, by a method according thereto, or by a combination of these and ordinary methods, with the use of 3,6-dichloro-2-pyridine carboxamide, 4-methoxythiophenol, 3-mercapto-1,2,4-triazole and 4-amino-pyrimidine.

$^1$HNMR (CDCl$_3$)

δ: 3.86 (3H, s), 6.98 (2H, d, J=8.8 Hz), 7.02 (1H, d, J=8.4 Hz), 7.22 (1H, d, J=8.4 Hz), 7.46 (2H, d, J=8.8 Hz), 8.38 (1H, dd, J=5.9, 0.8 Hz), 8.41 (1H, s), 8.65 (1H, d, J=5.9 Hz), 8.93 (1H, d, J=0.8 Hz)

ESI-MS (m/e): 438[M+H]$^+$

PRODUCTION EXAMPLE 64

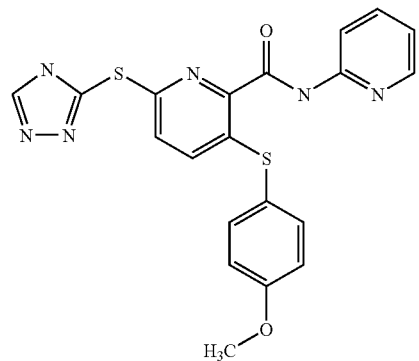

Manufacture of 3-(4-methoxy-phenylsulfanyl)-6-(4H-[1,2,4]triazole-3-yl-sulfanyl)-N-(pyridine-2-yl)-2-pyridine carboxamide Compound of Production Example 64 can be produced by the same method as Production Example 58, by a method according thereto, or by a combination of these and ordinary methods, with the use of 3,6-dichloro-2-pyridine carboxamide, 4-methoxythiophenol, 3-mercapto-1,2,4-triazole and 2-amino-pyridine.

$^1$HNMR (CDCl$_3$)

δ: 3.85 (3H, s), 6.97 (2H, d, J=8.8 Hz), 6.99 (1H, d, J=8.8 Hz), 7.05 (1H, dd, J=8.5, 4.5 Hz), 7.18 (1H, d, J=8.8 Hz), 7.46 (2H, d, J=8.8 Hz), 7.73 (1H, ddd, J=8.5, 8.5, 1.5 Hz), 8.29 (1H, dd, J=4.5, 1.5 Hz), 8.31 (1H, s), 8.41 (1H, d, J=8.5 Hz)

ESI-MS (m/e): 437[M+H]$^+$

PRODUCTION EXAMPLE 65

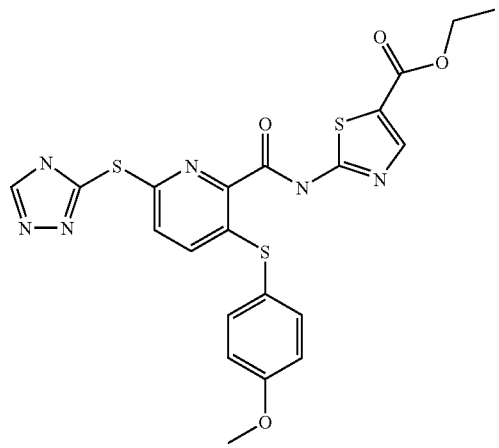

Manufacture of 3-(4-methoxy-phenylsulfanyl)-6-(4H-[1,2,4]triazole-3-yl-sulfanyl)-N-(5-etoxycarbonyl-thiazole-2-yl)-2-pyridine carboxamide Compound of Production Example 65 can be produced by the same method as Production Example 58, by a method according thereto, or by a combination of these and ordinary methods, with the use of 3,6-dichloro-2-pyridine carboxamide, 4-methoxythiophenol, 3-mercapto-1,2,4-triazole and 2-amino-5-etoxycarbonyl-thiazole.

$^1$HNMR (CDCl$_3$) δ: 1.37 (3H, t, J=7.0 Hz), 3.86 (3H, s), 4.34 (2H, q, J=7.0 Hz), 6.98 (2H, d, J=8.8 Hz), 7.00 (1H, d, J=8.5 Hz), 7.20 (1H, d, J=8.5 Hz), 7.46 (2H, d, J=8.8 Hz), 8.11 (1H, s), 8.36 (1H, s)

ESI-MS (m/e): 515[M+H]$^+$

PRODUCTION EXAMPLE 66

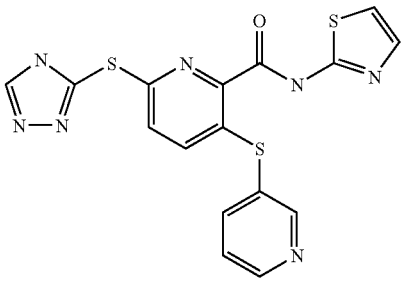

Manufacture of 3-(pyridine-3-yl-sulfanyl)-6-(4H-[1,2,4]triazole-3-yl-sulfanyl)-N-(thiazole-2-yl)-2-pyridine carboxamide Anisole (0.40 ml; 0.390 mmol) and 5 ml of trifluoroacetic acid were added to 152 mg (0.390 mmol) of 6-chloro-3-(4-methoxy-phenylmethylsulfanyl)-N-(thiazole-2-yl)-2-pyridine carboxamide produced by the same method as Production Example 1 and the reaction solution was stirred at 60° C. for 5 hours and stirred for one night thereafter at room temperature. The reaction solution was concentrated in vacuo to give a 3-thiol derivative as an orange-colored oily substance.

To a solution (3 ml) of the above-produced 3-thiol derivative in 2-propanol were added 62 μl (1.10 mmol) of ethylene glycol, 141 mg (1.02 mmol) of potassium carbonate, 114 mg (0.560 mmol) of 3-iodopyridine and 5.3 mg (0.030 mmol) of copper iodide and the reaction solution was stirred at 80° C. for one night. The reaction solution was filtered through Celite and the filtrate was partitioned by chloroform and water. The organic layer was washed with water, dried and concentrated in vacuo. The resulting residue was purified by a thin-layer silica gel chromatography (hexane:ethyl acetate=1:1) to give 28 mg (yield: 21%) of a 6-chloro derivative as a light yellow solid.

After 22 mg (0.22 mmol) of 3-mercapto-1,2,4-triazole were added to a solution (1 ml) of 25 mg (0.22 mmol) of potassium tert-butoxide in N,N-dimethylformamide, a solution (3 ml) of 28 mg (0.080 mmol) of the above-produced 6-chloro derivative in N,N-dimethylformamide was dropped thereinto and, after completion of the dropping, the reaction solution was stirred at 120° C. for 2 hours. Water was added to the reaction solution followed by extracting with chloroform. The organic layer was washed with water, dried and concentrated in vacuo. The resulting residue was purified by a thin-layer silica gel chromatography (chloroform:methanol=9:1) to give 12 mg (yield: 37%) of the title compound as a light yellow solid.

$^1$HNMR (CDCl$_3$) δ: 6.96 (1H, d, J=8.8 Hz), 7.05 (1H, d, J=3.6 Hz), 7.22 (1H, d, J=8.8 Hz), 7.40-7.43 (1H, m), 7.47 (1H, d, J=3.6 Hz), 7.87-7.90 (1H, m), 8.32 (1H, s), 8.64-8.66 (1H, m), 8.70-8.71 (1H, m)

ESI-MS (m/e): 414[M+H]$^+$

Compounds of Production Examples 67 and 68 were obtained by the same method as the above Production Example 66. Analytical data of those compounds are shown hereunder.

PRODUCTION EXAMPLE 67

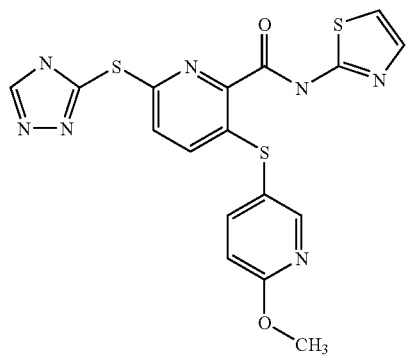

Manufacture of 3-(6-methoxy-pyridine-3-yl-sulfanyl)-6-(4H-[1,2,4]triazole-3-yl-sulfanyl)-N-(thiazole-2-yl)-2-pyridine carboxamide Compound of Production Example 67 can be produced by the same method as Production Example 66, by a method according thereto, or by a combination of these and ordinary methods, with the use of 6-chloro-3-(4-methoxy-phenylmethylsulfanyl)-N-(thiazole-2-yl)-2-pyridine carboxamide, 6-methoxy-3-iodopyridine and 3-mercapto-1,2,4-triazole.

$^1$HNMR (CDCl$_3$) δ: 4.00 (3H, s), 6.87 (1H, d, J=8.7 Hz), 7.00-7.11 (2H, m), 7.26 (1H, d, J=8.4 Hz), 7.46 (1H, d, J=3.3 Hz), 7.77 (1H, dd, J=2.4, 8.7 Hz), 8.35 (1H, d, J=2.4 Hz), 8.38 (1H, s)

ESI-MS (m/e): 444[M+H]$^+$

PRODUCTION EXAMPLE 68

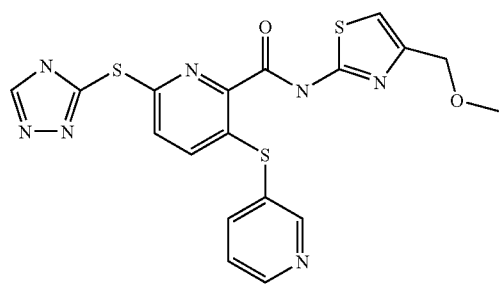

Manufacture of 3-(pyridine-3-yl-sulfanyl)-6-(4H-[1,2,4]triazole-3-yl-sulfanyl)-N-(4-methoxymethyl-thiazole-2-yl)-2-pyridine carboxamide Compound of Production Example 68 can be produced by the same method as Production Example, by a method according thereto, or by a combination of these and ordinary methods, with the use of 3,6-dichloro-N-(4-methoxy-phenylmethylsulfanyl)-N-(4-methoxymethyl-thiazole-2-yl)-2-pyridine carboxamide, 3-iodopyridine and 3-mercapto-1,2,4-triazole which can be obtained by the same method as Production Example 1.

$^1$HNMR (CDCl$_3$)

δ: 3.49 (3H, s), 4.56 (2H, s), 6.94 (1H, s), 6.97 (1H, d, J=8.8 Hz), 7.27 (1H, d, J=8.8 Hz), 7.43 (1H, dd, J=7.6 Hz, 3.3 Hz) 7.93 (1H, d, J=7.6 Hz), 8.38 (1H, s), 8.71 (1H, d, J=4.8 Hz), 8.77 (1H, s)

ESI-MS (m/e): 458[M+H]$^+$

PRODUCTION EXAMPLE 69

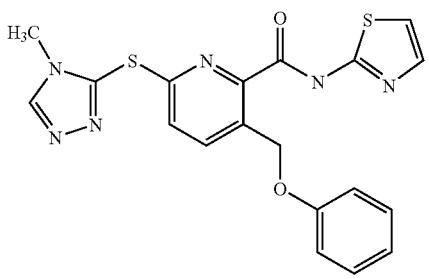

Manufacture of 3-phenyloxymethyl-6-(4-methyl-4H-[1,2,4]triazole-3-yl-sulfanyl)-N-(thiazole-2-yl)-2-pyridine carboxamide 3-Chloroperbenzoic acid (6.30 g; 21.0 mmol) was added to a solution (50 ml) of 3.50 g (14.0 mmol) of 2-cyano-3-tert-butyldimethylsilyloxymethylpyridine in chloroform followed by heating to reflux for one night. A saturated aqueous solution of sodium hydrogen carbonate was added to the reaction solution followed by extracting with chloroform and the organic layer was washed with water, a saturated aqueous solution of sodium hydrogen carbonate and a saturated aqueous saline solution followed by drying and concentrating. The resulting residue was purified by a silica gel column chromatography (hexane:ethyl acetate=2:1) to give 1.50 g (yield: 41%) of an N-oxide as a white solid.

A solution (10 ml) of 1.50 g (5.70 mmol) of the resulting N-oxide substance in phosphorus oxychloride was stirred at 80° C. for 1 hour. The reaction solution was concentrated in vacuo, a saturated aqueous solution of sodium hydrogen carbonate was added to the residue followed by extracting with chloroform and the organic layer was washed with a saturated aqueous solution of sodium hydrogen carbonate and a saturated aqueous saline solution. After drying and concentrating, the resulting residue was purified by a silica gel column chromatography (hexane:ethyl acetate=2:1) to give 625 mg (yield: 58%) of 2-chloro-5-chloromethyl-6-cyanopyridine as a white solid. Phenol (30 mg; 0.32 mmol) and 44 mg (0.32 mmol) of sodium hydrogen carbonate were added to a solution (5 ml) of 50 mg (0.27 mmol) of 2-chloro-5-chloromethyl-6-cyanopyridine in acetonitrile followed by stirring at room temperature for 8 hours and 30 minutes. Water was added to the reaction solution followed by extracting with ethyl acetate. The organic layer was washed with a saturated aqueous saline solution, dried and concentrated in vacuo and the resulting residue was purified by a thin-layer column chromatography (hexane:ethyl acetate=6:1) to give 61 mg (yield: 93%) of 2-chloro-6-cyano-5-phenoxymethylpyridine as a white solid.

3-mercapto-4-methyl-4H-1,2,4-triazole (44 mg; 0.380 mmol) and 52 mg (0.380 mmol) of potassium carbonate were added to a solution (5 ml) of 61 mg (0.249 mmol) of the resulting 2-chloro-6-cyano-5-phenoxymethylpyridine in N,N-dimethylformamide followed by stirring at 100° C. for one night. Water was added to the reaction solution followed by extracting with ethyl acetate and the organic layer was washed with water, a saturated aqueous solution of sodium hydrogen carbonate and a saturated aqueous saline solution. After drying and concentrating, the resulting residue was purified by a thin-layer column chromatography (chloroform:methanol=10:1) to give 4.4 mg (yield: 5%) of a thiotriazole derivative.

A 1N aqueous solution (0.5 ml) of sodium hydroxide was added to an ethanolic solution (5 ml) of 4.4 mg (0.014 mmol) of the resulting thiotriazole derivative followed by heating to reflux for one night. To the reaction solution was added a 1N aqueous solution of hydrochloric acid to acidify followed by extracting with ethyl acetate and the organic layer was washed with a saturated aqueous saline solution. After drying and concentrating, 3 mg (0.028 mmol) of 2-aminothiazole, 4 mg (0.030 mmol) of N-hydroxybenzotriazole hydrate and 6 mg (0.030 mmol) of 1-(3-dimethylaminopropyl)-3-ethylcarbodiimide hydrochloride were successively added to a solution (3 ml) of the resulting residue in methylene chloride followed by stirring at room temperature for one night. To the reaction solution was added a saturated aqueous solution of sodium hydrogen carbonate followed by extracting with chloroform and the organic layer was washed with water, a saturated aqueous solution of sodium hydrogen carbonate and a saturated aqueous saline solution. After drying and concentrating, the resulting residue was purified by a thin-layer silica gel chromatography (chloroform:methanol=10:1) to give 2.8 mg (yield: 47%) of the title compound as a white solid.

$^1$HNMR (CDCl$_3$) δ: 3.79 (3H, s), 5.71 (2H, s), 6.97-7.02 (3H, m), 7.05 (1H, d, J=3.6 Hz), 7.30 (2H, t, J=7.6 Hz), 7.40 (1H, d, J=8.4 Hz), 7.54 (1H, d, J=3.6 Hz), 8.22 (1H, d, J=8.4 Hz), 8.50 (1H, s)

ESI-MS (m/e): 425[M+H]

A compound of Production Example 70 was produced by the same method as in the above Production Example 69. Analytical data of the compound are shown hereunder.

PRODUCTION EXAMPLE 70

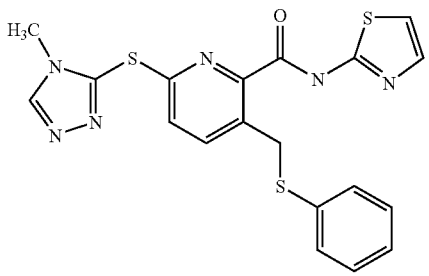

Manufacture of 3-phenylsulfanylmethyl-6-(4-methtyl-4H-[1,2,4]triazole-3-yl-sulfanyl)-N-(thiazole-2-yl)-2-pyridine carboxamide Compound of Production Example 70 can be produced by the same method as Production Example 69, by a method according thereto, or by a combination of these and ordinary methods, with the use of 2-cyano-3-tert-butyldimethylcyliloxymethylpyridine, thiophenol, 3-mercapto-4-methyl-4H-1,2,4-triazole and 2-aminothiazole.

$^1$HNMR (CDCl$_3$) δ: 3.77 (3H, s), 4.74 (2H, s), 7.04 (1H, d, J=3.2 Hz), 7.20 (1H, d, J=8.4 Hz), 7.24-7.28 (5H, m), 7.53 (1H, d, J=3.2 Hz), 7.58 (1H, d, J=8.4 Hz), 8.48 (1H, s)

ESI-MS (m/e): 441 [M+H]

PRODUCTION EXAMPLE 71

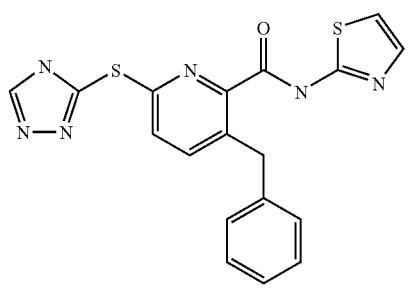

Manufacture of 3-phenylmethyl-6-(4H-[1,2,4]triazole-3-yl-sulfanyl)-N-(thiazole-2-yl)-2-pyridine carboxamide 3-benzoyl-2-pyridinecarboxylic acid (2.0 g; 8.8 mmol) was dissolved in 10 ml of methanol and 10 drops of concentrated sulfuric acid were dropped thereinto at room temperature followed by heating to reflux for a whole day and night. After cooling, methanol was evaporated therefrom followed by neutralizing with a saturated aqueous solution of sodium hydrogen carbonate. Extraction with chloroform was conducted followed by drying over sodium sulfate and concentrating to give 2.0 g of a crude product of 3-benzoyl-2-pyridinecarboxylate methyl ester.

The ester (2.0 g) was dissolved in 10 ml of chloroform and 3.57 g (20.7 mmol) of mCPBA were added thereto followed by heating to reflux for a whole day and night. After cooling, a saturated aqueous solution of sodium hydrogen carbonate was added to the reaction solution to make alkaline followed by extracting with chloroform. Drying over sodium sulfate and evaporation in vacuo were carried out to give a crude product of an N-oxide. To this crude product were added 10 ml of phosphorus oxychloride followed by stirring at 80° C. for 2 hours. After cooling, it was neutralized with a saturated aqueous solution of sodium hydrogen carbonate and extracted with ethyl acetate. After drying over sodium sulfate and evaporating in vacuo, purification was carried out by a silica gel column chromatography (ethyl acetate:hexane=1:2) to give 600 mg (yield: 26% in the three steps of the purification) of 3-benzoyl-6-chloro-2-pyridinecarboxylate methyl ester.

The chloro compound (300 mg; 1.10 mmol) was dissolved in 15 ml of methanol and 5 ml of 1N sodium hydroxide were added thereto followed by stirring at room temperature for 2 hours. After evaporation of methanol therefrom, the residue was neutralized with 1N hydrochloric acid and extracted with chloroform. This was dried over sodium sulfate and evaporated in vacuo to give 285 mg (yield: 100%) of a crude product of 3-benzoyl-6-chloro-2-pyridinecarboxylic acid.

The above-produced carboxylic acid (285 mg; 1.1 mmol) was dissolved in 10 ml of chloroform and 109 mg (1.1 mmol) of 2-aminothiazole, 221 mg (1.64 mmol) of N-hydroxybenzotriazole hydrate and 229 mg (1.2 mmol) of 1-(3-dimethylaminopropyl)-3-ethylcarbodiimide hydrochloride were added thereto followed by stirring at room temperature for a whole day and night. After addition of distilled water thereto, it was extracted with chloroform and dried over sodium sulfate. The residue obtained by evaporation of the solvent in vacuo was purified by a column chromatography (ethyl acetate:hexane=1:2) to give 225 mg (yield: 60% throughout the two steps) of 3-benzoyl-6-chloro-N-(thiazole-2-yl)-2-pyridine carboxamide.

The above-produced chloro compound (170 mg; 0.495 mmol) was dissolved in 3 ml of DMF and 55 mg (0.544 mmol) of 3-mercapto-1,2,4-triazole and 171 mg (1.24 mmol) of potassium carbonate were added thereto followed by stirring at 100° C. for a whole day and night. The reaction solution was cooled, DMF was evaporated therefrom and distilled water was added thereto followed by neutralizing with 1N hydrochloric acid and extracting with chloroform. After it was dried over sodium sulfate and evaporated in vacuo, the residue was purified by a silica gel column chromatography (methanol:chloroform=1:10) to give 101 mg (yield: 50%) of 3-benzoyl-6-(4H-[1,2,4]triazole-sulfanyl)-N-(thiazole-2-yl)-2-pyridine carboxamide.

The above-produced ketone compound (70 mg; 0.172 mmol) was suspended in 5 ml of methanol, 12.7 mg (0.343 mmol) of sodium borohydride were added thereto followed by stirring at room temperature for 30 minutes and the solvent was evaporated therefrom. To the resulting residue were added 99 mg (0.853 mmol) of triethylsilane and 5 ml of trifluoroacetic acid followed by stirring at 60° C. for 1 hour. After concentrating, it was partitioned by chloroform and a saturated aqueous solution of sodium hydrogen carbonate and the chloroform layer was dried over sodium sulfate. The residue obtained after concentration of the solvent was purified by a thin-layer silica gel chromatography for two times (methanol:chloroform=1:8 and ethyl acetate:acetone=2:1) to give 13.5 mg (yield: 20%) of the title compound.

$^1$HNMR (CDCl$_3$) δ: 4.63 (2H, s), 6.99 (1H, d, J=3.6 Hz), 7.18-7.29 (5H, m), 7.38 (1H, d, J=8.4 Hz), 7.41 (1H, dd, J=3.6 Hz), 7.45 (1H, d, J=8.4 Hz), 8.33 (1H, s)

ESI-MS (m/e): 395 [M+H]$^+$

PRODUCTION EXAMPLE 72

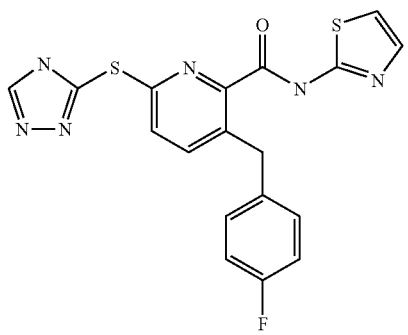

Manufacture of 3-(4-fluoro-phenylmethyl)-6-(4H-[1,2,4]triazole-3-yl-sulfanyl)-N-(thiazole-2-yl)-2-pyridine carboxamide $^1$HNMR (CDCl$_3$) δ: 4.60 (2H, s), 6.94-6.98 (2H, m), 7.01 (1H, d, J=3.6 Hz), 7.14-7.17 (2H, m), 7.40-7.46 (3H, m), 8.35 (1H, s)

ESI-MS (m/e): 413[M+H]$^+$

Compound of Production Example 72 can be produced by the same method as Production Example 71, by a method according thereto or by a combination of these and ordinary methods, with the use of 3-(4-fluoro benzoyl)-2-pyridinecarboxylic acid, 2-aminothiazole and 3-mercapto-1,2,4-triazole.

PRODUCTION EXAMPLE 73

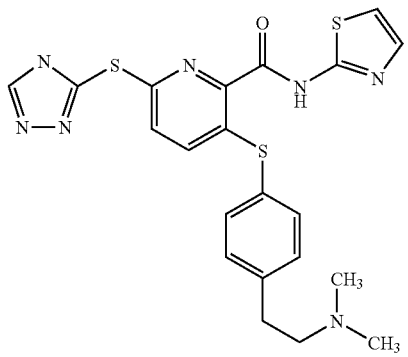

Manufacture of 3-(4-dimethylaminoethyl-phenylsulfanyl)-6-(4H)-[1,2,4]trizaole-3-ylsulfanyl)-N-(thiazole-2-yl)-2-pyridine carboxamide Compound of Production Example 73 can be produced by the same method as Production Example 1, by a method according thereto or by a combination of these and ordinary methods, with the use of 3,6-dichloro-2-pyridinecarboxylic acid, 2-amino-thiazole, 4-dimethylaminoethyl-thiophenol and 3-mercapto-1,2,4-triazole.

¹HNMR (CDCl₃) δ: 2.39 (6H, s), 2.68 (2H, m), 2.84 (2H, m), 7.00-7.05 (2H, m), 7.18 (1H, d, J=8.7 Hz), 7.28 (2H, d, J=8.4 Hz), 7.41-7.58 (3H, m), 8.32 (1H, s)

ESI-MS (m/e): 484[M+H]⁺

PRODUCTION EXAMPLE 74

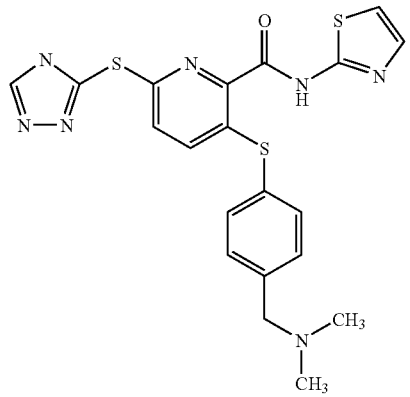

Manufacture of 3-(4-dimethylaminomethyl-phenylsufanyl)-6-(4H-[1,2,4]triazole-3-ylsulfanyl)-N-(thiazole-2-yl)-2-pyridine carboxamide Compound of Production Example 74 can be produced by the same method as Production Example 1, by a method according thereto, or by a combination of these and ordinary methods, with the use of 3,6-dichloro-2-pyridinecarboxylic acid, 2-amino-thiazole, 4-dimethylaminomethyl-thiophenol and 3-mercapto-1,2,4-triazole.

¹HNMR (CDCl₃) δ: 2.23 (6H, s), 6.96 (1H, d, J=8.8 Hz), 7.00 (1H, d, J=3.6 Hz), 7.11 (1H, d, J=8.8 Hz), 7.34 (2H, d, J=8.0 Hz), 7.43 (1H, d, J=3.6 Hz), 7.46 (2H, d, J=8.0 Hz), 8.29 (1H, s)

ESI-MS (m/e): 470[M+H]⁺

PRODUCTION EXAMPLE 75

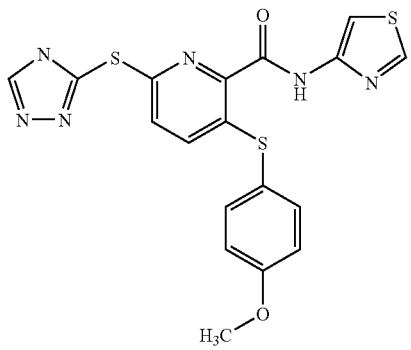

Manufacture of 3-(4-methoxy-phenylsulfanyl)-6-(4H-[1,2,4]triazole-3-ylsulfanyl)-N-(thiazole-4-yl)-2-pyridine carboxamide Compound of Production Example 75 can be produced by the same method as Production Example 1, by a method according thereto, or by a combination of these and ordinary methods, with the use of 3,6-dichloro-2-pyridinecarboxylic acid, 4-amino-thiazole, 4-methoxy-thiophenol and 3-mercapto-1,2,4-triazole.

¹HNMR (CDCl₃) δ: 3.85 (3H, s), 6.96 (2H, d, J=8.8 Hz), 6.98 (1H, d, J=8.8 Hz), 7.15 (1H, d, J=8.8 Hz), 7.46 (2H, d, J=8.8 Hz), 7.90 (1H, d, J=2.4 Hz), 8.34 (1H, s), 8.61 (1H, d, J=2.4 Hz),

ESI-MS (m/e): 443[M+H]⁺

PRODUCTION EXAMPLE 76

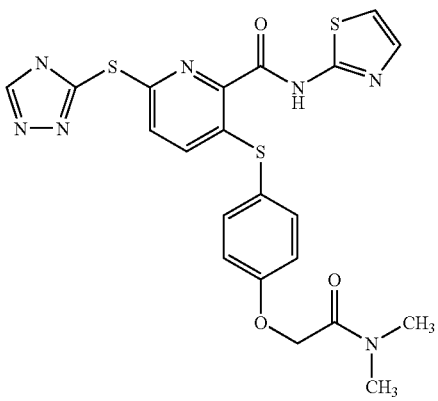

Manufacture of 3-(4-dimethylcarbamoylmethyloxyphenylsulfanyl)-6-(4H-[1,2,4]triazole-3-ylsulfanyl)-N-(thiazole-2-yl)-2-pyridine carboxamide Compound of Production Example 76 can be produced by the same method as Production Example 1, by a method according thereto, or by a combination of these and ordinary methods, with the use of 3,6-dichloro-2-pyridinecarboxylic acid, 2-amino-thiazole, 4-dimethylcarbamoylmethyloxy-thiophenol and 3-mercapto-1,2,4-triazole.

¹HNMR (CDCl₃) δ: 2.99 (3H, s), 3.09 (3H, s), 4.73 (2H, s), 6.99 (2H, d, J=8.8 Hz), 7.01-7.03 (1H, m), 7.03 (1H, d, J=3.6 Hz), 7.19 (2H, d, J=8.4 Hz), 7.45 (2H, d, J=8.8 Hz), 7.46 (2H, d, J=3.6 Hz), 8.30 (1H, s)

ESI-MS (m/e): 514[M+H]⁺

PRODUCTION EXAMPLE 77

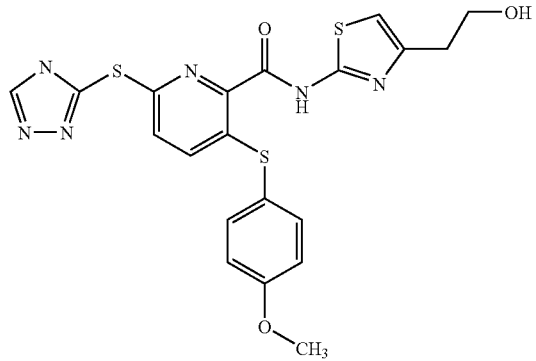

Manufacture of 3-(4-methoxy-phenylsufanyl)-6-(4H-[1,2,4]triazole-3-ylsulfanyl)-N-(4-hydroxyethyl-thiazole-2-yl)-2-pyridine carboxamide Compound of Production Example 77 can be produced by the same method as Production Example 1, by a method according thereto, or by a combination of these and ordinary methods, with the use of 3,6-dichloro-2-pyridinecarboxylic acid, 2-amino-4-hydroxyethyl-thiazole, 4-methoxy-thiophenol and 3-mercapto-1,2,4-triazole.

$^1$HNMR (CDCl$_3$) δ: 2.90 (2H, t, J=4.8 Hz), 3.83 (3H, s), 3.90 (2H, t, J=4.8 Hz), 6.65 (1H, s), 6.95 (2H, d, J=8.0 Hz), 6.97 (1H, d, J=8.8 Hz), 7.17 (1H, d, J=8.8 Hz), 7.43 (2H, d, J=8.0 Hz), 8.34 (1H, s)

ESI-MS (m/e): 487[M+H]$^+$

PRODUCTION EXAMPLE 78

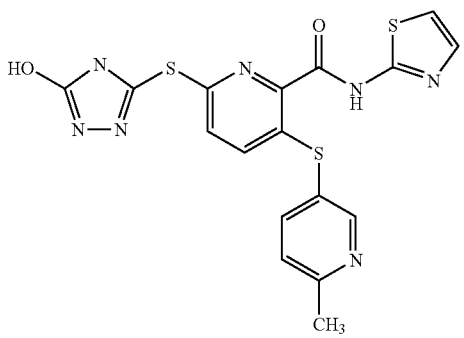

Manufacture of 3-(6-methyl-pyridine-3-ylsulfanyl)-6-(5-hydoxy-4H-[1,2,4]triazole-3-ylsulfanyl)-N-(thiazole-2-yl)-2-pyridine carboxamide Compound of Production Example 78 can be produced by the same method of Production Example 1, by a method according thereto, or by a combination of these and ordinary methods, with the use of 3,6-dichloro-2-pyridinecarboxylic acid, 2-amino-thiazole, 4-hydroxy-thiophenol and 5-hydroxy-3-mercapto-1,2,4-triazole.

$^1$HNMR (CDCl$_3$) δ: 2.65 (3H, s), 6.98-7.50 (5H, m), 7.82 (1H, m), 8.64 (1H, brs), ESI-MS (m/e): 444[M+H]$^+$

PRODUCTION EXAMPLE 79

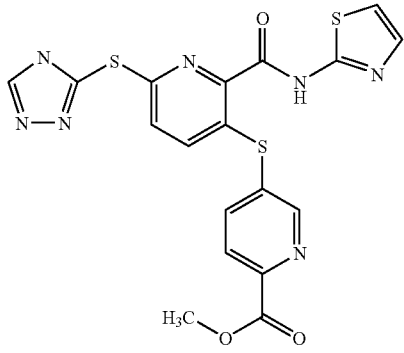

Manufacture of 3-(6-methoxycarbonyl-pyridine-3-ylsulfanyl)-6-(4H-[1,2,4]triazole-3-ylsulfanyl)-N-(thiazole-2-yl)-2-pyridine carboxamide Compound of Production Example 79 can be produced by the same method as Production Example 66, by a method according thereto, or by a combination of these and ordinary methods, with the use of 6-chloro-3-(4-methoxy-phenylmethylsulfanyl)-N-(thiazole-2-yl)-2-pyridine carboxamide, 5-iodo-3-methoxycarbonyl-piridine and 3-mercapto-1,2,4-triazole which can be obtained by the same method as Production Example 1.

$^1$HNMR (CDCl$_3$) δ: 4.01 (3H, s), 7.03 (1H, d, J=7.6 Hz), 7.05 (1H, d, J=3.6 Hz), 7.24 (1H, d, J=7.6 Hz), 7.47 (1H, d, J=3.6 Hz), 8.00 (1H, m), 8.16 (1H, d, J=8.0 Hz), 8.33 (1H, s), 8.79 (1H, m)

ESI-MS (m/e): 472[M+H]$^+$

PRODUCTION EXAMPLE 80

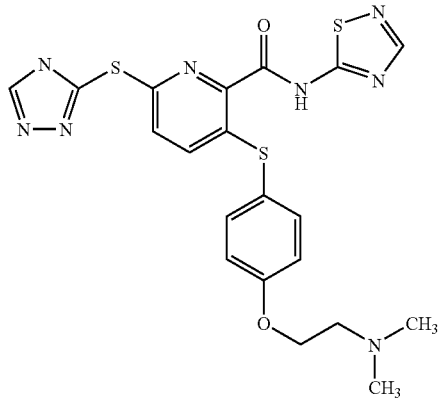

Manufacture of 3-(4-dimethylaminoethyloxy-phenylsulfanyl)-6-(4H-[1,2,4]triazole-3-ylsulfanyl)-N-([1,2,4]thiadiazole-5-yl)-2-pyridine carboxamide Compound of Production Example 80 can be produced by the same method as Production Example 1, by a method according thereto, or by a combination of these methods and ordinary methods, with the use of 3,6-dichloro-2-pyridinecarboxylic acid, 5-amino-1,2,4-thiadiazole, 4-dimethylaminoethyloxy-thiophenol and 3-mercapto-1,2,4-triazole.

$^1$HNMR (CDCl$_3$) δ: 2.42 (6H, s), 2.84 (2H, t, J=5.1 Hz), 4.13 (2H, t, J=5.1 Hz), 6.96 (2H, d, J=8.4 Hz), 7.00 (1H, d, J=8.8 Hz), 7.21 (1H, d, J=8.8 Hz), 7.43 (2H, d J=8.4 Hz), 8.35 (1H, s)

ESI-MS (m/e): 501 [M+H]$^+$

PRODUCTION EXAMPLE 81

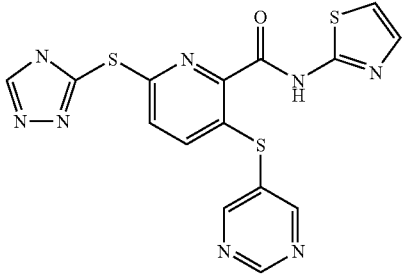

Manufacture of 3-(pyrimidine-5-ylsulfanyl)-6-(4H-[1,2,4]triazole-3-ylsulfanyl)-N-(thiazole-2-yl)-2-pyridine carboxamide Compound of Production Example 81 can be produced by the same method as Production Example 66, by a method according thereto, or by a combination of these and ordinary methods, with the use of 6-chloro-3-(4-methoxy-phenylmethylsufanyl)-N-(thiazole-2-yl)-2-pyridine carboxamide, 5-iodo-pyrimidine and 3-mercapto-1,2,4-triazole which can be obtained by the same method as Production Example 1.

$^1$HNMR (CDCl$_3$) δ: 6.95 (1H, d, J=8.4 Hz), 7.03 (1H, d, J=3.6 Hz), 7.22 (1H, d, J=8.4 Hz), 7.44 (1H, d, J=3.6 Hz), 8.33 (1H, s), 8.82 (2H, s), 9.20 (1H, s)

ESI-MS (m/e): 415[M+H]$^+$

PRODUCTION EXAMPLE 82

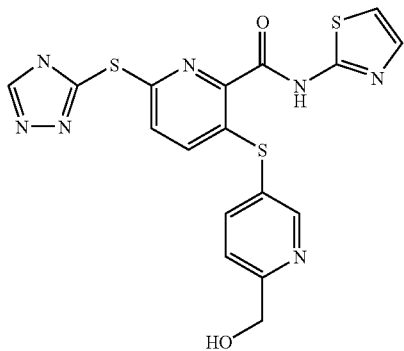

Manufacture of 3-(6-hydroxymethyl-pyridine-3-ylsulfanyl)-6-(4H-[1,2,4]triazole-3-ylsulfanyl)-N-(thiazole-2-yl)-2-pyridine carboxamide Compound of Production Example 82 can be produced by the same method as Production Example 1, by a method according thereof, or by a combination of these and ordinary methods, with the use of 3,6-dichloro-2-pyridinecarboxylic acid, 2-amino-thiazole, 4-hydroxymethyl-thiophenol and 3-mercapto-1,2,4-triazole.

$^1$HNMR (CDCl$_3$) δ: 4.86 (2H, s), 7.01 (1H, d, J=9.2 Hz), 7.07 (1H, d, J=3.2 Hz), 7.28 (1H, d, J=9.2 Hz), 7.41 (1H, d, J=7.6 Hz), 7.52 (1H, d, J=3.2 Hz), 7.90 (1H, m), 8.42 (1H, s), 8.74 (1H, m)

ESI-MS (m/e): 444[M+H]$^+$

PRODUCTION EXAMPLE 83

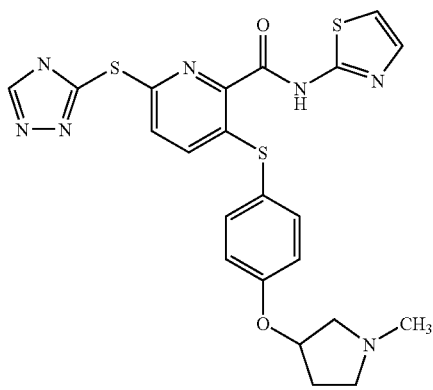

Manufacture of 3-[4-(1-methyl-pyrrolidine-3-yloxy)-phenylsulfanyl]-6-(4H[1,2,4]triazole-3-ylsulfanyl-N-(thiazole-2-yl)-2-pyridine carboxamide Compound of Production Example 83 can be produced by the same method as Production Example 1, by a method according thereto, or by a combination of these and ordinary methods, with the use of 3,6-dichloro-2-pyridinecarboxylic acid, 2-amino-thiazole, 4-(1-methyl-pyrrolidine-3-yl)-thiophenol and 3-mercapto-1,2,4-triazole.

$^1$HNMR (CDCl$_3$) δ: 1.90-1.98 (1H, m), 2.35 (3H, s), 2.25-2.35 (2H, m), 2.43-2.47 (1H, m), 2.80-2.83 (2H, m), 4.78-4.85 (1H, m), 6.85 (2H, d, J=8.4 Hz), 6.95 (1H, d, J=8.8 Hz), 7.00 (1H, d, J=3.6 Hz), 7.12 (1H, d, J=8.8 Hz), 7.38 (2H, d, J=8.4 Hz), 7.42 (1H, d, J=3.6 Hz), 8.29 (1H, s)

ESI-MS (m/e): 512[M+H]$^+$

PRODUCTION EXAMPLE 84

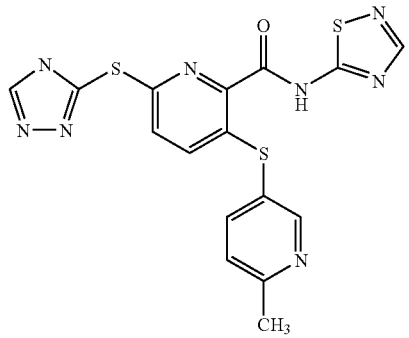

Manufacture of 3-(6-methyl-pyridine-3-ylsulfanyl)-6-(4H-[1,2,4]triazole-3-ylsulfanyl)-N-([1,2,4]thiadiazole-5-yl)-2-pyridine carboxamide Compound of Production Example 84 can be produced by the same method as Production Example 1, by a method according thereto, or by a combination of these and ordinary methods, with the use of 3,6-dichloro-2-pyridinecarboxylic acid, 5-amino-1,2,4-thiadiazole, 3-mercapto-6-methyl-pyridine and 3-mercapto-1,2,4-triazole.

$^1$HNMR (CDCl$_3$) δ: 2.65 (3H, s), 7.01 (1H, d, J=8.6 Hz), 7.26 (1H, d, J=8.6 Hz), 7.30 (1H, d, J=8.0 Hz), 7.78 (1H, dd, J=8.0, 2.2 Hz), 8.35 (1H, s), 8.42 (1H, s), 8.64 (1H, d, J=2.2 Hz)

ESI-MS (m/e): 429[M+H]$^+$

PRODUCTION EXAMPLE 85

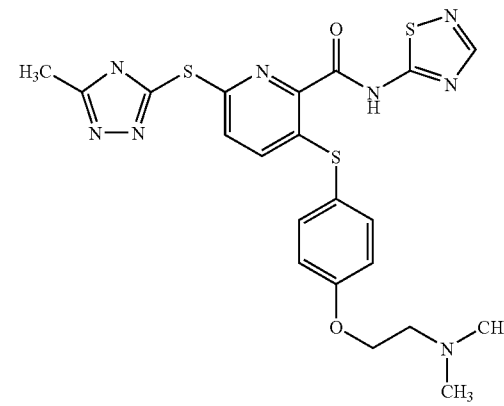

Manufacture of 3-(4-dimethylaminoethyloxy-phenylsulfanyl)-6-(5-methyl-4H-[1,2,4]triazole-3-ylsulfanyl)-N-([1,2,4]thiadiazole-5-yl)-2-pyridine carboxamide Compound of Production Example 85 can be produced by the same method as Production Example 1, by a method according thereof, or by a combination of these and ordinary methods, with the use of 3,6-dichloro-2-pyridinecarboxylic acid, 5-amino-1,2,4-thiadiazole, 4-dimethylaminoethyloxy-thiophenol and 3-mercapto-5-methyl-1,2,4-triazole.

$^1$HNMR (CDCl$_3$) δ: 2.40 (6H, s), 2.62 (6H, s), 2.81 (2H, t, J=5.5 Hz), 4.12 (2H, t, J=5.1 Hz), 6.96 (2H, d, J=8.5 Hz), 6.98 (1H, d, J=8.5 Hz), 7.20 (1H, d, J=8.5 Hz), 7.42 (2H, d, J=8.5 Hz), 8.34 (1H, s)

ESI-MS (m/e): 515[M+H]$^+$

PRODUCTION EXAMPLE 86

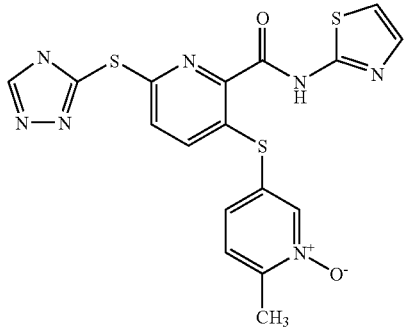

Manufacture of 3-(1-oxy-6-methyl-pyridine-3-ylsulfanyl)-6-(4H-[1,2,4]triazole-3-ylsulfanyl)-N-thiazole-2-yl)-2-pyridine carboxamide Compound of Production Example 86 can be produced by the same method as Production Example 1, by a method according thereof, or by a combination of these and ordinary methods, with the use of 3,6-dichloro-2-pyridine carboxylic acid, 2-amino-thiazole, 3-mercapto-6-methyl-1-oxy-pyridine and 3-mercapto-1,2,4-triazole.

$^1$HNMR (CDCl$_3$) δ: 2.60 (3H, s), 7.06 (1H, d, J=3.2 Hz), 7.12 (1H, d, J=8.4 Hz), 7.32 (1H, d, J=8.4 Hz), 7.39-7.39 (2H, m), 7.51 (1H, d, J=3.2 Hz), 8.44 (1H, s), 8.51 (1H, brs)

ESI-MS (m/e): 446[M+H]

PRODUCTION EXAMPLE 87

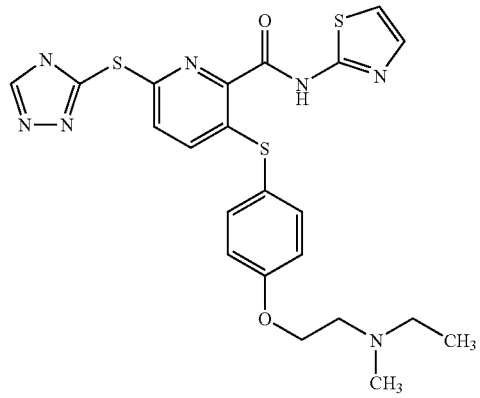

Manufacture of 3-4-diethylaminoethyloxy-phenylsulfanyl)-6-(4H-[1,2,4]triazole-3-ylsulfanyl)-N-(thiazole-2-yl)-2-pyridine carboxamide Compound of Production Example 87 can be produced by the same example as Production Example 1, by a method according thereof, or by a combination of these and ordinary methods, with the use of 3,6-dichloro-2-pyridinecarboxylic acid, 2-amino-thiazole, 4-diethylaminoethyloxy-thiophenol and 3-mercapto-1,2,4-triazole.

$^1$HNMR (CDCl$_3$) δ: 1.14 (6H, t, J=7.6 Hz), 2.73 (4H, q, J=7.6 Hz), 2.99 (2H, t, J=6.0 Hz), 6.99 (2H, d, J=8.8 Hz), 7.01 (1H, d, J=8.4 Hz), 7.07 (1H, d, J=4.0 Hz), 7.18 (1H, d, J=8.4 Hz), 7.46 (2H, d, J=8.8 Hz), 7.49 (1 H, d, J=4.0 Hz), 8.36 (1H, s)

ESI-MS (m/e): 528 [M+H]$^+$

PRODUCTION EXAMPLE 88

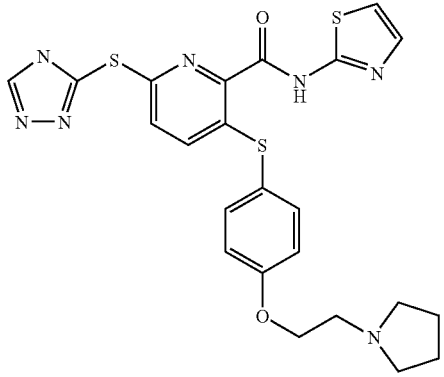

Manufacture of 3-(4-pyrrolidinoethyloxy-phenylsulfanyl)-6-(4-[1,2,4]triazole-3-ylsulfanyl)-N-(thiazole-2-yl)-2-pyridine carboxamide Compound of Production Example 88 can be produced by the same example as Production Example 1, by a method according thereto, or by a combination of these and ordinary methods, with the use of 3,6-dichloro-2-pyridinecarboxylic acid, 2-amino-thiazole, 4-pyrrolidinoethyloxy-thiophenol and 3-mercapto-1,2,4-triazole.

$^1$HNMR (CDCl$_3$) δ: 1.80-1.90 (4H, m), 2.70-2.80 (4H, m), 3.02 (2H, t, J=5.2 Hz), 4.18 (2H, t, J=5.2 Hz), 6.95 (2H, d, J=8.8 Hz), 6.97 (1H, d, J=7.02 (1H, d, J=3.6 Hz), 7.17 (1H, d, J=8.4 Hz), 7.42 (2H, d, J=8.8 Hz), 7.45 (1H, d, J=3.6 Hz), 8.29 (1H, s)

ESI-MS (m/e): 526[M+H]$^+$

PRODUCTION EXAMPLE 89

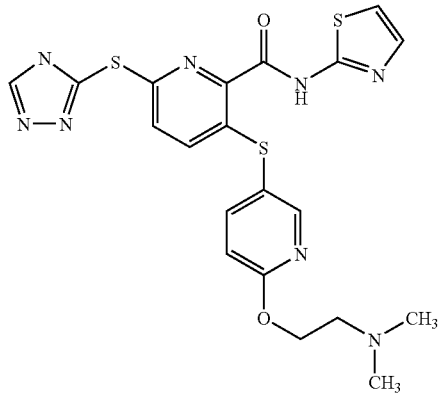

Manufacture of 3-(6-dimethylaminoethyloxy-pyridine-3-ylsulfanyl)-6-(4H-[1,2,4]triazole-3-ylsulfanyl)-N-(thiazole-2-yl)-2-pyridine carboxamide Compound of Production Example 89 can be produced by the same method as Production Example 1, by a method according thereof, or by a combination of these and ordinary methods, with the use of 3,6-dichloro-2-pyridinecarboxylic acid, 2-amino-thiazole, 3-mercapto-6-dimethylaminoethyloxy-pyridine and 3-mercapto-1,2,4-triazole.

$^1$HNMR (CDCl$_3$) δ: 2.41 (6H, s), 2.82 (2H, t, J=5.6 Hz), 4.48 (2H, t, J=5.6 Hz), 6.80 (1H, d, J=8.4 Hz), 6.98 (1H, d, J=8.4 Hz), 7.03 (1H, d, J=3.6 Hz), 7.23 (1H, d, J=8.4 Hz), 7.47 (1H, d, J=3.6 Hz), 7.63 (1H, dd, J=2.4, 8.4 Hz), 7.27 (1H, d, J=2.4 Hz), 8.36 (1H, s)

ESI-MS (m/e): 501 [M+H]$^+$

PRODUCTION EXAMPLE 90

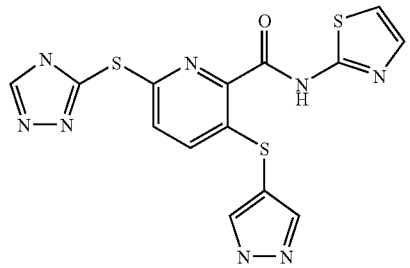

Manufacture of 3-(pyrazole-4-ylsulfanyl)-6-(4H-[1,2,4]triazole-3-ylsulfanyl)-N-(thiazole-2-yl)-2-pyridine carboxamide Compound of Production Example 90 can be produced by the same method as Production Example 66, by a method according thereto, or by a combination of these and ordinary methods, with the use of 6-chloro-3-(4-methoxy-phenylmethylsulfanyl)-N-(thiazole-2-yl)-2-pyridine carboxamide, 4-iodopyrazole and 3-mercapto-1,2,4-triazole which can be obtained by the same method as Production Example 1.

$^1$HNMR (CDCl$_3$) δ: 7.07 (1H, d, J=3.6 Hz), 7.18 (1H, d, J=8.4 Hz), 7.25 (1H, d, J=8.4 Hz), 7.49 (1H, d, J=3.6 Hz), 7.70 (2H, s), 8.35 (1H, s)

ESI-MS (m/e): 403[M+H]$^+$

PRODUCTION EXAMPLE 91

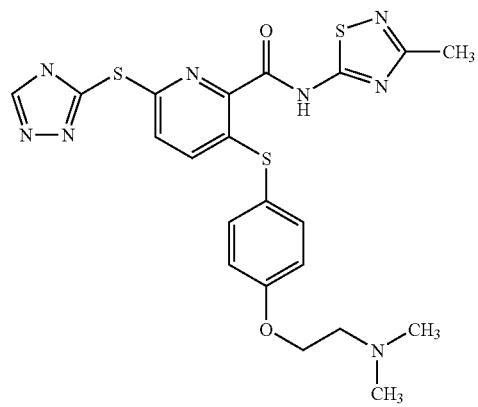

Manufacture of 3-(4-dimethyaminoethyloxy-phenylsulfanyl)-6-(4H-[1,2,4]triazole-3-ylsulfanyl)-N-(3-methyl-[1,2,4]thiadiazole-5-yl)-2-pyridine carboxamide Compound of Production Example 91 can be produced by the same method as Production Example 1, by a method according thereto, or by a combination of these and ordinary methods, with the use of 3-6-dichloro-2-pyridinecarboxylic acid, 5-amino-3-methyl-1,2,4-thiadiazole, 4-dimethylaminoethyloxy-thiophenol and 3-mercapto-1,2,4-triazole.

$^1$HNMR (CDCl$_3$) δ: 2.37 (6H, s), 2.61 (3H, s), 2.80 (2H, t, J=5.6 Hz), 4.12 (2H, t, J=5.6 Hz), 7.00 (2H, d, J=8.4 Hz), 7.02 (1H, d, J=8.8 Hz), 7.22 (1H, d, J=8.8 Hz), 7.45 (2H, d, J=8.4 Hz), 8.34 (1H, s)

ESI-MS (m/e): 515[M+H]$^+$

PRODUCTION EXAMPLE 92

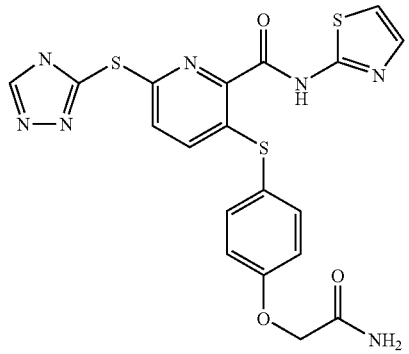

Manufacture of 3-(4-carbamoylmethyloxy-phenylsulfanyl)-6-(4H-[1,2,4]triazole-3-ylsulfanyl)-N-(thiazole-2-yl)-2-pyridine carboxamide Compound of Production Example 92 can be produced by the same method as Production Example 1, by a method according thereto, or by a combination of these and ordinary methods, with the use of 3,6-dichloro-2-pyridine carboxylic acid, 2-amino-thiazole, 4-carbamoylmethyloxy-thiophenol and 3-mercapto-1,2,4-triazole.

$^1$HNMR (CDCl$_3$) δ: 4.48 (2H, s), 6.95 (1H, d, J=8.4 Hz), 6.98 (2H, d, J=8.8 Hz), 7.02 (1H, d, J=3.6 Hz), 7.13 (1H, d, J=8.4 Hz), 7.44 (1H, d, J=3.6 Hz), 7.45 (2H, d, J=8.8 Hz), 8.33 (1H, s)

ESI-MS (m/e): 486[M+H]$^+$

PRODUCTION EXAMPLE 93

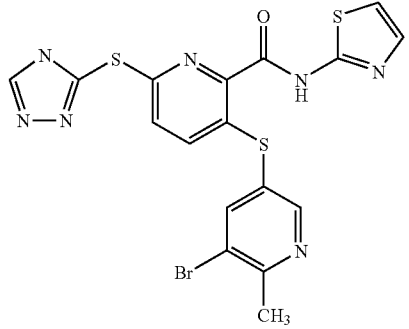

Manufacture of 3-(5-bromo-6-methyl-pyridine-3-ylsulfanyl)-6-(4H-[1,2,4]triazole-3-ylsulfanyl)-N-(thiazole-2-yl)-2-pyridine carboxamide Compound of Production Example 93 can be produced by the same example as Production Example 1, by a method according thereto, or by a combination of these and ordinary methods, with the use of 3,6-dichloro-2-pyridinecarboxylic acid, 2-amino-thiazole, 5-bromo-3-mercapto-6-methyl-pyridine and 3-mercapto-1,2,4-triazole.

$^1$HNMR (CDCl$_3$) δ: 2.72 (3H, s), 7.00 (1H, d, J=8.4 Hz), 7.05 (1H, d, J=3.6 Hz), 7.22-7.24 (1H, m), 7.48 (1H, d, J=3.6 Hz), 8.01 (1H, d, J=2.0 Hz), 8.33 (1H, s), 8.52 (1H, d, J=2.0 Hz)

ESI-MS (m/e): 505, 507[M+H]+

PRODUCTION EXAMPLE 94

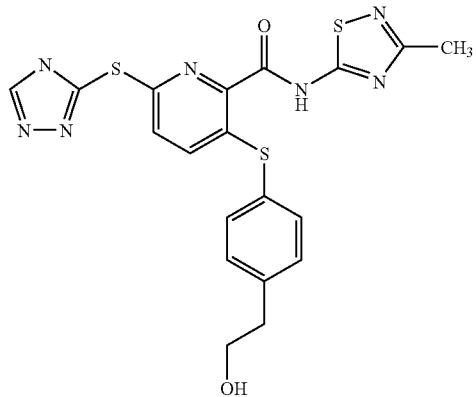

Manufacture of 3-[4-(2-hydroxyethyl-phenylsulfanyl)]-6-(4H-[1,2,4]triazole-3-ylsulfanyl)-N-(3-methyl-[1,2,4]-thiadiazole-5-yl)-2-pyridinecarboxylic acid Compound of Production Example 94 can be produced by the same method as Production Example 1, by a method according thereto, or by a combination of these and ordinary methods, with the use of 3,6-dichloro-2-pyridinecarboxylic acid, 5-amino-3-methyl-1,2,4-thiadiazole, 4-(2-hydroxyethyl)-thiophenol and 3-mercapto-1,2,4-triazole.

$^1$HNMR (CDCl$_3$) δ: 2.61 (3H, s), 2.91 (2H, t, J=6.8 Hz), 3.84 (2H, t, J=6.8 Hz), 7.07 (1H, d, J=8.4 Hz), 7.21 (1H, d, J=8.4 Hz), 7.35 (2H, d, J=8.0 Hz), 7.48 (2H, d, J=8.0 Hz), 8.36 (1H, s)

ESI-MS (m/e): 472[M+H]+

PRODUCTION EXAMPLE 95

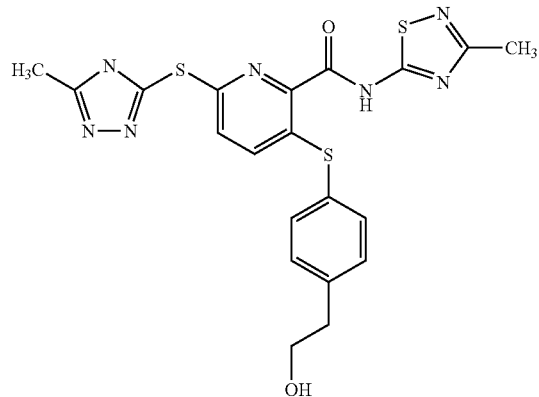

Manufacture of 3-4[4-(2-hydroxyethyl-phenylsulfanyl)]-6-(5-methyl-4H-[1,2,4]triazole-3-ylsulfanyl)-N-(3-methyl-[1,2,4]-thiadiazole-5-yl)-2-pyridine carboxamide Compound of Production Example 95 can be produced by the same example as Production Example 1, by a method according thereto, or by a combination of these and ordinary methods, with the use of 3,6-dichloro-2-pyridinecarboxylic acid, 5-amino-3-methyl-1,2,4-thiadiazole, 4-(2-hydroxyethyl)-thiophenol and 3-mercapto-5-methyl-1,2,4-triazole.

$^1$HNMR (CDCl$_3$) δ: 2.59 (3H, s), 2.59 (3H, s), 2.94 (2H, t, J=6.4 Hz), 3.94 (2H, t, J=6.4 Hz), 7.03 (1H, d, J=8.8 Hz), 7.21 (1H, d, J=8.8 Hz), 7.34 (2H, d, J=8.0 Hz), 7.49 (2H, d, J=8.0 Hz) ESI-MS (m/e): 486[M+H]$^+$

PRODUCTION EXAMPLE 96

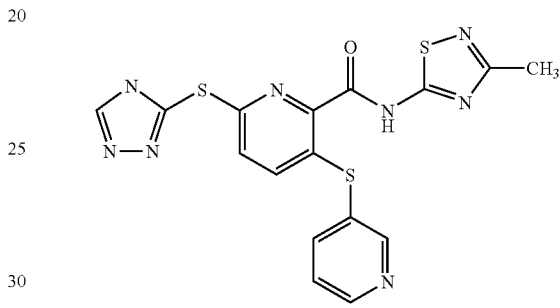

Manufacture of 3-(pyridine-3-ylsulfanyl)-6-(4H-[1,2,4]triazole-3-ylsulfanyl)-N-(3-methyl-[[1,2,4]-thiadiazole-5-yl]-2-pyridine carboxamide Compound of Production Example 96 can be produced by the same method as Production Example 1; by a method according thereto, or by a combination of these and ordinary methods, with the use of 3,6-dichloro-2-pyridinecarboxylic acid, 5-amino-3-methyl-1,2,4-thiadiazole, 3-mercapto-pyridine and 3-mercapto-1,2,4-triazole.

$^1$HNMR (CDCl$_3$) δ: 2.61 (3H, s), 7.00 (1H, d, J=8.8 Hz), 7.29 (1H, d, J=8.8 Hz), 7.41-7.44 (1H, m), 7.88-7.91 (1H, m), 8.41 (1H, s), 8.71-8.73 (1H, m), 8.76-8.77 (1H, m)

ESI-MS (m/e): 429[M+H]$^+$

PRODUCTION EXAMPLE 97

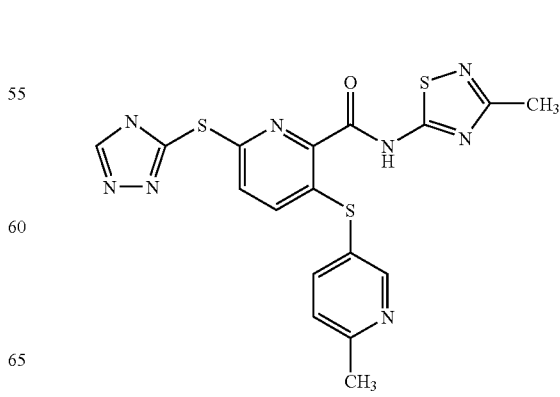

Manufacture of 3-(6-methyl-pyridine-3-ylsulfanyl)-6-(4H-[1,2,4]triazole-3-ylsulfanyl)-N-(3-methyl-[1,2,4]-thiadiazol-5-yl)-2-pyridine carboxamide Compound of Production Example 97 can be produced by the method as Production Example 1, by a method according thereto or by a combination of these and ordinary methods, with the use of 3,6-dichloro-2-pyridinecarboxylic acid, 5-amino-3-methyl-1,2,4-thiadiazole, 3-mercapto-6-methyl-pyridine and 3-mercapto-1,2,4-triazole.

$^1$HNMR (CDCl$_3$) δ: 2.62 (3H, s), 2.64 (3H, s), 7.02 (1H, d, J=8.0 Hz), 7.25 (1H, d, J=8.0 Hz), 7.31 (1H, d, J=8.0H), 7.78 (1H, dd, J=1.6 Hz, 8.0 Hz), 8.35 (1H, s), 8.60 (1H, d, J=1.6 Hz)

ESI-MS (m/e): 443[M+H]$^+$

PRODUCTION EXAMPLE 98

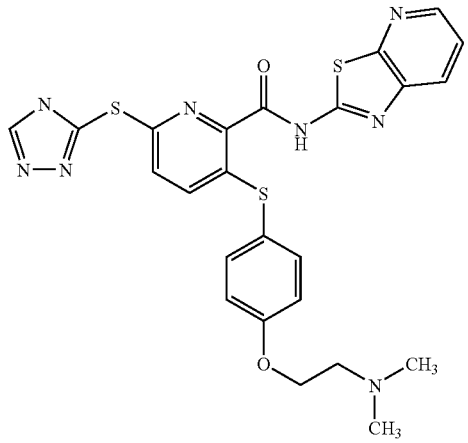

Manufacture of 3-(4-dimethylaminoethyloxy-phenylsulfanyl)-6-(4H-[1,2,4]triazole-3-ylsulfanyl)-N-(thiazolo[5,4-b]pyridine-2-yl)-2-pyridine carboxamide Compound of Production Example 98 can be produced by the same method as Production Example 1, by a method according thereto, or by a combination of these, with the use of 3,6-dichloro-2-pyridinecarboxylic acid, 2-amino-thiazolo[5,4-b]pyridine, 4-dimethylaminoethyloxy-thiophenol and 3-mercapto-1,2,4-triazole.

$^1$HNMR (CDCl$_3$) δ: 2.43 (6H, s), 2.70-2.88 (2H, m), 4.08-4.14 (2H, m), 6.88 (2H, d, J=8.4 Hz), 6.89-6.93 (1H, m), 7.13 (1H, d, J=8.8 Hz), 7.31-7.35 (1H, m), 7.38 (2H, d, J=8.8 Hz), 7.96 (1H, d, J=8.4 Hz), 8.37 (1H, s), 8.44 (1H, d, J=4.0 Hz)

ESI-MS (m/e): 551 [M+H]$^+$

PRODUCTION EXAMPLE 99

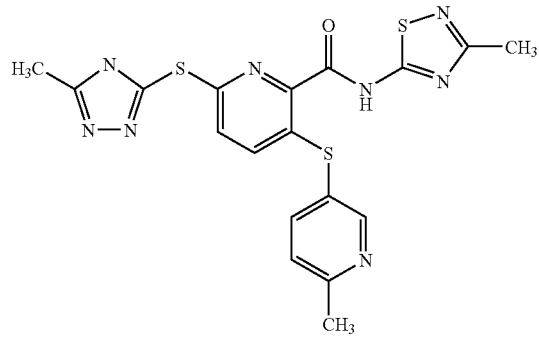

Manufacture of 3-(6-methyl-pyridine-3-ylsulfanyl)-6-(5-methyl-4H-[1,2,4]triazole-3-ylsulfanyl)-N-(3-methyl-[1,2,4]-thiadiazole-5-yl)-2-pyridine carboxamide Compound of Production Example 99 can be produced by the same method as Production Example 1, by a method according thereto, or by a combination of these and ordinary methods, with the use of 3,6-dichloro-2-pyridinecarboxylic acid, 5-amino-3-methyl-1,2,4-thiadiazole, 3-mercapto-6-methyl-pyridine and 3-mercapto-5-methyl-1,2,4-triazole.

$^1$HNMR (CDCl$_3$) δ: 2.60 (3H, s), 2.61 (3H, s), 3.64 (3H, s), 7.00 (1H, d, J=8.8 Hz), 7.20-7.36 (1H, m), 7.29 (1H, d, J=8.0 Hz), 7.77 (1H, dd, J=2.4, 8.0 Hz), 8.63 (1H, d, J=2.4 Hz)

ESI-MS (m/e): 457[M+H]$^+$

PRODUCTION EXAMPLE 100

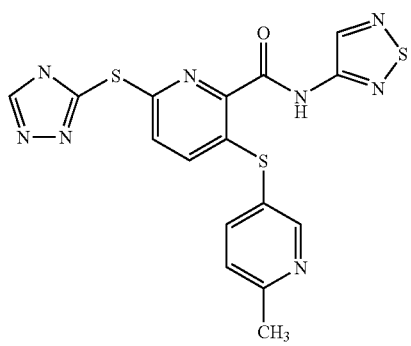

Manufacture of 3-(6-methyl-pyridine-3-ylsulfanyl)-6-(4H-[1,2,4]triazole-3-ylsulfanyl)-N-([1,2,5]thiadiazole-3-yl)-2-pyridinecarboxamide Compound of Production Example 100 can be produced by the same method as Production Example 1, by a method according thereto, or by a combination of these and ordinary methods, with the use of 3,6-dichloro-2-pyridinecarboxylic acid, 3-amino-1,2,5-thiadiazole, 3-mercapto-6-methyl-pyridine and 3-mercapto-1,2,4-triazole.

$^1$HNMR (CDCl$_3$) δ: 2.63 (3H, s), 6.99 (1H, d, J=8.8 Hz), 7.21 (1H, d, J=8.8 Hz), 7.29 (1H, d, J=8.1 Hz), 7.78 (1H, dd, J=8.1, 2.2 Hz), 8.37 (1H, s), 8.60 (1H, d, J=2.2 Hz), 9.38 (1H, s)

ESI-MS (m/e): 429[M+H]$^+$

PRODUCTION EXAMPLE 101

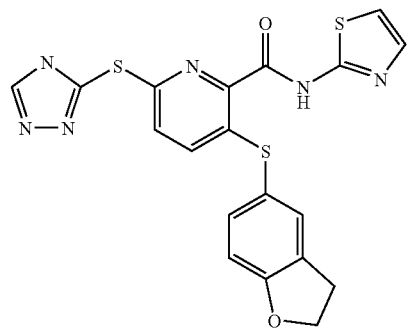

Manufacture of 3-(2,3-dihydrobenzofuran-5-ylsulfanyl)-6-(4H-[1,2,4]triazole-3-ylsulfanyl)-N-(thiazole-2-yl)-2-pyridine carboxamide Compound can be produced by the same method as Production Example 66, by a method according thereto, or by a combination of these and ordinary methods, with the use of 6-chloro-3-(4-methoxy-phenylmethylsulfanyl)-N-(thiazole-2-yl)-2-pyridine carboxamide, 5-iodo-2,3-dihydrobenzofuran and 3-mercapto-1,2,4-triazole, which were obtained by the same method of Production Example 1.

$^1$HNMR (CDCl$_3$) δ: 3.26 (2H, t, J=8.8 Hz), 4.66 (2H, t, J=8.8 Hz), 6.86 (1H, d, J=8.0 Hz), 7.02 (1H, d, J=3.2 Hz), 7.06 (1H, d, J=8.8 Hz), 7.22 (1H, d, J=8.8 Hz), 7.31 (1H, d, J=8.0 Hz), 7.35 (1H, brs), 7.45 (1H, d, J=3.2 Hz), 8.34 (1H, s)

ESI-MS (m/e): 455 [M+H]$^+$

PRODUCTION EXAMPLE 102

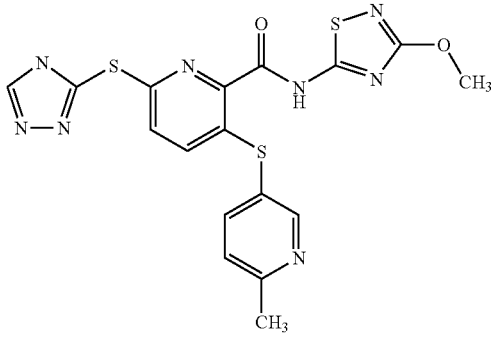

Manufacture of 3-(6-methyl-pyridine-3-ylsulfanyl)-6-(4H-[1,2,4]triazole-3-ylsulfanyl)-N-(3-methoxy-[1,2,4]-thiadiazole-5-yl)-2-pyridine carboxamide Compound of Production Example 102 can be produced by the same method as Production Example 1, by a method according thereto, or by a combination of these and ordinary methods, with the use of 3,6-dichloro-2-pyridinecarboxylic acid, 5-amino-3-methoxy-1,2,4-thiadiazole, 3-mercapto-6-methyl-pyridine and 3-mercapto-1,2,4-triazole.

$^1$HNMR (CDCl$_3$) δ: 2.65 (3H, s), 4.08 (3H, s), 6.90-7.05 (1H, m), 7.10-7.30 (2H, m), 7.70-7.80 (1H, m), 8.39 (1H, s), 8.63 (1H, brs)

ESI-MS (m/e): 459[M+H]$^+$

PRODUCTION EXAMPLE 103

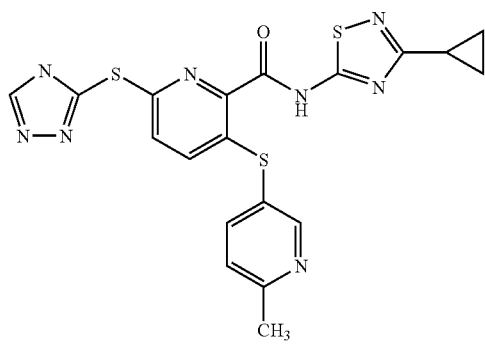

Manufacture of 3-(6-methyl-pyridine-3-ylsulfanyl)-6-(4H-[1,2,4]triazole-3-ylsulfanyl)-N-(3-cyclopropyl-[1,2,4]thiadiazole-5-yl)-2-pyridine carboxamide Compound of Production Example 103 can be produced by the same method as Production Example 1, by a method according thereto, or by a combination of these and ordinary methods, with the use of 3,6-dichloro-2-pyridine carboxylic acid, 5-amino-3-cyclopropyl-1,2,4-thiadiazole, 3-mercapto-6-methyl-pyridine and 3-mercapto-1,2,4-triazole.

$^1$HNMR (CDCl$_3$) δ: 0.90-1.20 (4H, m), 2.20-2.35 (1H, m), 2.64 (3H, s), 6.99 (1H, d, J=8.8 Hz), 7.20-7.30 (2H, m), 7.76 (1H, dd, J=2.4, 8.0 Hz), 8.38 (1H, s), 8.62 (1H, brs)

ESI-MS (m/e): 469[M+H]$^+$

PRODUCTION EXAMPLE 104

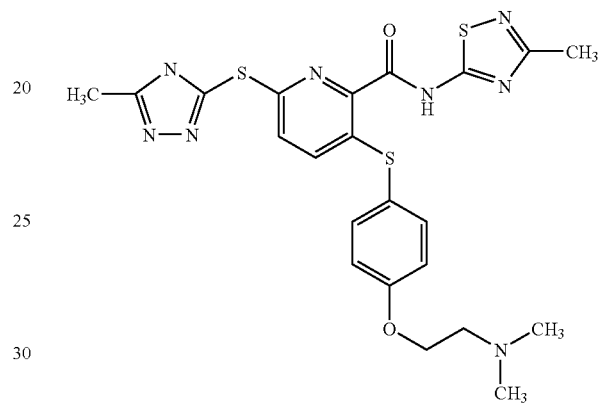

Manufacture of 3-(4-dimethylaminoethyloxy-phenylsulfanyl)-6-(5-methyl-4H-[1,2,4]triazole-3-ylsulfanyl)-N-(3-methyl-[1,2,4]thiadiazole-5-yl)-2-pyridine carboxamide Compound of Production Example 104 can be produced by the same method as Production Example 1, by a method according thereto, or by a combination of these and ordinary methods, with the use of 3,6-dichloro-2-pyridine carboxylic acid, 5-amino-3-methyl-1,2,4-thiadiazole, 4-dimethylaminoethyloxy-thiophenol and 3-mercapto-5-methyl-1,2,4-triazole.

$^1$HNMR (CDCl$_3$) δ: 2.41 (6H, s), 2.58 (3H, s), 2.59 (3H, s), 2.83 (2H, t, J=5.5 Hz), 4.12 (2H, t, J=5.5 Hz), 6.91 (2H, d, J=8.8 Hz), 6.94 (1H, d, J=8.6 Hz), 7.17 (1H, d, J=8.6 Hz), 7.40 (2H, d, J=8.8 Hz)

ESI-MS (m/e): 529[M+H]$^+$

PRODUCTION EXAMPLE 105

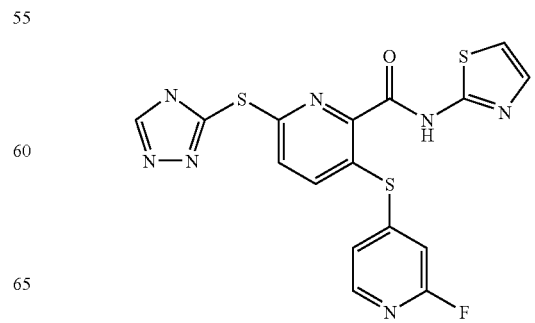

Manufacture of 3-(2-fluoro-pyridine-4-ylsulfanyl)-6-(4H-[1,2,4]triazole-3-ylsulfanyl)-N-(thiazole-2-yl)-2-pyridine carboxamide Compound of Production Example 105 can be produced by the same method as Production Example 66, by a method according thereto, or by a combination of these and ordinary methods, with the use of 6-chloro-3-(4-methoxy-phenylmethylsulfanyl)-N-(thiazole-2-yl)-2-pyridine carboxamide, 2-fluoro-4-iodo-pyridine and 3-mercapto-1,2,4-triazole which can be obtained by the same method as Production Example 1.

$^1$HNMR (CDCl$_3$) δ: 6.95-7.10 (2H, m), 7.20-7.26 (2H, m), 7.30-7.42 (1H, m), 7.40-7.50 (1H, m), 8.10-8.26 (1H, m), 8.38-8.45 (1H, m)

ESI-MS (m/e): 432[M+H]$^+$

PRODUCTION EXAMPLE 106

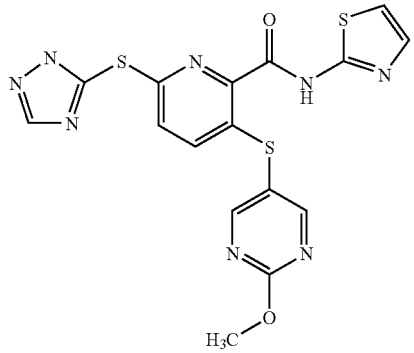

Manufacture of 3-(2-methoxy-pyrimidine-5-ylsulfanyl)-6-(2H-[1,2,4]triazole-3-ylsulfanyl)-N-(thiazole-2-yl)-2-pyridine carboxamide Compound of Production Example 106 can be produced by the same method as Production Example 66, by a method according thereto, or by a combination of these and ordinary methods, with the use of 6-chloro-3-(4-methoxy-phenylmethylsulfanyl)-N-(thiazole-2-yl)-pyridine carboxamide, 5-iodo-2-methoxy-pyrimidine and 3-mercapto-1,2,4-triazole which can be obtained by the same method as Production Example 1.

$^1$HNMR (CDCl$_3$) δ: 4.10 (3H, s), 7.02 (1H, d, J=8.4 Hz), 7.06 (1H, d, J=3.6 Hz), 7.32 (1H, d, J=8.4 Hz), 7.50 (1H, d, J=3.6 Hz), 8.39 (1H, s), 8.65 (2H, s)

ESI-MS (m/e): 445 [M+H]$^+$

PRODUCTION EXAMPLE 107

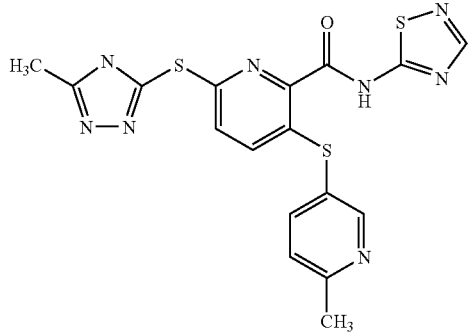

Manufacture of 3-(6-methyl-pyridine-3-ylsulfanyl)-6-(5-methyl-4H-[1,2,4]triazole-3-ylsulfanyl)-N-([1,2,4]-thiadiazole-5-yl)-2-pyridine carboxamide Compound of Production Example 107 can be produced by the same method as Production Example 1, by a method according thereto, or by a combination of these and ordinary methods, with the use of 3,6-dichloro-2-pyridinecarboxylic acid, 5-amino-1,2,4-thiadiazole, 3-mercapto-6-methyl-pyridine and 3-mercapto-5-methyl-1,2,4-triazole.

$^1$HNMR (CDCl$_3$) δ: 2.62 (3H, s), 2.64 (3H, s), 6.99 (1H, d, J=8.8 Hz), 7.20-7.35 (2H, m), 7.77 (1H, dd, J=2.0, 8.0 Hz), 8.35 (1H, s), 8.63 (1H, brs)

ESI-MS (m/e): 443[M+H]$^+$

PRODUCTION EXAMPLE 108

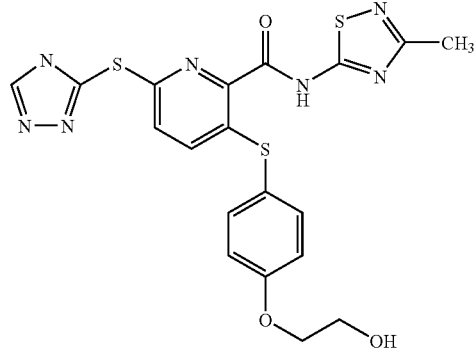

Manufacture of 3-(4-hydroxyethyloxy-phenylsulfanyl)-6-(4H-[1,2,4]triazole-3-ylsulfanyl)-N-(3-methyl-[1,2,4]-thiadiazole-5-yl)-2-pyridine carboxamide Compound of Production Example 108 can be produced by the same method as Production Example 1, by a method according thereto, or by a combination of these and ordinary methods, with the use of 3,6-dichloro-2-pyridinecarboxylic acid, 5-amino-3-methyl-1,2,4-thiadiazole, 4-hydroxyethyloxy-thiophenol and 3-mercapto-1,2,4-triazole.

$^1$HNMR (CDCl$_3$) δ: 2.63 (3H, s), 3.99 (2H, m), 4.13 (2H, m), 7.00-7.08 (3H, m), 7.25 (1H, d, J=8.4 Hz), 7.49 (2H, d, J=8.7 Hz), 8.36 (1H, s)

ESI-MS (m/e): 488[M+H]$^+$

PRODUCTION EXAMPLE 109

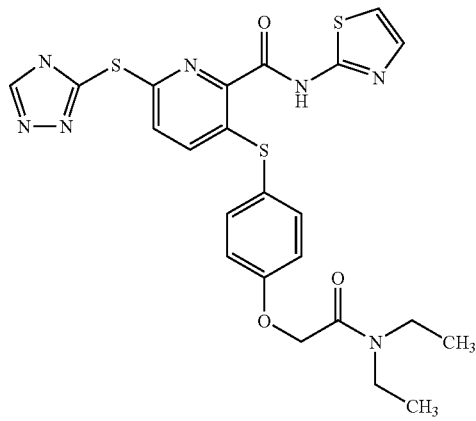

Manufacture of 3-(4-diethylcarbamoylmethyloxy-phenylsulfanyl)-6-(4H-[1,2,4]triazole-3-ylsulfanyl)-N-(thiazole-2-yl)-2-pyridine carboxamide Compound of Production Example 109 can be produced by the same method as Production Example 1, by a method according thereto, or by a combination of these and ordinary methods, with the use of 3,6-dichloro-2-pyridinecarboxylic acid, 2-amino-thiazole, 4-diethylcarbamoylmethyloxy-thiophenol and 3-mercapto-1,2,4-triazole.

$^1$HNMR (CDCl$_3$) δ: 2.72 (6H, s), 7.02 (1H, d, J=3.6 Hz), 7.03 (1H, d, J=8.0 Hz), 7.20 (1H, d, J=8.0 Hz), 7.44 (1H, d, J=3.6 Hz), 7.66 (2H, d, J=8.4 Hz), 7.78 (2H, d, J=8.4 Hz), 8.3 (1H, s)

ESI-MS (m/e): 542[M+H]$^+$

PRODUCTION EXAMPLE 110

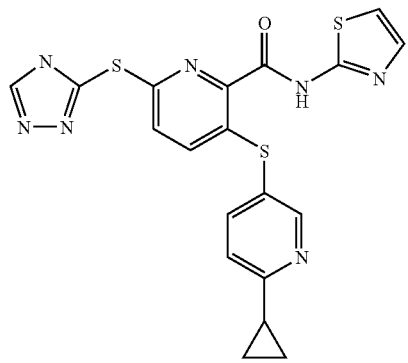

Manufacture of 3-(6-cyclopropyl-pyridine-3-ylsulfanyl)-6-(4H-[1,2,4]triazole-3-ylsulfanyl)-N-(thiazole-2-yl)-2-pyridine carboxamide Compound of Production Example 110 can be produced by the same method as Production Example 1, by a method according thereto, or by a combination of these and ordinary methods, with the use of 3,6-dichloro-2-pyridinecarboxylic acid, 2-amino-thiazole, 6-cyclopropyl-3-mercapto-pyridine and 3-mercapto-1,2,4-triazole.

$^1$HNMR (CDCl$_3$) δ: 0.70-1.38 (4H, m), 1.98-2.18 (1H, m), 6.96-7.08 (2H, m), 7.46 (1H, d, J=3.2 Hz), 7.70 (1H, dd, J=2.0, 8.4 Hz), 8.36 (1H, s), 8.56 (1H, d, J=2.0 Hz)

ESI-MS (m/e): 453[M+H]$^+$

PRODUCTION EXAMPLE 111

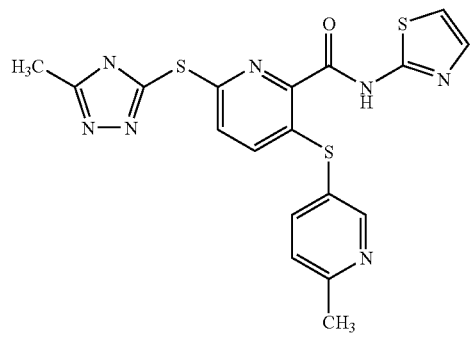

Manufacture of 3-(6-methyl-pyridine-3-ylsulfanyl)-6-(5-methyl-4H-[1,2,4]triazole-3-ylsulfanyl)-N-(thiazole-2-yl)-2-pyridine carboxamide Compound of Production Example 111 can be produced by the same method as Production Example 1, by a method according thereto, or by a combination of these and ordinary methods, with the use of 3,6-dichloro-2-pyridinecarboxylic acid, 2-amino-thiazole, 3-mercapto-6-methyl-pyridine and 3-mercapto-5-methyl-1,2,4-triazole.

$^1$HNMR (CDCl$_3$) δ: 2.57 (3H, s), 2.64 (3H, s), 6.96 (1H, d, J=8.8 Hz), 7.02 (1H, d, J=3.6 Hz), 7.20 (1H, d, J=8.8 Hz), 7.25-7.29 (1H, m), 7.46 (1H, d, J=3.6 Hz), 7.76 (1H, dd, J=2.4, 7.6 Hz), 8.63 (1H, brs)

ESI-MS (m/e): 442[M+H]$^+$

PRODUCTION EXAMPLE 112

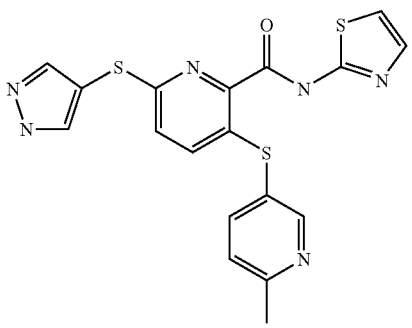

Manufacture of 3-(6-methyl-pyridine-3-ylsulfanyl)-6-(pyrazole-4-ylsulfanyl)-N-(thiazole-2-yl)2-pyridine carboxamide Compound of Production Example 112 can be produced by the same method as Production Example 1, by a method according thereto, or by a combination of these and ordinary methods with the use of 3,6-dichloro-2-pyridinecarboxylic acid, 2-amino-thiazole, 3-mercapto-6-methyl-pyridine and 4-mercapto-pyrazole.

$^1$HNMR (CDCl$_3$) δ: 2.62 (3H, s), 6.88 (1H, m), 7.05 (1H, m), 7.24 (1H, d, J=8.9 Hz), 7.30-7.68 (3H, m), 7.72 (1H, dd, J=1.1, 8.9 Hz), 7.76-7.82 (1H, m), 8.60 (1H, d, J=1.1 Hz)

ESI-MS (m/e): 427[M+H]$^+$

PRODUCTION EXAMPLE 113

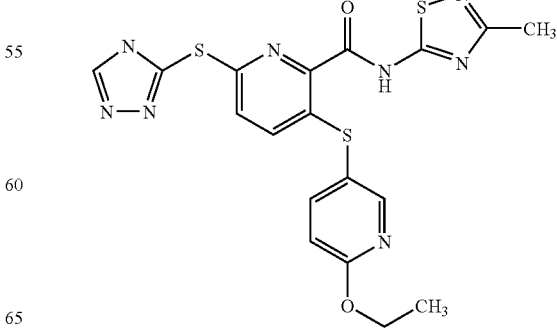

Manufacture of 3-(6-ethoxy-pyridine-3-ylsulfanyl)-6-(4H-[1,2,4]triazole-3-ylsulfanyl)-N-(3-methyl-[1,2,4]-thiadiazole-5-yl)-2-pyridine carboxamide Compound of Production Example 113 can be produced by the same method as Production Example 1, by a method according thereto, or by a combination of these and ordinary methods, with the use of 3,6-dichloro-2-pyridinecarboxylic acid, 5-amino-3-hydroxy-1,2,4-thiadiazole, 6-ethoxy-3-mercapto-pyridine and 3-mercapto-1,2,4-triazole.

¹HNMR (CDCl₃) δ: 1.43 (3H, t, J=6.9 Hz), 2.06 (3H, s), 4.42 (2H, q, J=6.9 Hz), 6.85 (1H, d, J=9.0 Hz), 7.08 (1H, d, J=9.0 Hz), 7.29 (1H, d, J=9.0 Hz), 7.69 (1H, dd, J=9.0, 2.1 Hz), 8.31 (1H, d, J=2.1 Hz), 8.37 (1H, s)

ESI-MS (m/e): 473[M+H]⁺

PRODUCTION EXAMPLE 114

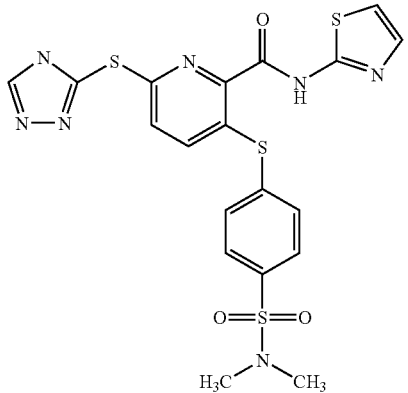

Manufacture of 3-(4-dimethylaminosulfonyl-phenylsulfanyl)-6-(4H-[1,2,4]triazole-3-ylsulfanyl)-N-(thiazole-2-yl)-2-pyridine carboxamide Compound of Production Example 114 can be produced by the same method as Production Example 1, by a method according thereto, or by a combination of these and ordinary methods, with the use of 3,6-dichloro-2-pyridinecarboxylic acid, 2-amino-thiazole, 4-dimethylaminosulfonyl-thiophenol and 3-mercapto-1,2,4-triazole.

¹HNMR (CDCl₃) δ: 2.72 (6H, s), 7.02 (1H, d, J=3.6 Hz), 7.03 (1H, d, J=8.0 Hz), 7.20 (1H, d, J=8.0 Hz), 7.44 (1H, d, J=3.6 Hz), 7.66 (2H, d, J=8.4 Hz), 7.78 (2H, d, J=8.4 Hz), 8.33 (1H, s)

ESI-MS (m/e): 520[M+H]⁺

PRODUCTION EXAMPLE 115

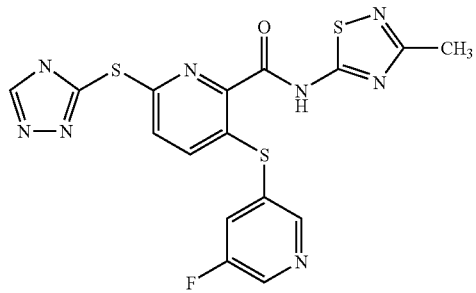

Manufacture of 3-(5-fluoro-pyridine-3-ylsulfanyl)-6-(4H-[1,2,4]triazole-3-ylsulfanyl)-N-(3-methyl-[1,2,4]thiadiazole-5-yl)-2-pyridine carboxamide ¹HNMR (CDCl₃) δ: 2.59 (3H, s), 7.02 (1H, d, J=8.8 Hz), 7.30 (1H, d, J=8.4 Hz), 7.60-7.75 (1H, m), 8.41 (1H, s), 8.50-8.65 (2H, m)

ESI-MS (m/e): 447 [M+H]⁺

Compound of Production Example 115 can be produced by the same method as Production Example 1, by a method according thereto, or by a combination of these and ordinary methods, with the use of 3,6-dichloro-2-pyridinecarboxylic acid, 5-amino-3-methyl-1,2,4-thiadiazole, 5-fluoro-3-mercapto-pyridine and 3-mercapto-1,2,4-triazole.

PRODUCTION EXAMPLE 116

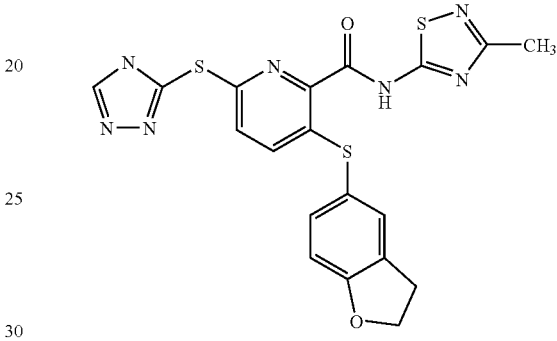

Manufacture of 3-(2,3-dihydrobenzofuran-5-ylsulfanyl)-6-(4H-[1,2,4])triazole-3-ylsulfanyl)-N-(3-methyl-[1,2,4]thiadiazole-5-yl)-2-pyridine carboxamide Compound of Production Example 116 can be produced by the same method as Production Example 66, by a method according thereto, or by a combination of these and ordinary methods, with the use of 6-chloro-3-(4-methoxy-phenylmethylsulfanyl)-N-(3-methyl-1,2,4-thiadiazole-5-yl)-2-pyridine carboxamide, 5-iodo-2,3-dihydrobenzofuran and 3-mercapto-1,2,4-triazole which can be obtained by the same method as Production Example 1.

¹HNMR (CDCl₃) δ: 2.61 (3H, s), 3.25 (2H, t, J=8.4 Hz), 4.65 (2H, t, J=8.4 Hz), 6.85 (1H, d, J=8.4 Hz), 7.05 (1H, d, J=8.4 Hz), 7.06-7.33 (3H, m), 7.78 (1H, dd, J=2.4, 8.5 Hz), 8.31 (1H, s)

ESI-MS (m/e): 470[M+H]⁺

PRODUCTION EXAMPLE 117

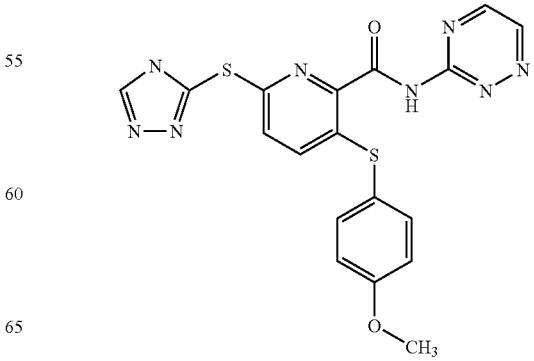

Manufacture of 3-(4-methoxy-phenylsulfanyl)-6-(4H-[1,2,4]triazole-3-ylsulfanyl)-N-([1,2,4]-triazine-3-yl)-2-pyridine carboxamide Compound of Production Example 117 can be produced by the same method as Production Example 1, by a method according thereof, or by a combination of these and ordinary methods, with the use of 3,6-dichloro-2-pyridinecarboxylic acid, 3-amino-1,2,4-triazine, 4-methoxy-thiophenol and 3-mercapto-1,2,4-triazole.

$^1$HNMR (CDCl$_3$) δ: 3.84 (3H, s), 6.95 (2H, d, J=8.8 Hz), 7.00 (1H, d, J=8.8 Hz), 7.17 (1H, d, J=8.8 Hz), 7.44 (2H, d, J=8.8 Hz), 8.40 (1H, s), 8.63 (1H, d, J=2.4 Hz), 8.96 (1H, d, J=2.4 Hz)

ESI-MS (m/e): 439[M+H]$^+$

PRODUCTION EXAMPLE 118

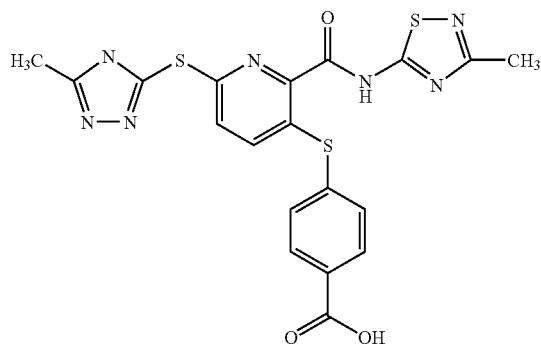

Manufacture of 3-(4-carboxy-phenylsulfanyl)-6-(5-methyl-[1,2,4]triazole-3-ylsulfanyl)-N-(3-methyl-[1,2,4]thiadiazole-5-yl)-2-pyridine carboxamide Compound of Production Example 118 can be produced by the same method as Production Example 1, by a method according thereto, or by a combination of these and ordinary methods, with the use of 3,6-dichloro-2-pyridinecarboxylic acid, 5-amino-3-methyl-1,2,4-thiadiazole, 4-carboxy-thiophenol and 3-mercapto-5-methyl-1,2,4-triazole.

$^1$HNMR (CDCl$_3$) δ: 2.46 (3H, s), 2.52 (3H, s), 7.00 (1H, d, J=8.8 Hz), 7.13 (1H, d, J=8.8 Hz), 7.52 (2H, d, J=7.8 Hz), 8.01 (2H, d, J=8.0 Hz)

ESI-MS (m/e): 486[M+H]$^+$

PRODUCTION EXAMPLE 119

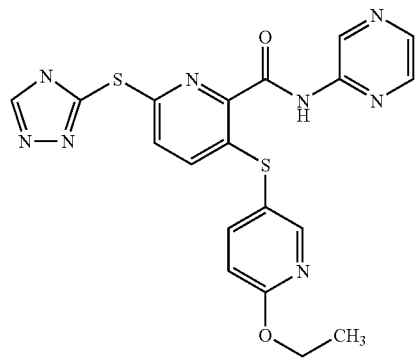

Manufacture of 3-(6-ethoxy-pyridine-3-ylsulfanyl)-6-(4H-[1,2,4]triazole-3-ylsulfanyl)-N-(pyrazin-2-yl)-2-pyridine carboxamide Compound of Production Example 119 can be produced by the same method as Production Example 1, by a method according thereto, or by a combination of these and ordinary methods, with the use of 3,6-dichloro-2-pyridine carboxylic acid, 2-amino-pyradine, 6-ethoxy-3-mercapto-pyridine and 3-mercapto-1,2,4-triazole.

$^1$HNMR (CDCl$_3$) δ: 1.43 (3H, t, J=6.9 Hz), 4.41 (2H, q, J=6.9 Hz), 6.83 (1H, d, J=8.7 Hz), 7.06 (1H, d, J=8.7 Hz), 7.27 (1H, d, J=8.7 Hz), 7.69 (1H, m), 8.29-8.35 (2H, m), 8.40 (1H, m), 8.42 (1H, s), 9.75 (1H, m)

ESI-MS (m/e): 453[M+H]$^+$

PRODUCTION EXAMPLE 120

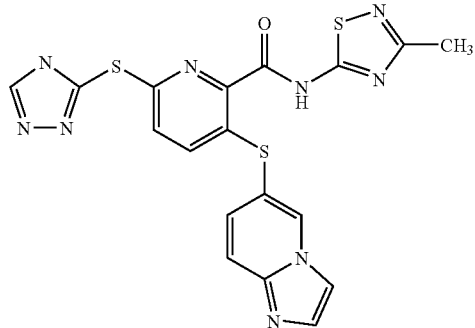

Manufacture of 3-(imidazo-[1,2-a]-pyridine-6-ylsulfanyl)-6-(4H[1,2,4]triazole-3-ylsulfanyl)-N-(3-methyl-[1,2,4]-thiadiazole-5-yl)-2-pyridine carboxamide Compound of Production Example 120 can be produced by the same method as Production Example 66, by a method according thereto, or by a combination of these and ordinary methods, with the use of 6-chloro-3-(4-methoxy-phenylmethylsulfanyl)-N-(3-methyl-1,2,4-thiadiazole-5-yl)-2-pyridine carboxamide, 6-iodo-imidazo-[1,2-a]-pyridine and 3-mercapto-1,2,4-triazole which can be obtained by the same method as Production Example 1.

$^1$HNMR (DMSO-d$_6$) δ: 3.30 (3H, s), 7.10-7.40 (3H, m), 7.60-7.80 (2H, m), 7.97 (1H, s), 8.60-8.80 (1H, m), 8.93 (1H, s)

ESI-MS (m/e): 468[M+H]$^+$

PRODUCTION EXAMPLE 121

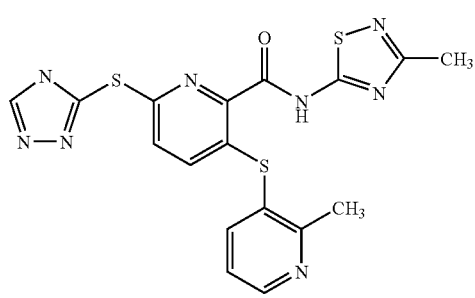

Manufacture of 3-(2-methyl-pyridine-3-ylsulfanyl)-6-(4H-[1,2,4]triazole-3-ylsulfanyl)-N-(3-methyl-[1,2,4]thiadiazole-5-yl)-2-pyridine carboxamide Compound of Production Example 121 can be produced by the same method as Production Example 1, by a method according thereof, or by a combination of these and ordinary methods, with the use of 3,6-dichloro-2-pyridinecarboxylic acid, 5-amino-3-methyl-1,2,4-thiadiazole, 3-mercapto-2-methyl-pyridine and 3-mercapto-1,2,4-triazole.

$^1$HNMR (CDCl$_3$) δ: 2.59 (3H, s), 2.62 (3H, s), 6.84 (1H, d, J=8.8 Hz), 7.20-7.35 (2H, m), 7.80-7.92 (1H, m), 8.43 (1H, s), 8.60-8.68 (1H, m)

ESI-MS (m/e): 443[M+H]$^+$

PRODUCTION EXAMPLE 122

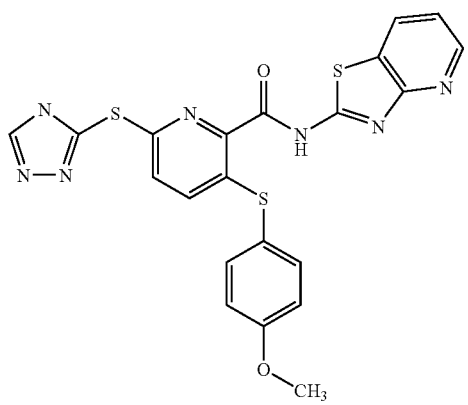

Manufacture of 3-(4-methoxy-phenylsulfanyl)-6-(4H-[1,2,4]triazole-3-ylsulfanyl)-N-(thiazolo[4,5-b]pyridine-2-yl)-2-pyridine carboxamide Compound of Production Example 122 can be produced by the same method as Production Example 1, by a method according thereof, or by a combination of these and ordinary methods, with the use of 3,6-dichloro-2-pyridinecarboxylic acid, 2-amino-thiazolo[4,5-b]pyridine, 4-methoxy-thiophenol and 3-mercapto-1,2,4-triazole.

$^1$HNMR (CDCl$_3$) δ: 3.88 (3H, s), 7.01 (2H, d, J=8.8 Hz), 7.03 (1H, d, J=8.0 Hz), 7.02-7.26 (1H, m), 7.50 (2H, d, J=8.8 Hz), 8.23 (1H, d, J=8.0 Hz), 8.52 (1H, s), 8.59 (1H, s)

ESI-MS (m/e): 494[M+H]$^+$

PRODUCTION EXAMPLE 123

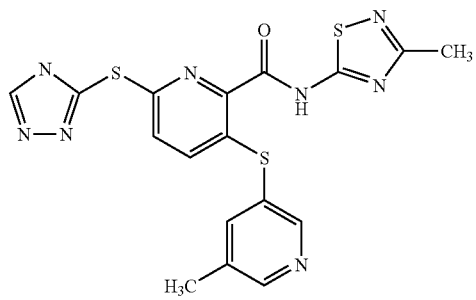

Manufacture of 3-(5-methyl-pyridine-3-ylsulfanyl)-6-(4H-[1,2,4]triazole-3-ylsulfanyl)-N-(3-methyl-[1,2,4]thiadiazole-5-yl)-2-pyridine carboxamide Compound of Production Example 123 can be produced by the same method as Production Example 1, by a method according thereto, or by a combination of these and ordinary methods, with the use of 3,6-dichloro-2-pyridinecarboxylic acid, 5-amino-3-methyl-1,2,4-thiadiazole, 3-mercapto-5-methyl-pyridine and 3-mercapto-1,2,4-triazole.

$^1$HNMR (CDCl$_3$) δ: 2.40 (3H, s), 2.60 (3H, s), 6.99 (1H, d, J=8.4 Hz), 7.22-7.30 (1H, m), 7.71 (1H, s), 8.40 (1H, s), 8.55 (2H, m)

ESI-MS (m/e): 443[M+H]$^+$

PRODUCTION EXAMPLE 124

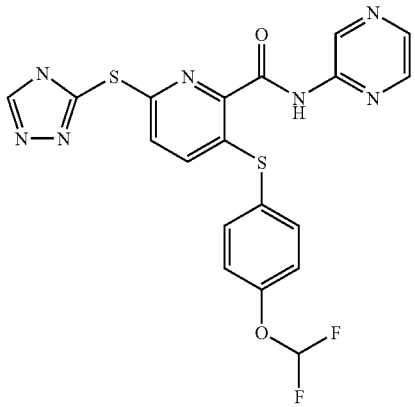

Manufacture of 3-(4,4-difluoromethyloxy-phenylsulfanyl)-6-(4H-[1,2,4]triazole-3-ylsulfanyl)-N-(pyridine-2-yl)-2-pyridine carboxamide Compound of Production Example 124 can be produced by the same method as Production Example 1, by a method according thereto, or by a combination of these and ordinary methods, with the use of 3,6-dichloro-2-pyridinecarboxylic acid, 2-amino-pyradine, 4,4-difluoromethyloxy-thiophenol and 3-mercapto-1,2,4-triazole.

$^1$HNMR (CDCl$_3$) δ: 6.62 (1H, t, J=73 Hz), 7.05 (1H, d, J=9.0 Hz), 7.20-7.30 (3H, m), 7.60 (2H, d, J=8.7 Hz), 8.30-8.43 (2H, m), 8.41 (1H, brs), 9.78 (1H, brs)

ESI-MS (m/e): 474[M+H]$^+$

PRODUCTION EXAMPLE 125

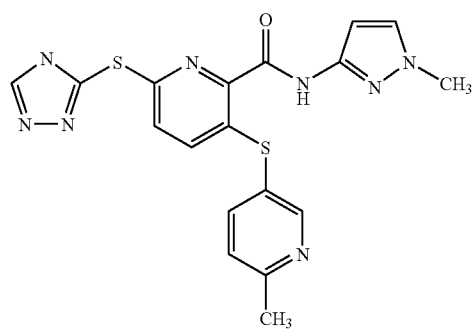

125

Manufacture of 3-(6-methyl-pyridine-3-ylsulfanyl)-6-(4H-[1,2,4]triazole-3-ylsulfanyl)-N-(1-methyl-1H-[1,2]-pyrazole-3-yl)-2-pyridine carboxamide Compound of Production Example 125 can be produced by the same method as Production Example 1, by a method according thereto, or by a combination of these and ordinary methods, with the use of 3,6-dichloro-2-pyridine carboxylic acid, 3-amino-1-methyl-1H-[1,2]pyrazole, 3-mercapto-6-methyl-pyridine and 3-mercapto-1,2,4-triazole.

$^1$HNMR (CDCl$_3$) δ: 2.64 (3H, s) 3.89 (3H, s), 6.91 (1H, m), 6.97 (1H, d, J=8.4 Hz), 7.17-7.36 (3H, m), 7.79 (1H, m), 8.31 (1H, s), 8.63 (1H, m)

ESI-MS (m/e): 425[M+H]$^+$

PRODUCTION EXAMPLE 126

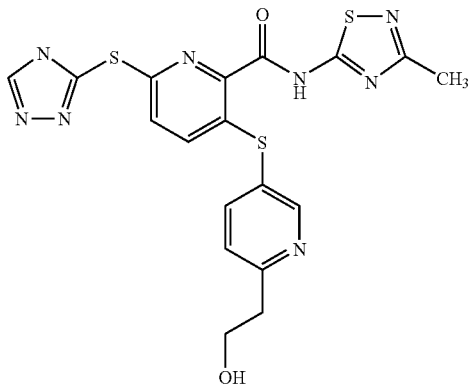

Manufacture of 3-(6-hydroxyethyl-pyridine-3-ylsulfanyl)-6-(4H[1,2,4]triazole-3-ylsulfanyl)-N-(3-methyl-[1,2,4]thiadiazole-5-yl)-2-pyridine carboxamide Compound of Production Example 126 can be produced by the same method as Production Example 1, by a method according thereto, or by a combination of these and ordinary methods, with the use of 3,6-dichloro-2-pyridinecarboxylic acid, 5-amino-3-methyl-1,2,4-thiadiazole, 6-hydroxyethyl-3-mercapto-pyridine and 3-mercapto-1,2,4-triazole.

$^1$HNMR (CDCl$_3$) δ: 2.57 (3H, s), 3.04 (2H, t, J=6.0 Hz), 3.97 (2H, t, J=6.0 Hz), 6.98 (1H, d, J=8.8 Hz), 7.20 (1H, d, J=8.8 Hz), 7.30 (1H, d, J=8.0 Hz), 7.78 (1H, dd, J=2.4, 8.0 Hz), 8.32 (1H, s), 8.57 (1H, d, J=2.4 Hz)

ESI-MS (m/e): 473[M+H]$^+$

PRODUCTION EXAMPLE 127

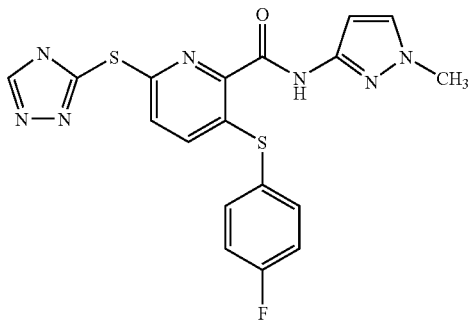

126

Manufacture of 3-(4-fluoro-phenylsulfanyl)-6-(4H-[1,2,4]triazole-3-ylsulfanyl)-N-(1-methyl-1H-[1,2]-pyrazole-3-yl)-2-pyridine carboxamide Compound of Production Example 127 can be produced by the same method as Production Example 1, by a method according thereto, or by a combination of these and ordinary methods, with the use of 3,6-dichloro-2-pyridinecarboxylic acid, 3-mercapto-1-methyl-1H-[1,2]pyrazole, 4-fluoro-thiophenol and 3-mercapto-1,2,4-triazole.

$^1$HNMR (CDCl$_3$) δ: 3.85 (3H, s), 6.89 (1H, brs), 6.97 (1H, d, J=8.7 Hz), 7.11-7.21 (3H, m), 7.30 (1H, d, J=8.7 Hz), 7.57 (2H, m), 8.35 (1H, s)

ESI-MS (m/e): 428[M+H]$^+$

PRODUCTION EXAMPLE 128

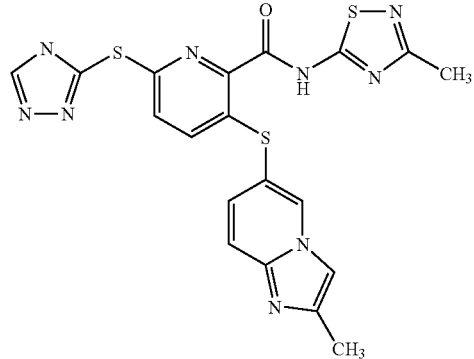

Manufacture of 3-(2-methyl-imidazo-[1,2-a]-pyridine-6-ylsulfanyl)-6-(4H-[1,2,4]triazole-3-ylsulfanyl)-N-(3-methyl-[1,2,4]-thiadiazole-5-yl)-2-pyridine carboxamide Compound of Production Example 128 can be produced by the same method as Production Example 1, by a method according thereto, or by a combination of these and ordinary methods, with the use of 3,6-dichloro-2-pyridinecarboxylic acid, 5-amino-3-methyl-1,2,4-thiadiazole, 6-mercapto-2-methyl-imidao-[1,2-a]pyridine and 3-mercapto-1,2,4-triazole.

$^1$HNMR (DMSO-d$_6$) δ: 2.34 (3H, s), 2.50 (3H, s), 7.10-7.20 (2H, m), 7.28 (1H, d, J=8.4 Hz), 7.49 (1H, d, J=9.2 Hz), 7.70 (1H, s), 8.70 (1H, brs), 8.83 (1H, s)

ESI-MS (m/e): 482[M+H]$^+$

PRODUCTION EXAMPLE 129

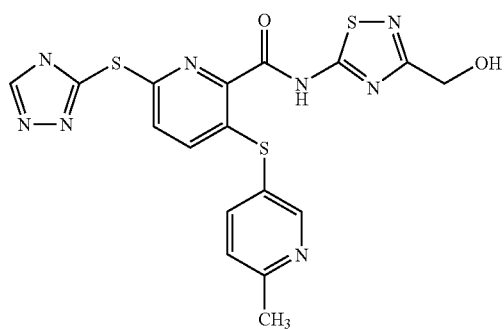

Manufacture of 3-(6-methyl-pyridine-3-ylsulfanyl)-6-(4H-[1,2,4]triazole-3-ylsulfanyl)-N-(3-hydroxymethyl-[1,2,4]-thiadiazole-5-yl)-2-pyridine carboxamide Compound of Production Example 129 can be produced by the same method as Production Example 1, by a method according thereto, or by a combination of these and ordinary methods, with the use of 3,6-dichloro-2-pyridinecarboxylic acid, 5-amino-3-methyl-1,2,4-thiadiazole, 3-mercapto-6-methyl-pyridine and 3-mercapto-1,2,4-triazole.

$^1$HNMR (CDCl$_3$) δ: 2.59 (3H, s), 4.65 (2H, s), 6.97 (1H, d, J=8.4 Hz), 7.23 (1H, d, J=8.4 Hz), 7.26 (1H, d, J=7.6 Hz), 7.74 (1H, dd, J=2.0, 7.6 Hz), 8.34 (1H, s), 8.54 (1H, d, J=2.0 Hz)

ESI-MS (m/e): 459[M+H]$^+$

PRODUCTION EXAMPLE 130

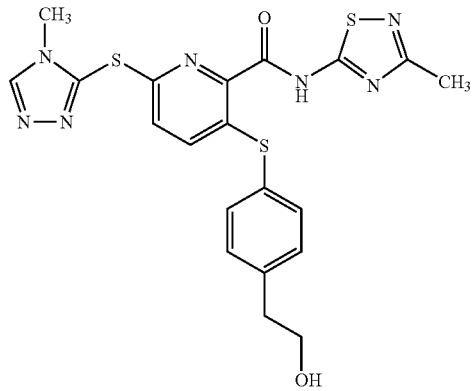

Manufacture of 3-[4-(2-hydroxyethyl)-phenylsulfanyl]-6-(4-methyl-4H-[1,2,4]triazole-3-ylsulfanyl)-N-(3-methyl-[1,2,4]-thiadiazole-5-yl)-2-pyridine carboxamide Compound of Production Example 130 can be produced by the same method as Production Example 1, by a method according thereto, or by a combination of these and ordinary methods, with the use of 3,6-dichloro-2-pyridinecarboxylic acid, 5-amino-3-methyl-1,2,4-thiadiazole, 4-hydroxyethyl-thiophenol and 3-mercapto-4-methyl-1,2,4-triazole.

$^1$HNMR (CDCl$_3$) δ: 2.61 (3H, s), 2.93 (2H, t, J=6.4 Hz), 3.72 (3H, s), 3.92 (2H, t, J=6.4 Hz), 7.06 (1H, d, J=8.4 Hz), 7.11 (1H, d, J=8.4 Hz), 7.35 (2H, d, J=8.0 Hz), 7.47 (2H, d, J=8.0 Hz), 8.38 (1H, s)

ESI-MS (m/e): 486[M+H]$^+$

PRODUCTION EXAMPLE 131

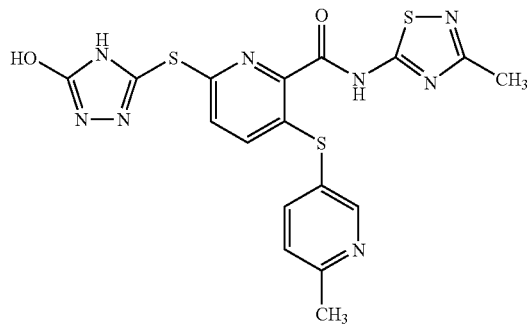

Manufacture of 3-(6-methyl-pyridine-3-ylsulfanyl)-6-(5-hydroxy-4H-[1,2,4]triazole-3-ylsulfanyl)-N-(3-methyl-[1,2,4]-thiadiazole-5-yl)-2-pyridine carboxamide Compound of Production Example 131 can be produced by the same method as Production Example 1, by a method according thereto, or by a combination of these and ordinary methods, with the use of 3,6-dichloro-2-pyridinecarboxylic acid, 5-amino-3-methyl-thiadiazole, 3-mercapto-6-methyl-pyridine and 5-hydroxy-3-mercapto-1,2,4-triazole.

$^1$HNMR (DMSO-d$_6$) δ: 2.53 (3H, s), 2.65 (3H, s), 7.13-7.71 (3H, m), 7.84-7.98 (1H, m), 8.43-8.63 (1H, m)

ESI-MS (m/e): 459[M+H]$^+$

PRODUCTION EXAMPLE 132

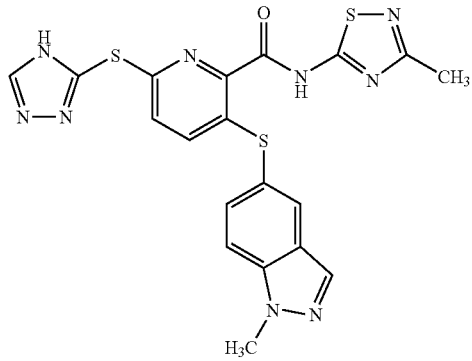

Manufacture of 3-(1-methyl-1H-indazole-5-ylsulfanyl)-6-(4H-[1,2,4]triazole-3-ylsulfanyl)-N-(3-methyl-[1,2,4]-thiadiazole-5-yl)-2-pyridine carboxamide Compound of Production Example 132 can be produced by the same method as Production Example 1, by a method according thereto, or by a combination of these and ordinary methods, with the use of 3,6-dichloro-2-pyridinecarboxylic acid, 5-amino-3-mercapto-1,2,4-thiadiazole, 5-mercapto-1-methyl-1H-indazole and 3-mercapto-1,2,4-triazole.

$^1$HNMR (CDCl$_3$) δ: 2.53 (3H, s), 4.03 (3H, s), 6.87 (1H, d, J=8.8 Hz), 7.06 (1H, d, J=8.8 Hz), 7.39-7.45 (2H, m), 7.94 (2H, m), 8.27 (1H, s)

ESI-MS (m/e): 482[M+H]$^+$

PRODUCTION EXAMPLE 133

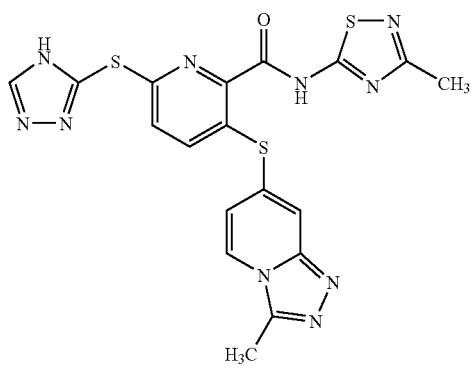

Manufacture of 3-(3-methyl-[1,2,4]-triazolo-[4,3-a]-pyridine-7-ylsulfanyl)-6-(4H-[1,2,4]triazol-3-ylsulfanyl)-N-(3-methyl-[1,2,4]-thiadiazole-5-yl)-2-pyridine carboxamide Compound of Production Example 133 can be produced by the same method as Production Example 1, by a method according thereto, or by a combination of these and ordinary methods, with the use of 3,6-dichloro-2-pyridinecarboxylic acid, 5-amino-3-mercapto-1,2,4-thiadiazole, 7-mercapto-3-methyl-[1,2,4]-triazoleo-[4,3-a]-pyridine and 3-mercapto-1,2,4-triazole.

$^1$HNMR (DMSO-d$_6$) δ: 2.49 (3H, s), 2.67 (3H, s), 6.82-6.87 (1H, m), 7.19 (1H, d, J=8.8 Hz), 7.57 (1H, d, J=8.8 Hz), 7.86 (1H, s), 8.35 (1H, d, J=7.2 Hz), 8.70-8.90 (1H, brs)

ESI-MS (m/e): 483 [M+H]$^+$

PRODUCTION EXAMPLE 134

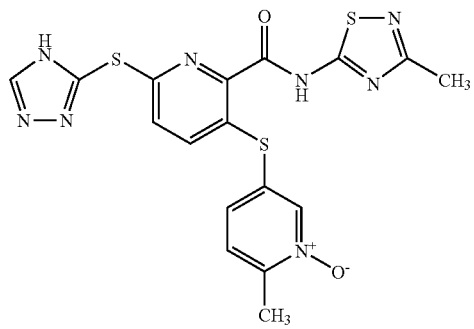

Manufacture of 3-(1-oxy-6-methyl-pyridine-3-ylsulfanyl)-6-(4H-[1,2,4]triazole-3-ylsulfanyl)-N-(3-methyl-[1,2,4]thiadiazole-5-yl)-2-pyridine carboxamide Compound of Production Example 134 can be produced by the same method as Production Example 1, by a method according thereto, or by a combination of these and ordinary methods, with the use of 3,6-dichloro-2-pyridinecarboxylic acid, 5-amino-3-methyl-thiadiazole, 3-mercapto-6-methyl-1-oxy-pyridine and 3-mercapto-1,2,4-triazole.

$^1$HNMR (CDCl$_3$) δ: 2.58 (3H, s), 2.61 (3H, s), 7.16 (1H, d, J=8.4 Hz), 7.32 (1H, d, J=8.4 Hz), 7.40-7.45 (2H, m), 8.38 (1H, s), 8.43 (1H, brs)

ESI-MS (m/e): 459[M+H]$^+$

PRODUCTION EXAMPLE 135

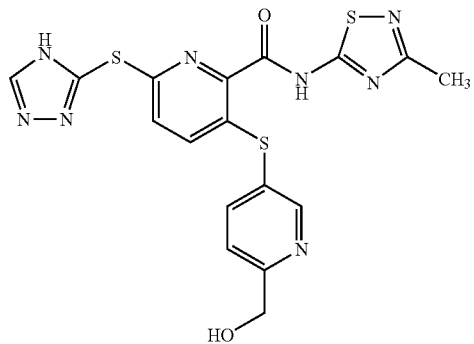

Manufacture of 3-(6-hydroxymethyl-pyridine-3-ylsulfanyl)-6-(4H-[1,2,4]triazole-3-ylsulfanyl)-N-(3-methyl-[1,2,4]-thiadiazole-5-yl)-2-pyridine carboxamide Compound of Production Example 135 can be produced by the same method as Production Example 1, by a method according thereto, or by a combination of these and ordinary methods, with the use of 3,6-dichloro-2-pyridinecarboxylic acid, 5-amino-3-methyl-thiadiazole, 6-hydroxymethyl-3-mercapto-pyridine and 3-mercapto-1,2,4-triazole.

$^1$HNMR (CDCl$_3$) δ: 2.62 (3H, s), 4.80 (2H, s), 7.01 (1H, d, J=8.8 Hz), 7.26 (1H, d, J=8.8 Hz), 7.56 (1H, d, J=8.0 Hz), 7.91 (1H, dd, J=8.0 Hz, 1.2 Hz), 8.36 (1H, s), 8.65 (1H, d, J=1.2 Hz)

ESI-MS (m/e): 459[M+H]

PRODUCTION EXAMPLE 136

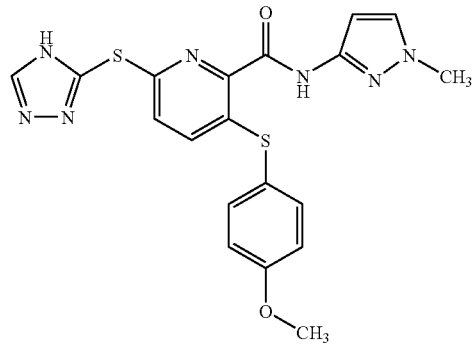

Manufacture of 3-(4-methoxy-phenylsulfanyl)-6-(4H-[1,2,4]triazole-3-ylsulfanyl)-N-(1-methyl-1H-[1,2]-pyrazole-3-yl)-2-pyridine carboxamide Compound of Production Example 136 can be produced by the same method as Production Example 1, by a method according thereto, or by a combination of these and ordinary methods, with the use of 3,6-dichloro-2-pyridinecarboxylic acid, 3-amino-1-methyl-1H-[1,2]pyrazole, 4-methoxy-thiophenol and 3-mercapto-1,2,4-triazole.

$^1$HNMR (CDCl$_3$) δ: 3.82 (3H, s), 3.83 (3H, s), 6.80 (1H, d, J=2.4 Hz), 6.93 (1H, d, J=8.4 Hz), 6.94 (2H, d, J=8.8 Hz), 7.08 (1H, d, J=8.4 Hz), 7.25 (1H, d, J=2.4 Hz), 7.43 (2H, d, J=8.8 Hz), 8.32 (1H, s)

ESI-MS (m/e): 440[M+H]$^+$

PRODUCTION EXAMPLE 137

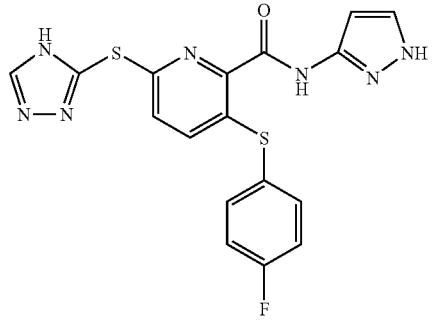

Manufacture of 3-(4-fluoro-phenylsulfanyl)-6-(4H-[1,2,4]triazole-3-ylsulfanyl)-N-(1H-[1,2]-pyrazole-3-yl)-2-pyridine carboxamide Compound of Production Example 137 can be produced by the same method as Production Example 1, by a method according thereto, or by a combination of these and ordinary methods, with the use of 3,6-dichloro-2-pyridinecarboxylic acid, 3-amino-1H-[1,2]pyrazole, 4-fluorothiophenol and 3-mercapto-1,2,4-triazole.

¹HNMR (CDCl3) δ: 6.87 (1H, bs), 6.94 (1H, d, J=8.4 Hz), 7.12-7.18 (3H, m), 7.45-7.53 (3H, m), 8.30 (1H, s)

ESI-MS (m/e): 414[M+H]⁺

PRODUCTION EXAMPLE 138

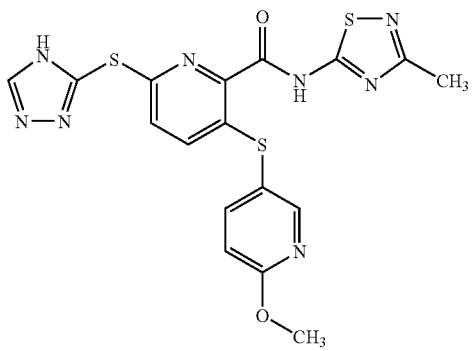

Manufacture of 3-(6-methoxy-pyridine-3-ylsulfanyl)-6-(4H-[1,2,4]triazole-3-ylsulfanyl)-N-(3-methyl-[1,2,4]-thiadiazole-5-yl)-2-pyridine carboxamide Compound of Production Example 138 can be produced by the same method as Production Example 1, by a method according thereto, or by a combination of these and ordinary methods, with the use of 3,6-dichloro-2-pyridinecarboxylic acid, 5-amino-3-methyl-thiadiazole, 3-mercapto-6-methoxy-pyridine and 3-mercapto-1,2,4-triazole.

¹HNMR (CDCl₃) δ: 2.63 (3H, s), 4.00 (3H, s), 6.88 (1H, d, J=8.7 Hz), 7.07 (1H, d, J=8.7 Hz), 7.29 (1H, d, J=8.7 Hz), 7.70 (1H, dd, J=8.7, 2.1 Hz), 8.31-8.40 (2H, m)

ESI-MS (m/e): 459[M+H]⁺

PRODUCTION EXAMPLE 139

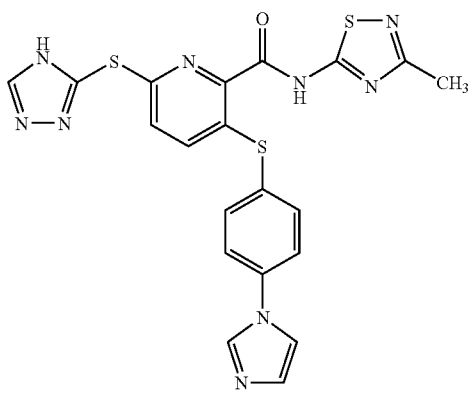

Manufacture of 3-[4-(1H-imidazole-1yl)]-phenylsulfanyl)-6-(4H-[1,2,4]triazole-3-ylsulfanyl)-N-(3-methyl-[1,2,4]-thiadiazole-5-yl)-2-pyridine carboxamide Compound of Production Example 139 can be produced by the same method as Production Example 1, by a method according thereto, or by a combination of these and ordinary methods, with the use of 3,6-dichloro-2-pyridinecarboxylic acid, 5-amino-3-methyl-1,2,4-thiadiazole, 4-(1H-imidazole-1-yl)thiophenol and 3-mercapto-1,2,4-triazole.

¹HNMR (CDCl₃) δ: 2.57 (3H, s), 7.03 (1H, d, J=8.8 Hz), 7.16 (2H, brs), 7.31 (1H, brs), 7.48 (1H, d, J=8.4 Hz), 7.65 (2H, d, J=8.4 Hz), 7.92 (1H, s), 8.32 (1H, s)

ESI-MS (m/e): 494[M+H]⁺

PRODUCTION EXAMPLE 140

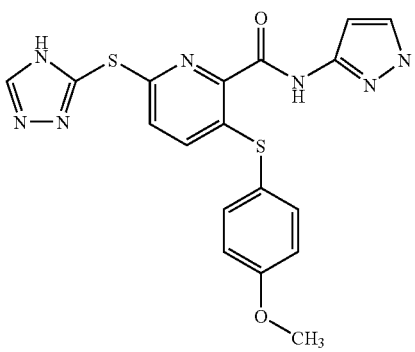

Manufacture of 3-(4-methoxy-phenylsulfanyl)-6-(4H-[1,2,4]triazole-3-ylsulfanyl)-N-(1H-[1,2]-pyrazole-3-yl)-2-pyridine carboxamide Compound of Production Example 140 can be produced by the same method as Production Example 1, by a method according thereto, or by a combination of these and ordinary methods, with the use of 3,6-dichloro-2-pyridinecarboxylic acid, 3-amino-1H-[1,2]-pyrazole, 4-methoxy-thiophenol and 3-mercapto-1,2,4-triazole.

¹HNMR (CDCl3) δ: 6.86 (1H, d, J=2.6 Hz), 6.98 (2H, d, J=8.8 Hz), 6.99 (1H, d, J=8.8 Hz), 7.17 (1H, d, J=8.8 Hz), 7.47 (2H, d, J=8.8 Hz), 7.50 (1H, d, J=2.6 Hz), 8.34 (1H, s)

ESI-MS (m/e): 426[M+H]⁺

PRODUCTION EXAMPLE 141

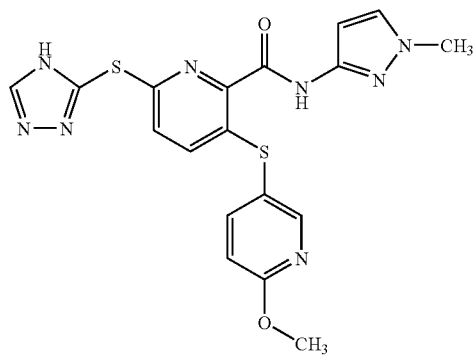

Manufacture of 3-(6-methoxy-pyridine-3-ylsulfanyl)-6-(4H-[1,2,4]triazole-3-ylsulfanyl)-N-(1-methyl-1H-pyrazole-3-yl)-2-pyridine carboxamide Compound of Production Example 141 can be produced by the same method as Production Example 1, by a method according thereto, or by a combination of these and ordinary methods, with the use of 3,6-dichloro-2-pyridinecarboxylic acid, 3-amino-1-methyl-1H-pyrazole, 3-mercapto-6-methoxy-pyridine and 3-mercapto-1,2,4-triazole.

$^1$HNMR (CDCl$_3$) δ: 3.81 (3H, s), 3.95 (3H, s), 6.76 (1H, d, J=2.4 Hz), 6.80 (1H, d, J=8.4 Hz), 6.93 (1H, d, J=8.4 Hz), 7.10 (1H, d, J=8.4 Hz), 7.25 (1H, d, J=2.4 Hz), 7.65 (1H, dd, J=8.4 Hz, 2.0 Hz), 8.28 (1H, d, J=2.0 Hz), 8.36 (1H, s), 10.11 (1H, s)

ESI-MS (m/e): 441 [M+H]

PRODUCTION EXAMPLE 142

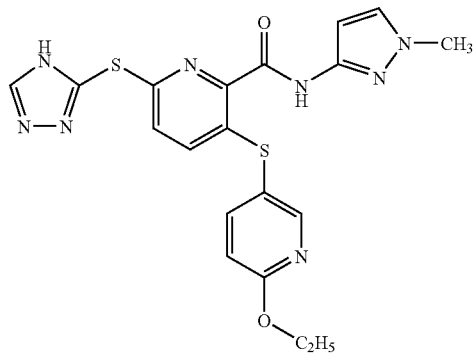

Manufacture of 3-(6-ethoxy-pyridine-3-ylsulfanyl)-6-(4H-[1,2,4]triazole-3-ylsulfanyl)-N-(1-methyl-1H-pyrazole-3-yl)-2-pyridine carboxamide Compound of Production Example 142 can be produced by the same method as Production Example 1, by a method according thereto, or by a combination of these and ordinary methods, with the use of 3,6-dichloro-2-pyridinecarboxylic acid, 3-amino-1-methyl-1H-pyrazole, 3-mercapto-6-ethoxy-pyridine and 3-mercapto-1,2,4-triazole.

$^1$HNMR (CDCl$_3$) δ: 1.43 (3H, t, J=6.9 Hz), 3.87 (3H, s), 4.42 (2H, q, J=6.9 Hz), 6.83 (1H, d, J=8.7 Hz), 6.93 (1H, d, J=2.1 Hz), 7.02 (1H, d, J=8.7 Hz), 7.22 (1H, d, J=8.7 Hz), 7.32 (1H, d, J=2.1 Hz), 7.69 (1H, dd, J=8.7, 2.4 Hz), 8.25-8.39 (2H, m)

ESI-MS (m/e): 455[M+H]$^+$

PRODUCTION EXAMPLE 143

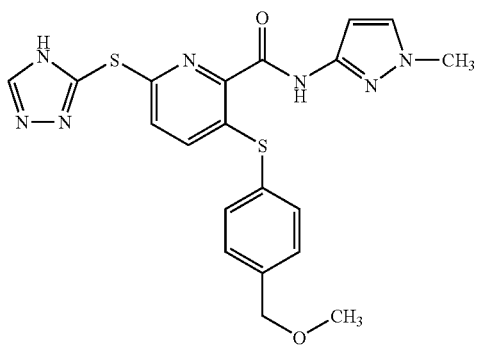

Manufacture of 3-(4-methoxymethyl-phenylsulfanyl)-6-(4H-[1,2,4]triazole-3-ylsulfanyl)-N-(1-methyl-1H-pyrazole-3-yl)-2-pyridine carboxamide Compound of Production Example 143 can be produced by the same method as Production Example 1, by a method according thereto, or by a combination of these and ordinary methods, with the use of 3,6-dichloro-2-pyridinecarboxylic acid, 3-amino-1-methyl-1H-pyrazole, 4-methoxymethyl-thiophenol and 3-mercapto-1,2,4-triazole.

$^1$HNMR (CDCl$_3$) δ: 3.45 (3H, s), 3.82 (3H, s), 4.49 (2H, s), 6.83 (1H, d, J=2.0 Hz), 6.96 (1H, d, J=8.8 Hz), 7.09 (2H, d, J=8.8 Hz), 7.25 (1H, d, J=2.0 Hz), 7.40 (2H, d, J=7.6 Hz), 7.51 (2H, d, J=7.6 Hz), 8.31 (1H, s), 10.14 (1H, s)

ESI-MS (m/e): 440[M+H]$^+$

PRODUCTION EXAMPLE 144

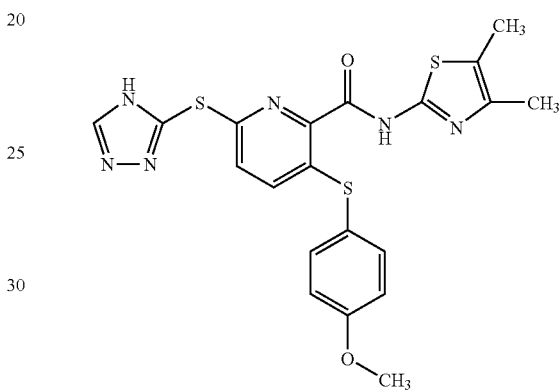

Manufacture of 3-(4-methoxy-phenylsulfanyl)-6-(4H-[1,2,4]triazole-3-yl-sulfanyl)-N-(4,5-dimethylthiazole-2-yl)-2-pyridine carboxamide Compound of Production Example 144 can be produced by the same method as Production Example 1, by a method according thereto, or by a combination of these and ordinary methods, with the use of 3,6-dichloro-2-pyridinecarboxylic acid, 2-amino-4,5-dimethyl-thiazole, 4-methoxy-thiophenol and 3-mercapto-1,2,4-triazole.

$^1$HNMR (CDCl$_3$) δ: 2.29 (3H, s), 2.33 (3H, s), 3.87 (3H, s), 6.98-7.03 (3H, m), 7.21 (1H, d, J=8.6 Hz), 7.48 (2H, d, J=8.6 Hz), 8.29 (1H, s)

ESI-MS (m/e): 471 [M+H]$^+$

PRODUCTION EXAMPLE 145

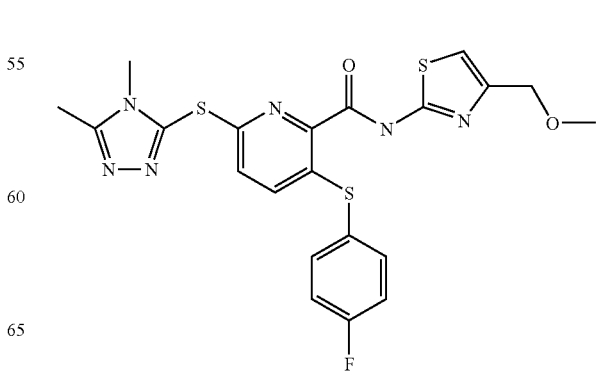

Manufacture of 3-(4-fluoro-phenylsulfanyl)-6-(4,5-dimethyl-4H-[1,2,4]triazole-3-yl-sulfanyl)-N-(4-methoxymethyl-thiazole-2-yl)-2-pyridine carboxamide Compound of Production Example 145 can be produced by the same method as Production Example 1, by a method according thereto, or by a combination of these and ordinary methods, with the use of 3,6-dichloro-2-pyridinecarboxylic acid, 2-amino-4-methoxymethyl-thiazole, 4-fluoro-thiophenol and 3-mercapto-4,5-dimethyl-1,2,4-triazole.

$^1$HNMR (CDCl$_3$) δ: 2.60 (3H, s), 3.47 (3H, s), 3.62 (3H, s), 4.50 (2H, s), 6.93 (1H, s), 6.98 (1H, d, J=8.8 Hz), 7.07 (1H, d, J=8.8 Hz), 7.16 (2H, dd, J=8.8, 8.8 Hz), 7.53 (2H, dd, J=5.2, 8.8 Hz)

ESI-MS (m/e): 503[M+H]$^+$

PRODUCTION EXAMPLE 146

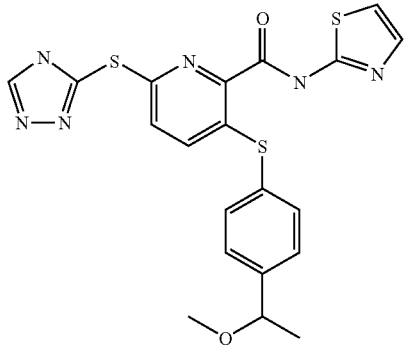

Manufacture of 3-(4-(1-methoxyethyl)-phenylsulfanyl)-6-(4H-[1,2,4]triazole-3-yl-sulfanyl)-N-(thiazole-2-yl)-2-pyridine carboxamide Compound of Production Example 146 can be produced by the same method as Production Example 1, by a method according thereto, or by a combination of these and ordinary methods, with the use of 3,6-dichloro-2-pyridinecarboxylic acid, 2-amino-thiazole, 4-(1-methoxyethyl)-thiophenol and 3-mercapto-1,2,4-triazole.

$^1$HNMR (CDCl$_3$) δ: 1.27 (3H, d, J=6.4 Hz), 3.30 (3H, s), 4.36 (1H, d, J=6.4 Hz), 7.03 (1H, d, J=3.6 Hz), 7.05 (1H, d, J=8.8 Hz), 7.23 (1H, d, J=8.8 Hz), 7.41 (2H, d, J=8.0 Hz), 7.47 (1H, d, J=3.6 Hz), 7.54 (2H, d, J=8.0 Hz), 8.35 (1H, s)

ESI-MS (m/e): 471 [M+H]$^+$

PRODUCTION EXAMPLE 147

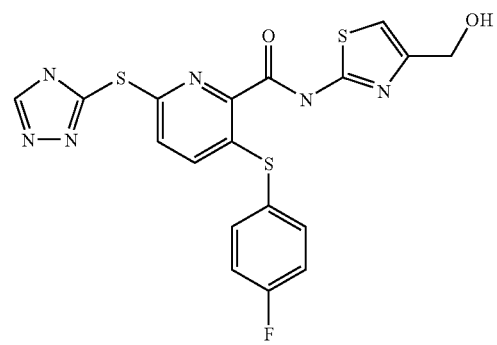

Manufacture of 3-(4-fluoro-phenylsulfanyl)-6-(4H-[1,2,4]triazole-3-yl-sulfanyl)-N-(4-hydroxymethyl-thiazole-2-yl)-2-pyridine carboxamide Compound of Production Example 147 can be produced by the same method as Production Example 1, by a method according thereto, or by a combination of these and ordinary methods, with the use of 3,6-dichloro-2-pyridinecarboxylic acid, 2-amino-4-hydroxymethyl-thiazole, 4-fluoro-thiophenol and 3-mercapto-1,2,4-triazole.

$^1$HNMR (CDCl$_3$) δ: 4.60 (2H, s), 6.84 (1H, s), 6.93 (1H, d, J=8.8 Hz), 7.06-7.16 (3H, m), 7.40-7.60 (2H, m), 8.31 (1H, s)

ESI-MS (m/e): 461 [M+H]$^+$

PRODUCTION EXAMPLE 148

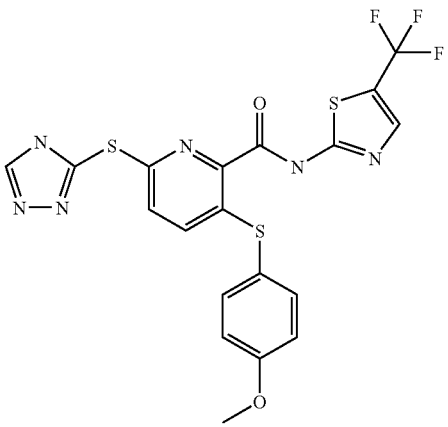

Manufacture of 3-(4-methoxy-phenylsulfanyl)-6-(4H-[1,2,4]triazole-3-yl-sulfanyl)-N-(5-trifluoromethylthiazole-2-yl)-2-pyridine carboxamide Compound of Production Example 148 can be produced by the same method as Production Example 1, by a method according thereto, or by a combination of these and ordinary methods, with the use of 3,6-dichloro-2-pyridinecarboxylic acid, 2-amino-5-trifluoromethyl-thiazole, 4-methoxy-thiophenol and 3-mercapto-1,2,4-triazole.

$^1$HNMR (CDCl$_3$) δ: 3.86 (3H, s), 6.97-7.05 (3H, m), 7.22-7.27 (1H, m), 7.47 (2H, d, J=8.8 Hz), 7.80 (1H, s), 8.39 (1H, s)

ESI-MS (m/e): 509[M–H]$^-$

PRODUCTION EXAMPLE 149

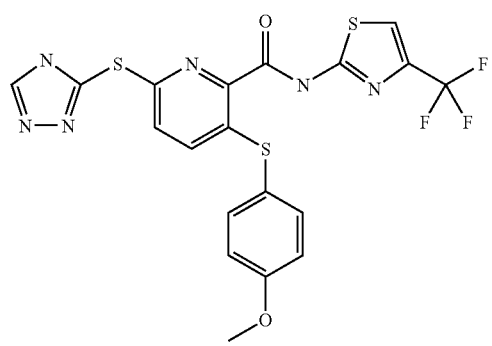

Manufacture of 3-(4-methoxy-phenylsulfanyl)-6-(4H-[1,2,4]triazole-3-yl-sulfanyl)-N-(4-trifluoromethylthiazole-2-yl)-2-pyridine carboxamide Compound of Production Example 149 can be produced by the same method as Production Example 1, by a method according thereto, or by a combination of these and ordinary methods, with the use of 3,6-dichloro-2-pyridinecarboxylic acid, 2-amino-4-trifluoromethyl-thiazole, 4-methoxy-thiophenol and 3-mercapto-1,2,4-triazole.

$^1$HNMR (CDCl$_3$) δ: 3.85 (3H, s), 6.96-7.00 (3H, m), 7.17 (1H, d, J=8.0 Hz), 7.44-7.47 (3H, m), 8.37 (1H, s)

ESI-MS (m/e): 511 [M+H]$^+$

PRODUCTION EXAMPLE 150

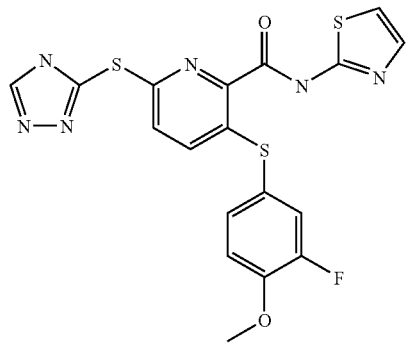

Manufacture of 3-(3-fluoro-4-methoxy-phenylsulfanyl)-6-(4H-[1,2,4]triazole-3-yl-sulfanyl)-N-(thiazole-2-yl)-2-pyridine carboxamide Compound of Production Example 150 can be produced by the same method as Production Example 1, by a method according thereto, or by a combination of these and ordinary, methods, with the use of 3,6-dichloro-2-pyridinecarboxylic acid, 2-amino-thiazole, 3-fluoro-4-methoxy-thiophenol and 3-mercapto-1,2,4-triazole.

$^1$HNMR (CDCl$_3$) δ: 3.95 (3H, s), 7.01-7.06 (3H, m), 7.23-7.32 (3H, m), 7.47 (1H, d, J=4.0 Hz), 8.32 (1H, s)

ESI-MS (m/e): 461 [M+H]$^+$

PRODUCTION EXAMPLE 151

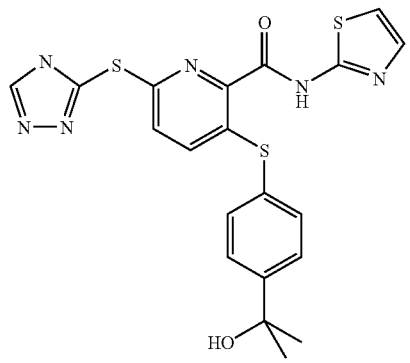

Manufacture of 3-[4-(1,1-dimethyl-1-hydroxymethyl)-phenylsulfanyl]-6-(4H-[1,2,4]triazole-3-yl-sulfanyl)-N-(thiazole-2-yl)-2-pyridine carboxamide Compound of Production Example 151 can be produced by the same method as Production Example 1, by a method according thereto, or by a combination of these and ordinary methods, with the use of 3,6-dichloro-2-pyridinecarboxylic acid, 2-amino-thiazole, 4-(1,1-dimethyl-1-hydroxymethyl)-thiophenol and 3-mercapto-1,2,4-triazole.

$^1$HNMR (CDCl$_3$) δ: 1.63 (6H, s), 6.99-7.03 (2H, m), 7.18 (1H, d, J=8.4 Hz), 7.39 (1H, d, J=3.6 Hz), 7.51 (2H, d, J=8.4 Hz), 7.58 (2H, d, J=8.4 Hz), 8.30 (1H, s)

ESI-MS (m/e): 471 [M+H]$^+$

PRODUCTION EXAMPLE 152

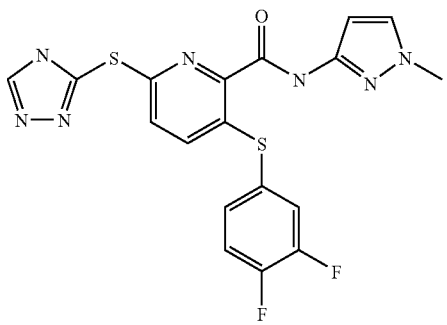

Manufacture of 3-(3,4-difluoro-phenylsulfanyl)-6-(4H-[1,2,4]triazole-3-ylsulfanyl)-N-(1-methyl-1H-[1,2]pyrazole-3-yl)-2-pyridine carboxamide Compound of Production Example 152 can be produced by the same method as Production Example 1, by a method according thereto, or by a combination of these and ordinary methods, with the use of 3,6-dichloro-2-pyridinecarboxylic acid, 3-amino-1-methyl-1H-[1,2]pyrazole, 3,4-difluoro-thiophenol and 3-mercapto-1,2,4-triazole.

$^1$HNMR (CDCl$_3$) δ: 3.84 (3H, s), 6.82 (1H, d, J=2.0 Hz), 6.94 (1H, d, J=8.8 Hz), 7.15 (1H, d, J=8.8 Hz), 7.20-7.41 (4H, m), 8.33 (1H, s)

ESI-MS (m/e): 446[M+H]$^+$

PRODUCTION EXAMPLE 153

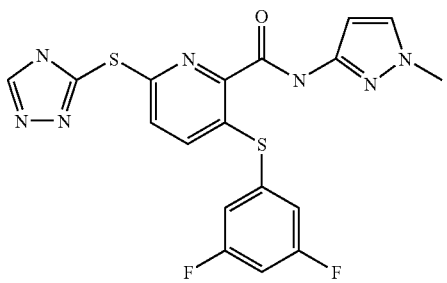

Manufacture of 3-(3,5-difluoro-phenylsulfanyl)-6-(4H-[1,2,4]triazole-3-ylsulfanyl)-N-(1-methyl-1H-[1,2]-pyrazole-3-yl)-2-pyridine carboxamide Compound of Production Example 153 can be produced by the same method as Production Example 1, by a method according thereto, or by a combination of these and ordinary methods, with the use of 3,6-dichloro-2-pyridinecarboxylic acid, 3-amino-1-methyl-1H-[1,2]pyrazole, 3,5-difluorothiophenol and 3-mercapto-1,2,4-triazole.

$^1$HNMR (CDCl$_3$) δ: 3.81 (3H, s), 6.81 (1H, d, J=2.8 Hz), 6.83-6.90 (1H, m), 7.04-7.06 (2H, m), 7.16 (1H, d, J=8.8 Hz), 7.27 (1H, d, J=2.8 Hz), 8.27 (1H, s)

ESI-MS (m/e): 446[M+H]$^+$

PRODUCTION EXAMPLE 154

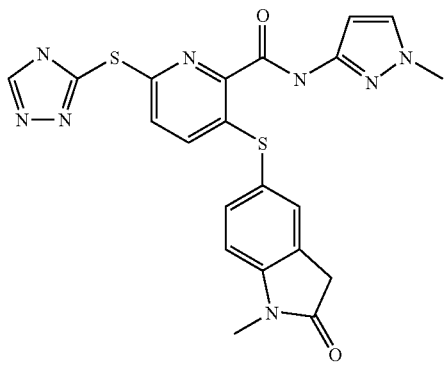

Manufacture of 3-(1-methyl-2-oxo-2,3-dihydro-1H-indole-5-ylsulfanyl)-6-(4H-[1,2,4]triazole-3-ylsulfanyl)-N-(1-methyl-1H-[1,2]-pyrazole-3-yl)-2-pyridine carboxamide Compound of Production Example 154 can be produced by the same method as Production Example 1, by a method according thereto, or by a combination of these and ordinary methods, with the use of 3,6-dichloro-2-pyridinecarboxylic acid, 3-amino-1-methyl-1H-[1,2]pyrazole, 5-mercapto-1-methyl-1,3-dihydro-indole-2-on and 3-mercapto-1,2,4-triazole.

$^1$HNMR (CDCl$_3$) δ: 3.15 (3H, s), 3.48 (2H, s), 3.76 (3H, s), 6.75 (1H, d, J=2.4 Hz), 6.83 (1H, d, J=8.0 Hz), 6.88 (1H, d, J=8.8 Hz), 7.02 (1H, d, J=8.8 Hz), 7.23 (1H, d, J=2.4 Hz), 7.31 (1H, d, J=1.6 Hz), 7.41 (1H, dd, J=8.0, 1.6 Hz), 8.22 (1H, s)

ESI-MS (m/e): 479[M+H]$^+$

PRODUCTION EXAMPLE 155

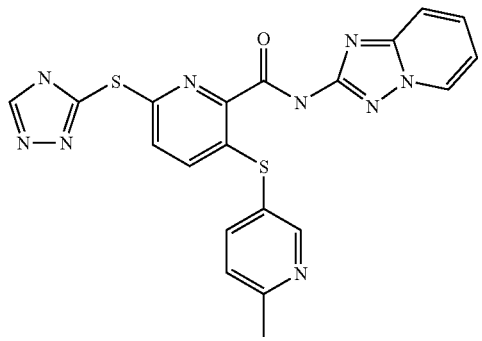

Manufacture of 3-(6-methyl-pyridine-3-sulfanyl)-6-(4H-[1,2,4]triazole-3-ylsulfanyl)-N-[1,2,4]triazoleopyridine-2-yl)-2-pyridine carboxamide Compound of Production Example 155 can be produced by the same method as Production Example 1, by a method according thereto, or by a combination of these and ordinary methods, with the use of 3,6-dichloro-2-pyridinecarboxylic acid, 2-amino-[1,2,4]triazoropyridine, 3-mercapto-6-methyl-pyridine and 3-mercapto-1,2,4-triazole.

$^1$HNMR (CDCl$_3$) δ: 2.58 (3H, s), 6.93 (1H, d, J=8.8 Hz), 7.01 (1H, t, J=6.4 Hz), 7.16 (1H, d, J=8.8 Hz), 7.24 (1H, d, J=8.0 Hz), 7.51-7.60 (2H, m), 7.73 (1H, dd, J=8.0, 2.4 Hz), 8.32 (1H, s), 8.53 (1H, s), 8.60 (1H, d, J=6.4 Hz)

ESI-MS (m/e): 462[M+H]$^+$

PRODUCTION EXAMPLE 156

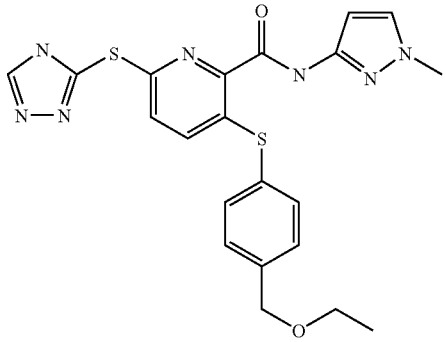

Manufacture of 3-(4-ethoxymethyl-phenylsulfanyl)-6-(4H-[1,2,4]triazole-3-ylsulfanyl)-N-(1-methyl-1H-[1,2]-pyrazole-3-yl)-2-pyridine carboxamide Compound of Production Example 156 can be produced by the same method as Production Example 1, by a method according thereto, or by a combination of these and ordinary methods, with the use of 3,6-dichloro-2-pyridinecarboxylic acid, 3-amino-1-methyl-1H-[1,2]pyrazole-4-ethoxymethyl-thiophenol and 3-mercapto-1,2,4-triazole.

$^1$HNMR (CDCl$_3$) δ: 1.28 (3H, t, J=6.8 Hz), 3.60 (2H, q, J=6.8 Hz), 3.83 (3H, s), 4.54 (2H, s), 6.85 (1H, d, J=2.0 Hz), 6.98 (1H, d, J=8.8 Hz), 7.10 (1H, d, J=8.8 Hz), 7.26 (1H, d, J=2.0 Hz), 7.41 (2H, d, J=8.0 Hz), 7.51 (2H, d, J=8.0 Hz), 8.31 (1H, s)

ESI-MS (m/e): 468[M+H]$^+$

PRODUCTION EXAMPLE 157

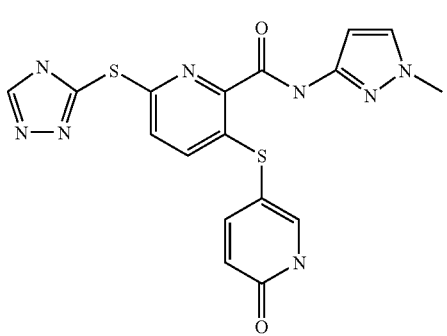

Manufacture of 3-(6-oxo-1,6-dihydro-pyridine-3-ylsulfanyl)-6-(4H-[1,2,4]triazole-3-ylsulfanyl)-N-(1-methyl-1H-[1,2]-pyrazole-3-yl)-2-pyridine carboxamide Compound of Production Example 157 can be produced by the same method as Production Example 1, by a method according thereto, or by a combination of these and ordinary methods, with the use of 3,6-dichloro-2-pyridinecarboxylic acid, 3-amino-1-methyl-1H-[1,2]pyrazole, 3-mercapto-6-methoxy-pyridine and 3-mercapto-1,2,4-triazole.

$^1$HNMR (CDCl$_3$) δ: 3.86 (3H, s), 6.63 (1H, d, J=9.3 Hz), 6.85 (1H, d, J=2.1 Hz), 7.21 (1H, d, J=9.0 Hz), 7.27 (1H, d, J=9.0 Hz), 7.33 (1H, m), 7.45 (1H, brd, J=9.3 Hz), 7.58 (1H, d, J=2.1 Hz), 8.35 (1H, s)

ESI-MS (m/e): 427[M+H]$^+$

PRODUCTION EXAMPLE 158

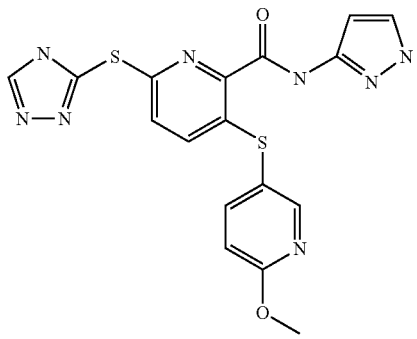

Manufacture of -(6-methoxy-pyridine-3-ylsulfanyl)-6-(4H-[1, 2,4]triazole-3-ylsulfanyl)-N-(1H-[1,2]-pyrazole-3-yl)-2-pyridine carboxamide Compound of Production Example 158 can be produced by the same method as Production Example 1, by a method according thereto, or by a combination of these and ordinary methods, with the use of 3,6-dichloro-2-pyridinecarboxylic acid, 3-amino-1-methyl-1H-[1,2]pyrazole, 3-mercapto-6-methoxy-pyridine and 3-mercapto-1,2,4-triazole.

$^1$HNMR (CDCl$_3$) δ: 4.00 (3H, s), 6.84-6.94 (2H, m), 7.02 (1H, d, J=9.0 Hz), 7.22 (1H, d, J=9.0 Hz), 7.52 (1H, m), 7.70 (1H, m), 8.31-8.40 (2H, m)

ESI-MS (m/e): 427[M+H]$^+$

PRODUCTION EXAMPLE 159

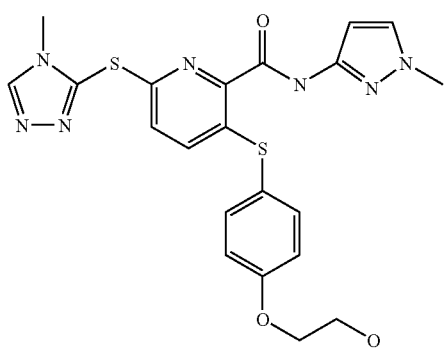

Manufacture of 3-(4-hydroxyethyloxy-phenylsulfanyl)-6-(4-methyl-4H-[1, 2,4]triazole-3-ylsulfanyl)-N-(1-methyl-1H-[1,2]-pyrazole-3-yl)-2-pyridine carboxamide Compound of Production Example 159 can be produced by the same method as Production Example 1, by a method according thereto, or by a combination of these and ordinary methods, with the use of 3,6-dichloro-2-pyridine carboxylic acid, 3-amino-1-methyl-1H-[1,2]pyrazole, 4-hydroxyethyloxy-thiophenol and 3-mercapto-1,2,4-triazole.

$^1$HNMR (CDCl$_3$) δ: 3.73 (3H, s), 3.85 (3H, s), 4.00 (2H, m), 4.13 (2H, m), 6.87 (1H, d, J=2.1 Hz), 6.95-7.06 (3H, m), 7.24-7.31 (2H, m), 7.46 (2H, d, J=8.7 Hz), 8.41 (1H, s)

ESI-MS (m/e): 484[M+H]$^+$

As hereunder, process for the production of the compounds used for the manufacture of the compounds concerning the present invention will be mentioned as Reference Examples 1 to 6.

REFERENCE EXAMPLE 1

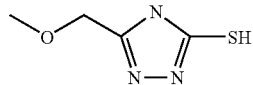

Manufacture of 5-methoxymethyl-3-mercapto-1,2,4-triazole

Methoxyacetyl chloride (2.82 g; 0.023 mol) was added to a solution (15 ml) of 2.09 g (0.0230 mol) of thiosemicarbazide in pyridine followed by stirring for a whole day and night at room temperature. The reaction solution was concentrated and 10 ml of methanol and 8 ml of a 25 wt % methanolic solution of sodium methoxide were added thereto followed by heating to reflux for a whole day and night. After cooling to room temperature, the solvent was evaporated and concentrated hydrochloric acid was added thereto to acidify. The solid separated out therefrom was filtered, washed with distilled water and dried to give 1.0 g (yield: 33%) of the title compound.

$^1$H-NMR (DMSO) δ: 3.24 (3H, s), 4.29 (2H, s)

ESI-MS (m/e): 146 [M+H]$^+$

REFERENCE EXAMPLE 2

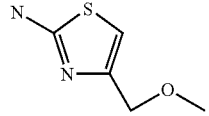

Manufacture of 2-amino-4-methoxymethylthiazole

To a solution (120 ml) of 13.4 g (106 mmol) of dichloroacetone were added 8.06 g (106 mmol) of thiourea followed by stirring at 55° C. for 3 hours. The reaction solution was concentrated and 200 ml of methanol and 15.1 g (125 mmol) of magnesium sulfate were added to the resulting white solid followed by heating to reflux for 3 days. The reaction mixture was filtered through Celite and the filtrate was concentrated and partitioned by chloroform and a saturated aqueous solution of sodium hydrogen carbonate. After the organic layer was dried and concentrated, the resulting residue was purified by a silica gel column chromatography (ethyl acetate) and by crystallization from a mixed solvent of hexane and ethyl acetate (4:1) to give 6.59 g (yield: 43%) of the title compound as a yellow solid.

$^1$H-NMR (CDCl$_3$) δ: 3.44 (3H, s), 4.34 (2H, s), 6.45 (1H, s)
ESI-MS (m/e): 145 [M+H]$^+$

REFERENCE EXAMPLE 3

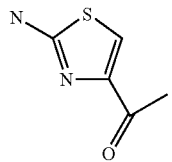

Manufacture of 4-acetyl-2-aminothiazole

To a solution (30 ml) of 1.30 g (5.14 mmol) of 2-(tert-butyloxycarbonylamino)-4-carboxythiazole in N,N-dimethylformamide were added 660 mg (6.77 mmol) of N,O-dimethylhydroxylamine hydrochloride, 1.40 ml (9.96 mmol) of triethylamine, 1.10 g (8.14 mmol) of N-hydroxybenzotriazole hydrate and 1.60 g (8.35 mmol) of 1-(3-dimethylaminopropyl)-3-ethylcarbodiimide hydrochloride successively followed by stirring at room temperature for 5 days. The reaction solution was concentrated, ethyl acetate was added to the residue and the mixture was washed with a 1N aqueous solution of hydrochloric acid, water and a saturated aqueous saline solution, dried and concentrated in vacuo to give 1.35 g (yield: 91%) of an amide compound as an oily substance. A solution (40 ml) of 920 g (3.20 mmol) of the resulting amide compound in tetrahydrofuran was cooled to −78° C. and 18.0 ml (18.0 mmol) of a solution of methyl lithium in diethyl ether were added thereto followed by stirring for 7 hours. To the reaction solution was added a saturated aqueous solution of ammonium chloride followed by extracting with ethyl acetate. The organic layer was washed with water, dried and concentrated to give 666 mg (yield: 86%) of an acetyl compound as an oily substance.

Trifluoroacetic acid (5 ml) was added to a solution (10 ml) of the above-produced acetyl compound in chloroform followed by stirring at room temperature for one and a half hour. The reaction solution was concentrated, neutralized with a saturated aqueous solution of sodium hydrogen carbonate and filtered to give 149 mg (yield: 59%) of the title compound as a white solid.

$^1$H-NMR (CDCl$_3$) δ: 2.48 (3H, s), 7.35 (1H, s)
ESI-MS (m/e): 143 [M+H]$^+$

REFERENCE EXAMPLE 4

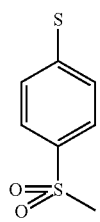

Manufacture of 4-methylsulfonylbenzenethiol

A 35% aqueous hydrogen peroxide (18 ml) and 180 mg (0.72 mmol) of methyl trioxolenium were added to a solution (150 ml) of 5.0 g (36 mmol) of 4-methylthiophenol in chloroform followed by stirring at room temperature for 30 minutes. Manganese dioxide was added to the reaction solution under ice-cooling followed by stirring at room temperature for 4 hours and a saturated aqueous saline solution was added thereto followed by extracting with chloroform. The organic layer was washed with a saturated aqueous saline solution, dried and concentrated to give 5.0 g (yield: 81%) of 4-methylsulfonylphenol as a white solid.

1,4-diazabicyclo[2.2.2]octane (6.5 g; 58 mmol) and 5.4 g (44 mmol) of dimethylthiocarbamoyl chloride were added to a solution (100 ml) of 5.0 g (29 mmol) of the resulting 4-methylsulfonylphenol in N,N-dimethylformamide followed by stirring at 75° C. for 4 hours. Water was added to the reaction solution followed by extracting with ethyl acetate. The organic layer was washed with water, a saturated aqueous solution of sodium hydrogen carbonate and a saturated aqueous saline solution. The residue obtained after drying and concentrating was recrystallized from a mixed solvent of hexane and chloroform to give 4.8 g (yield: 63%) of O-4-methylsulfonylphenyl dimethylthiocarbamate as white solid.

The resulting O-4-methylsulfonylphenyl dimethylthiocarbamate (4.8 g; 18 mmol) was stirred at 180° C. for 10 hours and, after returning it to room temperature, 10 ml of methanol were added thereto. To the reaction solution were added 10 ml of a 2N aqueous solution of sodium hydroxide followed by heating to reflux for 8 hours and 30 minutes. To the reaction solution was added a 1N aqueous solution of hydrochloric acid followed by extracting with ethyl acetate. The organic layer was washed with a saturated aqueous saline solution, dried and concentrated and the resulting residue was purified by a silica gel column chromatography (hexane:ethyl acetate=2:1; chloroform:methanol=10:1) to give 3.6 g (yield: 100%) of the title compound as a white solid.

$^1$H-NMR (CDCl$_3$) δ: 3.04 (3H, s), 3.69 (1H, s), 7.63 (2H, d, J=7.6 Hz), 7.87 (2H, d, J=7.6 Hz)

REFERENCE EXAMPLE 5

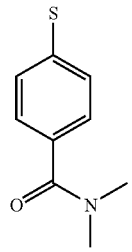

Manufacture of 4-dimethylcarbamoylbenzenethiol

To a solution (50 ml) of 1.30 g (5.14 mmol) of 4-methylthiobenzoic acid in tetrahydrofuran were added 1.50 g (6.77 mmol) of carbonyldiimidazole and 4.70 ml (8.35 mmol) of a solution of dimethylamine in tetrahydrofuran successively followed by stirring at room temperature for two and a half hours. To the reaction solution was added ethyl acetate followed by washing with a 1N aqueous solution of hydrochloric acid and a saturated aqueous saline solution. The organic layer was dried and concentrated to give 960 mg of a crude product of an amide compound as an oily substance.

3-chloroperbenzoic acid (980 mg; 4.90 mmol) was slowly added, at room temperature, to a solution (50 ml) of the above-produced amide compound in chloroform followed by stirring for 1 hour. To the reaction solution was added a saturated aqueous solution of sodium hydrogen carbonate followed by stirring for 30 minutes and extracting with ethyl acetate. The organic layer was washed with water and a saturated aqueous saline solution, dried and concentrated to give 910 mg of a crude product of a sulfoxide compound as an oily substance.

To a solution (20 ml) of the above-produced sulfoxide compound in chloroform were added 1.56 ml (13.4 mmol) of 2,6-lutidine and 1.80 ml (12.9 mmol) of trifluoroacetic acid anhydride successively followed by stirring at room temperature for 1 hour. The reaction solution was concentrated and 5 ml of triethylamine and 5 ml of methanol were added thereto followed by stirring for 30 minutes. The reaction solution was concentrated and to the resulting residue was added diethyl ether followed by washing with a 1N aqueous solution of hydrochloric acid and a saturated aqueous solution of sodium hydrogen carbonate. The organic layer was dried and concentrated to give 487 mg (yield: 62%) of the title compound as an orange-colored oily compound. The resulting crude product was used for the next reaction without purification.

$^1$H-NMR (CDCl$_3$) δ: 3.03 (3H, s), 3.14 (3H, s), 7.22-7.38 (3H, m), 7.46-7.52 (1H, m)

ESI-MS (m/e): 182 [M+H]$^+$

REFERENCE EXAMPLE 6

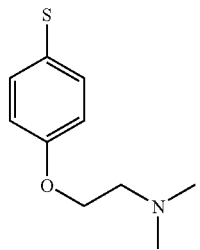

Manufacture of
4-dimethylaminoethyloxy-benzenethiol

Dimethylaminoethyl chloride hydrochloride (2.40 g; 17.1 mmol) and 5.83 g (42.2 mmol) of potassium carbonate were successively added to a solution (70 ml) of 3.00 g (13.6 mmol) of 4-iodophenol in N,N-dimethylformamide followed by stirring at 70° C. for 15 hours. The reaction solution was diluted with water and extracted with ethyl acetate. The organic layer was washed with water and a saturated aqueous saline solution, dried and concentrated. The resulting residue was purified by a silica gel column chromatography (chloroform:methanol=30:1) to give 840 mg (yield: 21%) of an iodine derivative as an oily substance.

Ethylene glycol (120 μl; 2.15 mmol), 305 mg (2.21 mmol) of potassium carbonate, 150 μl (1.08 mmol) of 4-methoxy-toluenethiol and 20 mg (0.105 mmol) of copper iodide were added to a solution (8 ml) of 317 mg (1.08 mmol) of the above-produced iodine derivative in 2-propanol and the reaction solution was heated to reflux for 40 hours. The reaction solution was filtered through Celite and the filtrate was partitioned by chloroform and a saturated aqueous saline solution. The organic layer was dried and concentrated in vacuo to give 298 mg of an oily substance. To the oily substance were successively added 180 μl of anisole and 1.5 ml of trifluoroacetic acid followed by stirring at 70° C. for 2 hours. The reaction solution was concentrated and the resulting crude product was used for the next reaction without purification.

ESI-MS (m/e): 198 [M+H]$^+$

INDUSTRIAL APPLICABILITY

A novel 2-pyridine carboxamide derivative of the present invention represented by the formula (I) shows an excellent glucokinase activity and, therefore, it is useful for treatment and/or prevention of diabetes mellitus, complications of diabetes mellitus or obesity in the field of medicine.

The invention claimed is:
1. A compound of the formula (I):

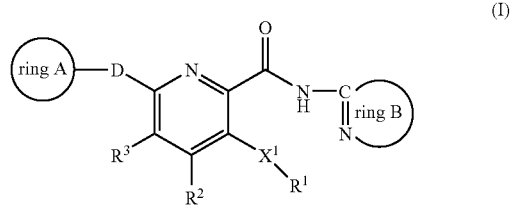

or a pharmaceutically acceptable salt thereof, wherein:

$X^1$ represents N, S or O, or a divalent saturated hydrocarbon group of 1 to 6 carbon atoms (when the carbon number of the divalent saturated hydrocarbon group is 2 or more, one of the carbon atoms therein may be replaced by a nitrogen atom, oxygen atom or sulfur atom);

$R^1$ represents a 6- to 10-membered aryl group, a cycloalkyl group of 3 to 7 carbon atoms, or a lower alkyl group (wherein $R^1$ may be substituted on $R^1$ by 1 or 2 groups selected from the group consisting of amino group, lower alkyl group (the hydrogen atom of the lower alkyl group may be substituted by hydroxy group, lower alkoxy group, halogen atom, carbamoyl group, mono- or di-lower alkyl carbamoyl group, carboxyl group alkoxy carboyl group, alkanoyl group, amino group, mono- or di-lower alkylamino group), lower alkoxy group (the hydrogen atom of the methylene group or methyl group constituting the lower alkoxy group may be substituted by hydroxyl group, halogen atom, carbamoyl group, mono- or di-loweralkyl carbamoyl group, carboxyl group alkoxy carboyl group, alkanoyl group, amino group, mono- or di-lower alkylamino group), carbamoyl group, lower alkylcarbamoyl group, di-lower alkylcarbamoyl group, carbamoylamino group, carbamoyloxy group, carboxyl group, cyano group, sulfamoyl group, trifluoromethyl group, halogen atom group, hydroxy group, formyl group, $C_2$-$C_6$ alkanoyl group, N-$C_2$-$C_6$ alkanoylamino group, $C_1$-$C_6$ alkylthio group, N-$C_1$-$C_6$ alkylsulfamoyl group, N,N-di-$C_1$-$C_6$ alkylsulfamoyl group, $C_1$-$C_6$ alkylsulfinyl group, $C_1$-$C_6$ alkylsulfonyl group, N-$C_1$-$C_6$ alkylsulfonylamino group, $C_1$-$C_6$ alkoxycarbonyl group, N-$C_1$-$C_6$ alkylamino group and N,N-di-$C_1$-$C_6$ alkylamino group);

D represents S;

$R^2$ and $R^3$ are the same or different, each representing a hydrogen atom, lower alkyl group, lower alkoxy group or halogen atom;

the formula (II):

(II)

represents a 1,2,4-triazolyl group, which may have on the ring 1 or 2 groups selected from the group consisting of lower alkyl group, lower alkoxy group, trifluoromethyl group, hydroxy group, hydroxyalkyl group (the hydrogen atom of the hydroxy group of the hydroxyalkyl group may further be substituted by a lower alkyl group) and halogen atom;

the formula (III):

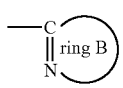
(III)

represents a 1,3,4-thiadiazolyl group optionally substituted with 1 or 2 substituents selected from the group consisting of lower alkyl group, lower alkoxy group, halogen atom, trifluoromethyl group, hydroxyalkyl group (the hydrogen atom of the hydroxy group in the hydroxyalkyl group may further be substituted by a lower alkyl group), aminoalkyl group (the amino may be substituted by a lower alkyl group), alkanoyl group, carboxyl group, alkoxycarbonyl group and cyano group).

2. The compound according to claim 1, wherein both $R^2$ and $R^3$ are hydrogen atoms.

3. A compound according to claim 1, wherein ring A is a 1,2,4-triazolyl group, which may contain on the ring 1 or 2 groups selected from the group consisting of lower alkyl group, lower alkoxy group, trifluoromethyl group, hydroxy group, hydroxyalkyl group (the hydrogen atom of the hydroxy group in the hydroxyalkyl group may further be substituted by a lower alkyl group) and halogen atom.

4. A compound according to claim 1, wherein $X^1$ is selected from the group consisting of nitrogen atom, sulfur atom, oxygen atom, —CH$_2$—, —N—CH$_2$—, —S—CH$_2$—, —O—CH$_2$—, —CH$_2$—N—, —CH$_2$—O— and —CH$_2$—S—.

5. A compound according to claim 1, wherein $R^1$ is a 6- to 10-membered aryl group, or a cycloalkyl group of 3 to 7 carbons.

6. A compound according to claim 5, wherein $R^1$ is a 6- to 10-membered aryl group.

7. A compound according to claim 2, wherein the substituent of the ring A is a hydrogen atom, lower alkyl group, lower alkoxy group, hydroxy group, or hydroxy lower alkyl group (the hydrogen atom of the hydroxy group of the hydroxy lower alkyl group may further be substituted by a lower alkyl group).

8. A compound according to claim 3, wherein the substituent of the ring B is a hydrogen atom, lower alkyl group, halogen atom, hydroxyalkyl group, aminoalkyl group, or alkanoyl group.

9. A compound according to claim 1, wherein the substituent in $R^1$ is a hydrogen atom, hydroxyalkyl group, lower alkyl group, lower alkoxy group, carbamoyl group, alkylcarbamoyl group, dialkylcarbamoyl group, cyano group, trifluoromethyl group, halogen atom, $C_2$-$C_6$ alkanoyl group, N—$C_2$-$C_6$ alkanoylamino group, $C_1$-$C_6$ alkylsulfonyl group, $C_1$-$C_6$ alkylamino group, or aminoalkyl group.

10. A pharmaceutical composition comprising a compound in accordance with claim 1 in combination with a pharmaceutically acceptable carrier.

11. A compound according to claim 1, selected from the group consisting of:
   3-(4-methoxy-phenylsulfanyl)-6-(4H-[1,2,4]triazol-3-yl-sulfanyl)-N-([1,3,4]thiadiazol-2-yl)-2-pyridine carboxamide,
   3-(4-methoxy-phenylsulfanyl)-6-(4H-[1,2,4]triazol-3-yl-sulfanyl)-N-([1,3,4]thiadiazol-2-yl)-2-pyridine carboxamide,
or a pharmaceutically acceptable salt thereof.

12. A pharmaceutical composition comprising a compound in accordance with claim 11 in combination with a pharmaceutically acceptable carrier.

13. A method of treating type II diabetes in a mammalian patient in need of such treatment comprising administering to the patient a compound in accordance with claim 1 in an amount that is effective to treat type II diabetes.

14. A method of treating type II diabetes in a mammalian patient in need of such treatment comprising administering to the patient a compound in accordance with claim 11 in an amount that is effective to treat type II diabetes.

* * * * *

UNITED STATES PATENT AND TRADEMARK OFFICE
CERTIFICATE OF CORRECTION

| | | |
|---|---|---|
| PATENT NO. | : 7,629,362 B2 | Page 1 of 1 |
| APPLICATION NO. | : 10/545424 | |
| DATED | : December 8, 2009 | |
| INVENTOR(S) | : Mitsuya et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 884 days.

Signed and Sealed this

Eighteenth Day of January, 2011

David J. Kappos
*Director of the United States Patent and Trademark Office*